(12) United States Patent
Schultz et al.

(10) Patent No.: US 12,097,345 B2
(45) Date of Patent: Sep. 24, 2024

(54) INFUSION CATHETER AND METHODS OF USE

(71) Applicant: Penumbra, Inc., Alameda, CA (US)

(72) Inventors: Robert D. Schultz, Emeryville, CA (US); Justin M. Olshavsky, Berkeley, CA (US); Bridget C. Vaughan, Berkeley, CA (US); Corey Teigen, Rosholt, SD (US); Scott Teigen, West Fargo, ND (US); Michael E. Salamy, Poway, CA (US); Nitika S. Chellappa, San Jose, CA (US); Akhilesh R. R. Yeluru, San Jose, CA (US); Annam K. Quraishi, Sunnyvale, CA (US); Melissa E. R. Jones, Calgary (CA); Aurko J. Shaw, Dayton, OH (US); Matthew W. L. Sprinkel, San Francisco, CA (US); Anderson S. Lee, Encinitas, CA (US); Evan T. Koretsky, San Francisco, CA (US); Steve Loisel, Castro Valley, CA (US); Robyn Shaffer, Kensington, CA (US)

(73) Assignee: Penumbra, Inc., Alameda, CA (US)

(*) Notice: Subject to any disclaimer, the term of this patent is extended or adjusted under 35 U.S.C. 154(b) by 946 days.

(21) Appl. No.: 17/031,511

(22) Filed: Sep. 24, 2020

(65) Prior Publication Data

US 2021/0100987 A1  Apr. 8, 2021

Related U.S. Application Data

(63) Continuation-in-part of application No. PCT/US2019/035071, filed on May 31, 2019.
(Continued)

(51) Int. Cl.
*A61M 25/10* (2013.01)
*A61M 25/00* (2006.01)

(52) U.S. Cl.
CPC .... *A61M 25/1018* (2013.01); *A61M 25/0026* (2013.01); *A61M 25/005* (2013.01);
(Continued)

(58) Field of Classification Search
CPC ........... A61M 25/0026; A61M 25/005; A61M 2025/1052; A61M 2025/0037;
(Continued)

(56) References Cited

U.S. PATENT DOCUMENTS 5,478,309 A * 12/1995 Sweezer ............. A61M 1/3659
604/6.14
5,885,238 A  3/1999 Stevens et al.
(Continued)

FOREIGN PATENT DOCUMENTS

CN  1864760 A  11/2006
CN  105579045 A  5/2016
(Continued)

OTHER PUBLICATIONS

International Search Report and Written Opinion in PCT/US2020/052550 dated Dec. 10, 2020.
(Continued)

*Primary Examiner* — Laura A Bouchelle
*Assistant Examiner* — Sarah Dympna Grasmeder
(74) *Attorney, Agent, or Firm* — Haley Guiliano LLP

(57) ABSTRACT

Venous infusion catheter assemblies and methods of use are described herein. A catheter assembly may comprise an elongated body having a proximal end and a distal end, with an expandable occlusion element disposed on the elongated catheter body. A catheter may include a first infusion lumen extending to a proximal infusion port positioned on the
(Continued)

catheter body proximally of the occlusion element and a second infusion lumen extending to a distal infusion port. Some embodiments may use a suction lumen extending to at least one suction port. When the catheter is introduced into vasculature of a patient, the suction port may be positioned in the patient's superior vena cava or right atrium to draw blood, the distal infusion port is positioned to direct normothermic or hyperthermic fluid toward the patient's heart, and the proximal infusion port is positioned to create a flow of hypothermic fluid in the patient's cerebral vasculature.

30 Claims, 90 Drawing Sheets

Related U.S. Application Data

(60) Provisional application No. 63/010,601, filed on Apr. 15, 2020, provisional application No. 62/954,363, filed on Dec. 27, 2019, provisional application No. 62/947,457, filed on Dec. 12, 2019, provisional application No. 62/905,104, filed on Sep. 24, 2019.

(52) U.S. Cl.
CPC ............ *A61M 2025/105* (2013.01); *A61M 2025/1052* (2013.01); *A61M 2025/1056* (2013.01); *A61M 2025/1079* (2013.01); *A61M 2025/1095* (2013.01); *A61M 2205/3334* (2013.01); *A61M 2205/3368* (2013.01); *A61M 2210/125* (2013.01); *A61M 2230/50* (2013.01)

(58) Field of Classification Search
CPC .. A61M 2025/1079; A61M 2025/1095; A61M 2025/0031; A61M 2025/0036; A61M 2025/0081; A61M 2025/001; A61M 2025/0023; A61M 2205/3334; A61M 2205/3368; A61M 2210/125; A61M 2230/50

See application file for complete search history.

(56) References Cited

U.S. PATENT DOCUMENTS

| | | | |
|---|---|---|---|
| 6,383,172 B1 | 5/2002 | Barbet | |
| 6,582,388 B1 | 6/2003 | Coleman et al. | |
| 6,652,565 B1 | 11/2003 | Shimada et al. | |
| 6,673,042 B1* | 1/2004 | Samson | A61M 29/02 606/198 |
| 6,726,651 B1* | 4/2004 | Robinson | A61M 1/3613 604/4.01 |
| 6,743,208 B1 | 6/2004 | Coyle | |
| 9,604,037 B2 | 3/2017 | Fischer, Jr. et al. | |
| 2001/0047163 A1* | 11/2001 | Samson | A61M 1/3613 604/509 |
| 2002/0052620 A1* | 5/2002 | Barbut | A61B 17/22 606/190 |
| 2002/0111584 A1* | 8/2002 | Walker | A61F 7/12 604/113 |
| 2002/0128586 A1* | 9/2002 | Barbut | A61M 1/3659 604/113 |
| 2003/0138350 A1* | 7/2003 | MacOviak | A61M 25/1011 604/4.01 |
| 2003/0139751 A1* | 7/2003 | Evans | A61M 25/0021 606/127 |
| 2003/0212304 A1 | 11/2003 | Lattouf | |
| 2004/0167467 A1* | 8/2004 | Harrison | A61F 7/12 604/113 |
| 2006/0009740 A1* | 1/2006 | Higgins | A61M 25/001 604/525 |
| 2006/0253071 A1 | 11/2006 | Zattera | |
| 2008/0125746 A1 | 5/2008 | Shapland et al. | |
| 2010/0233021 A1 | 9/2010 | Silwa et al. | |
| 2013/0000642 A1* | 1/2013 | Fearnot | A61M 16/0493 128/204.15 |
| 2013/0345628 A1 | 12/2013 | Berger et al. | |
| 2014/0114242 A1* | 4/2014 | Eckle | A61B 17/12031 604/96.01 |
| 2015/0283353 A1* | 10/2015 | Kohn | A61F 7/0097 607/104 |
| 2016/0158489 A1* | 6/2016 | Wu | A61M 25/003 604/509 |
| 2016/0271161 A1 | 9/2016 | Dobson | |
| 2016/0346452 A1* | 12/2016 | Gilbert | A61M 1/3666 |
| 2017/0164605 A1* | 6/2017 | Tillman | A61M 1/32 |
| 2018/0214303 A1 | 8/2018 | Dabrowiak et al. | |
| 2019/0117944 A1 | 4/2019 | Nitzan et al. | |
| 2021/0123009 A1* | 4/2021 | Yeo | C12M 35/02 |

FOREIGN PATENT DOCUMENTS

| | | | |
|---|---|---|---|
| CN | 108671362 A | 10/2018 | |
| EP | 1915943 A1 | 4/2008 | |
| WO | 2001/37921 A1 | 5/2001 | |
| WO | 2011/097295 A1 | 8/2011 | |
| WO | 2012/110598 A1 | 8/2012 | |
| WO | WO-2016126369 A1 * | 8/2016 | ........ A61M 25/0013 |
| WO | 2019/232488 A1 | 12/2019 | |

OTHER PUBLICATIONS

Extended European Search Report for Application No. 19811134.6, dated Feb. 28, 2022 (8 pages).

* cited by examiner

FIG. 9 [Expanded Configuration]

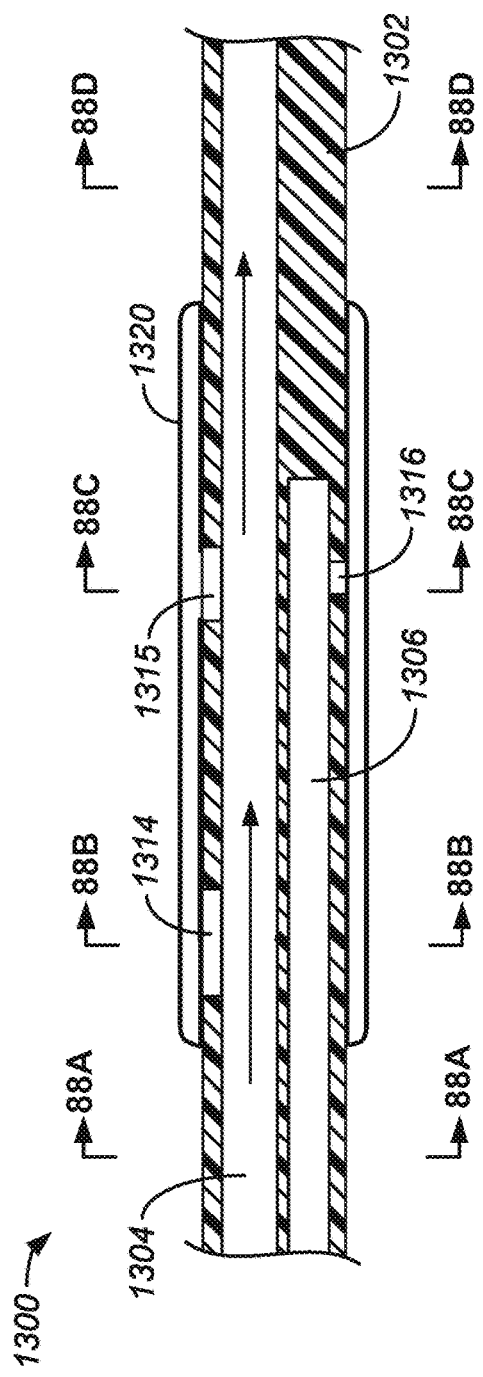
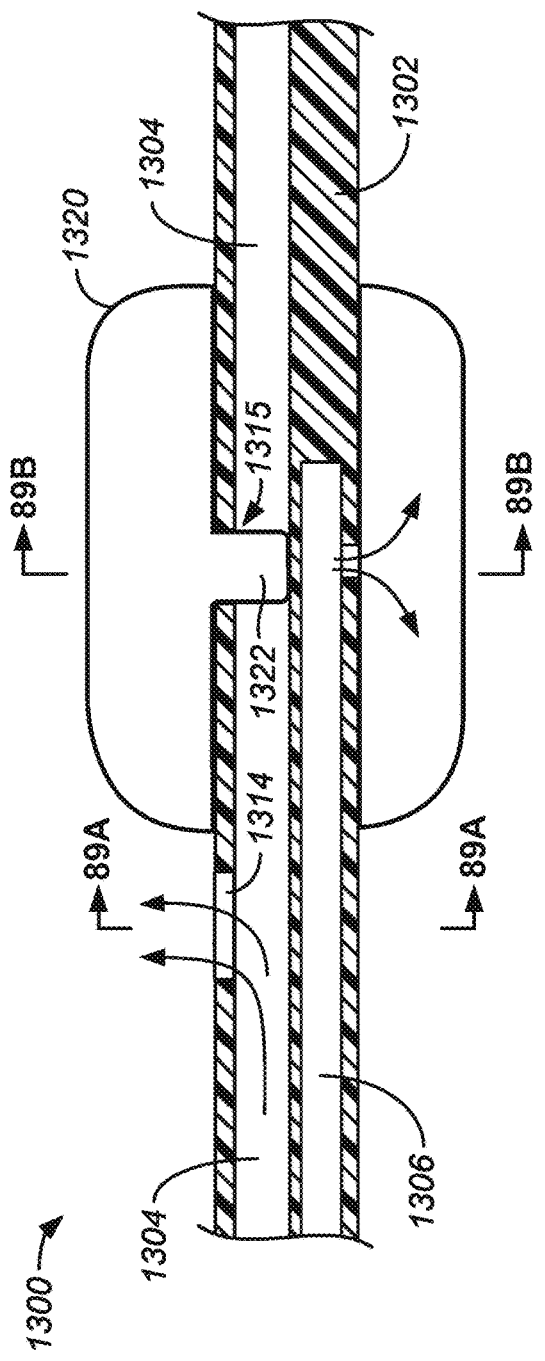
FIG. 87A
FIG. 87B

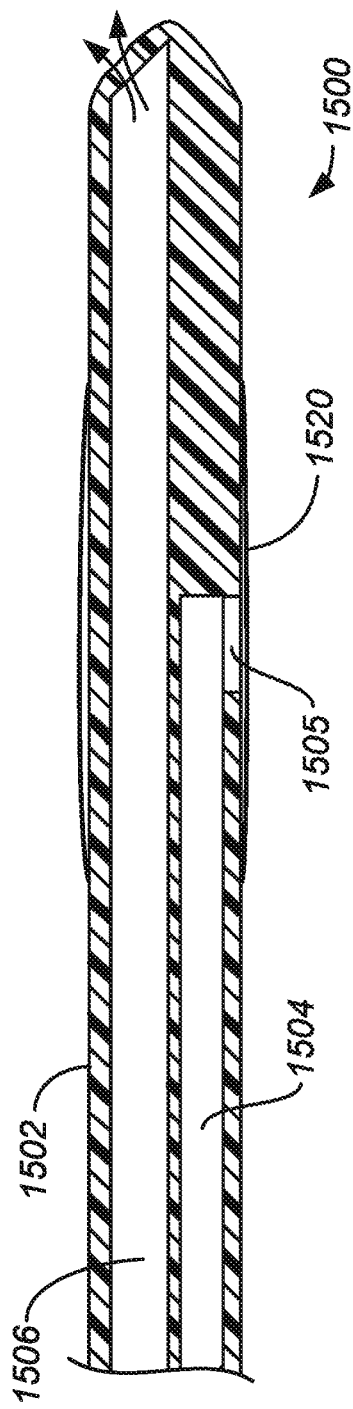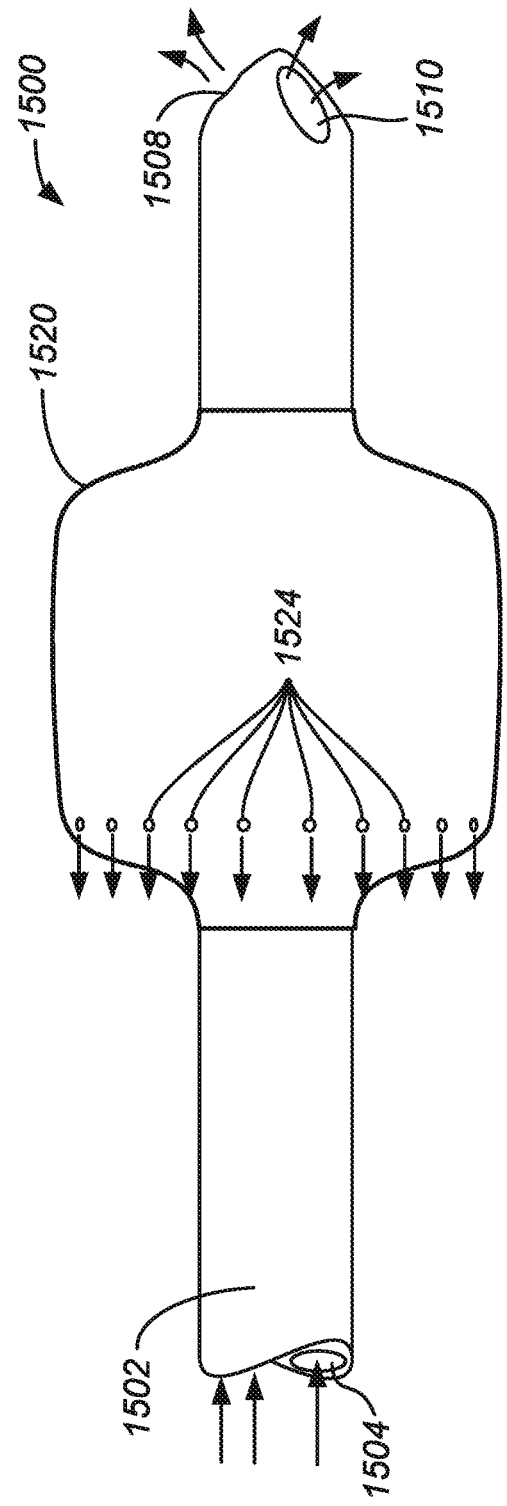

INFUSION CATHETER AND METHODS OF USE

RELATED APPLICATIONS

This application claims benefit to U.S. Provisional Application No. 62/905,104, filed on Sep. 24, 2019, U.S. Provisional Application No. 62/947,457, filed on Dec. 12, 2019, U.S. Provisional Application No. 62/954,363 filed on Dec. 27, 2019, and U.S. Provisional Application No. 63/010,601 filed on Apr. 15, 2020, and is a continuation-in-part of International Application No. PCT/US2019/035071, filed on May 31, 2019, which claims the benefit of U.S. Provisional Application No. 62/679,242, filed on Jun. 1, 2018, all of which are incorporated herein by reference.

BACKGROUND

The present disclosure relates generally to medical catheters, and more particularly to central venous catheters.

SUMMARY

Interruption of blood flow to the brain may result in permanent neurologic dysfunction or brain death and occurs in a number of clinical settings. Interrupted cerebral blood flow occurs in stroke, cardiac arrest, carotid endarterectomy, and stopped-heart cardiac surgery. Despite best practices, the substantial neuroprotection afforded to patients in cardiac surgery via therapeutic hypothermia has not yet become readily deployable outside of this unique and limited setting. For stroke and cardiac arrest patients, there exists a definitive clinical need for a novel point-of-care device and system to protect the brain and prevent disability and death.

Strokes occur due to the blockage (ischemic) or rupture (hemorrhagic) of arteries supplying the brain. Ischemic stroke describes those caused by blockages, typically atherosclerotic plaques or solid clots that become lodged in an artery. Brain injury in ischemic stroke occurs both due to the initial blockage, and a secondary mechanism, deemed 'reperfusion injury,' which results in additional injury upon reestablishment of blood flow. Existing treatments focus only on restoring blood flow to the endangered brain tissue, and include recombinant tissue plasminogen activator (tPA) and thrombectomy (mechanical clot removal). Administering therapeutic hypothermia in a timely fashion promises to mitigate both ischemic injury and reperfusion injury alike. Such treatment would be applicable to stroke patients in a variety of settings, such as during transport to a comprehensive stroke center, treatment during thrombectomy, and beyond. Additionally, therapeutic hypothermia delivered only to the brain, selective cerebral hypothermia, may confer additional benefit, as cooling of the body can have deleterious effects. These deleterious effects may include increased risk of pneumonia, increased coagulopathy, and bradycardia. Cooling the heart to levels around or below 32-33° C. is not considered safe, as doing so may lead to arrhythmias or complete stopping of the heart muscle, and coagulopathy. Selective cooling of the brain may allow for a reduction in the deleterious effects of systemic cooling and allow for deeper levels of hypothermia to be reached safely. An ideal solution would selectively cool the brain while leaving the body normothermic or near-normothermic.

Cardiopulmonary arrest, typically resulting from stopping of the heart but sometimes resulting from failure of a patient's respiratory function, is a medical emergency where loss of blood flow to the brain can cause irreversible brain damage within as little as two minutes. Cardiopulmonary resuscitation (CPR) may be used to restore cardiopulmonary function and revive the patient, brain death and permanent neurologic dysfunction may still occur. While techniques such as extracorporeal membrane oxygenation (ECMO), a form of miniaturized heart lung bypass, are theoretically effective if administered immediately, such methods require time and subspecialized personnel to administer. The emergent setting of cardiac arrest is not conducive to such time and personnel intensive modalities. Though some therapeutic hypothermia is employed during recovery from cardiac arrest, such modalities are too delayed and shallow in their depth of cooling to substantially prevent neurologic damage; additionally, such post-arrest cooling occurs systemically, which is associated with adverse consequences.

The ability to intervene utilizing therapeutic hypothermia for neuroprotection may be desired to be quick, nonobstructive to workflow, and maintain physiologic safety. Existing hypothermic techniques may be cumbersome to employ or achieve only shallow and systemic bodily temperature reduction, which limits the extent of neuroprotection delivered by the therapy.

Therefore, a need exists to improve neuroprotection in settings of interrupted cerebral blood flow; an opportunity exists to do so via translation of a neuroprotection technique, retrograde cerebral perfusion (RCP), used in cardiac surgery. In particular, it would be desirable to provide a device and fluid delivery system to enable easily implemented hypothermic RCP, while maintaining systemic normothermia to allow for deeper and more protective cerebral cooling. A modified central venous catheter and associated fluid delivery system may allow for hypothermic retrograde cerebral perfusion for neuroprotection in relevant clinical indications.

Accordingly, methods, devices, and systems are described herein that enable point of care personnel in a hospital or elsewhere to protect patient's brain swiftly. Typically, only medical doctors can place catheters in the central venous or arterial systems. Therapeutic hypothermia through a catheter in the central vasculature could be delivered in a hospital setting, but would not be available in the out-of-hospital setting, where the majority of cardiac arrests and strokes occur. Existing systems do not enable EMTs, nurses, or other non-medical doctor medical professionals to place lines in the central vasculature. These medical professionals have earlier access to patients out of the hospital, in the field and during emergency transport.

A catheter and associated fluid delivery system may allow for hypothermic cerebral perfusion for neuroprotection in relevant clinical indications. A device allowing such therapy, associated cooling system, and methods of use may be explained herein. Furthermore, additional methods of use of such a device beyond cerebral cooling may be described. Lastly, an automated approach to device placement in the vasculature may be elucidated. At least some of these objectives may be met by the inventions described below.

In accordance with an aspect of the present disclosure, an infusion catheter comprises an elongated catheter body having one or more lumens, such as perfusion lumens, drug delivery lumens, inflation lumens, temperature probe accommodating lumen, and the like, extending longitudinally between a proximal end and a distal end. The elongated catheter body has at least one lateral port open to a perfusion lumen, with a proximal end of the perfusion lumen fluidly connectable to a source of fluid to be delivered, typically including a proximal hub with an inlet port. An expandable occlusion element, typically an inflatable balloon, is secured to an external surface of the elongated catheter body, and the at least one lateral port is located between the expandable occlusion element and the proximal end or hub. The expandable occlusion element can assume an expanded configuration and a contracted configuration, typically comprising a balloon structure fluidly connectable to a source of inflation fluid. In accordance with various embodiments, the perfusion lumens of the present invention may be available for perfusion of all types of media, including hypothermic and other preservative media, blood products, drugs, medicaments, and the like.

In some embodiments, a venous infusion catheter assembly may comprise an elongated catheter body having a proximal end and a distal end, with an expandable occlusion element disposed on the elongated catheter body. A catheter may include a first infusion lumen extending from the proximal end of the catheter body to a proximal infusion port positioned on the catheter body proximally of the occlusion element between the occlusion element and the proximal end of the catheter body. A catheter may also include a second infusion lumen extending from the proximal end of the catheter body to a distal infusion port positioned on the catheter body distally of the occlusion element. Some embodiments may use a suction lumen extending from the proximal end of the catheter body to at least one suction port positioned on the catheter body distally of the occlusion element. The proximal infusion port and the distal infusion port may be spaced relative to the occlusion element such that when the catheter is introduced into vasculature of a patient, the suction port is positioned in the patient's superior vena cava or right atrium to draw blood flowing through the patient's vena cava, the distal infusion port is positioned in the patient's superior vena cava or right atrium to direct normothermic or hyperthermic fluid toward the patient's heart, and the proximal infusion port is positioned in the patient's internal jugular vein to create a retrograde flow of hypothermic fluid in the patient's cerebral vasculature.

In some embodiments, a method for treating a patient comprises introducing a catheter into the patient's venous vasculature to position a first outlet port on the catheter at a location where blood flows into the patient's right atrium and a second outlet port on the catheter at a location where venous blood drains from the cerebral vasculature. One or more medicaments, drugs, or the like, may be delivered in an antegrade direction to the right atrium of the patient's heart through the first outlet port of the catheter at selected times. At other selected times, a preservative medium, such as a hypothermic fluid, may be delivered in a retrograde direction to the patient's cerebral vasculature through the second outlet port of the catheter. In this way, the catheter may be used in a manner analogous to a central venous catheter for delivering drugs and other medicaments to the patient's heart, for example in a hospital setting such as an intensive care unit. In the setting of ischemic stroke, the catheter may be used for the delivery of a cooling or other preservative medium to the patient's cerebral vasculature in addition to drug, medicament, and fluid delivery through its distal port, for a period of time; after a length of therapeutic hypothermia may be maintained, this catheter can remain in the patient's vein and additional lumens be used for drug, medicament, and fluid delivery to the central venous system. In some embodiments, while the cooled fluid is delivered to the patient's cerebral vasculature in a retrograde direction, warmed fluid may be simultaneously delivered to the patient's heart to keep it warm.

For instance, in some embodiments, treatment may comprise creating an occlusion in the patient's internal jugular vein with an expandable occlusion element disposed on a catheter having a proximal end and a distal end, and then drawing blood from the patient's superior vena cava through a suction port into a suction lumen extending through the catheter. In some cases, the suction port may be positioned on the distal end of the catheter and proximal to the distal infusion port and positioned in the patient's right atrium or superior vena cava.

Treatment may further include delivering from a first heat exchange assembly a hypothermic fluid through a first infusion lumen extending from the proximal end of the catheter body to a proximal infusion port and out the proximal infusion port to create a retrograde flow in the patient's cerebral vasculature and delivering a normothermic or hyperthermic fluid from, e.g., a second heat exchange, through a second infusion lumen extending from the proximal end of the catheter body to a distal infusion port and out the distal infusion port to direct the normothermic or hyperthermic fluid toward the patient's heart. In some cases, the proximal infusion port on the proximal end of the catheter is positioned in the patient's internal jugular vein and/or the distal infusion port on the distal end of the catheter is positioned in the patient's right atrium or superior vena cava at or near the patient's cavoatrial junction.

In some embodiments, a catheter assembly may comprise one or more extracorporeal circuits to, for example, cool fluid for infusion and delivery to one organ and warm fluids for infusion and delivery to another organ. A catheter assembly may comprise one or more heat exchange assemblies fluidly connected to a catheter, which may include a heat exchanger, a pump, and a heat exchange circuit. Connected to the heat exchange assembly may be a controller to facilitate adjustment of, e.g., temperature and flow rate of the heat exchange assembly. In some embodiments, a controller may receive temperature sensor data and flow rate data and, using a processor and memory, may determine and transmit adjustments to be made by each heat exchange assembly.

For instance, in some embodiments, treatment may comprise creating an occlusion in the patient's internal jugular vein with an expandable occlusion element disposed on a catheter having a proximal end and a distal end. A controller may receive a brain temperature based on a measurement of at least one cranial temperature sensor, receive a heart temperature based on a measurement of a temperature sensor positioned on or in the catheter distally of the occlusion element, receive a first flow rate from a first heat exchange assembly indicating a rate of flow from the catheter into the patient's cerebral vasculature, and receive a second flow rate from a second heat exchange assembly indicating a rate of flow from the catheter directed to the patient's heart. The controller may determine if the heart temperature is less than a second predetermined temperature and transmit a command to the second heat exchange assembly to increase the second flow rate if the heart temperature is less than the second predetermined temperature. The controller may also determine if the brain temperature is greater than a first predetermined temperature if the heart temperature is not less than the second predetermined temperature and, in response to determining the brain temperature is greater than the first predetermined temperature, transmit a command to the second heat exchange assembly to increase the second flow rate and transmit a command to the first heat exchange assembly to increase the first flow rate.

DRAWINGS

FIG. 87A illustrates an embodiment of a venous perfusion catheter, in accordance with some embodiments of the disclosure;

FIG. 87B illustrates an embodiment of a venous perfusion catheter, in accordance with some embodiments of the disclosure;

FIG. 91A illustrates an embodiment of a venous perfusion catheter, in accordance with some embodiments of the disclosure; and FIG. 91B illustrates an embodiment of a venous perfusion catheter, in accordance with some embodiments of the disclosure.

DETAILED DESCRIPTION

It is understood that the disclosures herein are in part described by their associated figure(s). Figures are intended to be representative of potential embodiments. As such, some embodiments typically appear as part of a five or six-lumen catheter, though it is understood that the disclosures may be incorporated in a catheter with a greater or fewer number of lumens as appropriate. Similarly, the enlarged images included for detail often show only the lumens necessary for the relevant disclosure; for example, a cross section may include one or more lumens as appropriate beyond those depicted in the cross section in the figures herein.

It is understood that within this disclosure, a proximal port may be referred to as the infusion port and vice versa. Additionally, what is described as the infusion lumen may be described as a common infusion/drug lumen. What is described as an infusion lumen or port is synonymous with what is described as a perfusion lumen or perfusion port respectively. What is described as the infusion lumen may also refer to the infusion port, the perfusion port, or the perfusion lumen. Similarly, one or more of the distal ports and suction port may refer to the same feature. What is described as the infusion lumen may be a lumen used solely for delivery of fluids through the infusion port, or may be a lumen which may be used for delivery of fluids through one or more exit ports, potentially a proximal infusion port in some configurations and a distal port in other configurations. The expandable occluder may also be described as the occlusive element, occlusion element, the expandable occlusive element, and is inclusive of the occlusive balloon or balloon described in some embodiments. It is understood that language including the catheter, device, infusion catheter, elongated catheter body, therapy delivery device, fluid delivery device, inlet catheter may all refer to the same device: the device(s) detailed below. What is described as the therapeutic fluid or therapeutic media may also be described as the infusion fluid, perfusion fluid, perfusate, or medicament, or media. Additionally, the cooling system, therapy system, therapy circulating system, the therapy delivery apparatus may all refer to the same system.

Figure 1A:
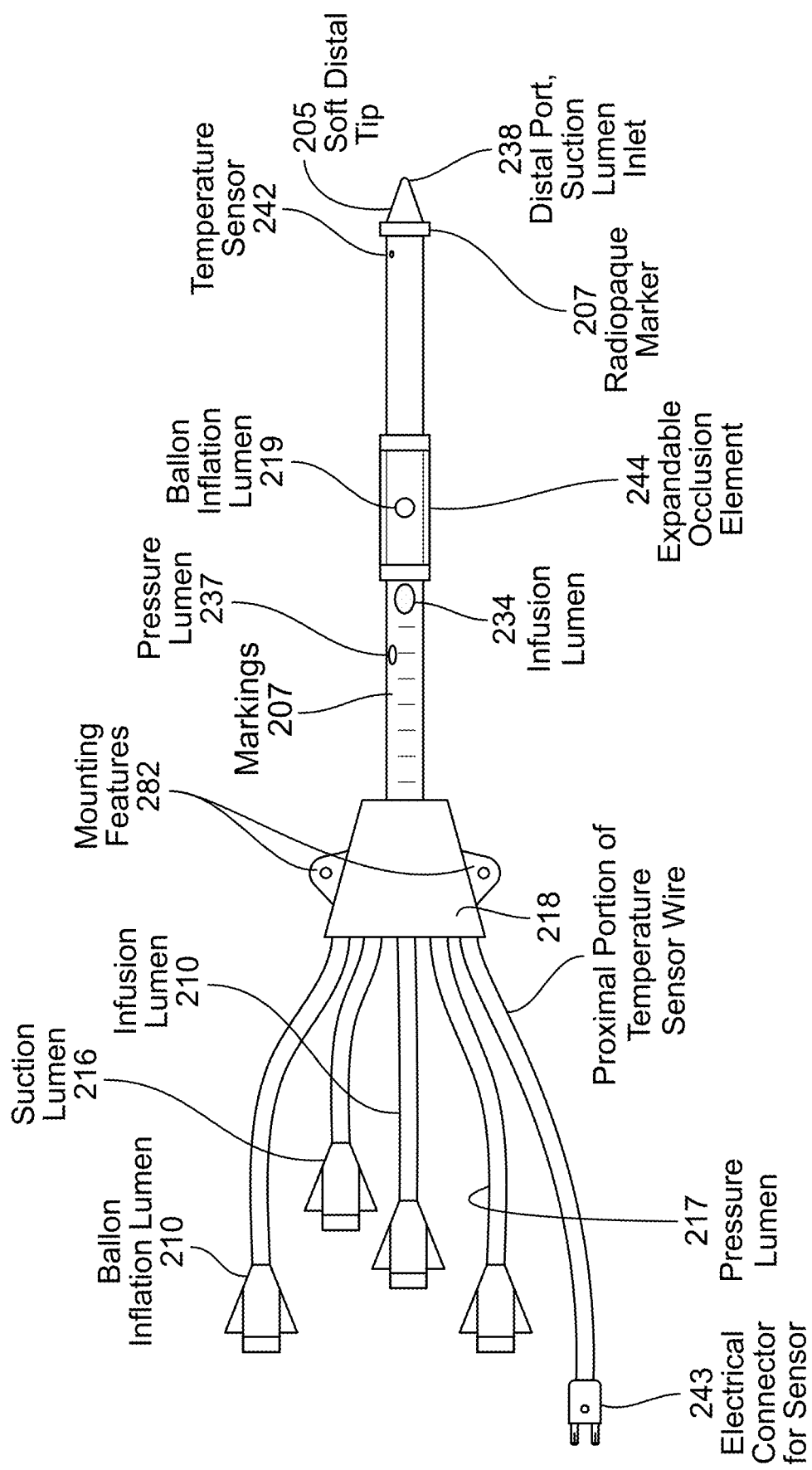
FIG. 1A depicts an exemplary external view of a catheter, in accordance with some embodiments of the disclosure.
Figure 1B:
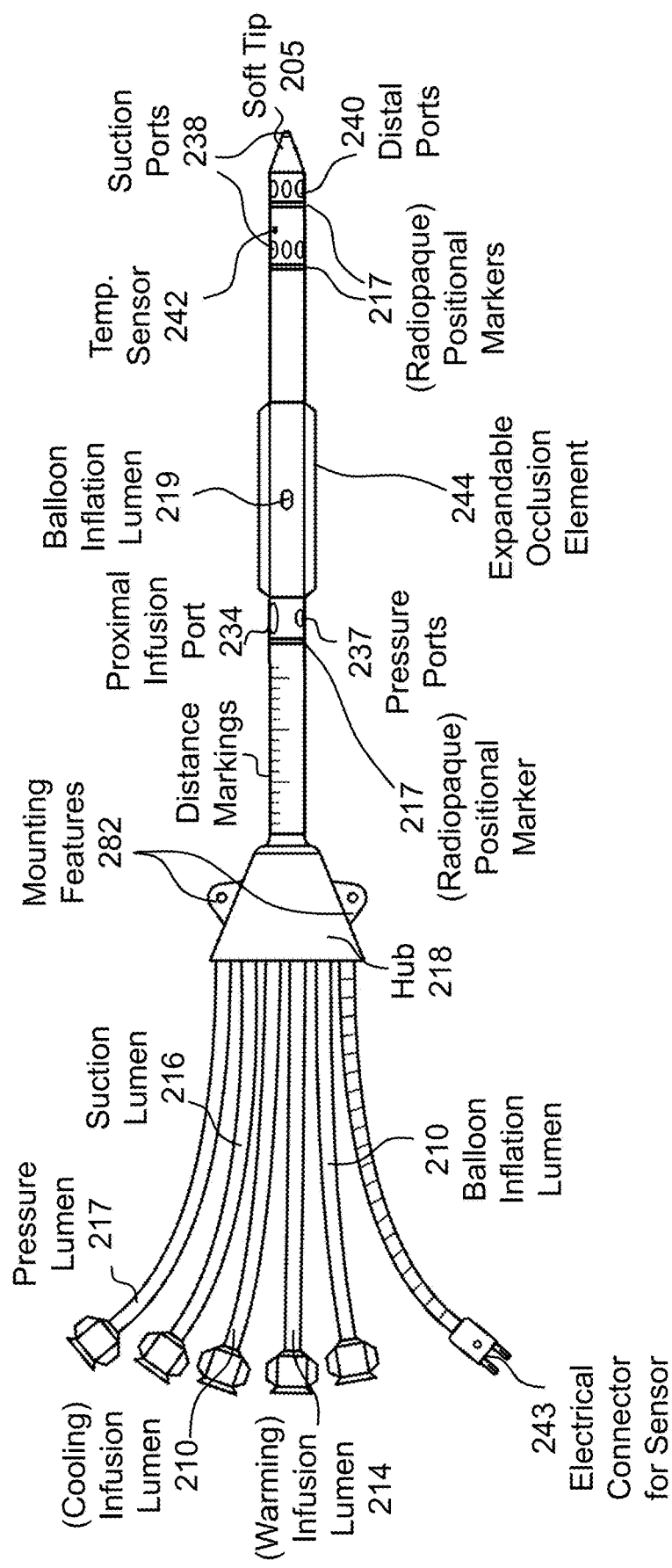
FIG. 1B depicts an exemplary external view of a catheter, in accordance with some embodiments of the disclosure.
Figure 2:
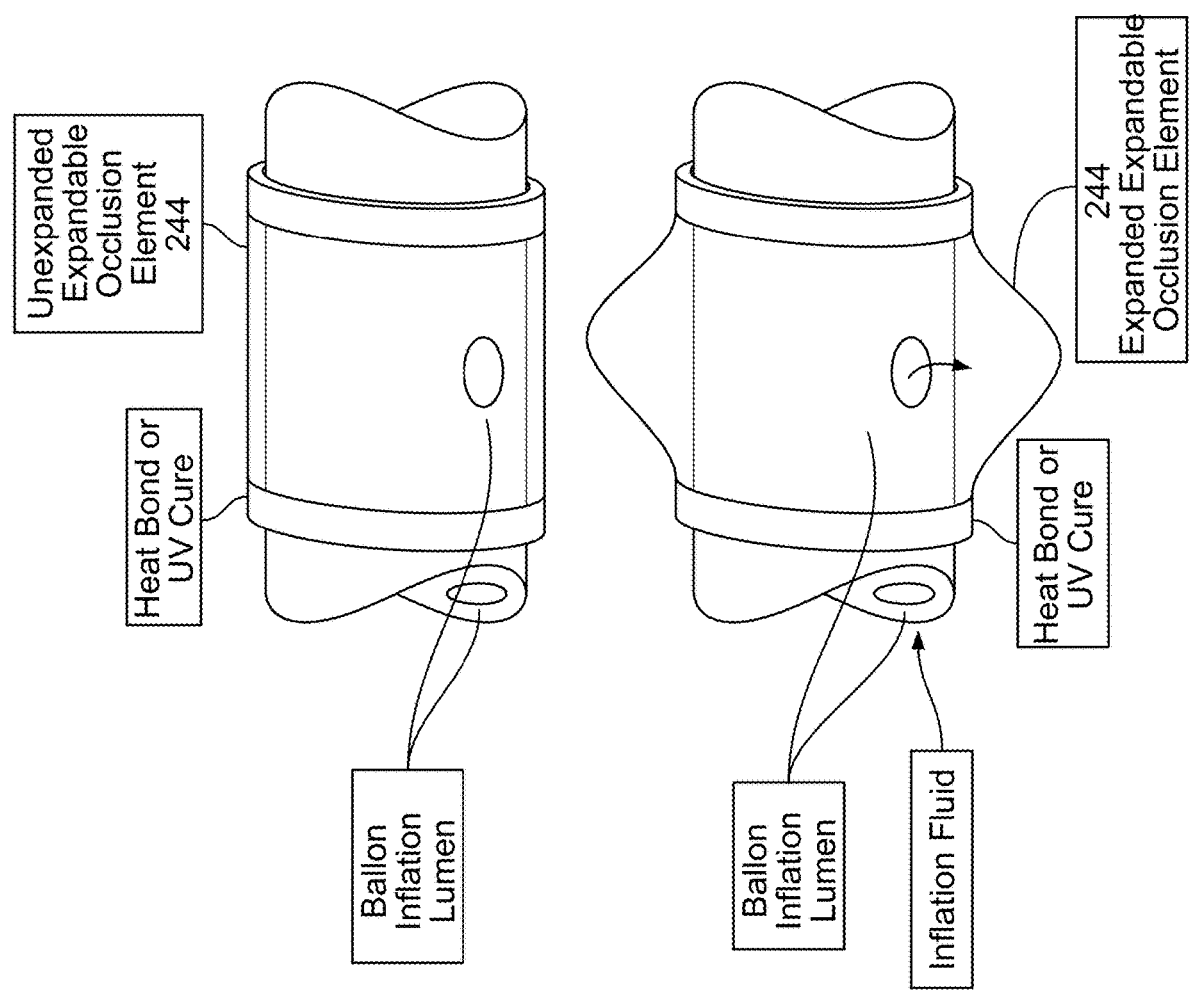
FIG. 2 is a detail view of a balloon on an infusion catheter of the present invention show in deflated and inflated configurations.
Figure 3A:
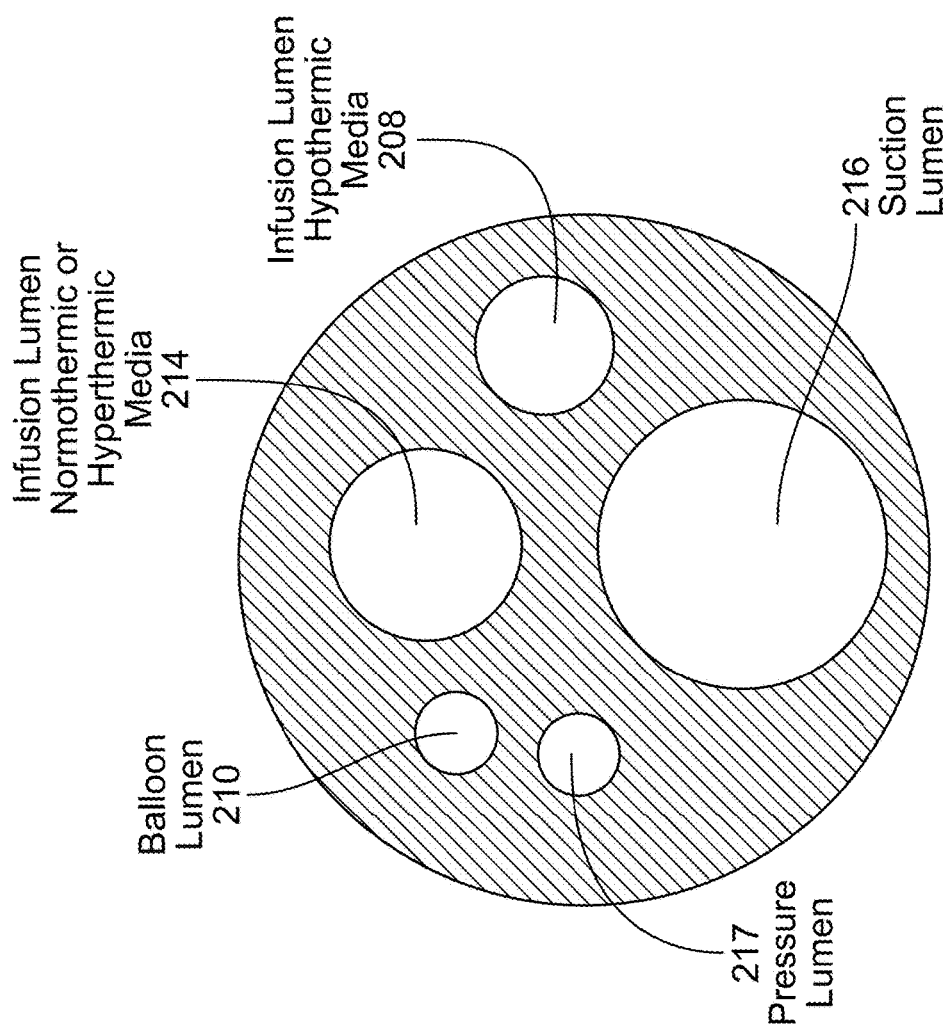
FIG. 3A depicts exemplary cross-sections of an infusion catheter of the present invention.

1.1 Aspects of an Infusion Catheter Device (See FIGS. 1-3)

FIG. 1A depicts an exemplary external view of a catheter, in accordance with some embodiments of the disclosure. In some embodiments as disclosed herein, an infusion catheter may comprise an elongated catheter body 202 having one or more lumens, extending longitudinally between a proximal end 206 and a distal end 204, and an expandable occlusion element is provided. The infusion catheter may also be known as an infusion cannula. The elongated catheter body 202 may have at least one port, which may be a lateral port, open to an infusion lumen, with a proximal end 206 of the infusion lumen fluidly connectable to a source of fluid to be delivered, typically including a proximal hub 218 with an inlet port. The one or more lumens may include lumens for infusion, suction, drug delivery, balloon inflation, temperature measurement, pressure measurement, lumens for central venous pressure measurement, and the like. FIG. 3 depicts exemplary cross-sections of an infusion catheter of the present invention. The cross section of the body of the catheter, as labeled herein, is an example of possible lumen geometries, but the shapes may be semicircular, oval, kidney-shaped, or some other shape or shapes to maximize flow rates and minimize risk of lumen collapse. The catheter may contain any number of combinations of these lumens. An expandable occlusion element, typically an inflatable balloon, may be secured to an external surface of the elongated catheter body 202, and the at least one lateral port may be located between the expandable occlusion element and the proximal end 206 or hub 218. The expandable occlusion element can assume an expanded configuration and an unexpanded configuration, typically comprising a balloon structure fluidly connectable to a source of inflation fluid. The device may be placed in a blood vessel, either a vein or artery of a patient, and may be used for delivering therapy. The infusion lumens may be available for infusion of all types of media, including hypothermic, normothermic, hyperthermic and other preservative media, blood products, drugs, medicaments, autologous blood and the like.

One or more temperature sensors may be disposed in the lumens, such as the suction, infusion, balloon, or pressure measuring lumens, or may be embedded into the material of the device. At least one suction lumen 216 port may be distal to the expandable occluder while at least one infusion lumen port may be proximal to the expandable occluder. There may be another one or more infusion lumen ports located distal to the suction lumen 216 port. The infusion lumen with the one or more ports proximal to the balloon may be used to infuse cooled hypothermic media at temperatures lower than a patient's body temperature. The infusion port distal to the expandable occluder may be used to infuse normothermic media, at temperatures at or near the temperature of a patient's body, or warmed hyperthermic media, at temperatures higher than a patient's body temperature. The one or more suction ports 238 may be distal to the expandable occluder, while the one or more infusion ports may be between the expandable occluding element and the inlet. One or more suction port 238 may be disposed just distal to the balloon, such that in the case of strong suction, if the catheter body 202 distal to the expandable occluder is suctioned into contact with the vessel wall, the suction port 238 closest to the expandable occluder may remain patent, as it may not become suctioned to the vessel wall due to the expandable occluder. One or more temperature sensors may be located on the catheter body 202. A temperature sensor disposed on or in the body of the catheter near the lateral suction ports 238 may inform an understanding of heart or brain temperature based on blood flow past the temperature sensor at this location in the body. A temperature sensor disposed on or in the body of the catheter near the distal end 204 of the catheter may inform an understanding of heart temperature based on blood flow past the sensor at this location. A temperature sensor may be threaded down its own lumen in the body of the catheter, or as in the primary embodiment discussed herein, may reside in another lumen of the catheter, such as the balloon inflation lumen, in order to conserve space in the catheter body 202 and minimize overall size of the device.

The entire body or a portion thereof of the elongated catheter may contain reinforcement to prevent collapse of the lumens; in particular the suction lumen 216 may be reinforced to prevent collapse, potentially due to suction. The outside of the infusion catheter may be reinforced, providing reinforcement to all of the lumens inside, the lumens themselves may be reinforced individually, or some combination of there may be used to reinforce the tubing. Suction may be applied using a specialized pump, associated system, or standard extracorporeal membrane oxygenation (ECMO) or heart-lung machine, for example, such as the temperature modulation system discussed in this document. The reinforced body may be reinforced using coiled material, such as stainless steel, to serve as the reinforcing agent. The coiled reinforcement may provide improved hoop strength and resistance to kink while maintaining the flexibility of the device. Braided reinforcement may also be used to reinforce the tubing. The proximal portions of the lumens, between the fluidic connectors and the mounting hub 218, may also be reinforced. In some embodiments, at least one hypotube may be used as reinforcement.

FIG. 1B depicts an exemplary external view of a catheter, in accordance with some embodiments of the disclosure. In some embodiments, such as depicted in FIG. 1B, a venous infusion catheter assembly may comprise an elongated catheter body 202 having a proximal end 206 and a distal end 204, with an expandable occlusion element 244 disposed on the elongated catheter body 202. A catheter may include a first infusion lumen extending from the proximal end 206 of the catheter body 202 to a proximal infusion port positioned on the catheter body 202 proximally of the occlusion element between the occlusion element and the proximal end 206 of the catheter body 202. A catheter may also include a second infusion lumen extending from the proximal end 206 of the catheter body 202 to a distal infusion port positioned on the catheter body 202 distally of the occlusion element. Some embodiments may use a suction lumen 216 extending from the proximal end 206 of the catheter body 202 to at least one suction port 238 positioned on the catheter body 202 distally of the occlusion element. The proximal infusion port and the distal infusion port may be spaced relative to the occlusion element such that when the catheter is introduced into vasculature of a patient, the suction port 238 is positioned in the patient's superior vena cava or right atrium to draw blood flowing through the patient's vena cava, the distal infusion port is positioned in the patient's superior vena cava or right atrium to direct normothermic or hyperthermic fluid toward the patient's heart, and the proximal infusion port is positioned in the patient's internal jugular vein to create a retrograde flow of hypothermic fluid in the patient's cerebral vasculature.

Figure 3B:
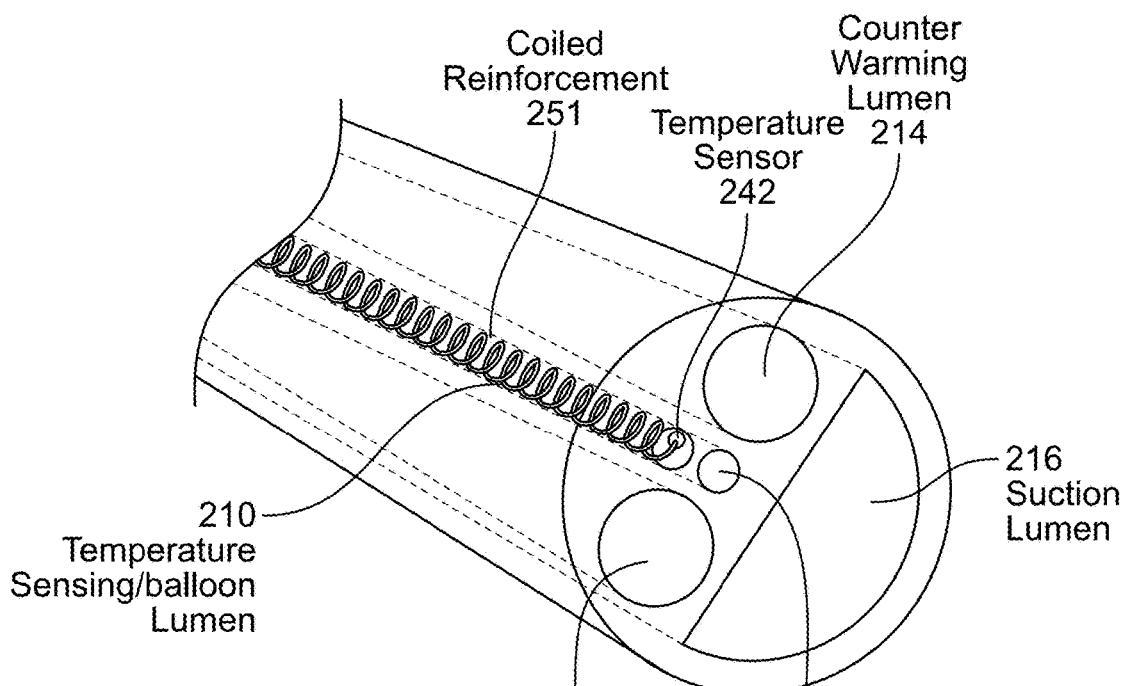
FIG. 3B depicts an exemplary cross-section of a catheter with a temperature sensor attached to a stabilizing wire, in accordance with some embodiments of the disclosure.

1.1.2 Temperature Sensor Attached to Stabilizing Wire (See FIG. 3B)

FIG. 3B depicts an exemplary cross-section of a catheter with a temperature sensor attached to a stabilizing wire, in accordance with some embodiments of the disclosure. In some embodiments, the reinforcing agent may consist of wire that may be in communication with a temperature sensor. The wire may serve as a coiled reinforcement, as depicted and described above, to provide improved hoop strength and resistance to kink while maintaining the flexibility of the device. The wire may take a variety of shapes or formations, such as a braided shape.

One or more temperature sensors may be used to measure the temperature at or near the distal end 204 of the device. In a particular instance, this distal end 204 sits at or near the cavoatrial junction, allowing for these temperature readings to act as a measure of the temperature close to the heart or to measure the temperature of the heart itself. One or more additional temperature sensors may be in the infusion catheter allowing for temperature measurements at other points of the device. In a potential embodiment, a temperature sensor may sit at or near the suction ports 238 of the catheter, allowing for an understanding of the blood temperature at this location, to sit at or near the right and left brachiocephalic vein anastomosis, at or near the superior vena cava. The one or more pressure sensing ports may be proximal to the expandable occluder, and may be used to measure the pressure generated by the flow of fluid out of one or more of the infusion lumens. Fluid may be suctioned out of the one or more suction lumen 216 ports and infused into the one or more infusion lumen ports after passing through an extracorporeal system, in which the fluid media may be modulated in temperature, oxygenated, or both. One or more infusion lumen may be in fluid communication with ports proximal to the expandable occluder, and may be known as the proximal infusion lumen or in some instances the cooling lumen, as it can be used to direct cooled media retrograde toward the brain. One or more infusion lumens may be in fluid communication with ports distal to the expandable occluder, and may be known as the distal infusion lumen or in some cases the counterwarming lumen, as this lumen may direct warmed media antegrade towards the heart. This distal infusion lumen may infuse normothermic or hyperthermic media which may warm or maintain the temperature of the heart when the device is being used to selectively cool the brain in a human patient. This may prevent the heart, the body, or both, from reaching temperatures known to be dangerously low. In other configurations, the one or more infusion ports may be distal to the expandable occlusion element, while the suction lumen 216 may be proximal to the expandable occlusion element. The one or more infusion and one or more suction ports 238 may have luer fluidic connectors or barbed fluidic connectors at their proximal end 206.

In some embodiments, an expandable occlusion element, typically an inflatable balloon, may be secured to an external surface of the elongated catheter body 202. The expandable occlusion element can assume an expanded configuration and a contracted configuration, typically comprising a balloon structure fluidly connectable to a source of inflation fluid. In some embodiments, the expandable occlusion element may be a sheath balloon, such that the balloon may be flush with the body of the catheter in its collapsed state, thereby allowing for smooth insertion into the vasculature, potentially using Seldinger technique in particular use cases. In some instances, the unexpanded diameter of the sheath balloon may be less than 30% greater than the outer diameter dimension of the infusion catheter. For example, if the outer diameter dimension of the infusion catheter is 3 mm, then the unexpanded diameter of the sheath balloon may be less than 3.9 mm. This may be advantageous when the device is placed in a blood vessel of a patient, to allow the device to slide through a small orifice without damaging the insertion site, and may minimize backbleeding risk. To accomplish this, the expandable occluder may be a balloon made of polyurethane, pebax, latex, or a similarly expansive material which can expand from less than 30% larger than the outer diameter of the venous infusion catheter in its collapsed state to 300% or more of the outer diameter of the venous infusion catheter in the inflated state. For example, if the outer diameter of the infusion catheter is 3 mm, the unexpanded diameter of the balloon may be less than 3.9 mm, and the balloon may have an expanded diameter of 11.7 mm or more. The balloon may be made using an extrusion process which yields thin-walled tubing. In some instances, the expandable occlusion element may be positioned so that the balloon inflation lumen can deliver fluid to inflate the expandable occlusion element. The expandable occlusion element may be thermally bonded to the body of the device, at a point in which it is positioned over the balloon inflation lumen, may be secured using UV curing adhesive, secured using another type of adhesive, secured using heat-shrinkable tubing, or some combination thereof, such that it covers the balloon inflation lumen. The balloon inflation lumen may have one or more outlet ports underneath the balloon. To inflate the expandable occlusion element, fluid, such as air, water, crystalloids, medical contrast medium, or similar may be infused through the balloon inflation lumen. The expandable occluder may be positioned such that it remains in the internal jugular vein and occludes the internal jugular vein upon inflation when placed in the human body, as opposed to occluding the superior vena cava, a subclavian vein, a brachiocephalic vein, or similar other venous structure. This may allow for flow in the vessel to be occluded superior to the superior vena cava and brachiocephalic vein, such that any infusion fluid administered proximal to the balloon may produce retrograde perfusion of the head instead of retrograde perfusion of the arm and head.

1.1.2.1 Visualization of Expandable Occluder (See FIG. 2)

FIG. 2 is a detail view of a balloon on an infusion catheter of the present invention show in deflated and inflated configurations. In a potential embodiment, it may be advantageous to visualize the expansion of the expandable occluder, as well as visualize when the expandable occluder is preventing flow in a vessel, readily. The elongated catheter may be placed using Seldinger technique under ultrasound guidance. Inflation of the expandable occluder may use agitated solution such that gas bubbles are dispersed in the fluid. As such, the agitated solution may be visible under ultrasound visualization, and may serve as an indicator that the occluder may have reached its expanded state. Agitated solution may be achieved by connecting two syringes and transferring fluid between them rapidly via a three way stop cock. Similarly, a specialized syringe may be used which introduces some gas into the fluid entering the balloon. Likewise, agitated solution may be accommodated by a specialized luer lock at the proximal end 206 of the balloon inflation lumen which would allow for inflow of air to similarly agitate the fluid flowing into the balloon.

In some embodiments, the infusion catheter device may have an antimicrobial coating. In some instances, this antimicrobial coating may function to reduce the risk of infection. This coating may also be lubricious to enable the device to slide smoothly when being placed in an orifice. In some instances, this coating may contain a silver based antimicrobial agent. This coating may only be applied to the portion of the device intended to pass through an orifice, such as a hole in the skin of a human body for placement of a medical device into a blood vessel.

In some embodiments, the device may have mounting features. The mounting features may allow the device to be fastened to an external object, such as the skin of a patient who may have the device in their vasculature. In some instances, the mounting features may be small orifices which allow suture or other similar mounting material to pass through the orifice and tied down to fasten this device to the external object. In other instances, the mounting features may be an adhesive that can stick to the external object. The mounting features may be added to the device through an additional manufacturing process, such as an overmolding process or the mounting of an assembly made by additive manufacturing. The mounting features may be made of a flexible material, so that they conform to an external object during mounting.

In some embodiments, the infusion catheter may be placed in an orifice using an insertion device. The insertion device may be an insertion sheath and may be of higher stiffness than the body of the infusion catheter. The insertion device may help expand the insertion orifice and may be of a larger diameter than the infusion catheter, if the infusion catheter is circular in shape. If the cross-sectional shape of the infusion catheter is a shape other than circular, the insertion device may be the same cross-sectional shape as the infusion catheter and may be the same size or slightly larger. The infusion catheter may be placed into an orifice, such as an orifice in human skin, by threading it through the insertion device. The insertion device may be made of peel-away material such that the insertion device can be peeled away and removed once the infusion catheter has been inserted into the orifice.

In some instances, the catheter may be insulated. The insulation may serve to maintain the temperature of fluids passing through the device, such as preventing the warming of a cool fluid in the device. Each lumen of the device may be insulated individually, or one or more lumens may be insulated, in any combination. In some embodiments, a lumen with warm fluid, which may be normothermic or warmed media such as blood, may be in close proximity to a lumen with cold fluid, which may be cooled media, such as blood. In these embodiments, insulation may help to maintain these lumens at their desired temperatures or to at least reduce temperature fluctuations. In one embodiment, a lumen carrying a warmer fluid, such as the counterwarming lumen carrying normothermic to hyperthermic 36-40° C. blood, may be partially or fully enclosed by an outer lumen that may be carrying an insulating medium to help prevent heat from transferring to lumens that may have a lower desired temperature, such as the proximal perfusion or cooling lumen carrying hypothermic 0-36° C. blood for example.

Figure 3C:
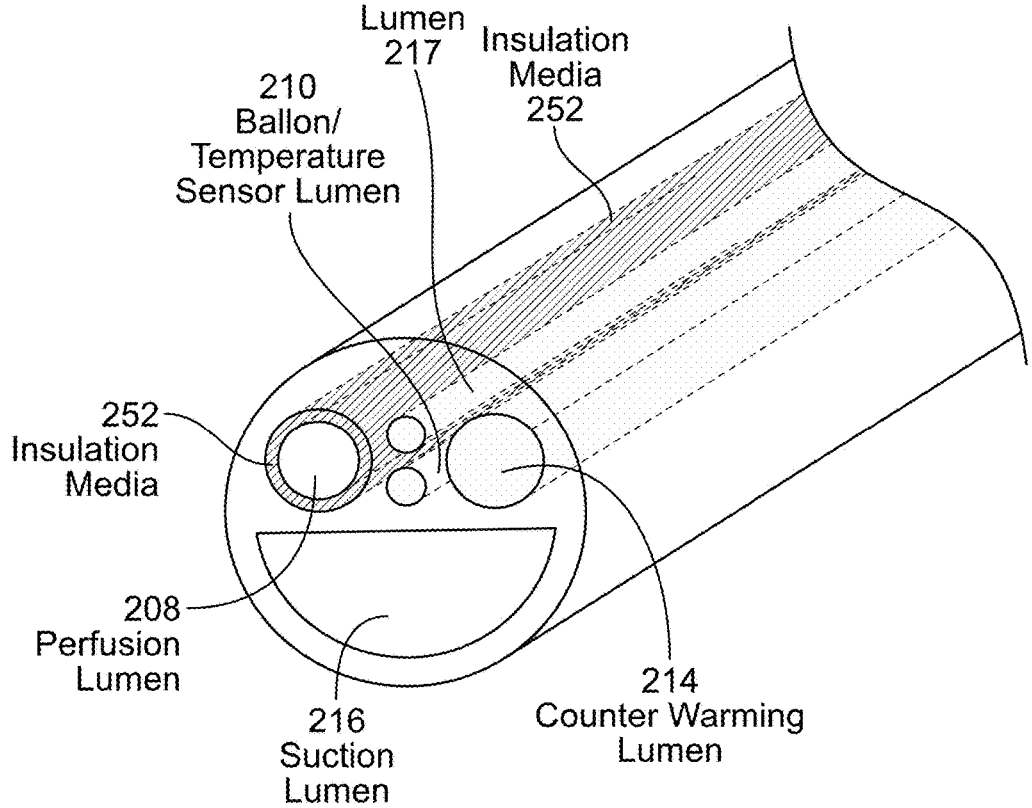
FIG. 3C depicts an exemplary cross-section of a catheter with an insulated lumen, in accordance with some embodiments of the disclosure.

1.1.3 Insulation of Infusion Catheter (See FIG. 3C)

FIG. 3C depicts an exemplary cross-section of a catheter with an insulated lumen, in accordance with some embodiments of the disclosure. In some embodiments, a lumen carrying a colder fluid may be partially or fully enclosed by an outer lumen that may be carrying an insulating medium. The labeled embodiment has one lumen insulated, the perfusion lumen, but any of the lumens may be insulated in other embodiments. Fluidic, potentially circulating, or solid material may be used for insulation. In some embodiments, lumen interiors may be coated with insulating materials such as rubber or foam to help prevent heat transfer. In other embodiments, a cylindrical sheath made of insulating material such as rubber or foam may be inserted into one or more lumens to help minimize heat transfer within the device.

In some instances, a guidewire may be able to pass through one or more lumens of the device. The guidewire may allow for the device to be placed more easily in the vessel of a patient. The guidewire may be flexible or rigid, depending on the intended placement location of the device. The guidewire may allow the device to be placed using Seldinger technique. The guidewire may pass through a lumen of the device, and the lumen in which the guidewire passes through may be the lumen with the distal-most outlet. The guidewire may pass through the lumen with a soft tip on its distal end 204.

In some embodiments, the one or more infusion lumens may have one or more ports disposed proximal to the expandable occlusion element. In such instances, all or some of the infused fluids may be delivered through the one or more proximal infusion ports, and the expandable occlusion element may be used to direct the flow in an antegrade, if unexpanded, or retrograde, if expanded, direction, as described in more detail herein.

In other embodiments, the one or more infusion lumens may have one or more ports disposed proximal to the expandable occlusion element and one or more ports disposed distal to the expandable occlusion element. In such instances, the infusion catheter typically further comprises a flow diverter, such as an internal valve, trap door, sliding fit tube, or other occluding structure disposed in the infusion lumen at a longitudinal position located between the at least one lateral port proximal of the external expandable occlusion element and the open distal end 204 and/or lateral ports distal to the external expandable occlusion element. In a first configuration, the flow diverter may block or redirect flow from the proximal outlet ports so that this flow is released from the ports distal to the external expandable occlusion element. In a second configuration, the flow diverter may block or redirect flow from the distal outlet port so that this flow is released from the ports proximal to the external expandable occlusion element. A tube with a sliding fit in this infusion lumen may be used to selectively open the and close the outlet ports.

In some embodiments, the device may have a lumen for measuring pressure proximal to the expandable occlusion element, a pressure lumen 217. This lumen may have a female luer lock connector on its proximal end 206 so that it may be connected to a pressure monitoring kit or apparatus. This lumen may also be the lumen in which the one or more of the one or more temperature sensors are placed.

In other embodiments, one or more sensors, potentially including but not limited to a temperature, pressure, or flow rate sensor or some combination thereof, may be integrated into the body of the catheter such that measurement of the fluid flowing through the catheter or through the vasculature may be assessed. In some instances, a temperature sensor may be disposed distal to the expandable occluder, and a pressure sensor may occur proximal to the expandable occluder. In some instances, the temperature sensor may be a thermocouple or a thermistor. The pressure sensor may be located external to the device and may be attached to an inlet hub 218 to measure the fluidic pressure in the lumen associated with the inlet hub 218. The pressure sensor may be a strain gage, or the pressure monitoring lumen may connect to a pressure monitoring system or apparatus to measure pressure. The proximal end 206 of the sensor, such as the temperature sensor, may be an electrical connector which may allow the sensor to communicate with other systems, such as the temperature modulation system described herein. The electrical connector may have, e.g., two pins.

In some embodiments, the distal tip 205 of the device may be tapered, soft, or some combination thereof, to reduce the possibility of injury to vessels in the body. A distal tip 205 may be made of the same material as the catheter body 202, but may be of a lower durometer. In some instances, the tip may not be a part of the device, but may be a part of an insert, which is inserted into the lumen having an outlet at the distal tip 205 of the device. The tipped insert may protrude from the distal tip 205 of the device, and may allow for ease of insertion without injury to vessels of the body. This tipped insert may be removed once the device has been placed in a vessel.

The body of the device may have positional markings that indicate how far the device can be inserted into an orifice, such as a fluid vessel of a human. These positional markings 207 may be radiopaque. These positional markings 207 may be made in ink and may be screen printed or pad printed onto the device. Additional marking may be placed on the proximal lumens or female luer connectors to indicate the flow rate that the lumen is certified to accommodate. In some embodiments, positional markers may be positioned on the catheter body 202 at or proximally adjacent to one or more lateral ports, such as a suction port 238, a proximal infusion port, or a distal infusion port. In some embodiments, positional markers may be positioned on the distal tip 205. Radiopaque markers may be placed on the device to allow for x-ray and fluoroscopy to be used to image the device. In some cases, ultrasonically opaque markers may be used.

In some instances, the device may contain an anti-leaking component, such as a grommet, used to plug a hole or orifice that the device can be inserted through, potentially in a vessel wall. The anti-leaking component may be made of rubber, silicone, polyurethane, or other similar flexible material. The anti-leaking component may be used to prevent leaking after the device has been placed into an orifice of a vessel containing fluid, especially once that vessel is experiencing an elevated pressure in comparison to its normal conditions.

In at least one embodiment, the infusion catheter may be provided in a kit such as a single-use kit. A kit may include at least one of the perfusion catheters of the present disclosure. A kit may optionally include at least one syringe, at least one needle, at least one suture, sterile dressings to be used by a doctor or other medical professional, sterile dressings for a patient, a facemask to be used by a doctor or other medical professional, a hairnet for a doctor or other medical professional, local anesthetic, a skin cleansing agent, at least one scalpel, at least one transduction probe, at least one guidewire, at least one skin dilator, at least one medical napkin, at least one needle driver, and at least one needle safety station for used needles and other sharps. The kit may also include caps, such as with luer connectors, and lumen clamps, to occlude one or more lumens of the device, which may be used with the perfusion catheters. The kit may include instructions on the use of the device. The kit may be packaged sterile and may come in a vacuum formed tray. The outer packaging may be made of plastic, paper, cardboard or some combination thereof.

1.2 An Infusion Catheter

In an embodiment, the infusion catheter may be used to achieve low temperatures (hypothermia) in the brain while maintaining normothermic temperatures or close to normothermic temperatures in the body with deep, quick cooling targeted at the brain. It may also be used to deliver oxygenated blood to the brain. The cooling system may be comprised of a catheter, and an extracorporeal cooling, warming, and oxygenation system. The infusion catheter may be placed in the patient's internal jugular (IJ) vein. Here, it may suction blood from the patient through a suction lumen 216 of the device, circulate it extracorporeally through a conditioning circuit which may include cooling, oxygenation, warming, or some combination thereof, and deliver conditioned blood back to the body; some of the suctioned blood may be conditioned in one way, while another portion is conditioned in another, before the conditioned blood is returned to the body through its respective lumen. Cooled blood, which may also be oxygenated, may be directed towards the patient's brain via the proximal perfusion lumen which outlets proximal to the occlusive element, flowing retrograde. Warmed blood, which may also be oxygenated, may be directed toward the patient's heart via a distal perfusion lumen which outlets distal to the occlusive element, flowing antegrade.

In some embodiments, a sterile, single-use intravascular five fluidic lumen occlusion balloon catheter and may be made with proprietary multi-lumen tubing and balloon. The proprietary tubing may be multi-lumen tubing and may be the portion of the device intended to be inserted into the vasculature. The balloon may be a sheath balloon and may sit as flush as possible with the device when it is not inflated. The balloon may be heat bonded, secured with UV cure or other adhesive, secured using heatshrink, or some combination thereof to fasten it to the external surface of the multi-lumen tubing. The device may contain a temperature sensor, near the distal end 204 of the device which measures the temperature at or near the heart or may be used to measure the temperature of fluid in a vein. The temperature sensor may have a proximal portion ending in an electrical connector to allow it to interface with external systems. The fluidic lumens may have fluidic connectors on the proximal portions of the lumens, to allow them to interface with external systems. The catheter may have a mounting hub 218 which connects the proximal fluidic lumens and the proximal portion of the temperature sensor to the multi-lumen intravascular extrusion. The tip of the device may be tapered, soft, or both tapered and soft, and/or of a lower durometer than the extrusion, to prevent damage to blood vessels. Each lumen may be in fluid communication with its respective outlet(s).

The device may contain a lumen, the balloon inflation lumen, which communicates with its one or more ports underneath the bonded sheath balloon. One or more ports may be skived or cut into the side of the balloon inflation lumen of the multi-lumen tubing underneath the balloon, and the lumen may be sealed distal to the one or more outlets. The balloon inflation lumen may contain the temperature sensor. The balloon inflation lumen may be used to inflate the balloon.

The device may contain a lumen, the pressure lumen 217, which communicates with its one or more ports proximal to the balloon. One or more ports may be skived or cut into the side of the pressure lumen 217 of the multi-lumen tubing proximal to the balloon, and the lumen may be sealed distal to the one or more outlets. The pressure lumen 217 may contain the temperature sensor. The pressure lumen 217 may be used to measure pressures generated by flow through the proximal infusion lumen or pressures generated by the body's venous system, or a combination thereof.

The device may contain a lumen, the suction lumen 216, which is capable of suctioning blood when attached to a source of suction. One or more ports may be skived or cut into the side of the suction lumen 216 of the multi-lumen tubing distal to the balloon, and the suction lumen 216 may be sealed distal to the one or more ports. The one or more outlets/inlets of this lumen may be at the distal tip 205 of the catheter. It may fit a 0.038-inch (approximately 0.97 mm) diameter guidewire to facilitate the device being placed. The distal inlet/outlet of this lumen may be a tapered soft tip at the distal end 204 of the device. If cooling is not being administered, and therefore the lumen is not being used for suction, this lumen may serve as a standard central venous catheter lumen, for delivery of drugs or fluids to the central venous system. The suction lumen 216 may be reinforced to prevent collapse when suction is being applied. The suction lumen 216 may be used to suction blood from the veins distal to the balloon and carry the blood to the inlet of the temperature modulation system.

The device may contain a lumen, known as the proximal infusion lumen or the cooling lumen, with its one or more ports proximal to the balloon. One or more ports may be skived or cut into the side of the cooling lumen of the multi-lumen tubing proximal to the balloon, and the cooling lumen may be sealed distal to the one or more ports. The cooling lumen may infuse cooled fluids through a port proximal to the balloon. This may serve the purpose of directing flow retrograde in a human vessel.

In some embodiments, one lumen may act, e.g., as a standard central venous catheter lumen for delivery of drugs or fluids to the central venous system. For instance, the outlet may be skived into the side of the catheter near the distal end 204 of the device, and the lumen may be sealed off distal to the outlet.

One lumen may be the infusion lumen, with its outlet proximal to the balloon. It may infuse fluids through a port proximal to the balloon. In some instances, it may be capable of communicating with more than one outlet port, one or more of which may be proximal to the balloon, and one or more of which may be distal. While the device is in use this lumen may communicate with only distal ports 240, or only proximal outlet ports at a time. This lumen may be capable of changing the port it communicates with based on input from the user. In a first orientation, when the balloon is inflated, the proximal ports may be open, and the distal ports 240 may be closed. This may serve the purpose of directing flow retrograde in a human vessel. In a second orientation, which may occur when the balloon is deflated, the proximal ports may be closed, and the distal ports 240 may be opened. This may allow for this lumen to serve as a standard central venous catheter lumen, for delivery of drugs or fluids to the central venous system. Both outlets may be skived into the side of the catheter, and the lumen may be sealed distal to the distal-most outlet. Several methods of switching outlet lumens have been devised herein.

The device may contain a lumen, known as the distal infusion lumen or the counterwarming lumen, with its one or more ports distal to the balloon. One or more ports may be skived or cut into the side of the cooling lumen of the multi-lumen tubing proximal to the balloon, and the counterwarming lumen and the distal port 240 of this lumen may be a tapered soft tip at the distal end 204 of the device. The counterwarming lumen may infuse normothermic or warmed fluids through the one or more ports distal to the balloon. This may serve the purpose of ensuring the temperature of the heart and/or body does not drop below desired levels. The counterwarming lumen may accommodate a guidewire to facilitate the device being placed.

The device may have a portion meant to enter the human body, the multi-lumen tubing, which may be distal to the mounting features. This portion may be a custom multi-lumen (e.g., four-lumen) extrusion. The lower extrusion may need an anti-microbial coating may be applied to this portion meant to enter the human body to prevent central line associated bloodstream infections (CLABSI). This multi-lumen tubing may have (radiopaque) markings 207 that allow the end user, which may be a healthcare professional placing the device, to determine how much of the lower tubing can be inserted into the patient. A tapered, soft, or tapered and soft tip may be added to this portion of the device. Radiopaque markers may be placed both at the distal tip 205 and just proximal to the proximal perfusion lumen. The sheath balloon may be thermally bonded to this tubing. The tubing may be reinforced using coiled reinforcement to provide increased hoop strength and kink resistance to the tubing. The coil may be made using stainless steel or nitinol. The sheath balloon may allow for occlusion of the jugular vein when inflated so that fluid administered to a proximal infusion port proximal to the balloon is directed retrograde, towards the brain.

The proximal portion of the device may comprise one or more upper lumens with female luer lock fluidic connectors, the cable and connector for the temperature sensor, and the cables for additional temperature sensors or other sensors. These lumens may be labeled to denote their function, and the labeling may be done using screen printing or pad printing. They may be of varying lengths, and their luer connectors may be of varying colors, such that they are easily distinguishable from one another.

The device may be placed in the internal jugular vein, between the medial and lateral heads of the sternocleidomastoid muscle and lateral to the carotid artery. The device may be placed using Seldinger technique under ultrasound guidance, with the device being inserted over a guidewire, and doppler ultrasound may be used to ensure occlusion of the vessel upon inflation of the balloon. A system for fully or partially automating the insertion of this catheter may be used to place the device.

Once the device is inserted, there may be backbleeding from the insertion point due to infusion through the proximal infusion lumen, which may lead to a local venous pressure of, e.g., 30 mm Hg to 60 mm Hg, or greater. To prevent fluid from leaking from this insertion point during use, the device may contain an anti-backbleeding mechanism, such as a rubber grommet.

In some instances, the proximal multi-lumen tubing may be the tubing profile pictured. The outer diameter may be 2.5-10 mm (7.5-30 Fr), with some embodiments being 6 mm (18 Fr). Two lumens may have surface areas in a fixed ratio of cross-sectional area, as these are the lumens that will be for suction and infusion. The total area of the suction lumen 216 may be 125% or more of the total area of the one or more infusion lumens, which may serve to reduce chatter and cavitation when attached to an extracorporeal circuit. In other embodiments, the outer diameter may be 1-5 mm (3-15 Fr), with the preferred embodiment being 3 mm (9 Fr). In this case, the size of one lumen may be 22 gauge (0.413 mm Dia), and one lumen may be an 18-gauge lumen (0.838 Dia). The multi-lumen tubing may be made of urethane, such as polyurethane.

The sheath balloon may have a 2.5-10 mm (7.5-30 Fr) inner diameter, with the preferred outer diameter being 6.1 mm (18.3 Fr) and may be slightly larger (0-25% larger) than the tubing. The balloon may have the ability to expand to an outer diameter 200% (or more) larger than the uninflated outer diameter when inflated. In other embodiments, the sheath balloon may have a 1-5 mm (3-15 Fr) inner diameter, e.g., with an outer diameter being 3.1 mm (9.3 Fr). The balloon may inflate to a targeted inflation diameter with 3-10 ml of fluid inserted. The target inflation diameter may be 10-30 mm, or larger. The balloon may be made of urethane, such as thinly extruded polyurethane. The balloon may be a compliant balloon. The balloon may have thin walls to remain as flush as possible with the tubing.

The soft tip may be heat bonded (reflowed) to the tubing. One lumen may continue through the soft tip such that it exits out of the distal tip 205 of the device, such that it can be used to insert the device over a guidewire. The soft tip may be a different color than the normal tubing so that it is distinguishable. The tip may be radiopaque.

The outlet ports on the device may be large enough such that they do not impede flow when the device is in use. The device may have pad print, or other markings that show the length of device inserted into the patient for a portion of the device, for instance at least 6 cm of the device. Length marking may be in 1 cm increments.

1.2.1 Pressure and Temperature

In some embodiments, a catheter may be placed in the internal jugular vein, an expandable occluder expanded such that the vein may be occluded, and hypothermic fluid may be delivered through this catheter retrograde toward the brain, and normothermic or hyperthermic fluid delivered through this catheter antegrade toward the heart. The pressure sensor, or pressure sensing lumen, of this device may sit in or near the internal jugular vein and may allow for the pressure in the internal jugular vein to be measured. This pressure sensor, and/or other sensors or probes, may send data to a data storage module to be recorded, or to the control system of an extracorporeal system, which may change its rate of flow or temperature of flow based on the sensor data or make an indication to let a user know to change a setting manually. The data storage or control system may be a part of the temperature modulation system described herein. In some embodiments, a change in flow rate or temperature of flow may be made to ensure cooling of the brain, as monitored by a tympanic probe or other proxy, of neuroprotective levels less than or equal to 32-33° C. The pressure sensor of the catheter may be used to monitor if the brain or venous system is experiencing pressures higher than may be considered safe. Using these sensors or other sources of data as input, the system may be able to maintain hypothermia in the brain, while maintaining brain or vein pressure below an established safety threshold pressure, such as a pressure of 25 mm Hg. The pressure threshold may be a time-weighted average of pressure readings.

In another embodiment, the one of the one or more temperature sensors of this device may sit in or near the cavoatrial junction or at the suction ports 238 of the device and may allow an inference of heart temperature to be measured by proxy. This temperature sensor, and/or other sensors or probes, may send data to a data storage module to be recorded, or to the control system of an extracorporeal system, or both, and the interpretation of this data may cause the system to change its rate of flow or temperature of the flow through the system based on the sensor data. It may also use this data to set an alarm or reminder to get the attention of a user and alert them that a change of a setting may be needed. Such a change in flow rate or temperature of flow, in a potential scenario, may be made to ensure the heart is maintained at a temperature warm enough to avoid arrhythmias, which may be greater than 32° C.

In other embodiments, the catheter device may use retrograde flow to provide selective cooling.

A pressure sensor or other means of measuring pressure may be integrated into the body of the catheter such that measurement of the fluid flowing through the vasculature may be assessed. One or more temperature sensors or other means of measuring temperature may be integrated into the body of the catheter such that temperature of the fluid flowing through the vasculature may be assessed. A control system may be implemented in which autologous blood may be pulled from a patient's venous system, modified through an extracorporeal circuit, and returned to the patient's venous system, possibly with a pump. Such modification to the blood may include temperature modulation, oxygenation or otherwise. The lumens of the catheter, or the catheter itself, may be insulated to avoid heat exchange.

Figure 4:
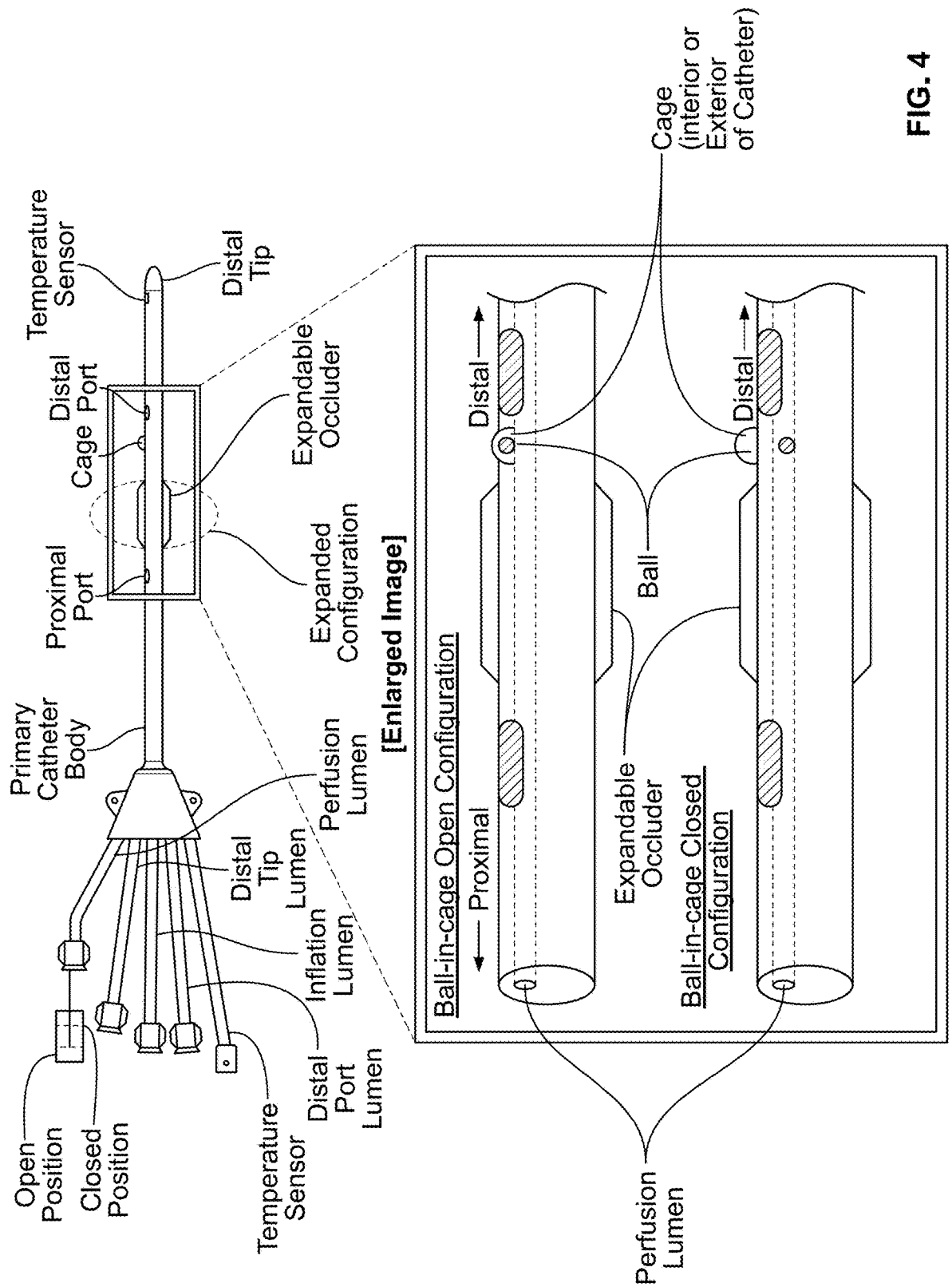
FIG. 4 depicts an illustrative scenario of providing treatment with a catheter using a caged spherical occluder, in accordance with some embodiments of the disclosure.

1.3 Additional Features of Infusion Catheter 1.3.1 Caged Spherical Occluder (See FIG. 4)

FIG. 4 depicts an illustrative scenario of providing treatment with a catheter using a caged spherical occluder, in accordance with some embodiments of the disclosure. In some embodiments, a spherical occluder may be in a position in which it may be non-occlusive to the lumen, such that fluid delivery through this lumen may exit through the distal port 240. In another configuration, the spherical occluder may be in a position in which it may be occlusive to the lumen such that fluid delivery through this lumen may exit through the proximal port. This may interrupt flow and may allow for the possibility of redirecting flow through a proximal port. The spherical occluder may be shifted upon user input, potentially using a pre-placed wire or other mechanism; such a shift may allow the occlusive-capable sphere to be moved such that it does not occlude the lumen, potentially into a cage located at the exterior of the catheter. The cage may be comprised of flexible material, such that the device may still have a flush outer surface; in which, the cage may not expand away from the surface of the device until desired by user.

Figure 5:
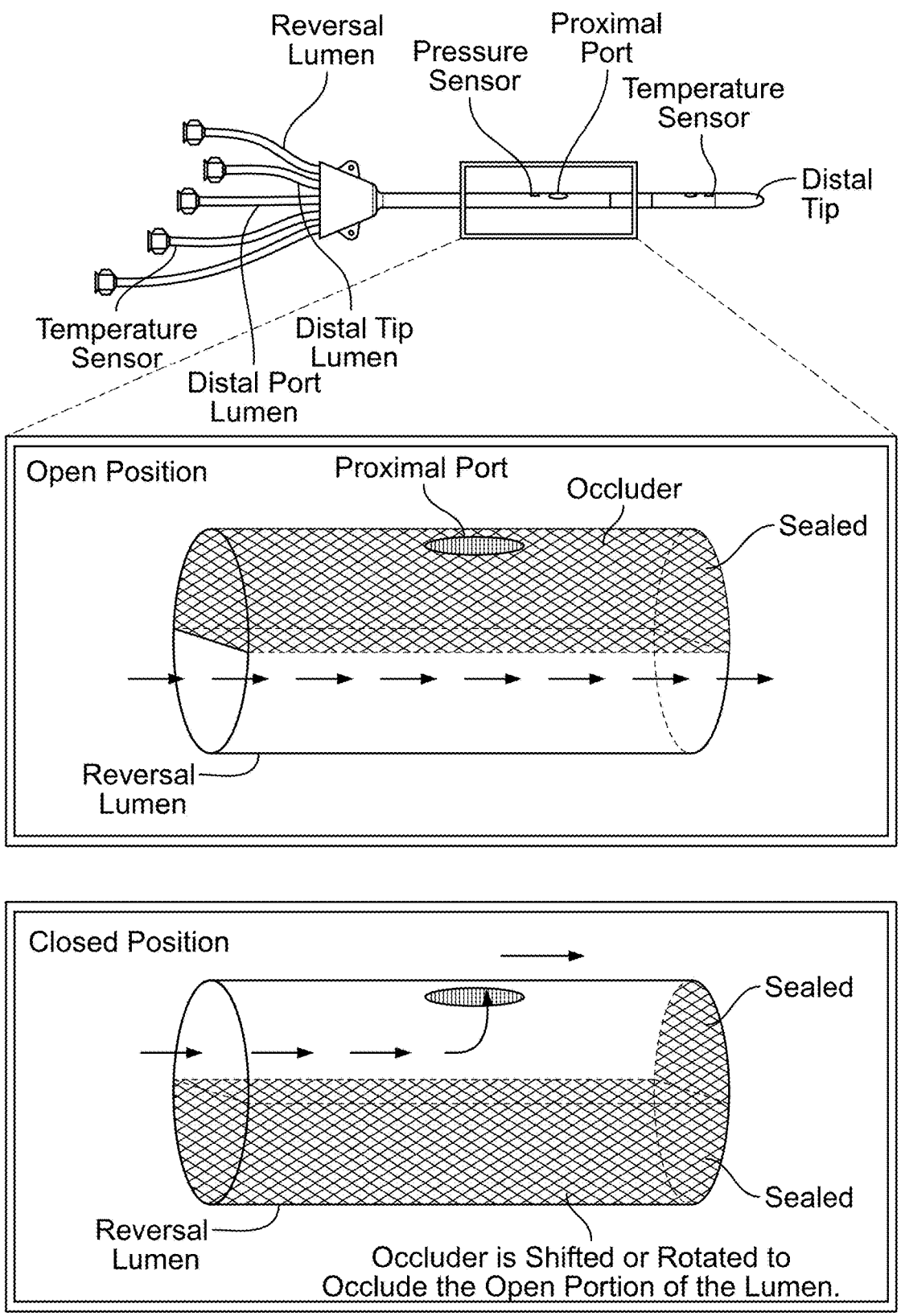
FIG. 5 depicts an illustrative scenario of providing treatment with a catheter using a hemicylindrical occluder, in accordance with some embodiments of the disclosure.

1.3.2 Hemicylindrical Occluder (See FIG. 5)

FIG. 5 depicts an illustrative scenario of providing treatment with a catheter using a hemicylindrical occluder, in accordance with some embodiments of the disclosure. A flow diverter can have a hemicylindrical apparatus, herein termed occluder in the associated figure. In one configuration, the occluder is oriented such that it occludes the perfusion port and flow administered through this lumen is directed to the distal port 240. In another configuration, the occluder is rotated 180°, and then occludes the distal port 240, and allows for fluid administered to exit the perfusion port.

Figure 6:
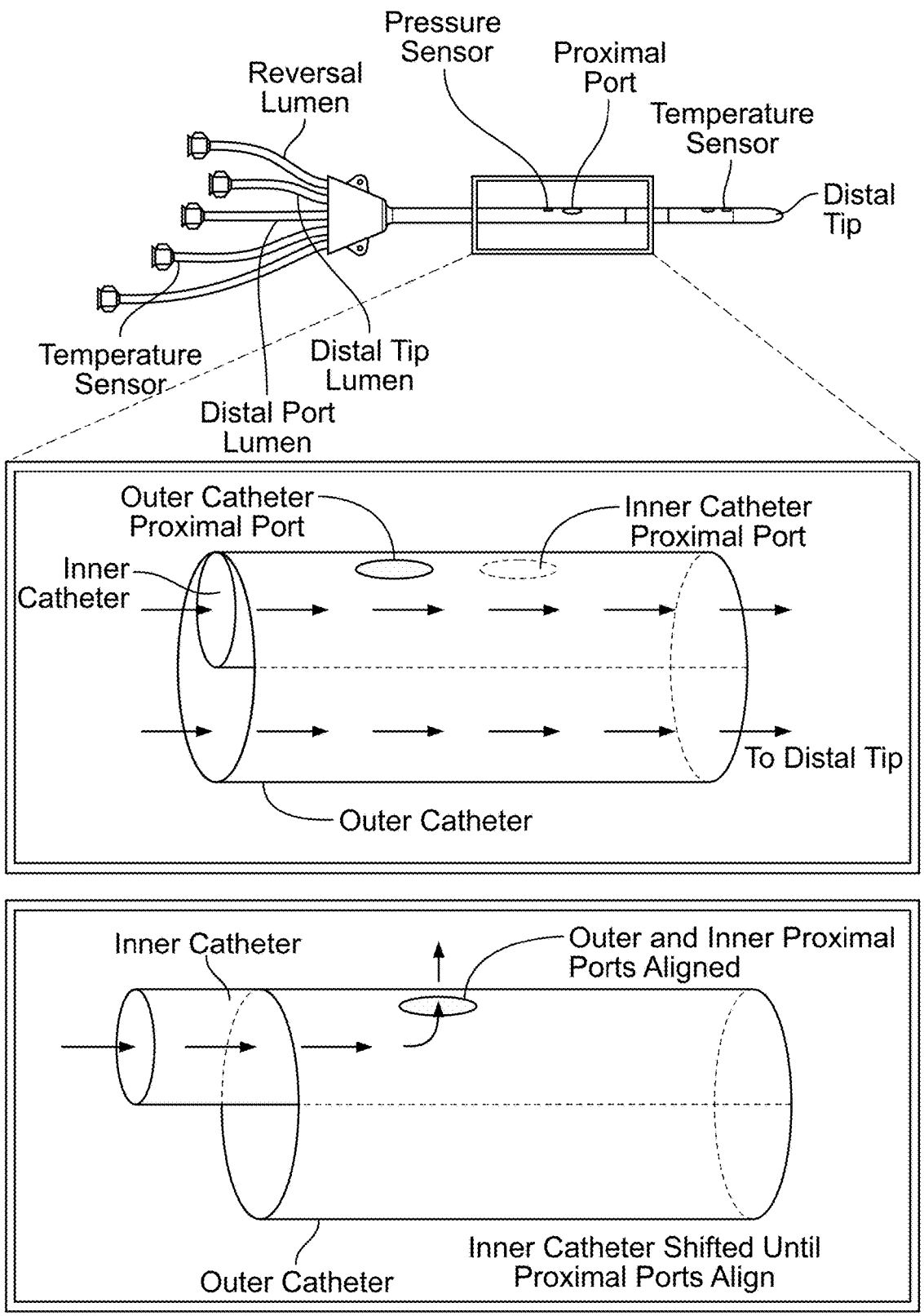
FIG. 6 depicts an illustrative scenario of providing treatment with a catheter using a removable inner lumen, in accordance with some embodiments of the disclosure.

1.3.3 Removable Inner Lumen (See FIG. 6)

FIG. 6 depicts an illustrative scenario of providing treatment with a catheter using a removable inner lumen, in accordance with some embodiments of the disclosure. In one embodiment, another catheter with a proximal port may be placed in the primary catheter in which it may be non-occlusive to the lumen, such that fluid delivery through this lumen may exit through the distal port 240. In another configuration, the secondary catheter may be in a position in which the proximal ports of the two catheters overlap or align such that fluid delivery through this lumen may exit through the proximal ports of both catheters. The secondary lumen may be shifted or rotated upon user input. This secondary inner lumen is removable and may be administered through any existing lumen of the primary catheter body 202, to preferentially direct fluid flow through a selected port or ports. This inner lumen may have openings which align with selected ports on the body of the primary catheter, thereby blocking fluid flow through ports which do not have an aligned port on the inner lumen.

1.3.4 Bent Tip for Inferior Vena Cava Entry

Figure 7:
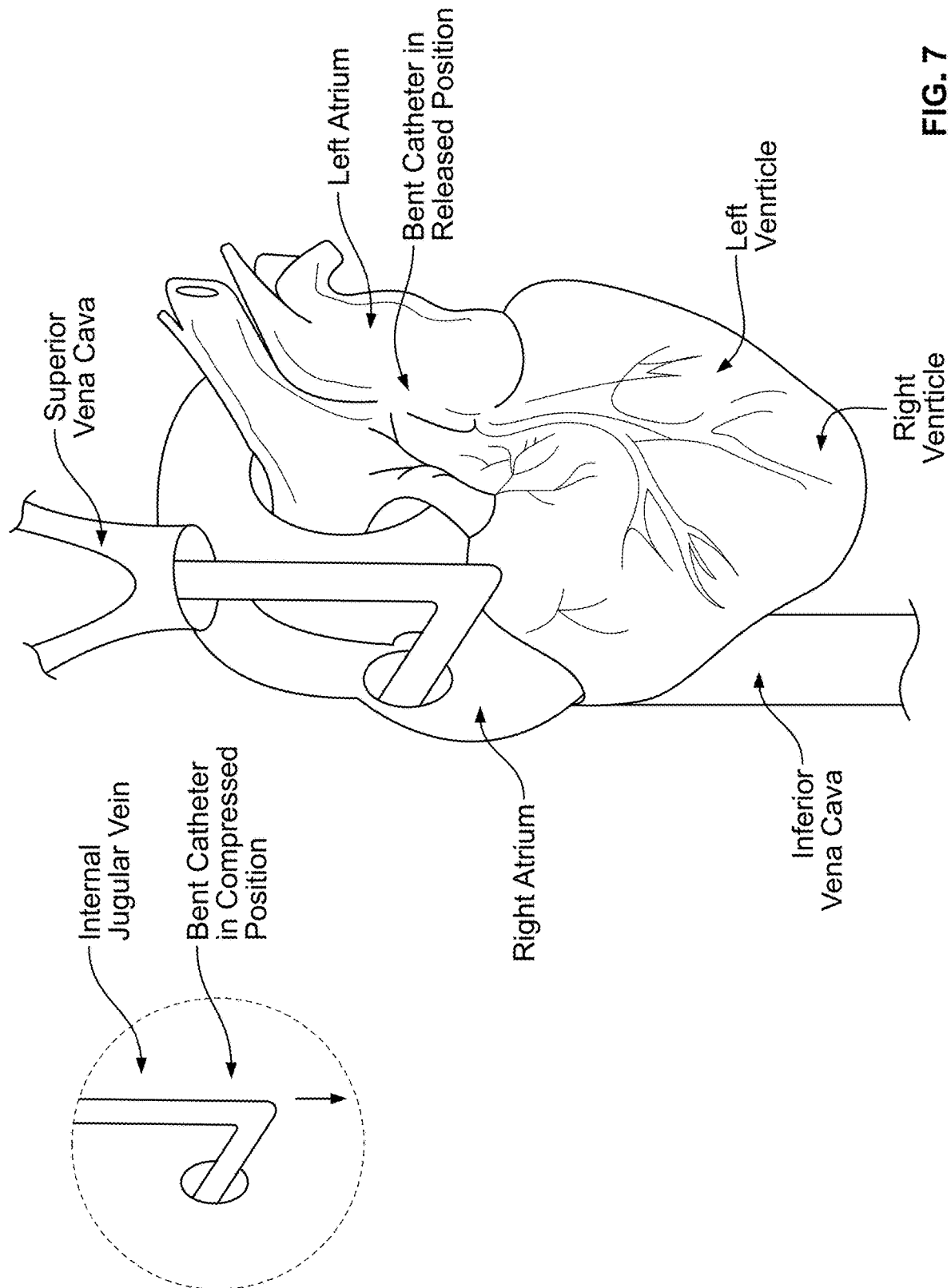
FIG. 7 depicts an illustrative scenario of providing treatment with a catheter using a bent tip for inferior vena cava entry, in accordance with some embodiments of the disclosure.

FIG. 7 depicts an illustrative scenario of providing treatment with a catheter using a bent tip for inferior vena cava entry, in accordance with some embodiments of the disclosure.

In some embodiments, the distal tip 205 of the device may have the capability of shifting between a compressed and released position as labeled above. In the compressed position, the distal tip 205 may be partially or fully bent in on itself to reduce the possibility of injury to vessels in the body. In the relaxed position, the bent portion of the catheter tip may increase its distance from the portion of the catheter tip that is not bent. The catheter tip may shift between the compressed and released position using an elongated wire inside of the catheter or by some other mechanism. If the catheter tip is extended into the right atrium, the released position of the catheter tip may facilitate entry of the catheter tip into the inferior vena cava.

1.3.5 Non-Occlusive Balloon for Mitigation of Potential Vessel Collapse

Figure 8:
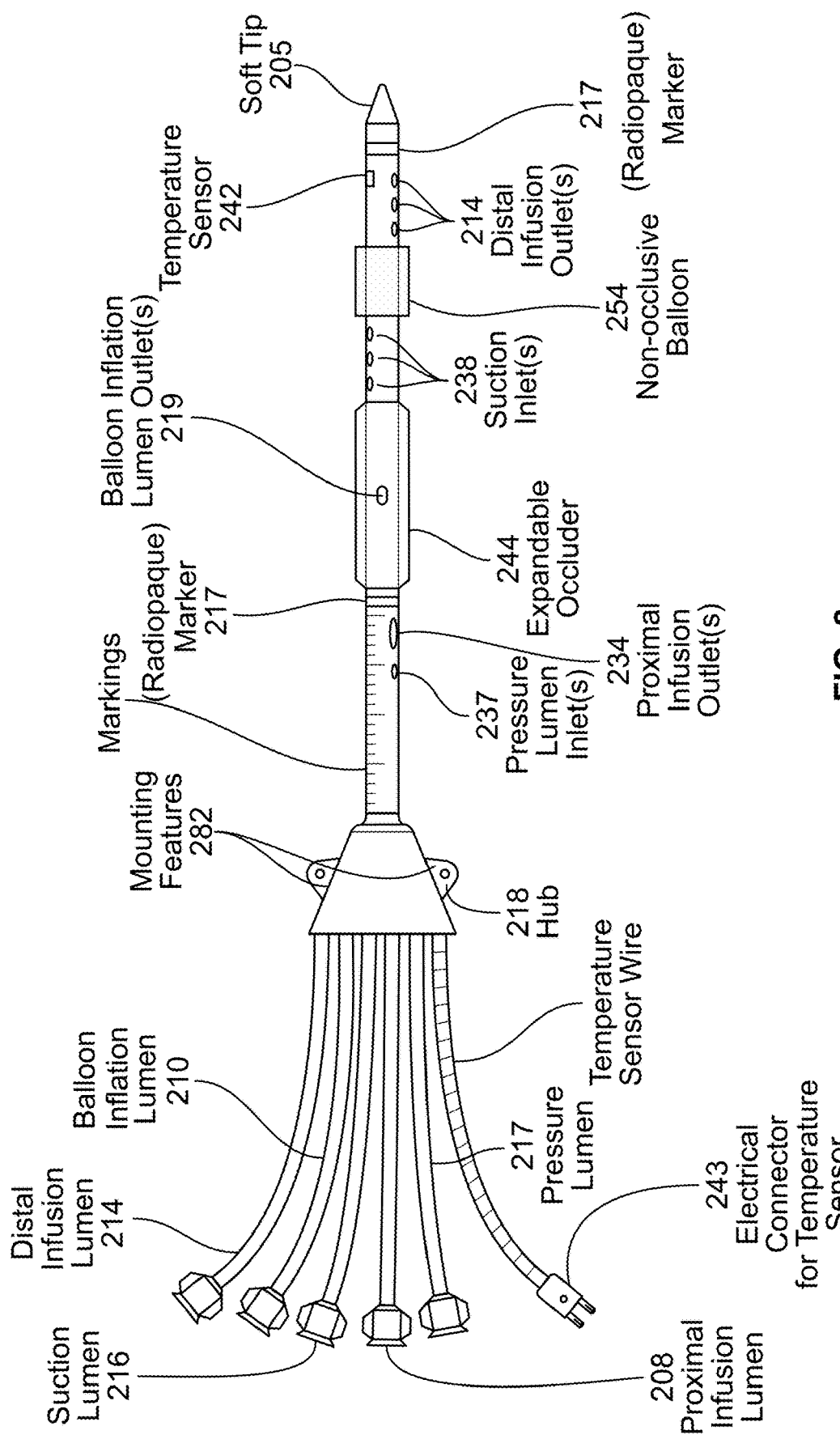
FIG. 8 depicts an exemplary external view of a catheter with a non-occlusive balloon, in accordance with some embodiments of the disclosure.
Figure 9:
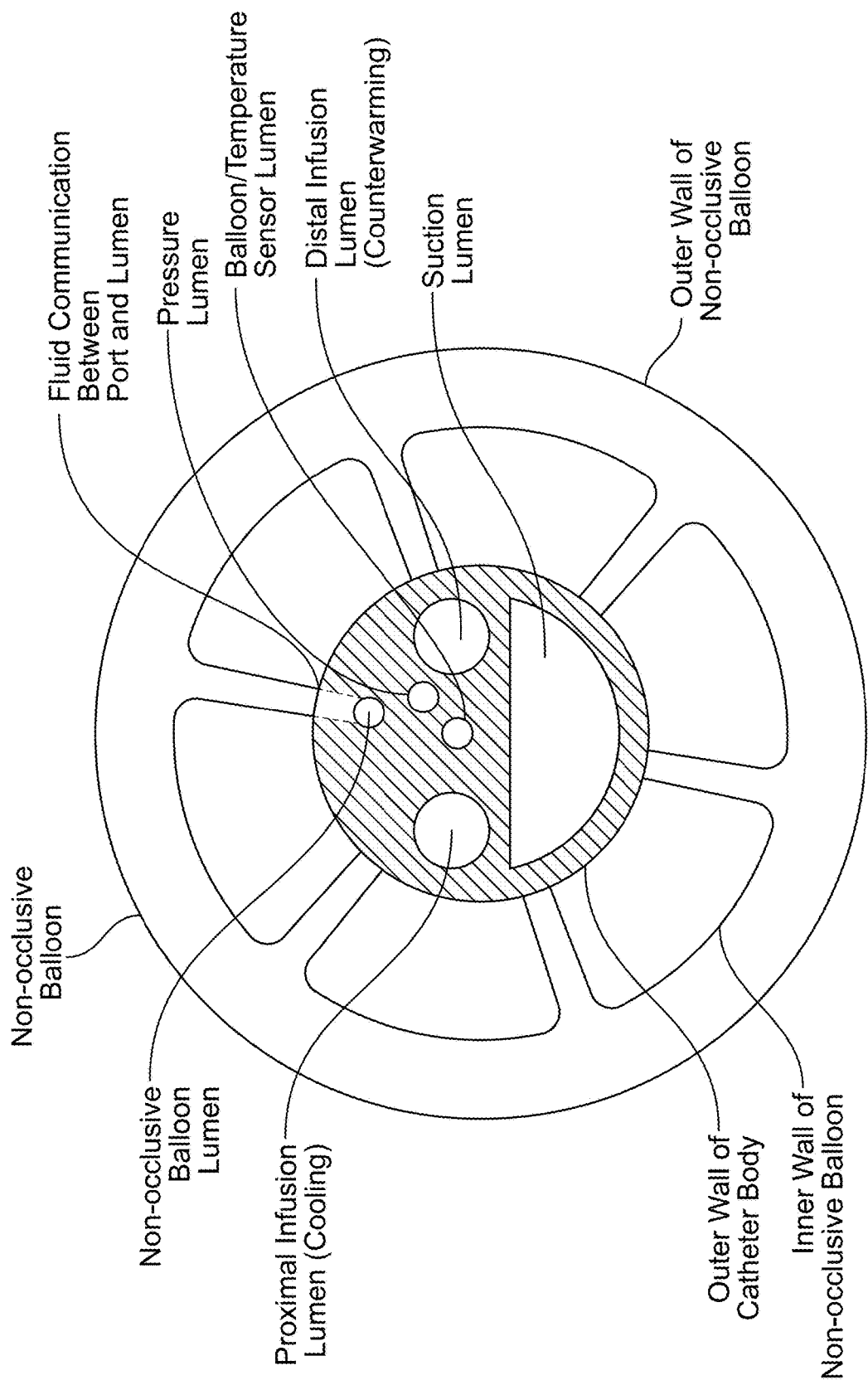
FIG. 9 depicts an exemplary cross-section of a catheter with a non-expanded non-occlusive balloon, in accordance with some embodiments of the disclosure.
Figure 10:
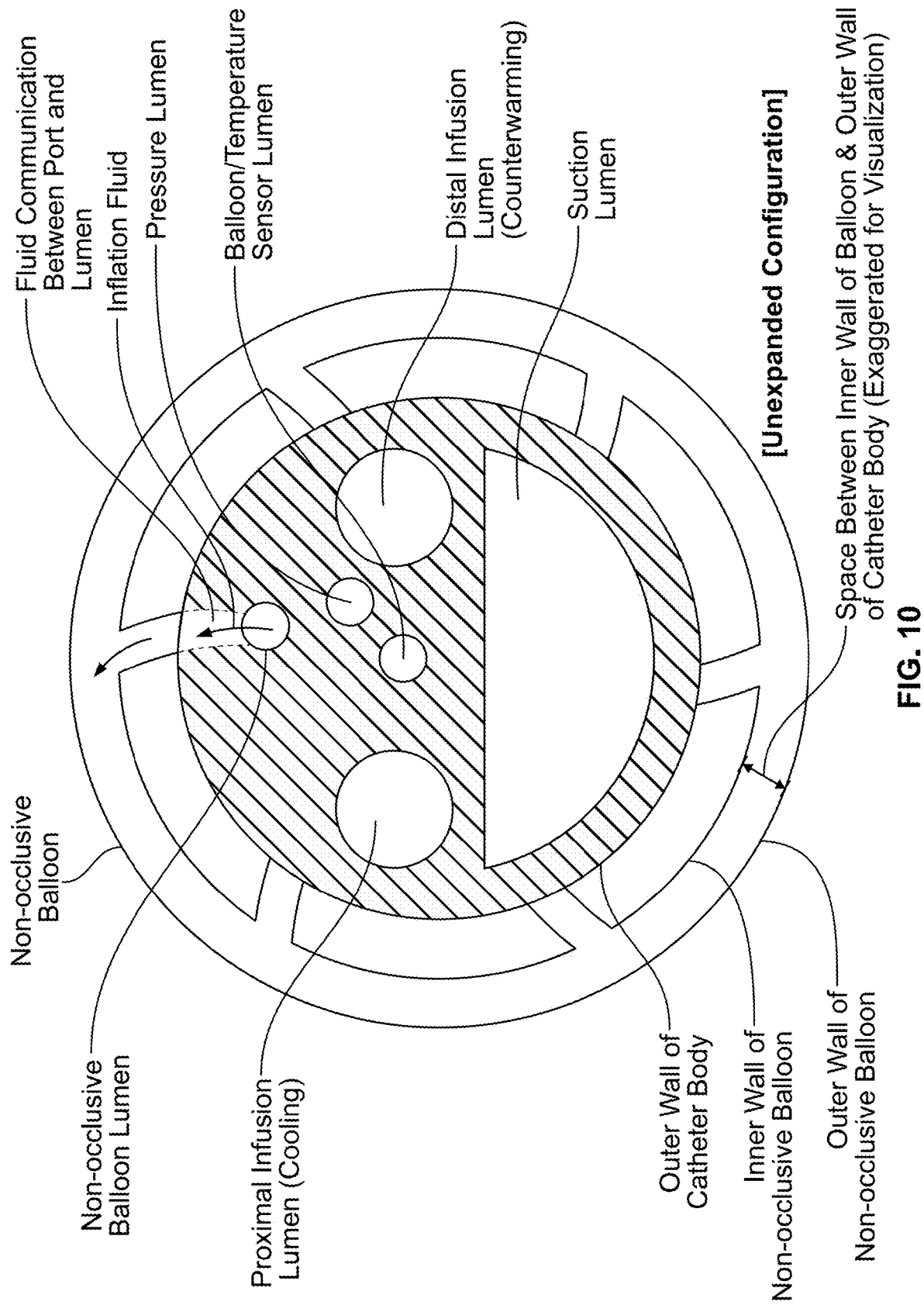
FIG. 10 depicts an exemplary cross-section of a catheter with an expanded non-occlusive balloon, in accordance with some embodiments of the disclosure.

FIG. 8 depicts an exemplary external view of a catheter with a non-occlusive balloon, in accordance with some embodiments of the disclosure. FIG. 9 depicts an exemplary cross-section of a catheter with a non-expanded non-occlusive balloon and FIG. 10 depicts an exemplary cross-section of a catheter with an expanded non-occlusive balloon, in accordance with some embodiments of the disclosure.

A non-occlusive balloon may be additionally disposed on the infusion catheter near the suction ports 238. This balloon may be inflated only during the retrieval of blood via the suction port 238, and distension of this balloon would result in structural support to the vessel wall and mitigation of potential vessel collapse around the body of the catheter. The balloon shall be disposed on the body of the catheter and will possess a distinct port for inflation. The balloon shall consist of multiple fluid channels connected by a single channel to the inflation lumen.

In its non-inflated state, the balloon and accompanying channels will lay flush against the outer wall of the VCL.

Once inflated, all fluid channels will become filled with fluid until the maximum wall tension of both the fluid channels and the outer wall of the balloon is reached. This will result in structural reinforcement of the vessel wall with mitigation of vessel collapse leading to cavitation of suctioned blood, while allowing for blood to flow proximally through a suction port 238 if desired.

1.3.6 Non-Occlusive Balloon for Mitigation of Risks

A similar non-occlusive balloon as previously described may instead be located on the distal side of the lateral distal infusion outlet(s), such that it provides a protective 'bumper' effect for the tip of the catheter. In this way, the tip of the catheter will minimally interact with the tissue around it, minimizing risk of perforation or damage. This may be particularly of interest in the embodiment of this infusion catheter in which the tip resides in the right atrium of the heart. Such a balloon may help prevent the tip of the catheter from traveling through the tricuspid valve to the ventricle additionally.

Figure 11:
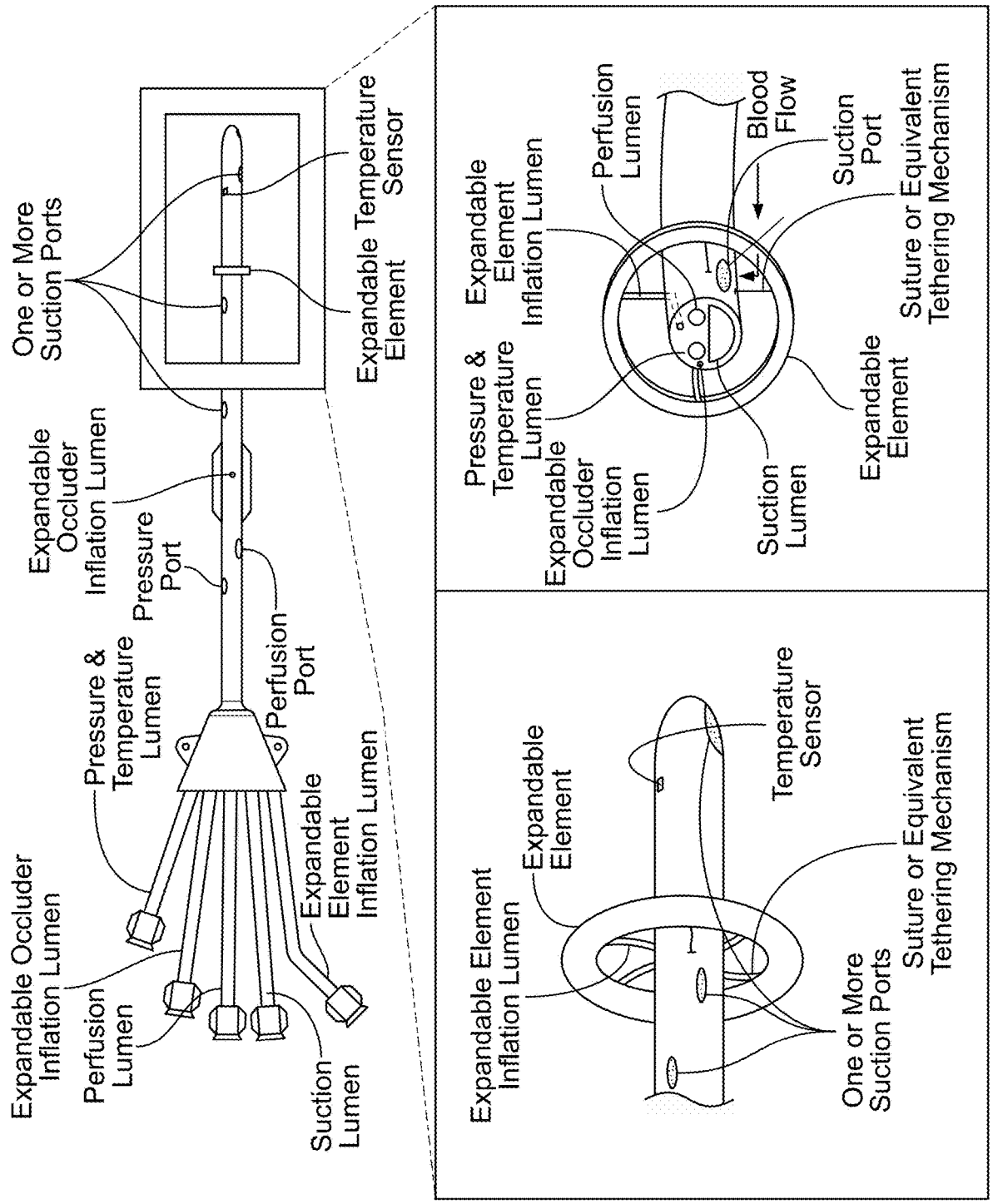
FIG. 11 depicts an exemplary external view of a catheter with an expandable element to facilitate suction, in accordance with some embodiments of the disclosure.

1.4 Expandable Element to Facilitate Suction (See FIG. 11)

FIG. 11 depicts an exemplary external view of a catheter with an expandable element to facilitate suction, in accordance with some embodiments of the disclosure. An expandable element, possibly an elastomeric balloon, may be disposed on the body of the catheter, in order to facilitate maintenance of an open flow path through the suction port 238 of a device. In its expanded configuration, the element may be a ringed geometry, such that it maintains the patency of the flow path of blood suctioned through a port on the body of the catheter, and may be of particular benefit in cases in which the suction applied may otherwise suction the device to the wall of the vessel in which it sits. The geometry may be such that it maintains patency of the vessel and creates distance between the primary body of the catheter and the vessel wall, such that fluid suctioned or delivered through suction ports 238 on the device have an available flow path. The inflation lumen may communicate inflation fluid between the primary body of the catheter and the expandable element. The expandable element may be further tethered to the body of the catheter with suture or equivalent tethering mechanisms.

2.0 System for Temperature Modulation System

2.1 System for Temperature Modulation (See FIGS. 12-15)

Figure 12:
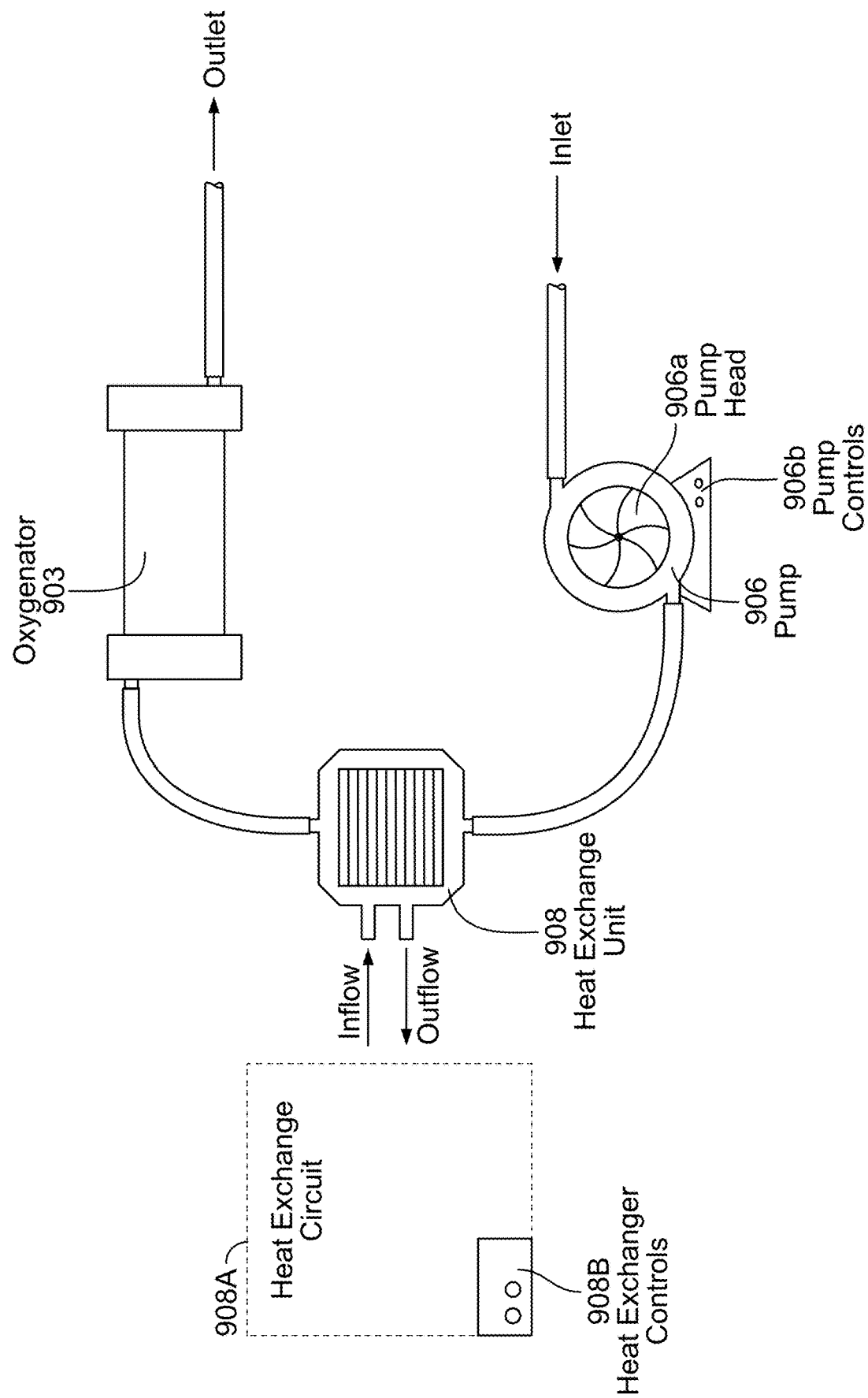
FIG. 12 illustrates a system suitable for incorporating a catheter, in accordance with some embodiments of the disclosure.

FIG. 12 illustrates a system suitable for incorporating a catheter, in accordance with some embodiments of the disclosure. In some embodiments, a system may provide for moving a fluid through a fluidic circuit and modulating the characteristics of said fluid. The system may be known as the therapy delivery system. The fluid movement may be created by one or more pumps or pumping mechanisms. The temperature characteristic of the fluid may be modulated by one or more heat exchangers or similar temperature modulation apparatuses. The oxygenation characteristics of the fluid may be modulated by one or more oxygenators. In some instances, a controller may be used to modulate aspects of the therapy delivery system. A console may be used to interface or interact with the therapy delivery system and monitor the system. The therapy delivery system may be connected to the infusion catheter, described herein, to deliver selective therapy to an organ or group of organs. Countermeasures to the selective therapy may be implemented if the therapy delivery system meets parameters which may be unfavorable for the patient, for instance, cooling too deeply, and these countermeasures may be controlled by the control system and monitored on the console.

In some embodiments, the fluid movement may be created by one or more pumps or pumping mechanisms, creating one or more fluidic circuits of the therapy delivery system. The pump or pumping mechanism may be used to create suction on one or more inlets of a fluidic circuit and expel fluid at one or more outlets of the fluidic circuit. The pump or pumping mechanism may flow in a first direction and a second direction, and the direction of flow may be switched at certain times. The direction and rate of the flow in the circuit may vary as a function of time. The pump may be a centrifugal pump or a peristaltic pump. A centrifugal pump may be used when the fluid being moved is blood or similar, to minimize the risk of hemolysis. For a centrifugal pump that comes into contact with blood or other bodily fluid, the pump head may be replaceable and disposable after a single use or after only a few uses. The disposable pump head may be manipulated by using a non-contact method of applying force, such as a magnetic drive. The pump may drive flow through the system at a flow rate between, e.g., 0 ml/min and 2 L/min. The pump circuit may contain safety mechanisms, such as pressure relief valves, check valves, or the like to ensure the circuit constantly operates under safe operating conditions, such as maintaining pressure in the circuit under a specified safe threshold. The flow rate or pressure provided by the pump may be regulated by a control system, discussed herein. In some instances, the pumping mechanism may be controlled by a human operator. In some scenarios where the pumping is under the control of a human operator, the pumping may be performed using fluid mechanical force inputs from the human operator. This mechanical force driven pump may be used when the system malfunctions or does not have the electrical energy input needed to run.

In some embodiments, the fluidic circuit may be coated with Heparin or other similar anti-clotting media to prevent the clotting of blood in the pump and fluidic circuit. Some or all of the fluid paths of the fluidic circuit may be insulated to minimize thermal communication of the fluid in the pump and fluidic circuit with the surrounding environment. Some or all of the fluid paths of the fluidic circuit may be partially or fully in contact with ice packs or gel ice packs, which may consist of a mixture of water and potentially one or more other fluids, such as propylene glycol, to help maintain cooled fluids in the circuit at their desired temperature.

The temperature of the fluid may be modulated by one or more heat exchangers or similar temperature modulation apparatuses. The temperature modulation apparatuses may heat or cool the fluid passing through the fluidic circuit. In some embodiments, one or more ancillary fluidic circuits may be in thermal communication with the one or more therapy delivery system fluidic circuits. In this embodiment, the point of thermal exchange between the one or more ancillary fluidic temperature modulation circuit and the fluidic circuit of the therapy delivery system may be a sterile heat exchange unit. The sterile heat exchange unit may be disposable and discarded after contact with the fluid of the fluidic circuit. The ancillary heat exchange circuits may thermally communicate with the one or more therapy delivery system fluidic circuits using thin metal plates, and the design of the therapy delivery system may use parallel flow or counter flow heat exchange mechanisms, a shell-and-tube heat exchange mechanism, a finned or unfinned tubular heat exchange mechanism, a U-tube heat exchange mechanism, a plate and frame heat exchange mechanism, another similar heat exchange mechanism, or some combination thereof. The ancillary fluidic heat exchange circuit may circulate water, refrigerant fluid, or some other fluid with properties optimized for heat transfer. The ancillary fluidic temperature modulation circuit may contain a compressor to drive fluid flow, running a refrigeration circuit and removing heat. The circuit may also contain a condenser and evaporator in thermal communication with the surroundings of the system. An expansion valve may be used to remove pressure from the fluid at one or several points in the fluidic circuit. The one or more ancillary fluidic temperature modulation circuits may contain one or more peltier devices to modify the temperature of fluid in the second fluidic circuit. The one or more ancillary fluidic temperature modulation circuits may use an ice bath as the source of cold fluid for circulation through a heat exchanger. The ancillary fluidic temperature modulation circuits may use a fan, heat fins, or other methods of increasing thermal energy transfer to dissipate heat from the temperature modulation apparatus, especially in the condenser and evaporator. Some or all of the fluid paths of the temperature modulation apparatus may be insulated to minimize thermal communication of the fluid in the system with the surrounding environment. The ancillary fluidic temperature modulation circuits may also contain a heating coil or other similar heating source to warm the fluid passing through the heat exchanger, in turn warming the all or some of the fluid passing through one or more of the therapy delivery system's fluidic circuit. One ancillary fluidic circuit may be used to cool all or some portion of blood passing through the therapy delivery system's fluidic circuit, and this cooled blood may be infused through the cooling lumen of the infusion catheter. One ancillary fluidic circuit may be used to warm or sustain the temperature of some or all the blood passing through the therapy delivery system's fluidic circuit, and this warm blood may be infused through the counterwarming lumen of the infusion catheter. A fluid flow regulating mechanism, such as one or more valves, may be used to dictate how much flow from the therapy delivery system's fluidic circuit, if any, is warmed or cooled by an ancillary circuit. For example, one or more valve or other fluid distribution systems may direct 20% of the flow coming in from the suction inlet to be cooled by a cooling ancillary circuit, while the other 80% of flow is directed to be warmed by a warming ancillary circuit. There may be two or more branches of flow, and any number of combinations and conditionings applied to these different flow paths.

The oxygenation characteristics of the fluid may be modulated by one or more oxygenators. The fluid in the fluidic circuit may pass through this oxygenator and be imbued with oxygen. The oxygenator may have sterile, disposable oxygenation units, which may be discarded after coming into contact with the fluid in the fluidic circuit.

Figure 13:
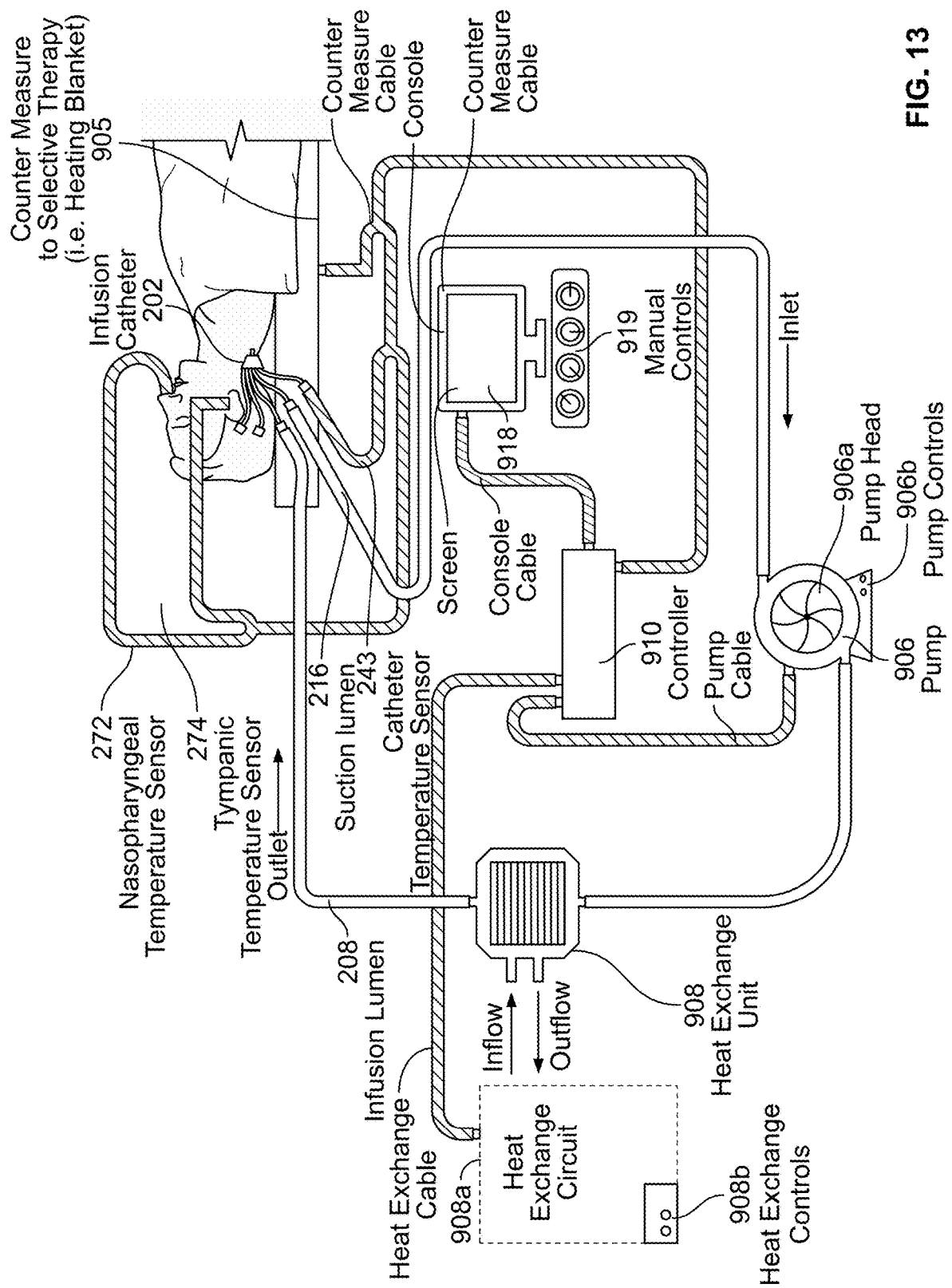
FIG. 13 illustrates a system using a controller suitable for incorporating a catheter, in accordance with some embodiments of the disclosure.
Figure 14:
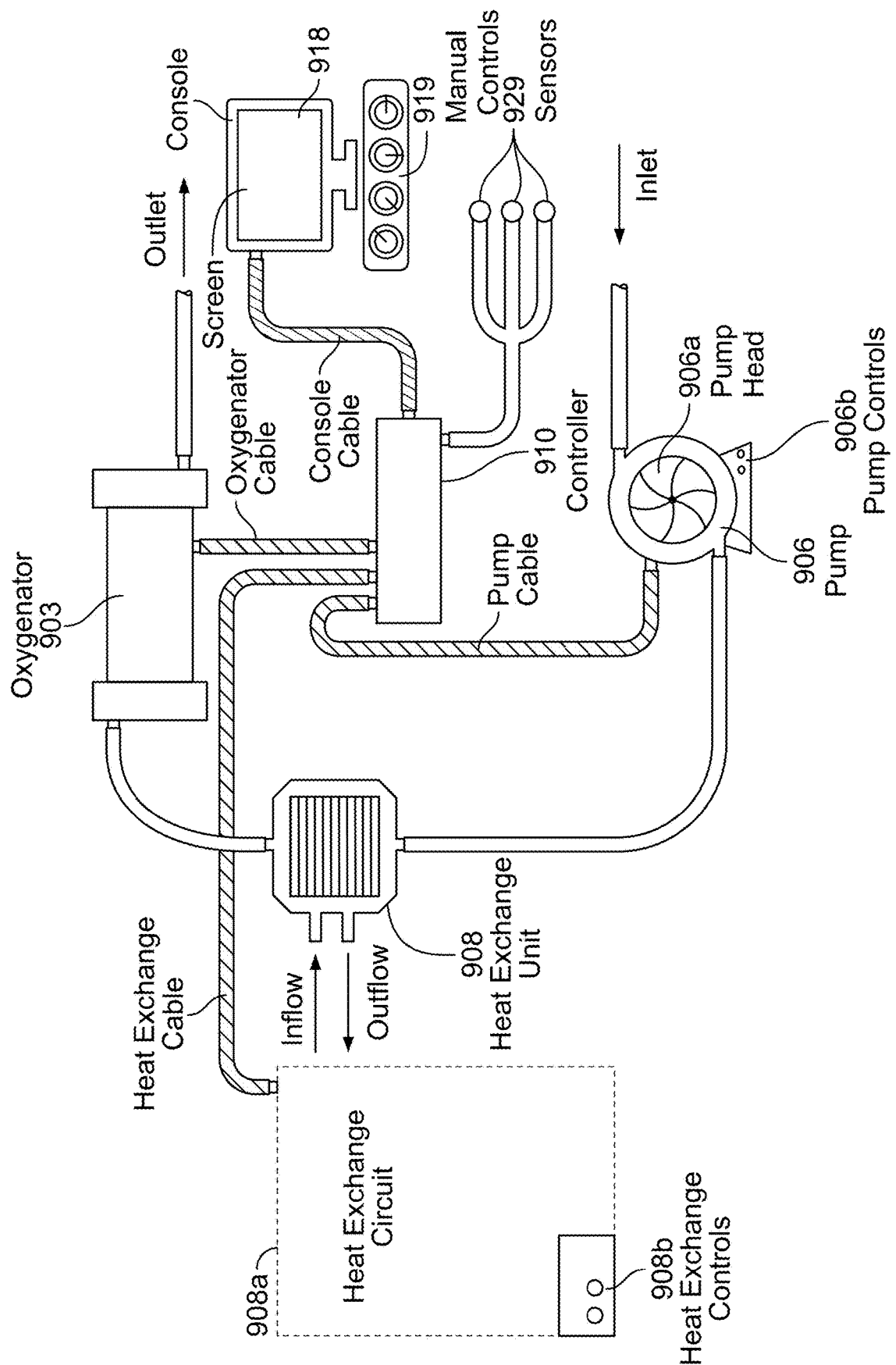
FIG. 14 illustrates a system using an oxygenator and a controller suitable for incorporating a catheter, in accordance with some embodiments of the disclosure.

FIG. 13 illustrates a system using a controller suitable for incorporating a catheter, in accordance with some embodiments of the disclosure. FIG. 14 illustrates a system using an oxygenator and a controller suitable for incorporating a catheter, in accordance with some embodiments of the disclosure. In some embodiments, a controller may be used to modulate aspects of the therapy delivery system. The controller may modulate the pressure of the fluid in the fluidic circuit, the temperature of the fluid, the flow rate of the fluid, the oxygenation of the fluid, a similar system property, or some combination thereof. The pump, heat exchanger, oxygenator (if present), and other system components, such as temperature, pressure, and flow sensors, may be in communication with the controller, and each connection may be made using one or more communication cables. When modulating the temperature of the fluid, the controller may modify aspects of the one or more ancillary fluidic heat exchange circuits, such as the flow rate, temperature, or pressure in the second fluidic circuit, which may be in thermal communication with the therapy delivery system. The controller may take input from sensors, such as temperature, pressure, flow sensors, or the like, and use these inputs to modify the therapy delivery system. The temperature measurements may be gathered using a tympanic, nasopharyngeal, tubing-embedded, or catheter-based sensors, or some combination thereof. The pressure inputs may be gathered via a catheter device and/or from sensors in associated tubing to which the system may be in fluid communication with. This controller may be a PID (proportional integral derivative) controller, a programmable logic controller (PLC), another control system, or the like. An algorithm may be used to control the characteristics of the cooling system based on the sensor inputs described previously. The algorithm may monitor the temperature of a target location, such as the temperature of one or more target organs or a region close to, or at a similar temperature to, these one or more target organs, and modulate the therapy delivery system to modify the temperature of the target location. The organ targeted for selective cooling may be the brain, and it may be targeted due to the presence of a stroke, in order to potentially deliver neuroprotection and reduce brain damage. The temperature of the heart may also be monitored, directly or indirectly, using a temperature sensor either in the body, external to the body, in the therapy delivery system (e.g., associated tubing), or otherwise strategically placed to ensure it does not drop below temperatures known to be dangerous, with temperatures approaching 33° C. increasing the likelihood of arrhythmias. In some embodiments, indirect measurement of heart temperature may be inferred via a temperature sensor placed on a catheter which may sit on or in the body of the catheter at or near the cavoatrial junction. An emergency cutoff temperature may be set such that if a particular temperature probe is measuring a temperature too low, temperature near or in the heart of 32° C. for example, the system slows the flow rate of fluid through the fluidic system or shuts off completely. In some embodiments, other metrics such as rate of cooling, historical cooling data, pressure data, or the like may be used to determine if the system needs to shut off. An algorithm may combine the known volume and temperature of cold and warm perfusate being administered, the known volume and temperature of the suctioned blood, and the temperature read from the device thermistor, possibly in addition to patient parameters such as body weight, heart rate, blood pressure, body temperature (rectal or bladder probe), in such a way to infer an expected heart temperature. This may be done with an understanding of the various known temperatures and volumes of delivery and suction to the heart, and a calculation of the resulting mixed temperature blood the heart will experience.

The emergency cutoff measurement may come from a temperature sensor measuring the temperature at or near the heart or in the fluid path of the therapy delivery system, and the slowing or stoppage of flow in response to a temperature too low may allow the system to prevent the heart from reaching dangerous temperatures, which may be below 32° C. The flow rate of warmed or normothermic blood through the counterwarming lumen may also be used to prevent the heart from reaching dangerous temperatures. Similarly, the control system may take inputs of the target temperature of a target organ to modulate flow rate or other parameters of the therapy delivery system. In some embodiments, the target temperature of the brain, as measured by a nasopharyngeal or tympanic membrane temperature probe, may be greater than or equal to 33° C., and the control system may increase the flow rate of cooled fluid, decrease the temperature of cooled fluid administered, or decrease the flow rate of warmed or normothermic counterwarming fluid in order to reach and maintain this target cerebral temperature. The temperature of the heart may be monitored, directly (e.g., with a temperature probe in the right atrium) or indirectly, to ensure the brain cooling is not causing dangerously cold temperatures in the heart, such as temperatures below 32° C.

In some embodiments, an algorithm may adjust the characteristics of the fluid system in response to the recanalization status of a blocked vessel. For example, in a stroke patient receiving thrombectomy, the cooling and flow of the system may be increased to decrease the temperature of the brain, allowing neuroprotective hypothermia to reduce the risk of reperfusion injury. The temperature of the brain, and the differential in temperature between the brain and body, may be modulated based on the medical state of the patient or the time after they have received some other treatment, such as thrombectomy. The control system may modulate the parameters of the system based on medical imaging. For example, a CT scan or MRI on a stroke patient may indicate the patient has a large volume of brain tissue that can be saved, in which case the controller may increase the flow rate of the cooling, decrease the temperature of the fluid, increase the oxygenation of the fluid, or otherwise adjust the system in order to better salvage the at-risk tissue.

In some embodiments, the temperature measured using nasopharyngeal or tympanic temperature probes near the brain may be used to increase the flow rate of the pump or decrease the temperature of the fluid in the therapy delivery system in order to decrease the temperature of the brain in accordance with the control system algorithm. The control system may also modulate the temperature and flow rate of the warmed fluid being delivered to the counterwarming port of the infusion catheter to increase or sustain the temperature of the heart. The control system may control the flow and temperature of the fluid to reach a specified target temperature in the brain and heart. If a temperature measurement at or near a target organ such as the heart, is too low as measured by a device placed in the central venous system of a patient, it may be desired to warm the target organ; the controller can decrease the flow rate of the pump, increase the temperature of the fluid, or reroute flow towards or away from the heart, as prescribed by a control algorithm. The pressure created by the output of the therapy delivery system may be monitored by a sensor on the infusion device, potentially a pressure sensor or pressure lumen 217 placed near the infusion port of the device. The system may decrease the flow rate or the pressure of the therapy delivery system to prevent overpressurization near the outlet of the therapy delivery system. In this example, the output infusion of the therapy delivery system may be in a human blood vessel, such as a vein, and the pressure measured may be the pressure created by the infusion into the vein to assess if the pressure or flow rate of the therapy delivery system needs to be decreased to reduce safety risks, such as edema in the case that the target organ is the brain.

A console may be used to interface or interact with the therapy delivery system and monitor the system. The console may be designed for ease-of-use by a human operator. The console may have a screen, such as a touchscreen or a display screen, which allows users to modulate characteristics of the system based on the information displayed on the screen. Alternatively, dials, buttons, and other mechanical control mechanisms may be used to modify characteristics of the fluid system. Temperature, pressure, flow and similar sensors may be operably connected to the cooling console through the controller, and measurements may be reported on the screen. The console may be able to gather and store data over time and to report on the value of sensor readings over a period of time. The console may be used by doctors or other medical professionals to monitor the temperature of either the heart, the temperature of the brain, or both, for a patient suffering from a stroke receiving therapy using the therapy delivery system. The console may alert care providers when conditions are reaching a dangerous level and prompt a change in the therapy delivery system parameters.

Figure 15:
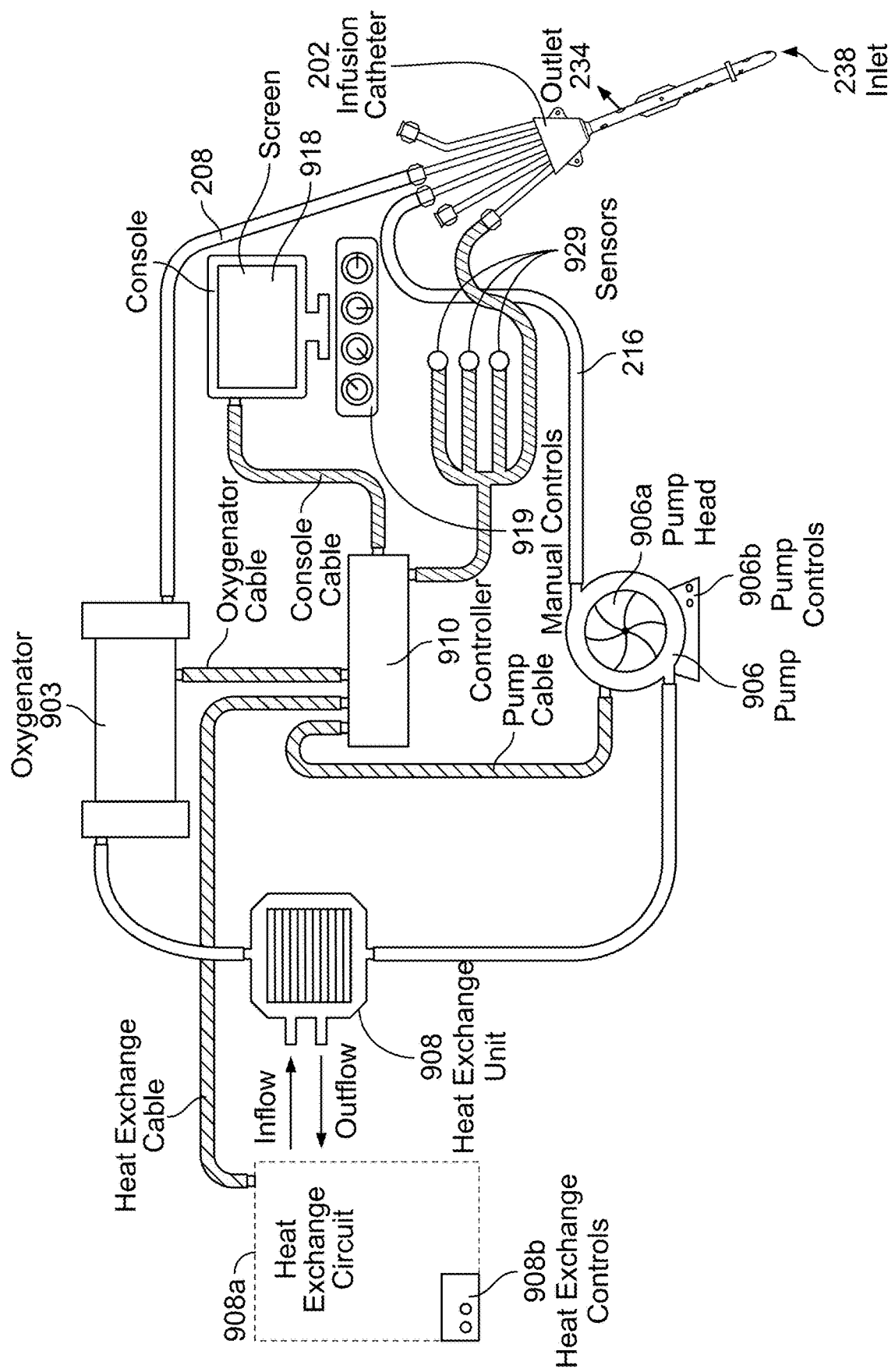
FIG. 15 illustrates a system using a controller incorporating a catheter, in accordance with some embodiments of the disclosure.

FIG. 15 illustrates a system using a controller incorporating a catheter, in accordance with some embodiments of the disclosure. In some instances, the therapy delivery apparatus may be fluidly connected to the infusion catheter previously described, at one or more points. The one or more of the inlet ports of the therapy delivery system may suction from the suction port 238 of the infusion catheter, and one or more of the outlet ports of the therapy delivery system may infuse fluid that may have been modulated in temperature, oxygenation status, or both through the infusion port of the infusion catheter. One infusion lumen of the infusion lumen, such as the infusion lumen that outlets proximal to the expandable occlusion element, may be connected to an outlet of the therapy delivery apparatus that delivers cooled fluid to this proximal infusion lumen, while another infusion lumen of the infusion catheter, such as the infusion lumen that outlets distal to the expandable occlusion element, may be connected to an outlet of the of the therapy delivery apparatus that delivers warmed or body temperature fluid to this distal infusion outlet. The one or more sensors of the infusion catheter may be in communication with the controller or another component of the therapy delivery system, in order to communicate measurements from the one or more sensors in the device. The therapy delivery system can control the temperature, flow rate, pressure, and oxygenation of the flow infused through the infusion catheter. In the embodiment in which cooling may be delivered to the brain of a stroke patient, the cooling may increase the vasodilation of arteries in the brain and therefore improve collateralization to the portion of the brain cut off from blood flow.

Figure 16:
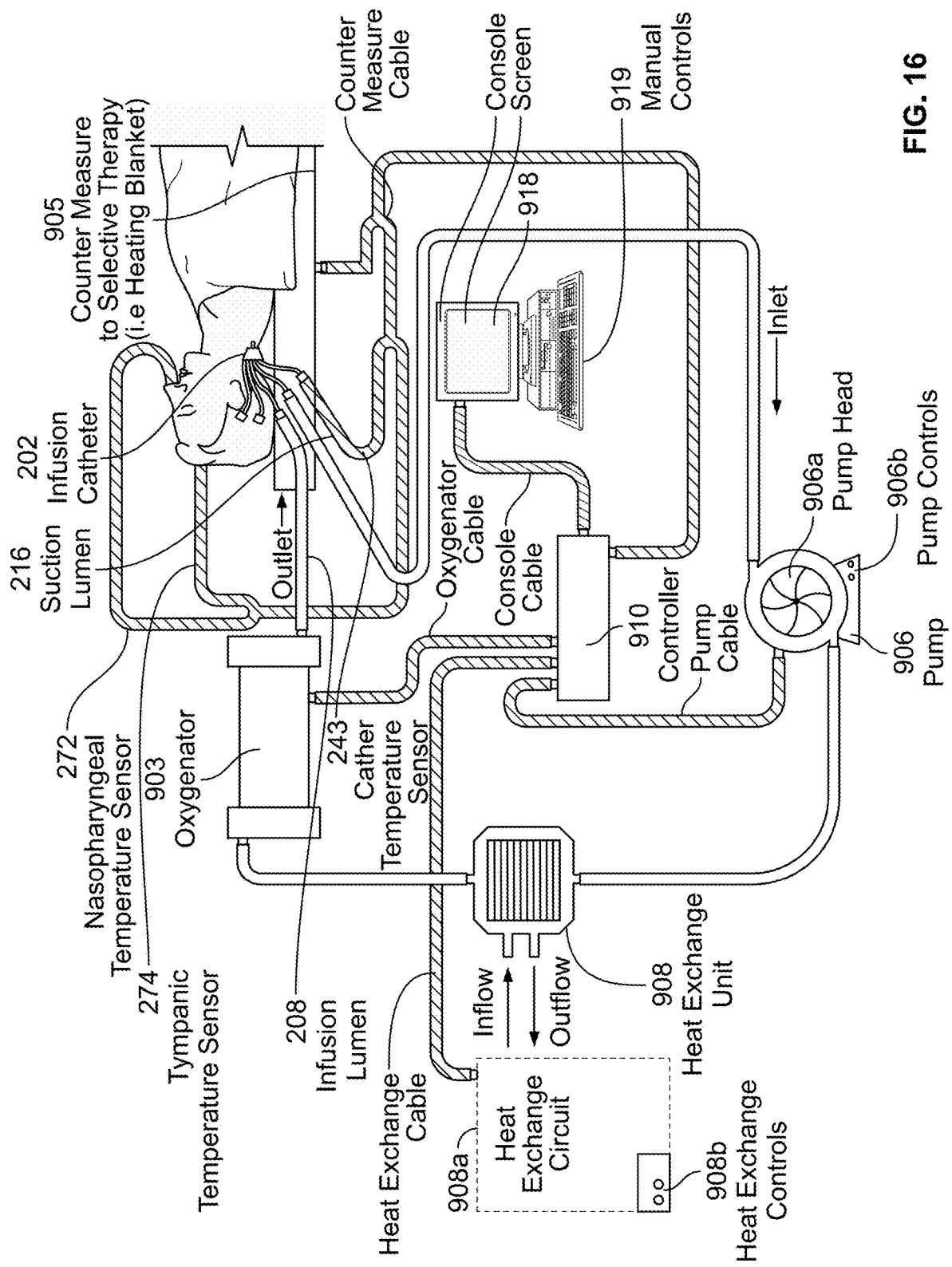
FIG. 16 illustrates a system using a controller incorporating a catheter used with a patient, in accordance with some embodiments of the disclosure.

FIG. 16 illustrates a system using a controller incorporating a catheter used with a patient, in accordance with some embodiments of the disclosure. In the embodiment of the combined infusion catheter and therapy delivery system, the infusion catheter may be placed in the central venous system of a patient, such as the internal jugular vein (or femoral vein), and may be used to selectively cool an organ, such as the brain. The system may be used to cool, oxygenate, or otherwise deliver therapy to the brain of a stroke patient to potentially reduce ischemic damage.

The expandable occluder may be inflated to occlude the vein in which the infusion catheter may be placed. In some embodiments, the expandable occluder, which may be a balloon, may be inflated with cold fluid such as saline, to augment cooling. The suction ports 238 of the therapy delivery system may be used to suction blood through the suction lumen 216 of the infusion catheter, run it through the fluidic circuit of the therapy delivery system, and infuse it through the one or more infusion ports of the infusion catheter. With the vein in which the infusion catheter may reside occluded by the catheter's expandable occluder, some of the infused fluid from the therapy delivery system, the fluid infused proximal to the expandable occlusion element, may be directed retrograde in the vessel. Some other portion of the fluid infused through the infusion catheter, the portion infused distal to the expandable occlusion element, may be directed antegrade in the vessel, towards the heart. This may enable selective brain therapy, in which oxygen may be delivered, the brain may be cooled, drugs may be delivered, some other therapeutic agent may be delivered or some combination thereof. The brain may be cooled to levels of hypothermia, 23-28° C., a temperature range known to substantially slow metabolism to provide neuroprotection during cardiac surgery. Alternatively, the brain can be cooled to 33° C. or lower, a temperature shown to be neuroprotective in animal studies. When cooling the brain to 33° C. or lower, it may be advantageous for the brain cooling to be completed quickly, in a time period of 0-30 minutes from initiation of cooling, to reduce the risk for reperfusion injury.

The pressure of the retrograde perfusion may be monitored to ensure it does not exceed levels known to be safe in the brain, such as a sustained intracranial pressures (ICP) greater than 25 mm Hg. To mitigate the potential for causing dangerously high levels of ICP, the expandable occluder may be unexpanded periodically in order to relieve pressure in the fluidic system that the device may be residing in. The cooling system may also control the flow of fluid into and out of the infusion device's expandable occluder port. The cooling system may circulate cold fluid in the expandable occluder of the device to increase the amount of cooling delivered to the selected organ. The connection points between the therapy delivery system and the infusion catheter may be luer connectors.

The combined system, the infusion catheter and the therapy delivery system, may be suited for delivery of selective cooling therapy during transit of a patient, such as in an ambulance. To enable this therapy, the therapy delivery system may need to fit in a container between 1-5 cubic feet in volume, which may be small enough to be placed on an ambulance. The therapy delivery system may be run on the power supply provided by the ambulance or by batteries. The infusion catheter may have features, such as ultrasound guidance that enables a user to ensure the device can be placed correctly, that make it safe to be inserted by an EMT, nurse, or other medical professional on the ambulance. The ultrasound guidance may include the use of doppler ultrasound to assess if the balloon is occluding the vessel, and may utilize inflating the balloon with agitated solution to aid in visual confirmation that the expandable occluder, which may be a balloon, may have been expanded. The infusion catheter may be tethered to the patient at one or more mounting points to ensure the infusion catheter remains in the correct placement position during the shocks and vibrations experienced in an ambulance ride.

Countermeasures to the selective therapy may be implemented if the therapy delivery system may be at risk of causing harm. For example, if the therapy delivery system is being used to selectively cool the brain, the heart may cool from the cooled fluid that has passed through the brain and made its way to the heart. In order to prevent the heart from cooling too deeply, countermeasures of warming may be used. In some embodiments, warm fluid may be delivered through a lumen of the infusion catheter, typically near the heart, in order to warm the tissues of the heart. In some embodiments, warmed or body temperature fluid may be infused through the counterwarming lumen of the infusion catheter to warm or sustain the temperature of the heart. This warmed or body temperature fluid may be delivered distal to the expandable occluder of the device, in the internal jugular, brachiocephalic, superior vena cava, the right atrium of the heart, or the inferior vena cava. A heating blanket, forced air heating system, heating pad, or similar may be used to deliver heat externally, through a patient's skin. These countermeasures to the selective therapy may be controlled by the control system, such that more of the countermeasure may be administered when a sensor may be measuring in a range deemed to be dangerous. For example, a temperature sensor in or near the heart may alert the control system that the heart may be reaching a dangerous level, so the control system may increase the countermeasure warming.

In another embodiment of the combined system, the infusion catheter may be placed in the arterial system of a patient, such as the carotid artery or femoral artery, and may be used to selectively cool an organ, such as a brain, or limb.

In at least one embodiment, the disposable components of the therapy delivery system may come in a prepackaged kit. The kit and the components inside it may be sterilized. The kit may include one or more disposable pump heads, one or more disposable heat exchangers, one or more oxygenation components, one or more temperature sensors, one or more pressure sensors, one or more pressure sensing apparatuses to measure pressure from an open lumen in a catheter, lengths of disposable tubing of one or more diameters, or some combination thereof. The heat exchanger and oxygenator, if present, may be one combined component which can function as both a heat exchanger and an oxygenator.

Figure 17A:
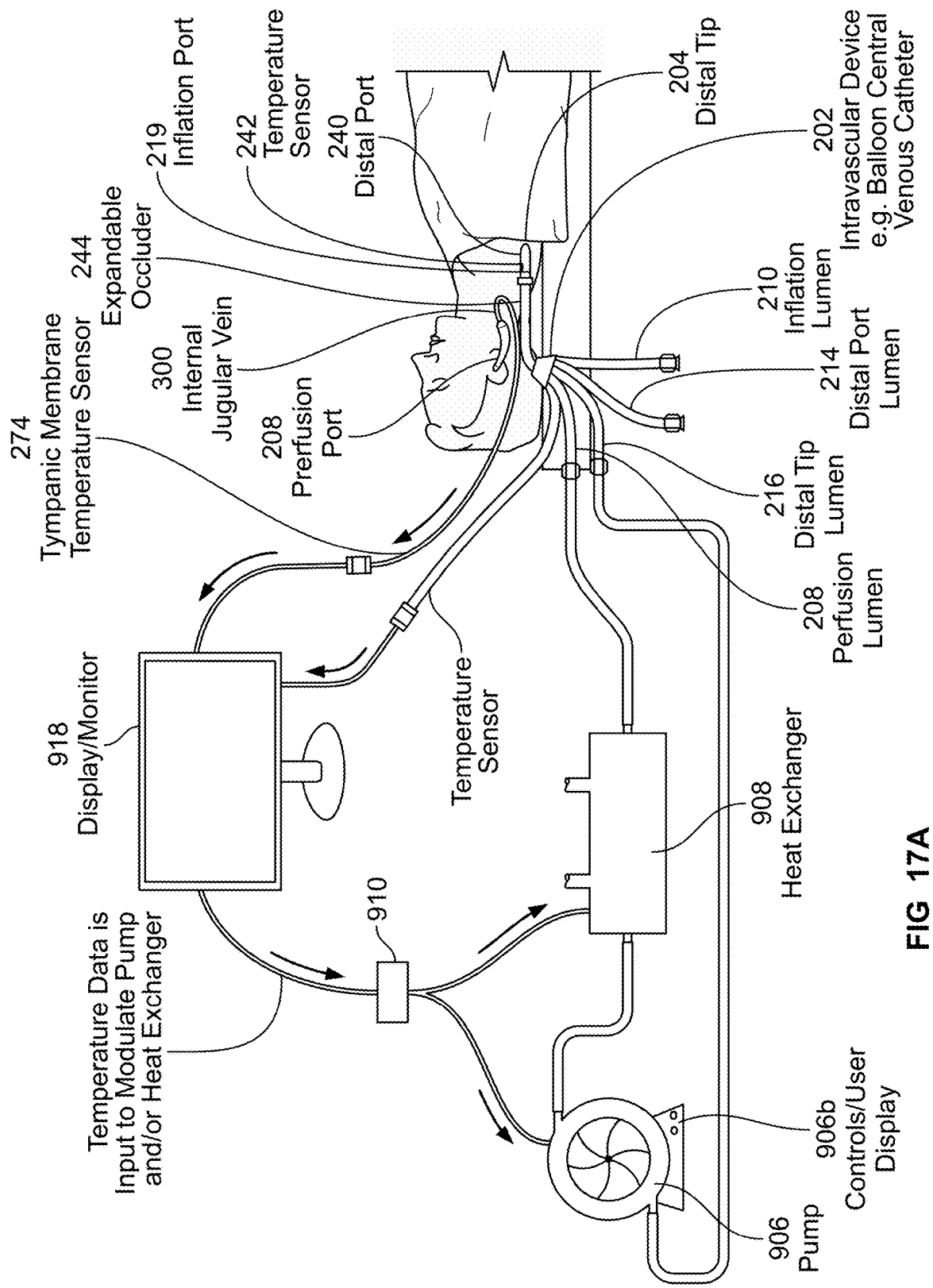
FIG. 17A illustrates a system using selective cooling with counterwarming of a heart, in accordance with some embodiments of the disclosure.
Figure 17B:
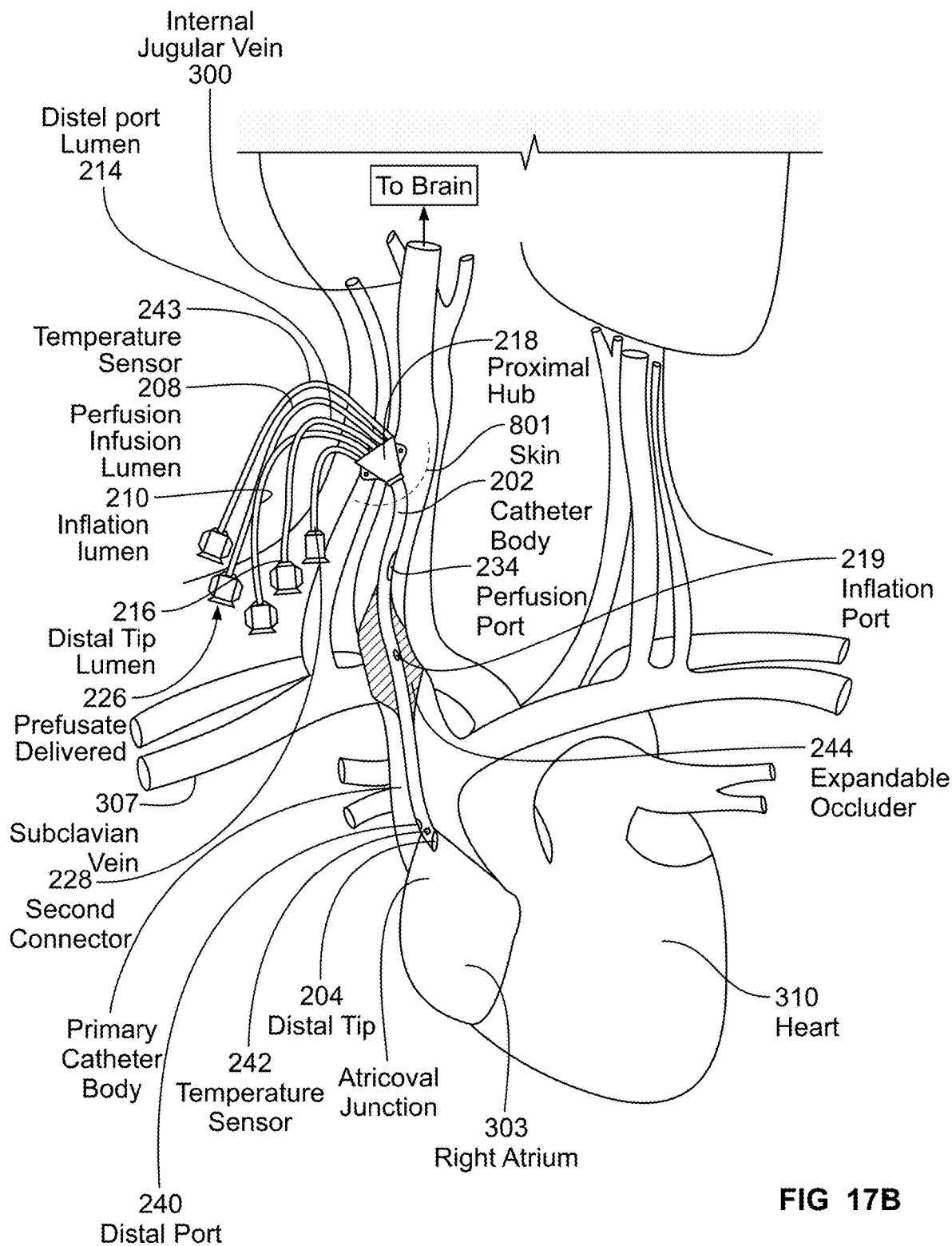
FIG. 17B illustrates a system using selective cooling with counterwarming of a heart with a catheter in a patient, in accordance with some embodiments of the disclosure.

2.2 Selective Cooling with Counterwarming of Heart (See FIGS. 17A-17B)

FIG. 17A illustrates a system using selective cooling with counterwarming of a heart, in accordance with some embodiments of the disclosure. A system may comprise a controllable pump or other method of producing a pressure head, a heat exchanger or other means of cooling media, a temperature sensor or other means of measuring body temperature, and a catheter or other type of intravenous access device, herein labeled 'catheter,' which may direct fluid in a preferential direction, such as towards the heart of a patient during a stroke or cardiac arrest. A temperature sensor near the heart may be used to monitor if the heart may be reaching a dangerously low temperature, such as a temperature at or under 32° C., which has been known to cause arrhythmias and ultimately arrest the heart. The system may suction blood or other fluid from one or more ports of the catheter; this fluid may be taken out of the original fluid system, such as the body, may be temperature-modulated by the heat exchanger, and the fluid may be perfused back into the original fluid system at a different temperature. The fluid perfused into the original fluid system, which may be the body, can be directed to a structure to be selectively warmed, such as the heart. The flow rate or another parameter of the pump system, which may be controllable either by a user, by a control system, or by other means, can be adjusted in response to input to the control system, such as input from temperature sensors. Sensors, such as nasopharyngeal, tympanic, or other temperature sensors, may be used as inputs to control a parameter of the system such as the flow rate of the pump or the cooling rate of the heat exchanger. Additional sensors, such as a temperature sensor measuring the temperature of the heart, may be used to determine if the flow rate or heat exchange rate should be modulated. The system may monitor both brain and heart temperature, directly or indirectly, of a patient, and the system may make recommendations to a user on how to modulate the system such that desired temperatures are maintained, such as sustaining a warm temperature in the heart to prevent arrhythmias, temperatures greater than 32° C. The system may contain a user interface to allow for control of the system and monitoring of important parameters, such as flow rate, temperature, and pressure of the perfusate. The catheter may contain additional lumens for delivery of drugs or other medicaments, pressure sensing, or other functions.

In practice, this system may have a heat exchanger that ensures blood remains 32° C. and can warm the blood to or above this temperature. This may be autologous blood and may be collected via the same catheter that delivers the temperature-modulated blood back to the patient. The pump may adjust its flow rate in a range of 0-2000 ml/min, for example, based on a one or more temperature sensor at or near the cavoatrial junction, disposed in or on the body of a catheter, or other sensor, which may be used as a proxy for heart temperature or the temperature of another organ. Temperature sensors in or on the infusion catheter may also be used to understand the temperature at other points in the vasculature. Furthermore, blood may be passed through an oxygenator in addition to or in place of a heat exchanger.

This system, coupled with a catheter, may be able to withdraw, temperature-modulate, and re-infuse autologous blood at one or more target temperatures or oxygenations to one or more target regions of the body.

FIG. 17B illustrates a system using selective cooling with counterwarming of a heart with a catheter in a patient, in accordance with some embodiments of the disclosure. In some embodiment, a catheter may be placed in the internal jugular vein. One example may include cooling a portion of the blood withdrawn via the suction ports 238 of the catheter extracorporeally, and reinfusing a portion of this blood, cooled and potentially oxygenated, via a port proximal to an occlusive body on the catheter, such that targeted brain cooling may be achieved. Simultaneously, warming (or maintenance at body temperature) of a portion of the blood potentially withdrawn via the device, and reperfusing via a port distal to the expandable occluder, such that warmed blood may be directed toward the heart preferentially may occur. As such, cooling proximal to the expandable occluder, and warming distal to the expandable occluder may be achieved for targeted cerebral cooling while maintaining near normothermia in the heart, for example. The pump may adjust its flow rate in a potential range of 0-2000 ml/min, for example, based on input from both a tympanic temperature, as a proxy for brain temperature, and a distal tip 205 of the catheter temperature sensor, as a proxy for heart temperature. Using these sensors or other sources of data as input, the system may be able to warm the heart enough to avoid arrhythmias, e.g., greater than 32° C.

2.3 Control System

Figure 18A:
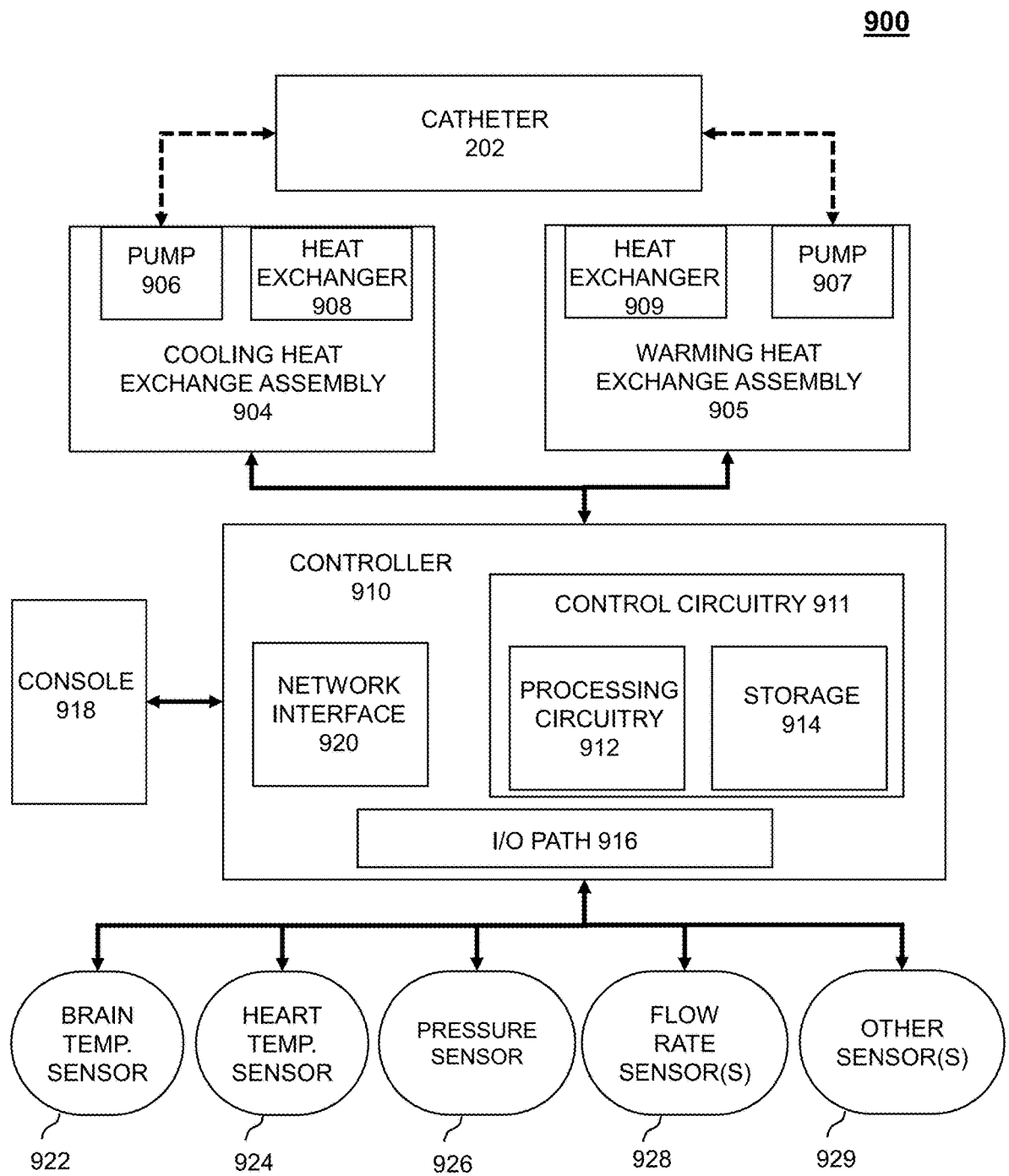
FIG. 18A is a block diagram of an illustrative system using a controller suitable for incorporating a catheter, in accordance with some embodiments of the disclosure.

FIG. 18A is a block diagram of an illustrative system using a controller suitable for incorporating a catheter, in accordance with some embodiments of the disclosure. FIG. 18A shows a diagram of illustrative devices of a system 900 that includes catheter 902, cooling heat exchange assembly 904, warming heat exchange assembly 905, controller 910, console 918, and several exemplary sensors including brain temperature sensor 922, heart temperature sensor 924, pressure sensor 926, flow rate sensor 928, and other sensors 929. These components may be housed on a local computing system or may be remote components in wired or wireless connection with a local computing system (e.g., a remote server, a cloud, a mobile device, a connected device, etc.). Generally in system 900, controller 910 controls temperature and pump flow rates of each of cooling heat exchange assembly 904 and warming heat exchange assembly 905 based on inputs received from sensors 922-929 and, e.g., instructions to maintain safe patient therapy.

Control circuitry 911 may be based on any suitable processing circuitry, such as processing circuitry 912. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, octa-core, or any suitable number of cores). In some embodiments, processing circuitry is distributed across multiple separate processors or processing units, for example, multiple of the same type of processing units (e.g., two INTEL CORE i7 processors) or multiple different processors (e.g., an INTEL CORE i5 processor and an INTEL CORE i7 processor). Some embodiments may use multiple controllers, with each controller, for instance, controlling at least one corresponding heat exchange assembly or other system component. In some embodiments, control circuitry 911 executes instructions stored in memory (e.g., storage 914). For example, the instructions may cause control circuitry 911 to control the performance of fluid heating and cooling operations described above and below.

Memory/storage 914 may be an electronic storage device that is part of control circuitry 911. As referred to herein, the phrase "electronic storage device" or "storage device" should be understood to mean any device for storing electronic data, computer software, instructions, and/or firmware, such as random-access memory, hard drives, optical drives, solid state devices, quantum storage devices, or any other suitable fixed or removable storage devices, and/or any combination of the same. Nonvolatile memory may also be used. The circuitry described herein may execute instructions included in software running on one or more general purpose or specialized processors.

Controller 910 may receive and send data via an input/output (I/O) path 916. I/O path 916 is communicatively connected to control circuitry 911, which includes processing circuitry 912 and storage (or memory) 914. Control circuitry 911 may send and receive commands, requests, and other suitable data using I/O path 916.

In some embodiments, controller 910 may use I/O path 916 to receive sensor data from (and/or send requests to), e.g., brain temperature sensor 922, heart temperature sensor 924, pressure sensor 926, flow rate sensor 928, and other sensors 929. In some embodiments, connections between components may be facilitated by one or more buses (e.g. peripheral component interconnects (PCI) bus, PCI-Express bus, or universal serial bus (USB)). With such buses, the computing environment may be capable of integrating numerous components, numerous PCBs, numerous remote computing systems. One or more system management controllers, e.g., control circuitry 911, may provide data transmission management functions between the buses and the components they integrate. Such management controllers may facilitate the arrangements orchestration of these components that may each utilize separate instructions within defined time frames to execute applications.

In some embodiments, I/O path 916 may function in conjunction with network interface 920. Network interface 920 may include an Ethernet connection or a component that forms a wireless 802.11b, g, a, or n connection to a local area network (LAN), wide area network (WAN), intranet, or internet. In some embodiments, controller 910 may communicate with console 918 via network interface 920. I/O path 916 may connect control circuitry 911 (and specifically processing circuitry 912) to one or more network interfaces 920, which in turn connect controller 910 to other devices on a network (e.g., sensors 922-929, heat exchange assemblies 904-905, console 918, etc.). Controller 910 may be connected to console 918 via I/O path 916 and/or network interface 920. Console 918 may include, for example, a monitor, dials, and/or input devices such as a mouse, keyboard touchscreen, etc. to facilitate creating, modifying, or accessing instructions for controller 910 and system 900.

In system 900, controller 910 is communicatively connected to cooling heat exchange assembly 904 and/or warming heat exchange assembly 905. Controller 910 may transmit instructions to each of cooling heat exchange assembly 904 and/or warming heat exchange assembly 905, such as setting temperature and/or flow rate of each heat exchange assembly.

In some embodiments, cooling heat exchange assembly 904 may be used to provide cooled fluid to catheter 202 to allow the cooled fluid to flow to the brain. Heat exchange assembly 904 includes pump 906 and heat exchanger 908. In some embodiments, heat exchange assembly 904 may incorporate a heat exchange circuit. In some embodiments, heat exchange assembly 904 may include one or more flow rate sensors, e.g., flow rate sensor(s) 928, to measure outlet flows.

In some embodiments, warming heat exchange assembly 905 may be used to provide normothermic or warmed fluid to catheter 202 to allow the warmed fluid to flow to the heart. Heat exchange assembly 905 includes pump 907 and heat exchanger 909. In some embodiments, heat exchange assembly 905 may incorporate a heat exchange circuit. In some embodiments, heat exchange assembly 905 may include one or more flow rate sensors, e.g., flow rate sensor(s) 928, to measure outlet flows. Some embodiments may not use counterwarming from warming heat exchange assembly 905.

System 900 may use many sensors to gather body and/or fluid temperature. For instance, brain temperature sensor 922 may include one or more thermistors placed in the patient's body. In some embodiments, brain temperature sensor 922 could be one or more of a nasopharyngeal temperature probe, a tympanic membrane temperature probe, or an intraparenchymal temperature probe. In some embodiments, an intracranial pressure (ICP) probe including a temperature sensor may be used. Other thermistors or temperature sensors on or near brain tissue may be used to approximate actual brain temperature. For instance, brain temperature may be estimated and/or measured by proxy. In some embodiments, for therapy, the brain temperature should be between 0 and 36° C. In some cases, such as using probes not as near the brain, the brain temperature may be approximated. For example, based on received sensor measurements, brain temperature may be inferred to be a few degrees warmer than the received brain temperature measurements.

Heart temperature sensor 924 may include one or more thermistors, such as a thermistor in or on a catheter that is inserted into the patient. For instance, catheter 902 may be a venous infusion catheter as described herein when the distal end 204 of the catheter is inserted in the patient's vena cava or right atrium. In some embodiments, heart temperature sensor 924 may be placed distally of an occlusion element. Some catheter embodiments may include heart temperature sensor 924 positioned distally of one or more suction ports 238. Positioning a heart temperature sensor 924 on or near the distal tip 205 of a catheter would allow for the distal end 204 to be in or near the cavoatrial junction and/or the right atrium of the heart. Placement of a thermistor near the cavoatrial junction and/or the right atrium can provide an approximate measurement of heart temperature. In some embodiments, placement of a thermistor in the superior vena cava, e.g., not in the cavoatrial junction, may also be suitable for use to approximate a measurement of heart temperature. In some embodiments, a temperature sensor may be placed in the suction tubing, e.g., tubing carrying blood from the catheter to one or more heat exchange assemblies.

Calculating an approximate heart temperature may be more precise than approximating brain temperature as cooling the brain has a wider range of temperatures than safe heart temperatures. Specifically, maintaining heart temperature above 32 degrees Celsius is considered safe and striving to keep the heart 36-37° C. is optimal. If a calculated heart temperature drops below 32° C., the pump 906 of cooling heat assembly 904 may be modulated to reduce or eliminate cold flow, while pump 907 of warming heat assembly 905 may continue or potentially increase. In some embodiments, if calculated heart temperature drops below 32° C., the cooling system may shut down.

Measuring and approximating heart temperature may be calculated in several ways. Some embodiments may use a thermistor on the catheter as proxy for heart temperature, where temperature may be estimated. For instance, if a temperature sensor in the vena cava reads greater than 34° C., heart temperature may be assumed to be at least 35° C. Some embodiments may use a thermistor in a suction lumen 216 as a proxy for heart temperature. Some embodiments may use both a thermistor on the device and a thermistor in the suction lumen 216, with the redundancy increasing safety.

Some embodiments may calculate an approximate heart temperature using measured return volumes and temperatures of the patient's superior vena cava and inferior vena cava. For example, based on these inputs, controller 910 may determine a mixed volume and temperature for fluid returning to the heart. For example, SVC fluid volume can be calculated based on the known volumes and temperatures of cold fluid delivered toward the brain and warm fluid delivered to the heart, along with the temperature of the SVC as measured by a thermistor on the device or in a suction lumen 216. IVC fluid volume can be determined based on the calculated SVC volume using an approximation that SVC is about 35% of cardiac output and IVC is 65% of cardiac output. Based on that proportion, IVC volume is approximately equal to the product of 65 and the SVC volume divided by 35. If the flow rate of the SVC is 350 ml/min, then the IVC flow rate may be assumed to be 650 ml/min. IVC blood temperature can be assumed to be the same as the body temperature, e.g., measured by an additional rectal, bladder, and/or esophageal probe. Heart temperature may be inferred by a combination of the assumed volume and temperature returned via the combination of the SVC and IVC. Generally, if the SVC return flow is above a safe threshold temperature for the heart, the heart can be assumed to be at or above this temperature, as the IVC flow will typically only warm the heart additionally, not cool it.

In some embodiments, other sensors 929 may include other temperature sensors to, for example, measure temperatures for safety and redundancy. In some embodiments, body temperature may be measured by a rectal temperature probe, bladder temperature probe, and/or esophageal temperature probe. Body temperature may be important for some calculations to heart temperatures. In some embodiments, tubing temperatures (e.g., thermistors in catheter lumens or in the tubing of the heat exchange circuit) may be used to verify for controller 910 that the desired temperature is being delivered to the body for cooling or warming. In some embodiments, other sensors 929 may measure flow rate in tubing and/or lumens, e.g., flow rate through a suction lumen 216. Pressure sensor 926 and/or other sensors 929 may include, e.g., an open pressure lumen 217 connected to a standard patient monitor.

Figure 18B:
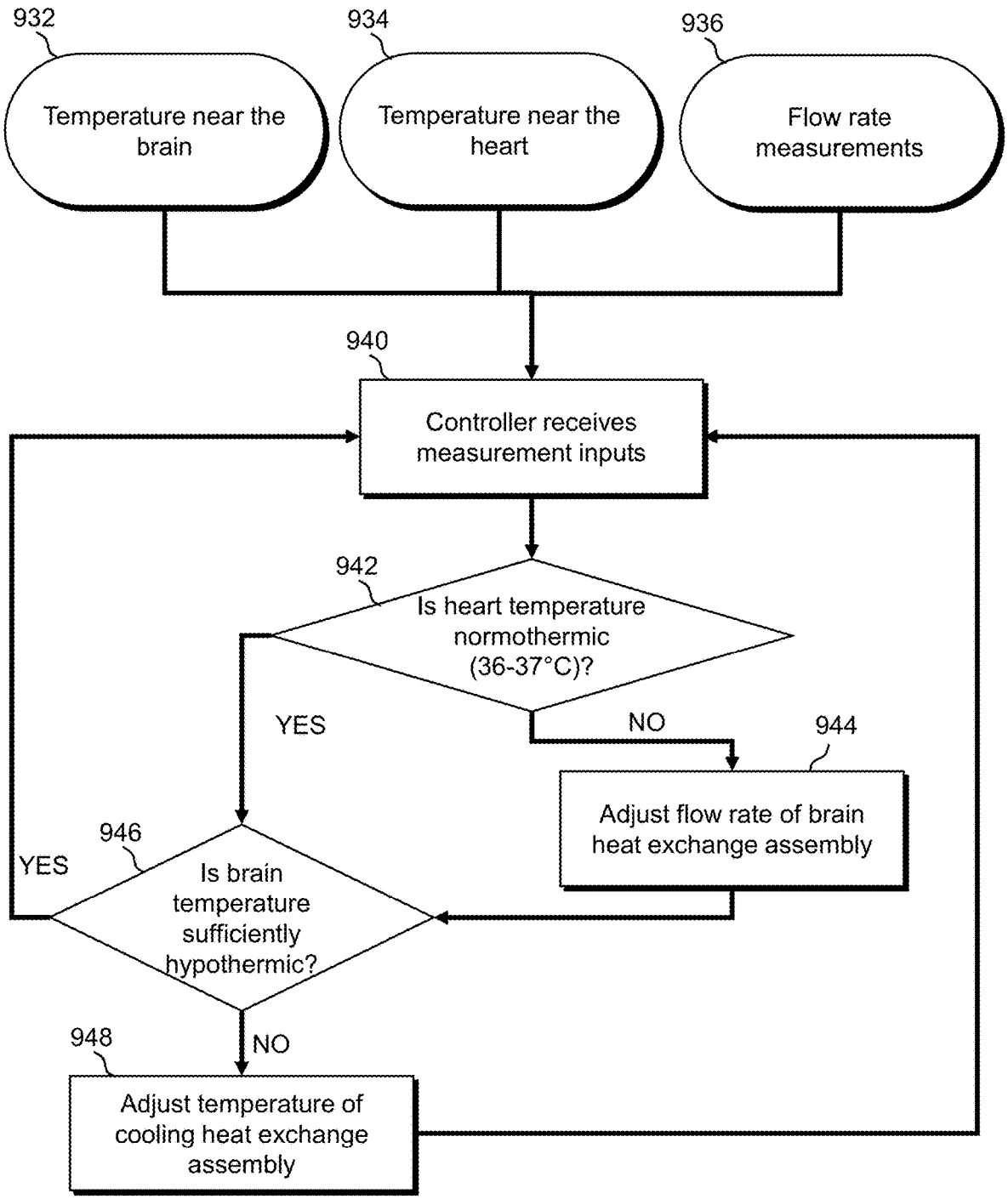
FIG. 18B depicts an illustrative flow diagram of a process for adjusting a therapeutic system using a controller and incorporating at least one heat exchange assembly, in accordance with some embodiments of the disclosure.

FIG. 18B depicts an illustrative flow diagram of a process for adjusting a therapeutic system using a controller and incorporating at least one heat exchange assembly, in accordance with some embodiments of the disclosure. In this case, a heat exchange assembly is controlled to cool fluid flowing to the brain while maintaining a safe heart temperature. Process 930 includes steps for analyzing sensor data to determine how to adjust flow rate and temperature of the heat exchange assembly. Some embodiments may utilize a control engine stored and executed by one or more of the processors and memory of a controller such as controller 910 or other device carrying out the steps of process 930 depicted in the flowchart of FIG. 18B. Some embodiments may use process 930 to initially set the temperatures and flow rates of a brain-cooling therapeutic system. Some embodiments may use process 930 to maintain and adjust the temperatures and flow rates of a brain-cooling therapeutic system.

At step 932, temperature is measured near the brain. For instance, brain temperature may be measured by brain temperature sensor 922 of FIG. 18A, which may include one or more thermistors placed in the patient's body. For instance, brain temperature may be estimated and/or measured by proxy, e.g., using nasopharyngeal and/or tympanic membrane temperature probes.

At step 934, temperature is measured near the heart. Heart temperature may be measured/calculated in several ways. For instance, heart temperature sensor 924 of FIG. 18A may be used. Heart temperature sensor 924 may include one or more thermistors, such as a thermistor in or on a catheter that is inserted into the patient so that the thermistor is on or near the distal tip 205 to allow for the distal end 204 to be in or near the cavoatrial junction and/or the right atrium of the heart. In some embodiments, heart temperature may be inferred based on temperatures and volumes measured for the superior vena cava (or the SVC and IVC combined), as discussed above.

At step 936, flow rates are measured. In some embodiments, flow rates may be set and/or measured by pumps that are part of a heat exchange assembly used to, e.g., cool the fluid flowing to the brain or warm the fluid flowing to the heart. In some embodiments, separate sensors may be used to determine flow rates in various veins or arteries.

At step 940, the controller receives measurements for brain temperature, heart temperatures and flow rates. In some embodiments, a controller, such as controller 910 of FIG. 18A, may receive sensor measurements via I/O path 916 and/or network interface 920.

At step 942, the controller determines if the heart temperature is normothermic. In some embodiments, if not measured directly, heart temperature may be calculated by the controller or by another processor prior to transmission to the controller. For safety purposes, it is important that heart temperature is around 36-37° C. In some cases, if heart temperature dips below a certain temperature, e.g., 32° C., such as if the occlusion element of the catheter unintentionally deflates, then all cooling should cease immediately with an emergency shut down.

At step 944, if the controller determines the heart temperature is not normothermic at step 942, then the flow rate of the cooling heat exchange assembly is adjusted by the controller. For instance, the controller may reduce the flow rate of a cooling heat exchange assembly creating a cool flow of fluid to the brain if the heart temperature becomes too low. In some embodiments, flow rate may be adjusted based on a received body temperature and proportionality of the flow rate of cold fluid of a set temperature flowing to the cerebral vasculature. In some embodiments, temperature may be adjusted. In some embodiments, the controller transmits a command to a heat exchange assembly to adjust the flow rate of the pump. For instance, controller 910 of FIG. 18A may transmit an instruction via I/O path 916 and/or network interface 920 to cooling heat exchange assembly 904 to set a flow rate of pump 906 and/or adjust temperature of heat exchanger 908. In some cases, while not very common when only cooling the brain, heart temperature may be too high, and the controller may increase the flow rate of a cooling heat exchange assembly creating a cool flow of fluid to the brain and that eventually drains to the heart.

After step 944, or if the controller determines the heart temperature is normothermic at step 942, the controller determines if the brain temperature is hypothermic, at step 946. As discussed throughout, hypothermic fluid may be delivered to the cerebral vasculature for therapeutic purposes. In some embodiments, brain temperature may be between 0° and 36° C. for cooling therapy. In some embodiments, target brain temperature for therapy may be around 32-33 degrees Celsius. In some embodiments, target temperature for therapy may be around 28 degrees Celsius. In some cases, fluid from the cooling heat exchange assembly may be approximately 6°–10° C. In some cases, a higher temperature fluid, such as 15° C. may be used.

At step 948, if the controller determines the brain temperature is not hypothermic, at step 946, then the temperature of the cooling heat exchange assembly may be adjusted by the controller. For instance, the controller may reduce the temperature setting of a cooling heat exchange assembly to create a cooler flow of fluid to the brain if the brain temperature is not low enough. In some cases, the controller may determine the brain temperature is not sufficiently cool enough for therapeutic purposes. For instance, a controller may set a heat exchange assembly to, e.g., 0°–2° C., and the fluid may ultimately reach the patient at approximately 6°–10° C. In some cases, a higher temperature, such as 15° C. may be warranted.

In some embodiments, at step 948, temperature may be adjusted based on a received body temperature and proportionality of the flow rate of cold fluid of a set temperature flowing to the cerebral vasculature. In some embodiments, the controller transmits a command to a heat exchange assembly to adjust the temperature of the heat exchanger. In some embodiments, flow rate may be adjusted. For instance, controller 910 of FIG. 18A may transmit an instruction via I/O path 916 and/or network interface 920 to cooling heat exchange assembly 904 to adjust temperature of heat exchanger 908 and/or set a flow rate of pump 906.

After step 946, or if the controller determines the brain temperature is (sufficiently) hypothermic at step 942, the controller receives new measurement inputs from the various sensors. Importantly, if the cooling heat exchange assembly used to create a cooling flow of fluid to the brain is adjusted, heart temperature should be reexamined. Of course, based on the newly received heart and brain temperatures, the controller can adjust the heat exchange assemblies again to maintain safe therapy.

Figure 18C:
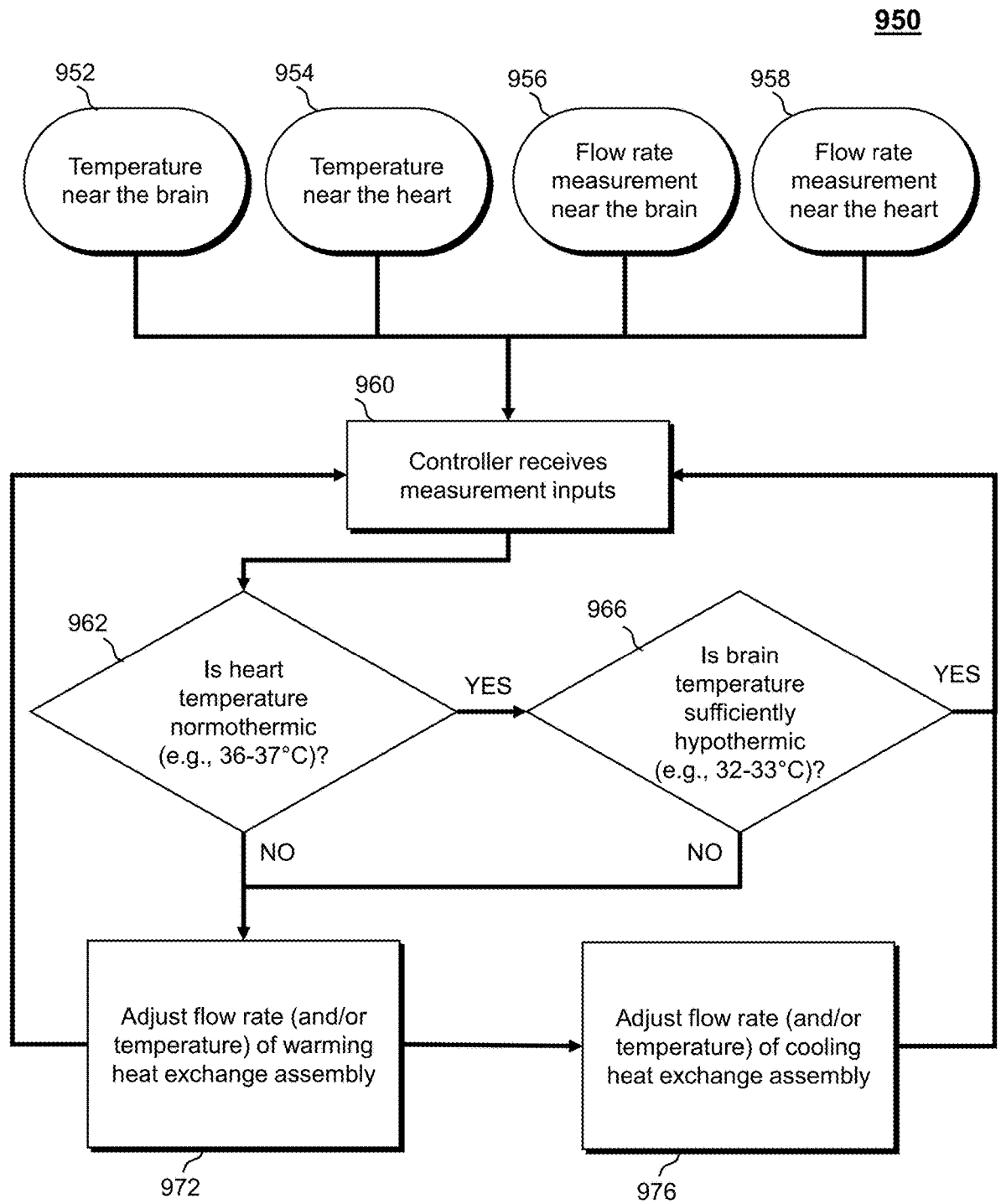
FIG. 18C depicts an illustrative flow diagram of a process for adjusting a therapeutic system using a controller and incorporating two heat exchange assemblies, in accordance with some embodiments of the disclosure.

FIG. 18C depicts an illustrative flow diagram of a process for adjusting a therapeutic system using a controller and incorporating two heat exchange assemblies, in accordance with some embodiments of the disclosure. In this case, a first heat exchange assembly is controlled to cool fluid flowing to the brain and a second heat exchange assembly is controlled to warm fluid flowing to the heart. Process 950 includes steps for analyzing sensor data to determine how to adjust flow rate and temperature of each heat exchange assembly. Some embodiments may utilize a control engine stored and executed by one or more of the processors and memory of a controller such as controller 910 or other device carrying out the steps of process 950 depicted in the flowchart of FIG. 18C. Some embodiments may use process 930 to initially set the temperatures and flow rates of a brain-cooling therapeutic system. Some embodiments may use process 930 to maintain and adjust the temperatures and flow rates of a brain-cooling therapeutic system.

At step 952, temperature is measured near the brain. For instance, brain temperature may be measured by brain temperature sensor 922 of FIG. 18A, which may include one or more thermistors placed in the patient's body. For instance, brain temperature may be estimated and/or measured by proxy, e.g., using nasopharyngeal and/or tympanic membrane temperature probes.

At step 954, temperature is measured near the heart. Heart temperature may be measured/calculated in several ways. For instance, heart temperature sensor 924 of FIG. 18A may be used. Heart temperature sensor 924 may include one or more thermistors, such as a thermistor in or on a catheter that is inserted into the patient so that the thermistor is on or near the distal tip 205 to allow for the distal end 204 to be in or near the cavoatrial junction and/or the right atrium of the heart. In some embodiments, heart temperature may be inferred based on temperatures and volumes measured for the SVC and IVC, as discussed above.

At step 956, rate of fluid flowing near the brain is measured. In some embodiments, flow rates may be set and/or measured by pumps that are part of a heat exchange assembly used to, e.g., cool the fluid flowing to the brain. In some embodiments, separate sensors may be used to determine flow rates in various veins or arteries.

At step 958, rate of fluid flowing near the heart is measured. In some embodiments, flow rates may be set and/or measured by pumps that are part of a heat exchange assembly used to, e.g., warm the fluid flowing to the heart. In some embodiments, separate sensors may be used to determine flow rates in various veins or arteries.

At step 960, the controller receives measurements for brain temperature, heart temperatures and flow rates. In some embodiments, a controller, such as controller 910 of FIG. 18A, may receive sensor measurements via I/O path 916 and/or network interface 920.

At step 962, the controller determines if the heart temperature is normothermic. In some embodiments, if not measured directly, heart temperature may be calculated by the controller or by another device prior to transmission to the controller. For safety purposes, it is important that heart temperature remains around 36-37° C. In some cases, if heart temperature dips below a certain temperature, e.g., 32° C., such as if the occlusion element of the catheter unintentionally deflates, then all cooling should cease immediately with an emergency shut down. If the controller determines the heart temperature is normothermic at step 962, then the controller determines if the brain temperature is hypothermic, at step 966. If the controller determines the heart temperature is not normothermic at step 962, then the controller decides to adjust with steps 972 and/or 976.

At step 966, the controller determines if the brain temperature is hypothermic, at step 966. As discussed throughout, hypothermic fluid may be delivered to the cerebral vasculature for therapeutic purposes. In some embodiments, brain temperature may be between 0° and 36° C. for cooling therapy. In some embodiments, target brain temperature for therapy may be around 32-33 degrees Celsius. In some embodiments, target temperature for therapy may be around 28 degrees Celsius. If the controller determines the brain temperature is sufficiently hypothermic at step 966, then the controller receives new measurement inputs and the cycle repeats. If the controller determines the brain temperature is sufficiently hypothermic at step 966, then the controller decides to adjust with steps 972 and/or 976.

At step 972, if the controller determines the heart temperature is not normothermic at step 942, then the flow rate of the warming heat exchange assembly may be adjusted by the controller. For instance, the controller may increase the flow rate of a warming heat exchange assembly creating a warming flow of fluid to the heart if the heart temperature becomes too low. In some embodiments, flow rate may be adjusted based on a received body temperature and proportionality of the flow rate of cold fluid of a set temperature flowing to the cerebral vasculature. In some embodiments, temperature may be adjusted. In some embodiments, the controller transmits a command to a heat exchange assembly to adjust the flow rate of the pump. For instance, controller 910 of FIG. 18A may transmit an instruction via I/O path 916 and/or network interface 920 to warming heat exchange assembly 905 to set a flow rate of pump 907. In some cases, heart temperature may be too high, and the controller may decrease the flow rate of a warming heat exchange assembly creating a warm flow of fluid to the heart. From there, the controller may make other adjustments in, e.g., step 972 and/or step 976, or the controller receives new measurement inputs from the various sensors at step 960 and the cycle repeats.

At step 972, if the controller determines that the heart temperature is not normothermic (step 962), then the flow rate and/or temperature of the warming heat exchange assembly may be adjusted by the controller. For instance, the controller may increase the temperature setting of a warming heat exchange assembly to create a warmer flow of fluid to the heart if the heart temperature is not high enough. For instance, a controller may set a heat exchange assembly to, e.g., 40°-42° C. In some embodiments, the controller transmits a command to a heat exchange assembly to adjust the flow rate of the pump. Warming flow rate may be increased, e.g., in increments of 50-75 ml/min until heart temperature increases minimally, e.g., 0.1-0.3° C. For instance, controller 910 of FIG. 18A may transmit an instruction via I/O path 916 and/or network interface 920 to warming heat exchange assembly 905 to set a temperature and/or adjust the flow rate of heat exchanger 909. From there, the controller may make other adjustments in, e.g., step 972 and/or step 976, or the controller receives new measurement inputs from the various sensors at step 960 and the cycle repeats.

At step 976, if the controller determines that the heart temperature is not normothermic (step 962) or that the brain temperature is not sufficiently hypothermic (step 966), then the flow rate of the cooling heat exchange assembly may be adjusted by the controller. In some embodiments, when the heart temperature is not normothermic (step 962), the controller may decrease the flow rate of a cooling heat exchange assembly to create less of a cool flow of fluid to the brain that would eventually drain to the heart.

In some embodiments when the brain temperature is not sufficiently hypothermic (step 966), the controller may increase the flow rate of a cooling heat exchange assembly creating a cool flow of fluid to the brain if the brain temperature is not sufficiently low. Prior to adjusting the flow rate of the cooling heat exchange assembly, warming flow rate may be increased, e.g., in increments of 50-75 ml/min until heart temperature increases minimally, e.g., 0.1-0.3° C. so that the heart temperature will not drop too quickly as cooling heat exchange assembly delivers more cool fluid to the brain. This cycle may be repeated until the brain temperature is on target for therapy, e.g., 32-33° C. or 28° C. in some cases.

In some embodiments, the controller may reduce the flow rate of a cooling heat exchange assembly creating a cool flow of fluid to the brain if the heart temperature becomes too low, (e.g., freezing). In some embodiments, flow rate of the cooling heat exchange assembly may be adjusted based on a received body temperature and proportionality of the flow rate of cold fluid of a set temperature flowing to the cerebral vasculature. Generally, the controller will modulate the flow rate of the warming heat exchange assembly prior and leave the cooling heat exchange assembly flow rate and temperature unchanged unless the heart temperature is not increasing quickly enough.

In some embodiments, temperature may be adjusted for the cooling heat exchange at step 976. In some embodiments, the controller transmits a command to a heat exchange assembly to adjust the flow rate of the pump. For instance, a controller may set a heat exchange assembly to, e.g., 0°-2° C., and the fluid may ultimately reach the patient at approximately 6°-10° C. In some cases, a higher temperature, such as 15° C. may be warranted.

In some embodiments, at step 976, controller 910 of FIG. 18A may transmit an instruction via I/O path 916 and/or network interface 920 to cooling heat exchange assembly 904 to set a flow rate of pump 906 and/or adjust temperature of heat exchanger 908. From there, the controller may make other adjustments in, e.g., step 972, or the controller receives new measurement inputs from the various sensors at step 960 and the cycle repeats.

After step 972 and/or step 976, or if the controller determines the brain temperature is (sufficiently) hypothermic at step 966, the controller receives new measurement inputs from the various sensors at step 960 and the cycle repeats. Importantly, if the cooling heat exchange assembly used to create a cooling flow of fluid to the brain and/or the warming heat exchange assembly is adjusted, heart temperature should be reexamined. Of course, based on the newly received heart and brain temperatures, the controller can adjust the heat exchange assemblies again to maintain safe therapy.

In some embodiments, a control system may be used to control temperatures of fluid flowing to, e.g., brain and body. A control system may consist of one or more proportional-integral-derivative (PID) controllers. One or more PID controllers may control a cooling heat exchange assembly and one or more PID controllers may control a warming heat exchange assembly. PID controllers may control a flow rate in a heat exchange assemblies, pressure, temperature of all or a portion of components in a heat exchange assembly, rotational speed of a pump in a heat exchange assembly, another similar metric, or some combination thereof. Controllers may work independently of one another, each having their own inputs and outputs, or be dependent on one another.

A PID controller controlling a cold heat exchange assembly may receive one or more sensor measurements as an input. One or more sensor inputs may include temperature inputs, pressure inputs, flow rate inputs, or other similar measurements. Temperature inputs may include a temperature of a brain, and may be measured using a nasopharyngeal temperature probe, tympanic temperature probe, intraparenchymal temperature probe in a brain, or some similar metric, as an input metric to be controlled by a PID. Pressure inputs may be measured in a first heat exchange assembly, or within a patient using a device such as a catheter. An output of a PID algorithm may be an electronic signal. An electronic signal may be an analog voltage. This analog voltage may be 0-5 V. This analog voltage may control a motor controller circuit, which in practice may be a circuit that converts AC power into DC power which may be used to power a motor. A motor may be attached to a pump, such as a pump in a first heat exchanger assembly, and an application of an output signal from a PID may control a flow rate of a pump. Increasing a flow rate of a pump in a first heat exchange assembly may cause a decrease in brain temperature, and therefore a decrease in an input value measured by a probe measuring temperature of the brain. A PID controller may increase or sustain levels of cool fluid flow until a temperature of a one or more input measurements has decreased to a previously defined setting. A set temperature may be a temperature known to be protective to brain tissues, such as 32-33° C. or lower. A pump may be limited in its maximum flow rate based on known levels of safe flow, such as 50-300 ml/min.

In some embodiments, a pressure sensor in a first heat exchange circuit may be capable of triggering a slowing or stopping of a flow in a circuit if pressures exceed a set threshold, for instance over 400 mmHg. A pressure sensor in a first heat exchange circuit may be capable of triggering a slowing or stopping of a flow in a circuit if pressures drop below a set threshold, for instance less than −300 mm Hg. A pressure sensor measuring a pressure value in a patient's vasculature, such as a pressure caused by infusion from a catheter in an internal jugular vein, may be capable of triggering a slowing or stopping of a flow in a circuit if a pressure is greater than a value known to be safe, for instance 30 mm Hg. A pressure over a known safe value threshold may trigger a pump to slow or stop completely instantly after exceeding the safe threshold, or it may only cause a slow or stopping of a pump when a safe value is exceeded for an extended period of time, such as 5 or 15 minutes of time where the value exceeds the threshold. A first heat exchange assembly pump may slow or stop when an input temperature, such as a temperature measuring at or near a heart, drops below a known safe value, such as 33° C.

A PID controller controlling a cold heat exchange assembly may receive one or more sensor measurements as an input. One or more sensor inputs may be temperature inputs, pressure inputs, flow rate inputs, or other similar measurements. A temperature inputs may be a temperature of a heart, and may be measured using a temperature probe in a catheter inside of a patient, from fluid suctioned from a patient, or some similar metric, as a input metric to be controlled by a PD. Pressure inputs may be taken either in a second heat exchange assembly. An output of a PID algorithm may be an electronic signal, such as analog voltage of 0-5 V. This analog voltage may control a motor controller circuit, which may be a circuit that converts AC power into DC power which may be used to power a motor. A motor may be attached to a pump, such as a pump in a second heat exchanger assembly, and a application of a output signal from a PID may control a flow rate of a pump. Increasing a flow rate of a pump in a second heat exchange assembly may cause an increase in heart temperature, and therefore an increase in an input value measured by a probe measuring a temperature of a heart. A PID controller may increase or sustain levels of flow until a temperature of one or more input measurements has increased to a setpoint previously defined. A setpoint temperature may be a temperature known to be safe for heart tissues, such as 33-37° C. A pump may be limited in its maximum flow rate based on known levels of safe flow, such as 500-2000 ml/min. A pressure sensor in a second heat exchange circuit may be capable of slowing or stopping a flow in a circuit if pressures exceed a set threshold, for instance over 400 mm Hg. A pressure sensor in a second heat exchange circuit may be capable of slowing or stopping a flow in a circuit if pressures drop below a set threshold, for instance less than −300 mm Hg. A first heat exchange assembly pump may slow or stop when an input temperature, such as a temperature measuring at or near a heart, drops below a known safe value, such as 33° C.

Figure 19:
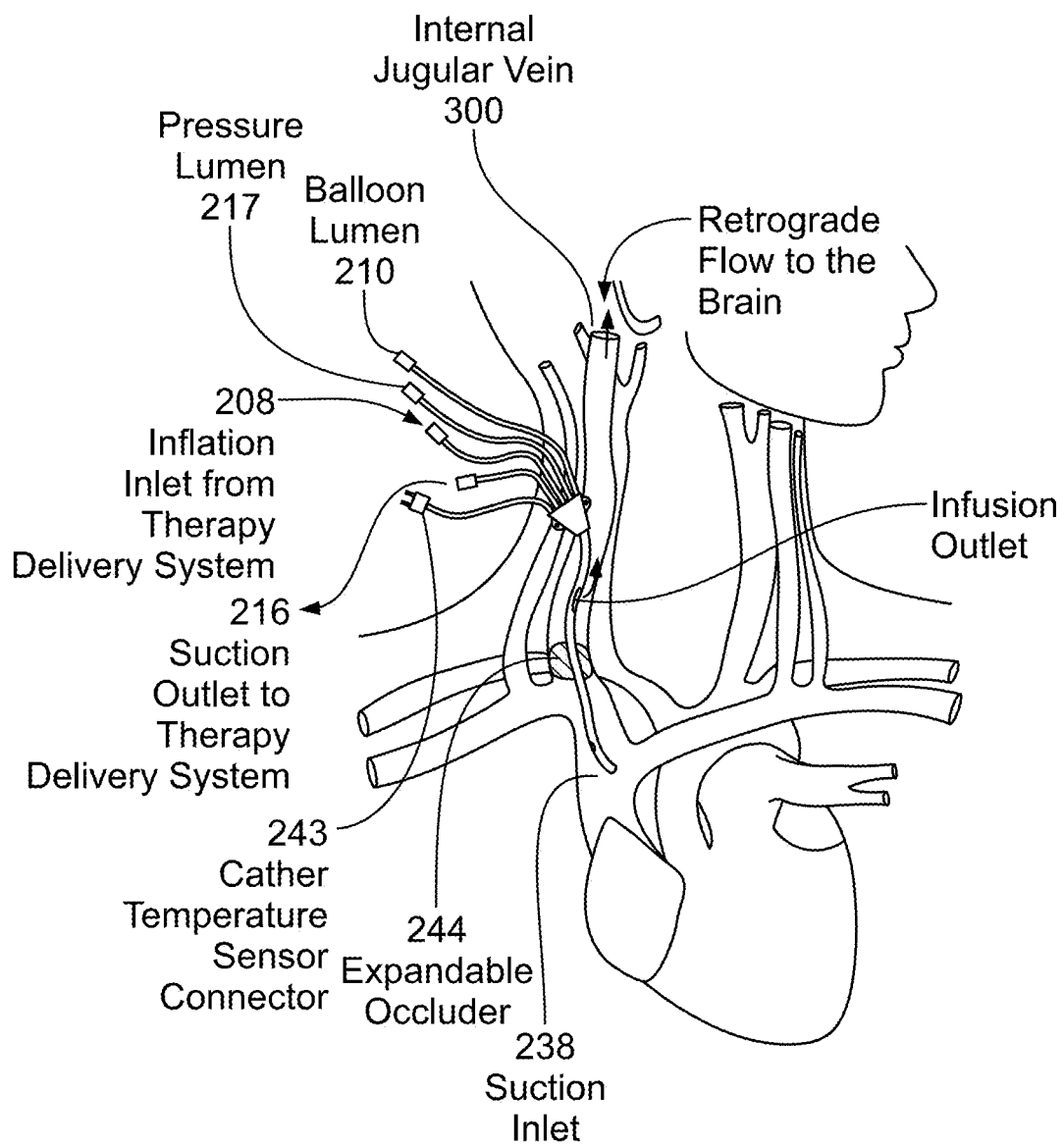
FIG. 19 illustrates a system for selective therapy incorporating a catheter used in a patient, in accordance with some embodiments of the disclosure.

3.0 Methods of Selective Target Organ Therapy 3.1 General Methods of Selective Therapy (See FIGS. 19, 16)

According to some embodiments, the present disclosure provides methods for selective therapy of a selected location of the body, comprising the use of one or more therapy delivery devices and a therapy delivery apparatus. The selected location may be an organ, group of organs, tissue, group of tissue, or similar anatomical target. FIG. 16 illustrates a system using a controller incorporating a catheter used with a patient and FIG. 19 illustrates a system for selective therapy incorporating a catheter used in a patient, in accordance with some embodiments of the disclosure. In some embodiments, the one or more therapy delivery devices may be catheters or cannulas, which may include elongated bodies having one or more lumens, such as infusion lumens for cooled fluid, infusion lumens for warmed or normothermic fluids, infusion lumens for drugs or other medicaments, suction lumen 216, balloon inflation lumens, temperature probe accommodating lumens, pressure sensing lumens and the like, or some combination thereof. The one or more lumens may extend longitudinally between a proximal end 206 and a distal end 204. One such therapy delivery device may be the catheter disclosed herein. The methods of therapy may entail connecting the therapy delivery apparatus to the one or more infusion catheters and using this system to deliver therapy to the selected location. The therapy may be an infusion of fluid, and the fluid may be delivered either in an antegrade direction or in a retrograde direction. The therapy may also involve the extracorporeal treatment of blood, saline, or some similar fluid by a therapy delivery apparatus, such as the therapy delivery system described herein. Typically, the one or more infusion lumens of the one or more infusion catheters may be available for perfusion of all types of therapeutic media, including hypothermic and other preservative media, hyperthermic or normothermic warmed media, blood products, drugs, medicaments, autologous blood and the like.

In practice, the selective therapy may entail the delivery of a therapeutic drug, therapeutic cooling, or delivery of oxygenated blood, or any combination thereof, to a selected location, such as the brain; in a particular scenario, the brain of a patient having a stroke. The therapy may also entail maintaining the temperature of a second selected location, such as the heart, at temperatures considered to not present gratuitous risk to a patient. The one or more therapy delivery devices may be a catheter or cannula described herein and this catheter may be placed in a vessel of a patient, such as a vessel in the central venous system, such as the internal jugular vein. The device may be inserted through the internal jugular vein, and the tip of the device may be located in a vein downstream from the insertion point, such as the distal region of the internal jugular vein, the brachiocephalic vein, the superior vena cava, the right atrium of the heart, or the inferior vena cava. The catheter may be connected to the one or more of the one or more outlets of the therapy delivery apparatus, which may be the therapy delivery system described herein. The configuration of the infusion catheter may allow some or all of the flow produced by the therapy delivery system, such as cooled blood to reach the brain in a selective manner, e.g., through retrograde or antegrade.

The catheter may also allow flow of a second medium, such as warmed blood, to reach the heart. The therapy may include, but is not limited to, lowering the temperature of the brain to therapeutic levels using retrograde infusion of cold deoxygenated blood suctioned from the suction port 238 of the infusion catheter that may have been extracorporeally cooled, retrograde delivery of drugs to the penumbral region of a patient having a stroke, retrograde delivery of oxygenated blood toward the brain of a patient having a stroke, antegrade delivery of saline, blood, or similar warm media towards the heart, or some combination thereof. In some embodiments, the infusion catheter may be placed using Seldinger technique in the internal jugular vein of a patient who may be having or may have had a stroke recently, the expandable occluder may be expanded to occlude the internal jugular vein proximal to the branch of the subclavian vein, blood may be suctioned from the suction lumen 216 of the infusion catheter via one or more ports distal to the expandable occluder; blood may be then circulated extracorporeally, with some portion cooled, some portion warmed, and potentially oxygenated or some combination thereof via the therapy delivery system, and then each portion of blood infused through the infusion port of the catheter, located proximal to the balloon (e.g., expandable occluder), for targeted delivery toward the brain of the patient, and through the distal infusion port of the infusion catheter, distal to the balloon, for delivery to or near the heart. With the internal jugular vein occluded, retrograde flow may be created from the fluid infused through this proximal infusion port such that it travels retrograde up the internal jugular and into the venous sinuses and vasculature of the brain, which may selectively cool the brain below normal body temperature, deliver oxygen, or deliver drugs or other medicaments. The cooling may be selective in the sense that the brain temperature may be decreased more significantly than the decrease in temperature elsewhere in the body, such as temperature measured rectally, in the heart, or in the esophagus. A warming blanket may be used to maintain warmth in the rest of the body. The fluid infused through the distal inlet may be directed to the heart, and this fluid may be warmed to maintain a safe temperature of the heart while the brain is selectively being cooled by the retrograde flow.

Infusion of therapeutic media may be a combination of fluids. In order to reduce viscosity, thereby improving flow rates, allowing for a more minimally sized device, blood may be mixed with normal saline or other crystalloid upon conditioning extracorporeally, before return to the body. As such, cooled saline may be infused, possibly up to 2 L, retrograde toward the brain, delivered either as a bolus or as a mixture with cooled blood via the proximal perfusion ports. Warmed saline may be infused, antegrade toward the heart, delivered as a bolus or as a mixture with warm blood via the distal perfusion ports.

In some embodiments, the system may be instituted before patient transfer, during patient transfer, after patient transfer, or some combination thereof. For instance, the system may be used to deliver therapy, such as therapeutic hypothermia, to a patient who has arrived at a first medical facility who may be intended to be transferred to a second medical facility. The therapy, such as neuroprotective therapy for patients with a stroke, may begin at the first location, and this therapy may reduce the brain damage incurred by this stroke patient during their transit from the first medical facility, such as a rural emergency room, to the second medical facility, such as a comprehensive stroke center. The therapy delivery may be continued on the vehicle used to transport the patient, which may be an ambulance, a car, a helicopter, or the like. Operators at the first center or in the transit vehicle may first place the one or more catheters in a patient's blood vessels, such as placing the catheter described herein in the internal jugular vein, connect the device to an extracorporeal circuit, and then control the circuit to provide therapy. Sensors may be placed on or in the patient, like temperature and pressure sensors, to monitor the patient during therapy. The therapy may be monitored from a console, and the therapy modulated in response to readouts from the sensors. The extracorporeal circuit may be the aspect of the system modulated, by changing the flow rate, heat transfer rate to the blood passing through, oxygenation status, or any combination thereof. Therapy may continue until (or after) the patient has reached the second medical center.

In some instances the device may be placed in the internal jugular vein and extend through the internal jugular vein, through the brachiocephalic vein, through the superior vena cava, with the distal tip 205 of the infusion catheter in or near the right atrium of the heart. In other instances, instead of being located in or near the right atrium of the heart, the proximal tip of the device may extend through the right atrium into the inferior vena cava. In still other instances, the device may not reach the right atrium, and the proximal tip may sit in the superior vena cava. Before beginning therapy, the balloon may be inflated, occluding the internal jugular vein. The ports of the suction lumen 216 may be located at or near the junction of the brachiocephalic veins, or in or near the superior vena cava. This suction port 238 may suction all or some portion of the blood returning to the heart from the upper body, and provide this suctioned blood to the inlet of the therapy delivery system. In this way, the cooled fluid that may be perfused retrograde to the brain before draining down the contralateral internal jugular vein, may be suctioned by the catheter before returning to the heart, thereby minimizing the effect of this potentially slightly cooled blood draining from the contralateral jugular vein. In the therapy delivery system, the suctioned blood may be cooled, warmed, oxygenated, infused with a drug or other medicament, or some combination thereof. A portion of the blood in the therapy delivery system may receive one type of modulation, such as cooling it to reduce temperature and oxygenation, while another portion of the blood in the therapy delivery system may receive a different type of modulation, such as warming of the blood to increase the temperature or no temperature modulation to leave it at or near body temperature. The one or more outlets of the therapy delivery system may connect to one or more inlets of the infusion catheter, and the conditioned blood may be infused back into the body via one or more infusion ports on the infusion catheter. For example, blood that has been conditioned to be warmed or normothermic by the therapy delivery system may be infused through the distal infusion lumen (the counterwarming lumen) of the infusion catheter, and blood that has been cooled, and potentially oxygenated, by the therapy delivery system may be infused through the proximal infusion lumen (the cooling lumen) of the infusion catheter. The proximal infusion port, or proximal outlet, may be located proximal to the balloon in the internal jugular vein, such that the fluid inserted through this lumen is directed retrograde towards the brain. The distal infusion port, or the distal outlet, may be located at or near the tip of the device, either in or near the right atrium of the heart, in or near the inferior vena cava, or in or near the superior vena cava, so that the warmed or normothermic blood flows directly toward the heart.

As such, the system suctions some or all of the blood returning to the heart from the upper half of the body, including the cooled blood which was infused inorder to cool the brain draining back to the heart from the contralateral veins. This suctioned blood may be conditioned in two or more portions; with one portion of this blood cooled and potentially oxygenated for retrograde infusion to continue brain cooling, and another portion of this blood to be returned to the heart at or above normothermia, such that the heart does not experience a drastic or dangerous decline in temperature while the brain is cooled.

In some embodiments, a second expandable occluder, which may be an elastomeric balloon, may be disposed on the body of the catheter such that it may partially or fully occlude the superior vena cava to better isolate the suction region, above this second occlude, from the counterwarming region, below this second occluder. This may be beneficial in the case that the cooled blood draining from the contralateral veins, after traveling through the venous vasculature of the brain after being infused through one internal jugular vein, is colder than desired upon reaching the superior vena cava. A sufficient volume of blood must be infused through the distal infusion ports to account for the reduced natural blood flow reaching the heart through the superior vena cava in this setting in which the second expandable occluder is deployed. Blood may be delivered at flow rates ranging from 1 ml/min to 1500 ml/min.

In some embodiments, blood may be suctioned from the inferior vena cava. In another embodiment, blood may be suctioned from the femoral vein, subclavian vein, cephalic vein, or some other similar vein.

In some embodiments, blood may be delivered to the right atrium. In other embodiments, blood may be delivered to the superior vena cava or the inferior vena cava.

In some instances, the infusion catheter may be positioned at a venous drainage structure, such as the internal jugular vein, of a target organ, such as the brain. When the expandable occluder is expanded, there may be one or more outlets, the proximal infusion port(s) and pressure port, on the target organ side of the expandable occluder. The infusion catheter's one or more suction ports 238 and distal infusion port(s) may both be located on the systemic side of the occlusion, distal to the expanded occluder.

3.1.1 Results of a Study on Selective Retrograde Cerebral Cooling

U.S. Provisional Patent Application No. 62/947,457, filed Dec. 12, 2019 and incorporated herein by reference, detailed a study titled "Selective Retrograde Cerebral Cooling in Complete Cerebral Circulatory Arrest," where selective retrograde cerebral cooling was used in pigs and human cadavers. In order to establish selective retrograde cerebral cooling, the chosen approach consisted of occluding, unilaterally, the internal jugular vein, and administering cold fluid cephalad to the region of occlusion, for targeted brain cooling. The perfusate circulates the venous sinuses before exiting the intracranial space via the contralateral internal jugular vein. The normothermic perfused cadaver study utilized a catheter facilitating this approach and demonstrated that the flow of cooled perfusate through the venous system was not in direct opposition with arterial inflow. Preferential movement of cooled fluids within the lower pressure venous system, was demonstrated, thereby minimizing risk of venous congestion.

In the animal experiencing 15 minutes of complete cerebral circulatory arrest, brain temperature reached 29.3° C. from 37.6° C. following administration of four liters of cooled saline over 20 minutes. Functionally, the animal was eating, drinking, and walking independently at 24 hours post-extubation, with an Neurological Deficit Score (NDS) of 26 indicating normal neurologic status. The functional outcomes at 24 hours for the animal undergoing 30 minutes of complete cerebral circulatory arrest were improved from the 15-minute animal, with an NDS of 10. In this animal, six liters of cooled normal saline were infused, and cerebral cooling from 36.8° C. to 31.9° C. was achieved. The final animal experienced 90 minutes of complete cerebral circulatory arrest, and was cooled to 25.4° C. from 37.4° C. Post-procedure, the animal experienced seizures, with a 24 hour NDS of 290, did not regain consciousness and was euthanized. Rectal temperature did not drop below 31.5° C. in all of the animals. Intravascular cooling through the internal jugular vein of the cadaver resulted in a reduction in cerebral temperature by intraparenchymal probe of 19° C. in 11 minutes, to a depth of 18° C. Cooled simulated blood flowed from the sight of administration in the right internal jugular vein to the contralateral jugular vein, as confirmed on fluoroscopy, via the dural sinus. The dural, transverse, sigmoid, superior sagittal, and petrosal sinuses as well as the facial vein were filled along this flow path.

The study of a normothermic perfused human cadaver demonstrates that retrograde cerebral perfusion for targeted brain cooling via a percutaneously placed intravenous catheter within the internal jugular vein is indeed feasible. Additionally, the notable speed (1.73° C./min in the cadaver versus 0.42° C./min in the 15-minute circulatory arrest porcine model) and depth of cooling (18° C. in the cadaver versus 25.4° C. in the porcine model) exceed those seen in porcine models with similar device flow rates. Though a living model is superior for its incorporation of metabolic heat generation among other factors, the results suggest that cooling through the human vasculature, notably the dural venous sinus system, may confer a more expedient route to deeper levels of hypothermia.

3.1.2 Alternating Pulling and Pushing

In some embodiments, the extracorporeal system may alternate, in response to user input or a sensor measurement of a physiologic parameter, between suctioning blood through the suction lumen 216, delivering warmed blood through the distal infusion ports, and delivering cooled blood through the proximal infusion port. This alternation may allow for more efficient therapy, such that the blood pulled via the device may be used for cooling the brain in one instance, during which no counterwarming is occurring; in a subsequent instance, blood suctioned from the device may be used for counterwarming the heart, during which little or no cooling is occurring. This cycle may occur in rapid succession and would be useful if the volume of blood and flow rate needed for sufficient cooling or counterwarming exceeds what is reasonable to pull at once from the suction ports 238 and use for simultaneous brain cooling and heart counterwarming. Additionally, in some embodiments of the catheter in which there is one lumen that serves as both the suction and counterwarming lumen, this alternation must occur.

In some methods the system may be instituted before, or during patient transfer, or some combination thereof. For instance, the system may be used to deliver therapy, such as therapeutic hypothermia, to a patient who has arrived at a first medical facility who may be intended to be transferred to a second medical facility. The therapy, such as neuroprotective therapy for patients with a stroke, may begin at the first location, and this therapy may reduce the brain damage incurred by this stroke patient during their transit from the first medical facility to the second medical facility. The therapy delivery may be continued on the vehicle used to transport the patient, which may be an ambulance, a car, a helicopter, or the like. Operators at the first center or in the transit vehicle may first place the one or more suction and reinfusion devices in a patient's blood vessels, such as a single suction and reinfusion catheter in the internal jugular vein, connect the device to an extracorporeal circuit, and then turn on the circuit to begin therapy. Sensors may be placed on the patient, like temperature and pressure sensors, to monitor the patient during therapy. The therapy may be monitored from a console, and the therapy modulated in response to readouts from the sensors. The extracorporeal circuit may be the aspect of the system modulated, by changing the flow rate, heat transfer rate to the blood passing through, or the like. Therapy may continue one the patient has reached the second medical center.

3.2 Single Catheter Infusion

In some embodiments, therapeutic fluid may be administered through veins or arteries supplying or draining an organ targeted for selective therapy through an inlet catheter, which may be the infusion catheter described herein. Flow and the characteristics of the flowing fluid in the inlet catheter may be modulated by the therapy delivery system, which may be in fluid communication with the catheter. Temperature sensors may be used in the catheter or on the body of the patient to monitor the temperature produced by the cooling, as described in the therapy delivery system description. Flow may be either retrograde or antegrade through the selected organ. The catheter may include an expandable occluder element to block off a blood vessel if desired. Blocking off the vessel may allow for administration of fluid retrograde in the vessel. The inlet catheter may be used to deliver drugs or other medicaments, crystalloids, colloids, blood products, or other therapeutic media in order to prevent damage to the selected organ. In the case of the selected organ being the brain, retrograde flow created in the internal jugular vein may be used to deliver a neuroprotective drug, or other neuroprotective agent, such as calcium antagonists, cell membrane stabilizers, serotonin-receptor antagonists, xenon, radical scavengers, or the like, to the brain of a patient, such as ischemic stroke patients. The retrograde flow may be advantageous, as it can reach the tissue being blocked from receiving normal blood flow by the clot, and therefore administered fluids may be delivered to therapeutic benefit. It is understood that depending on the target organ or tissue to which administered fluids are delivered via an infusion catheter, the desired flow may be antegrade or retrograde, arterial or venous, and any combination thereof.

3.2.1 Antegrade Approach (See FIGS. 16-21)

Figure 20:
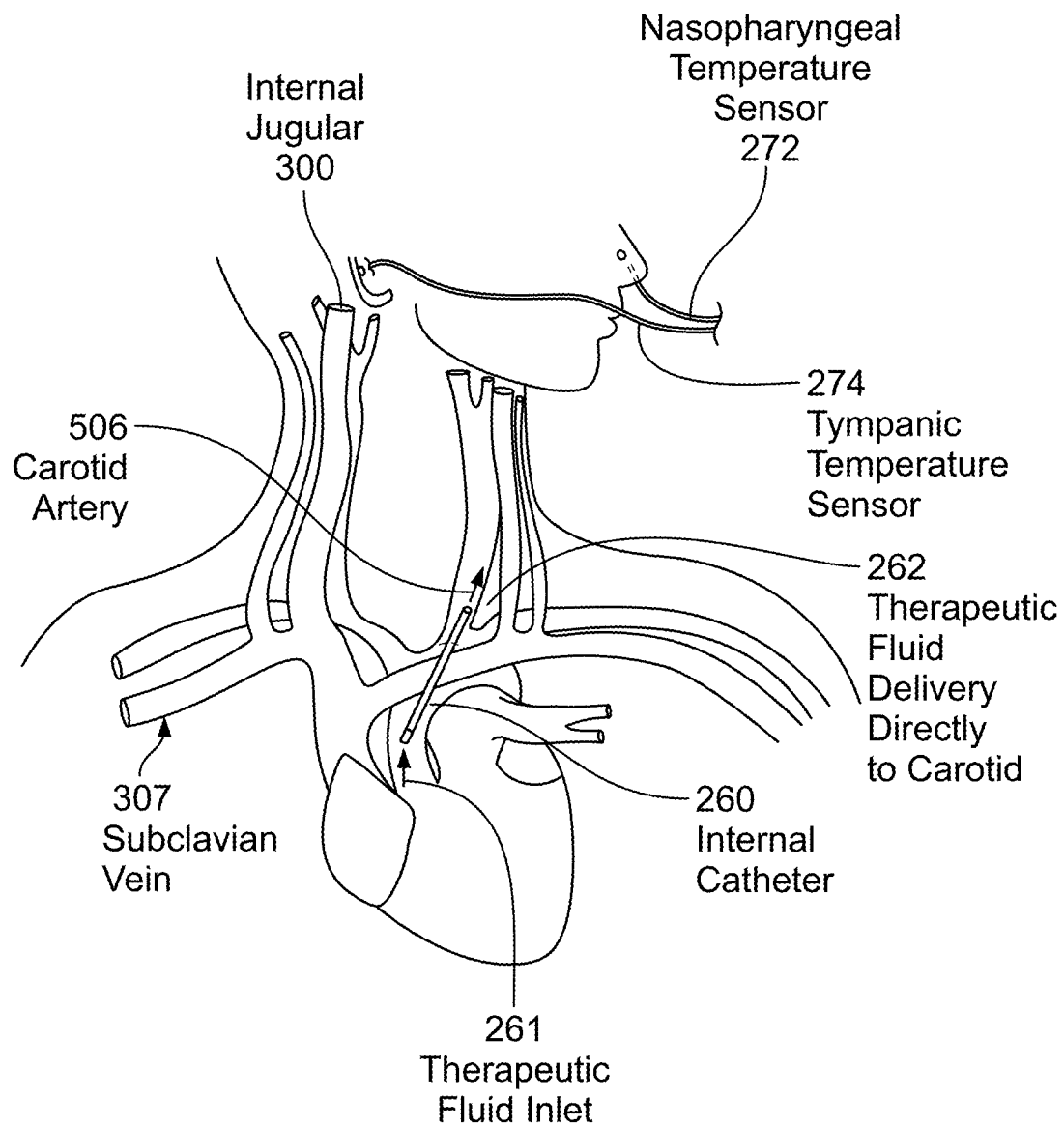
FIG. 20 illustrates a system using antegrade therapy with a catheter through the carotid artery of a patient, in accordance with some embodiments of the disclosure.
Figure 21:
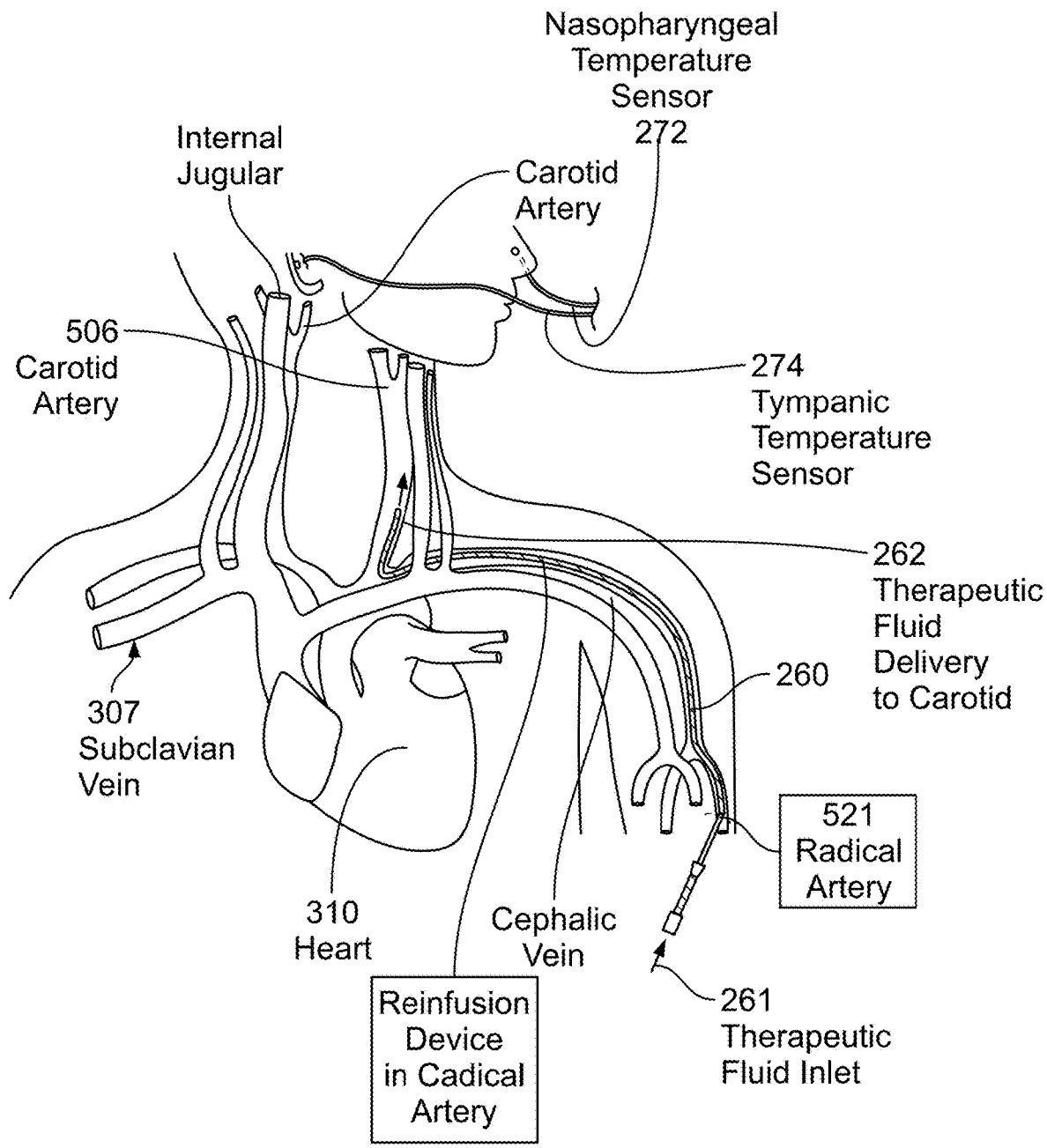
FIG. 21 illustrates a system using antegrade therapy with a catheter through the radial artery of a patient, in accordance with some embodiments of the disclosure.
Figure 22:
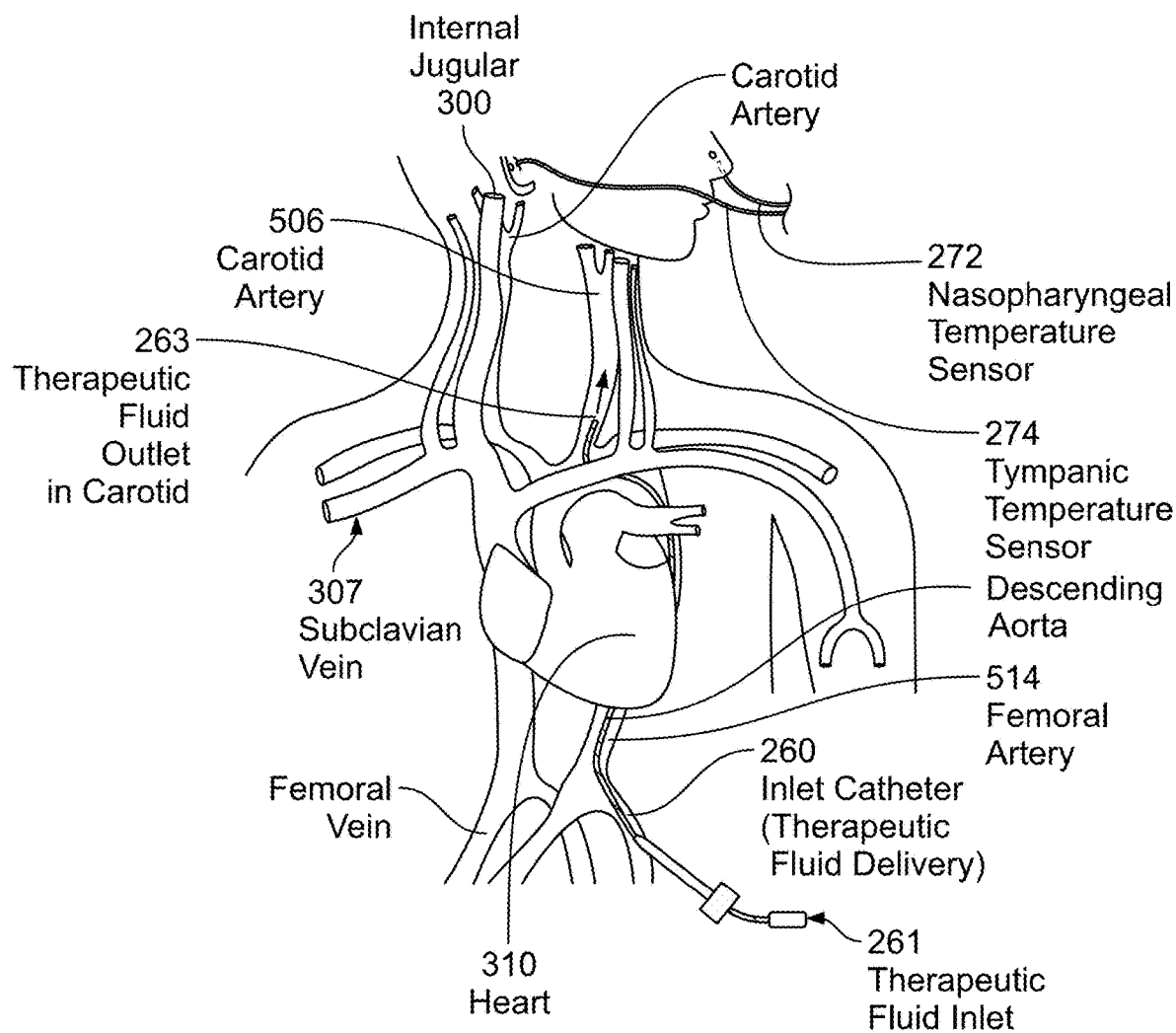
FIG. 22 illustrates a system using antegrade therapy with a catheter through the femoral artery of a patient, in accordance with some embodiments of the disclosure.

In the case of antegrade therapy, the catheter may be placed in the arteries delivering blood to the selected organ. The catheter may be the infusion catheter herein described, or a device containing all or some of the features of the infusion catheter described. The catheter may enter the body through a carotid artery, femoral artery, or through a peripheral artery such as the radial artery in the arm, in which case the catheter may need to be navigated to the desired location using a guidewire and fluoroscopic imaging guidance. FIG. 20 illustrates a system using antegrade therapy with a catheter through the carotid artery of a patient, FIG. 21 illustrates a system using antegrade therapy with a catheter through the radial artery of a patient, and FIG. 22 illustrates a system using antegrade therapy with a catheter through the femoral artery of a patient, in accordance with some embodiments of the disclosure. Therapeutic fluid, such as cooled autologous blood, oxygenated or non-oxygenated, or saline, may be infused through this catheter, flowing antegrade toward the target organ. In the case of cold autologous blood, the patient's own blood may be suctioned from another arterial or venous access site, cooled, oxygenated, and then infused through the infusion catheter.

Figure 23:
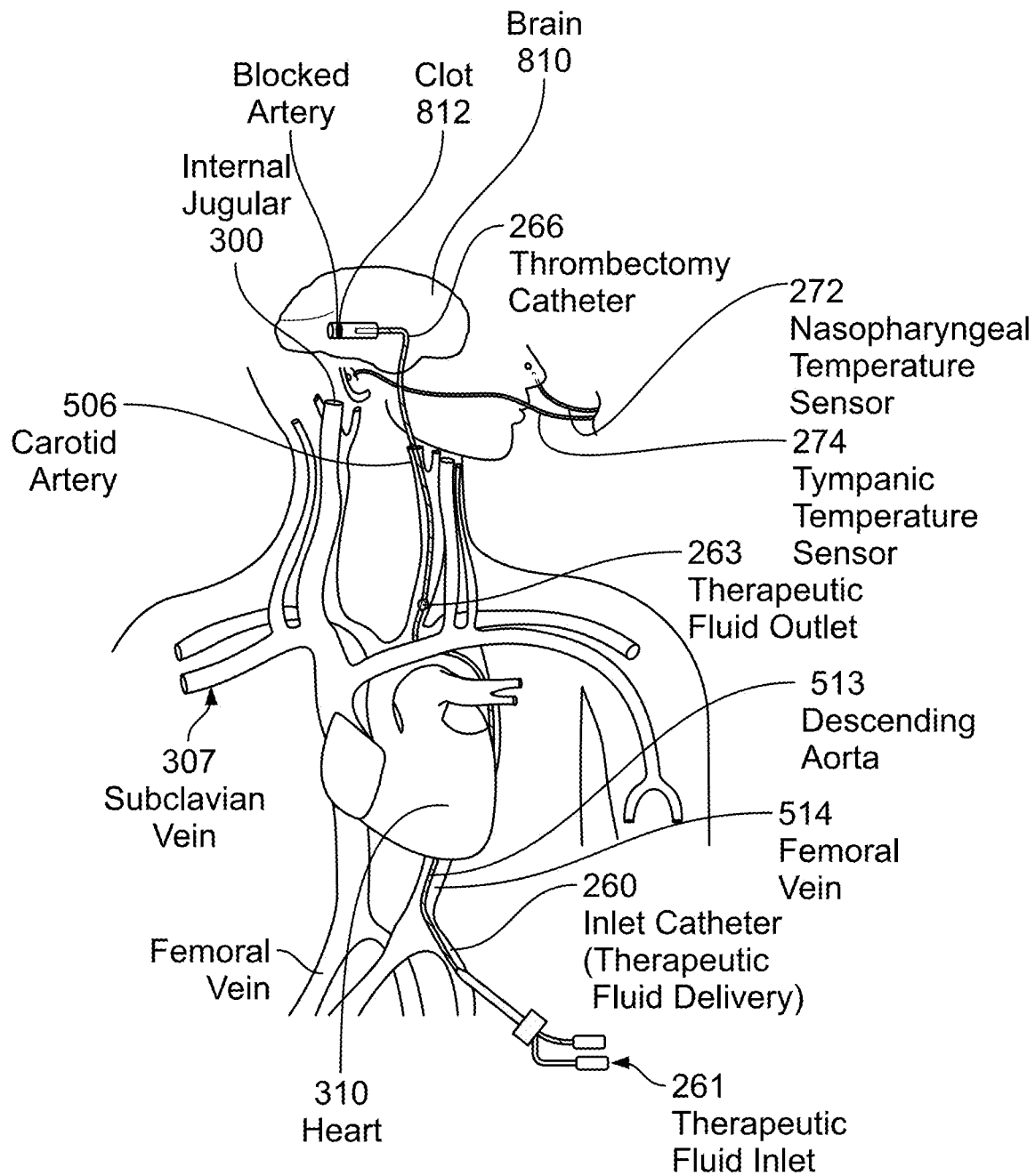
FIG. 23 illustrates a system using antegrade therapy with a catheter through the femoral artery into the carotid artery of a patient with thrombectomy, in accordance with some embodiments of the disclosure.

FIG. 23 illustrates a system using antegrade therapy with a catheter through the femoral artery into the carotid artery of a patient with thrombectomy, in accordance with some embodiments of the disclosure. In some embodiments, the brain may be the organ selected, and the therapy delivered may be hypothermic in nature. In this instance, the catheter may be placed in the carotid artery, which delivers blood to the brain, or in the arteries of the brain itself, especially the artery which may be occluded in the setting of ischemic stroke. Such therapy may be administered as an adjunct treatment to thrombectomy in the setting of ischemic stroke, with delivery of therapeutic fluid occurring initiated prior to, during, or following the thrombectomy, and continuing for a length of time, to maintain a target temperature in the brain for neuroprotection, possibly 25-33° C., for a number of hours.

Figure 24:
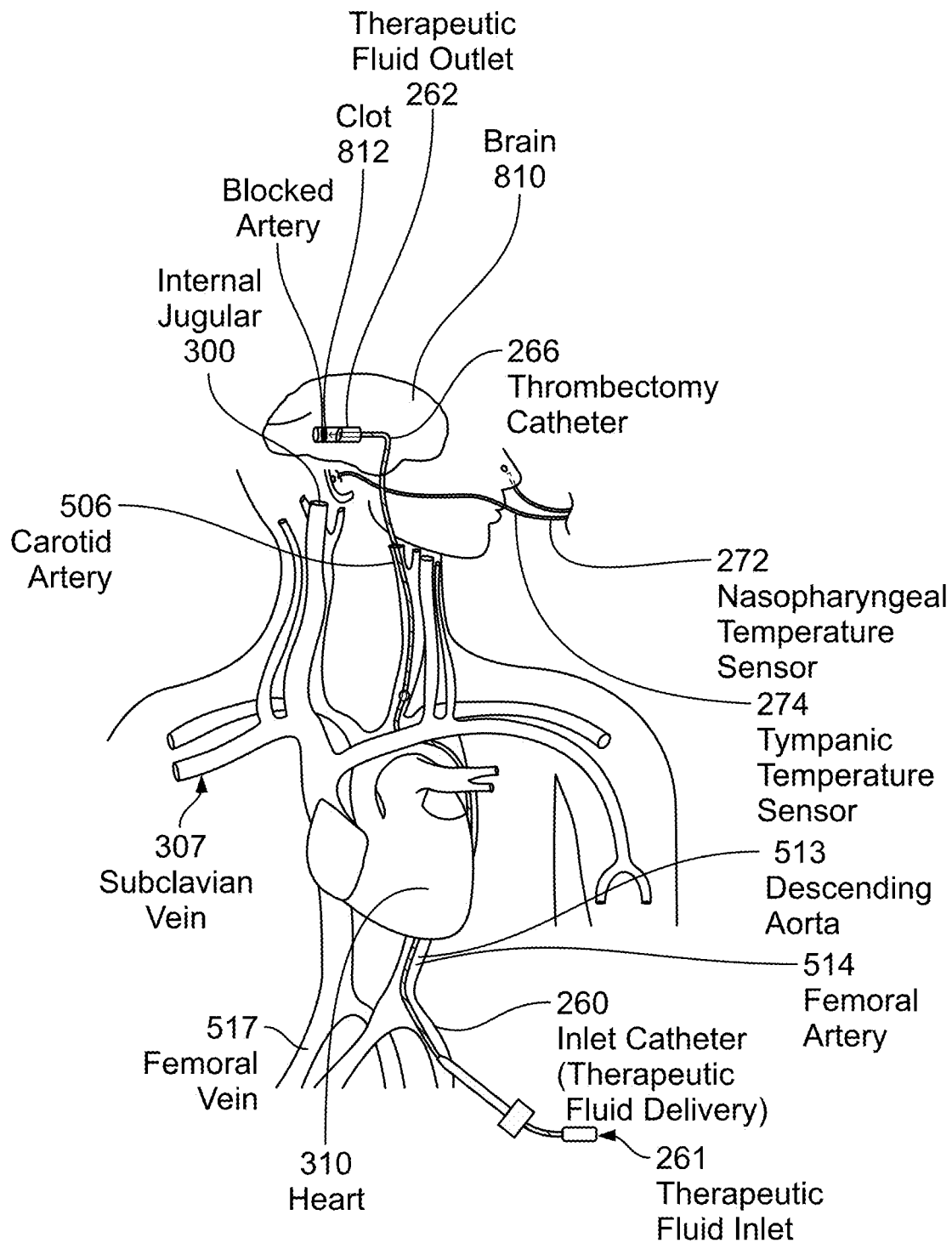
FIG. 24 illustrates a system using antegrade therapy with a catheter through the femoral artery into the brain of a patient with thrombectomy, in accordance with some embodiments of the disclosure.

FIG. 24 illustrates a system using antegrade therapy with a catheter through the femoral artery into the brain of a patient with thrombectomy, in accordance with some embodiments of the disclosure. In a particular setting, of ischemic stroke, the device may be advanced into the large vessel in which the occlusion occurs. The catheter may be placed via the femoral artery in parallel with a device such as a thrombectomy catheter to remove the clot causing the stroke, and infusion of therapeutic fluid may cool the brain prior to, during, or following clot removal.

Figure 25:
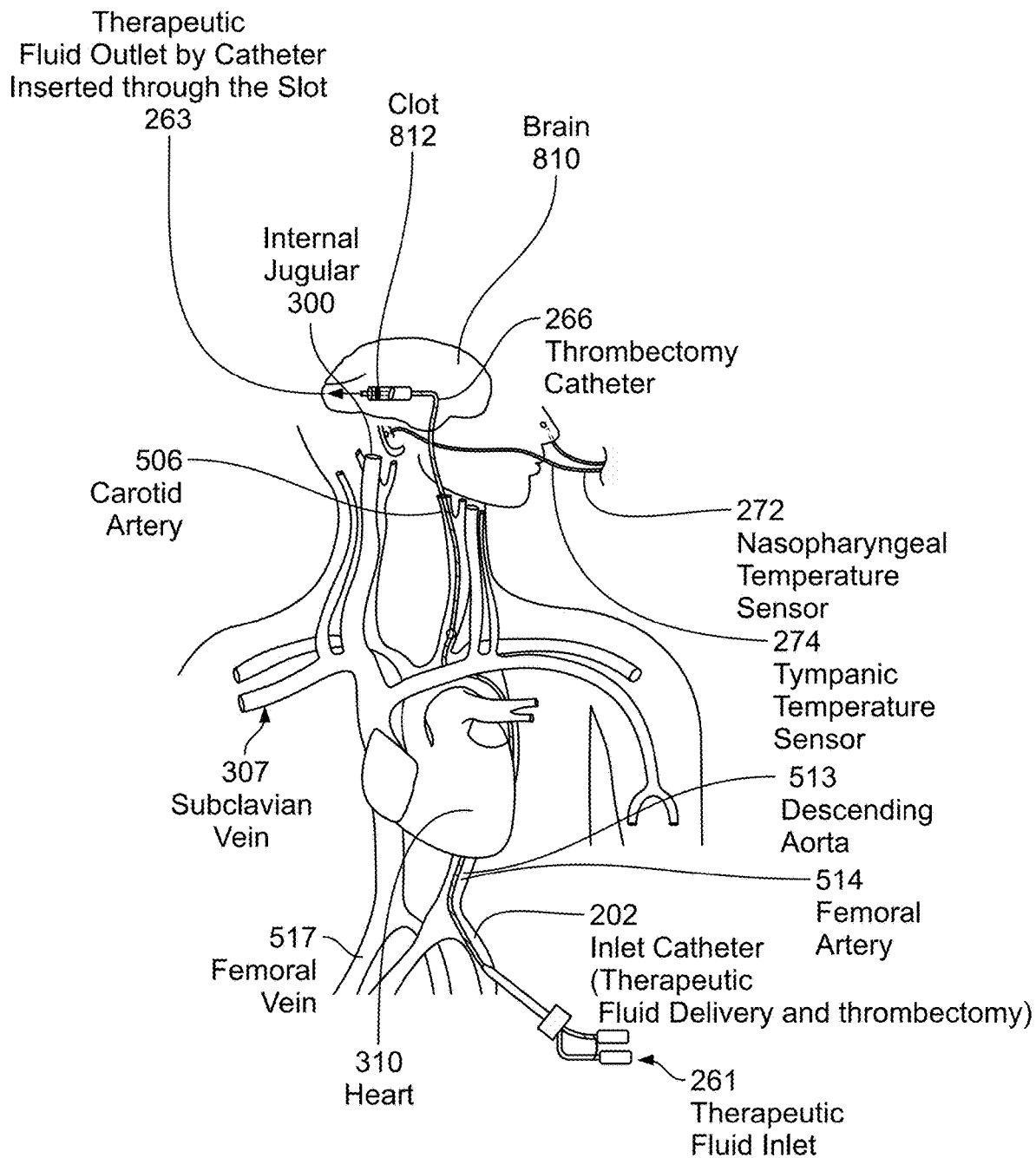
FIG. 25 illustrates a system using antegrade therapy with a catheter through the femoral artery into the brain of a patient past a blockage, in accordance with some embodiments of the disclosure.

FIG. 25 illustrates a system using antegrade therapy with a catheter through the femoral artery into the brain of a patient past a blockage, in accordance with some embodiments of the disclosure. In some instances, a catheter will be advanced past the clot, before the clot may have been removed, so that cooling of the ischemic core and penumbra can be better achieved to potentially save tissue and mitigate the risk of reperfusion injury before recanalization. The infusion of therapeutic fluid, which may include colloid, crystalloid, drugs, or blood product, possibly cooled to therapeutic levels, may occur with the use of a control system. The control system may infuse infusate until certain sensor readings are obtained, such as the temperature of a nasopharyngeal temperature probe, a tympanic membrane temperature probe, or a temperature probe in the catheter indicating that the selected organ has reached a target temperature. The target temperature may be 25-33° C.

3.2.2 Retrograde Approach (See FIGS. 26-30)

In the case of retrograde therapy, the infusion catheter may be placed in the veins draining the selected organ. In one instance, the brain may be the organ selected for therapy.

Figure 26:
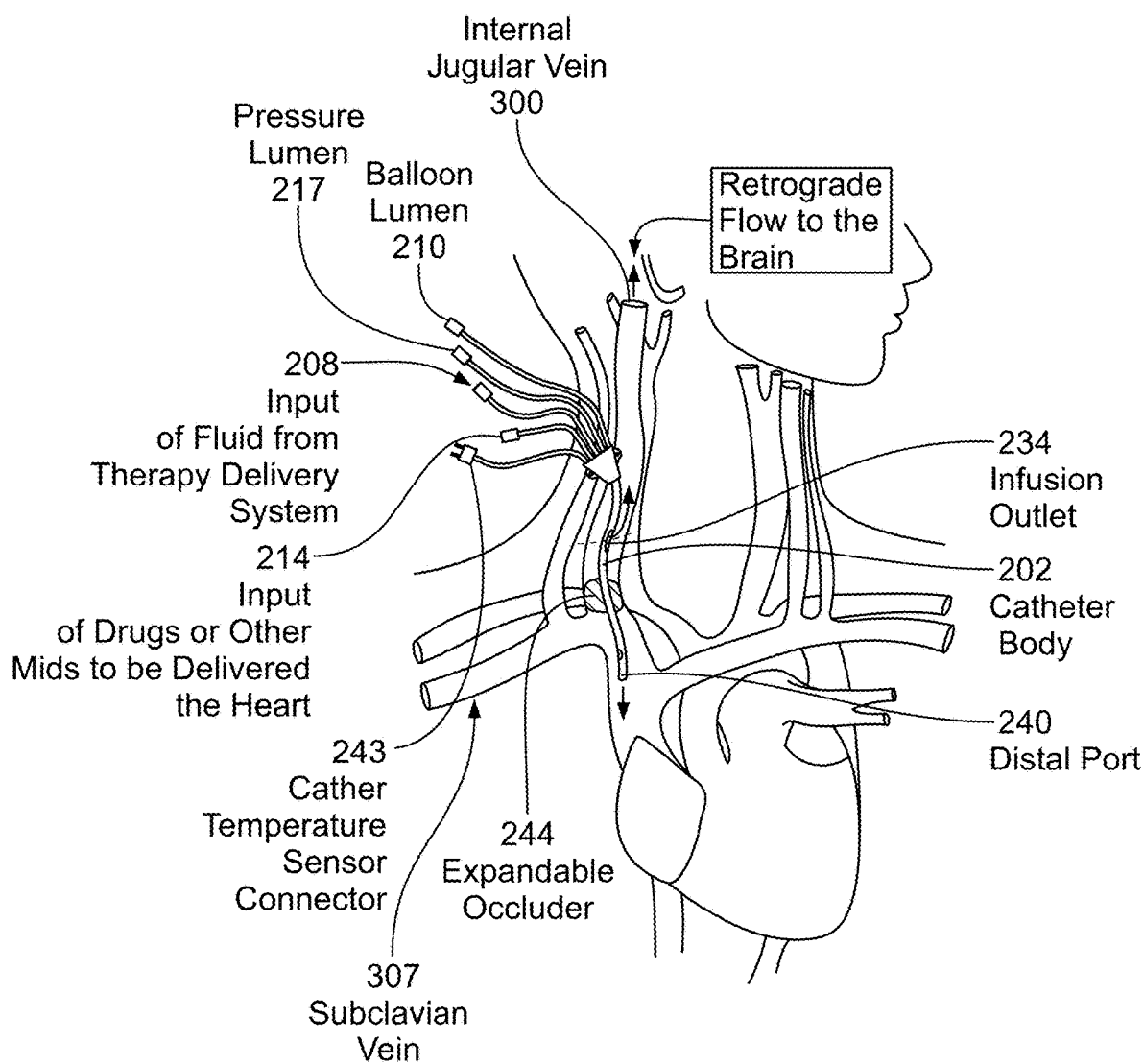
FIG. 26 illustrates a system using retrograde therapy with a catheter via internal jugular vein of a patient, in accordance with some embodiments of the disclosure.
Figure 27:
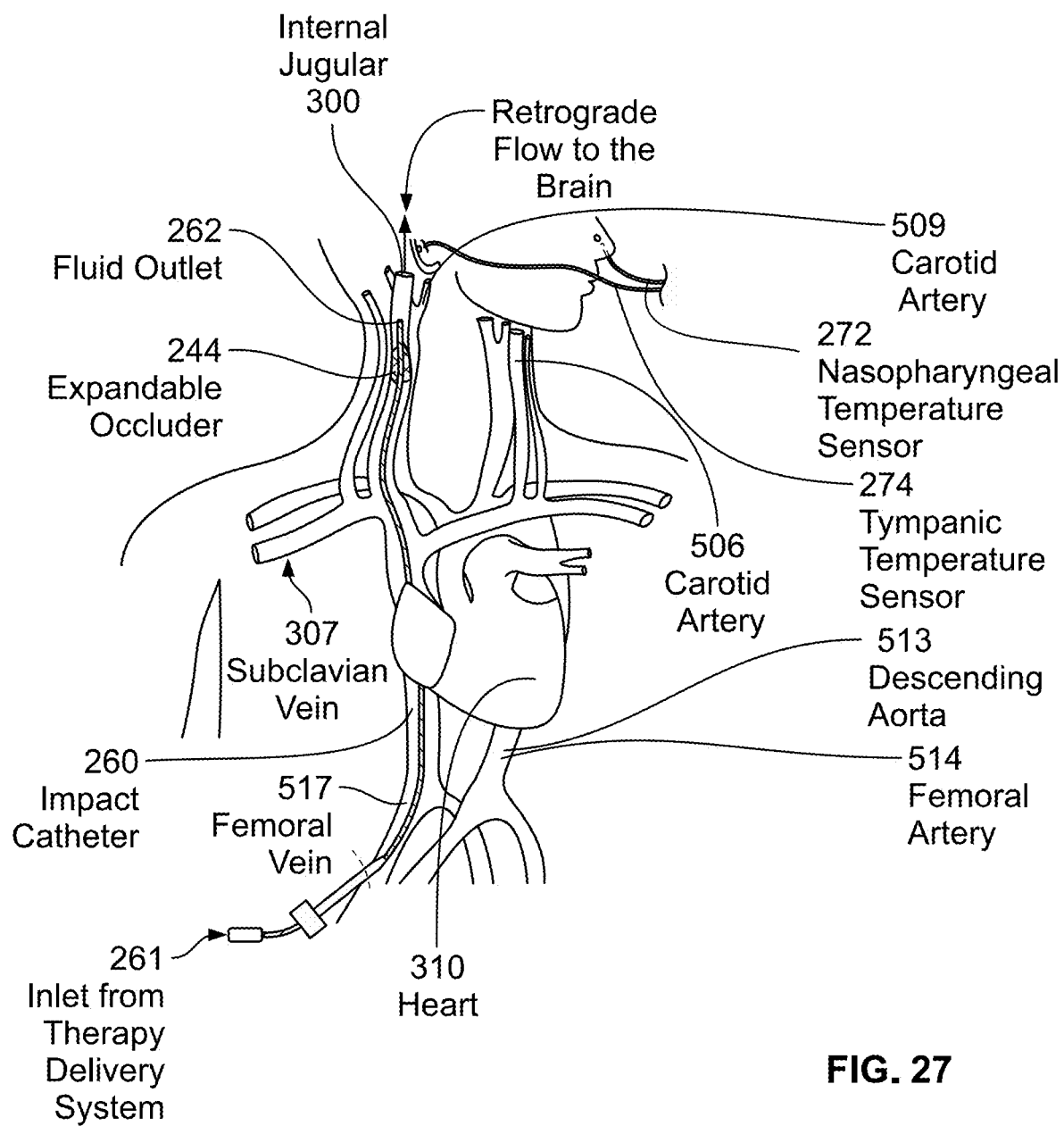
FIG. 27 illustrates a system using retrograde therapy with a catheter via femoral vein of a patient, in accordance with some embodiments of the disclosure.
Figure 28:
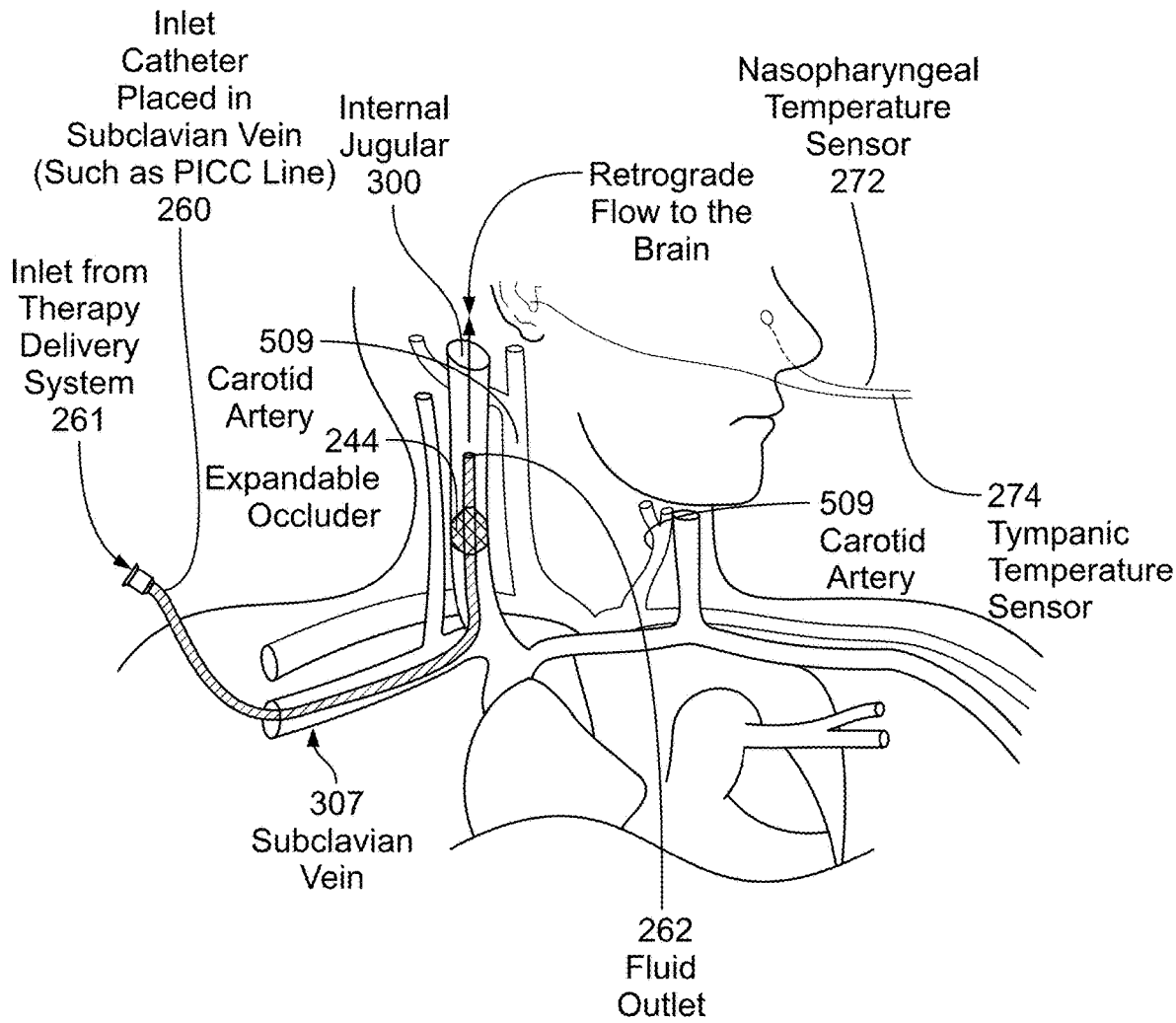
FIG. 28 illustrates a system using retrograde therapy with a catheter via subclavian vein of a patient, in accordance with some embodiments of the disclosure.
Figure 29:
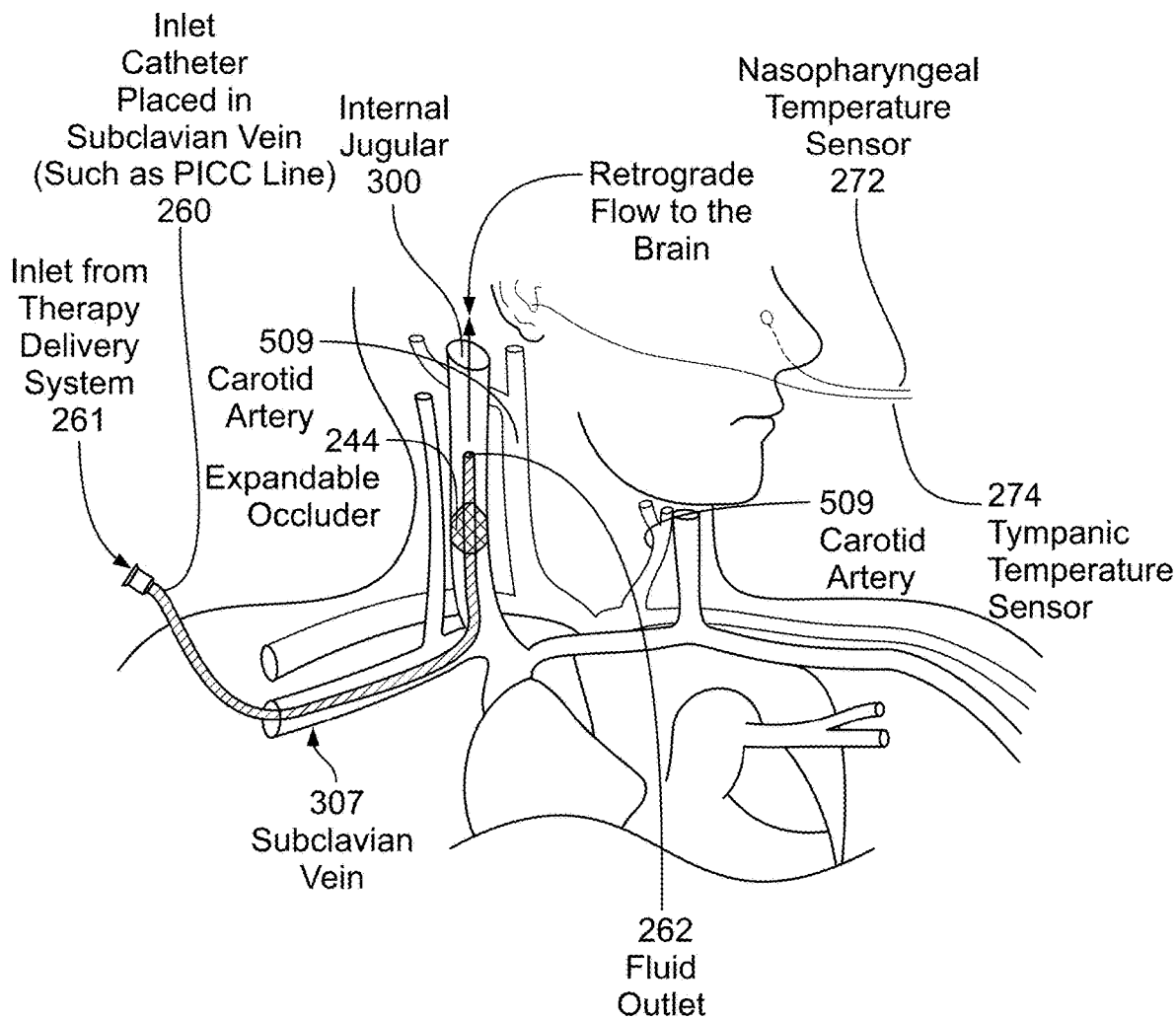
FIG. 29 illustrates a system using retrograde therapy with a catheter via cephalic vein of a patient, in accordance with some embodiments of the disclosure.
Figure 30:
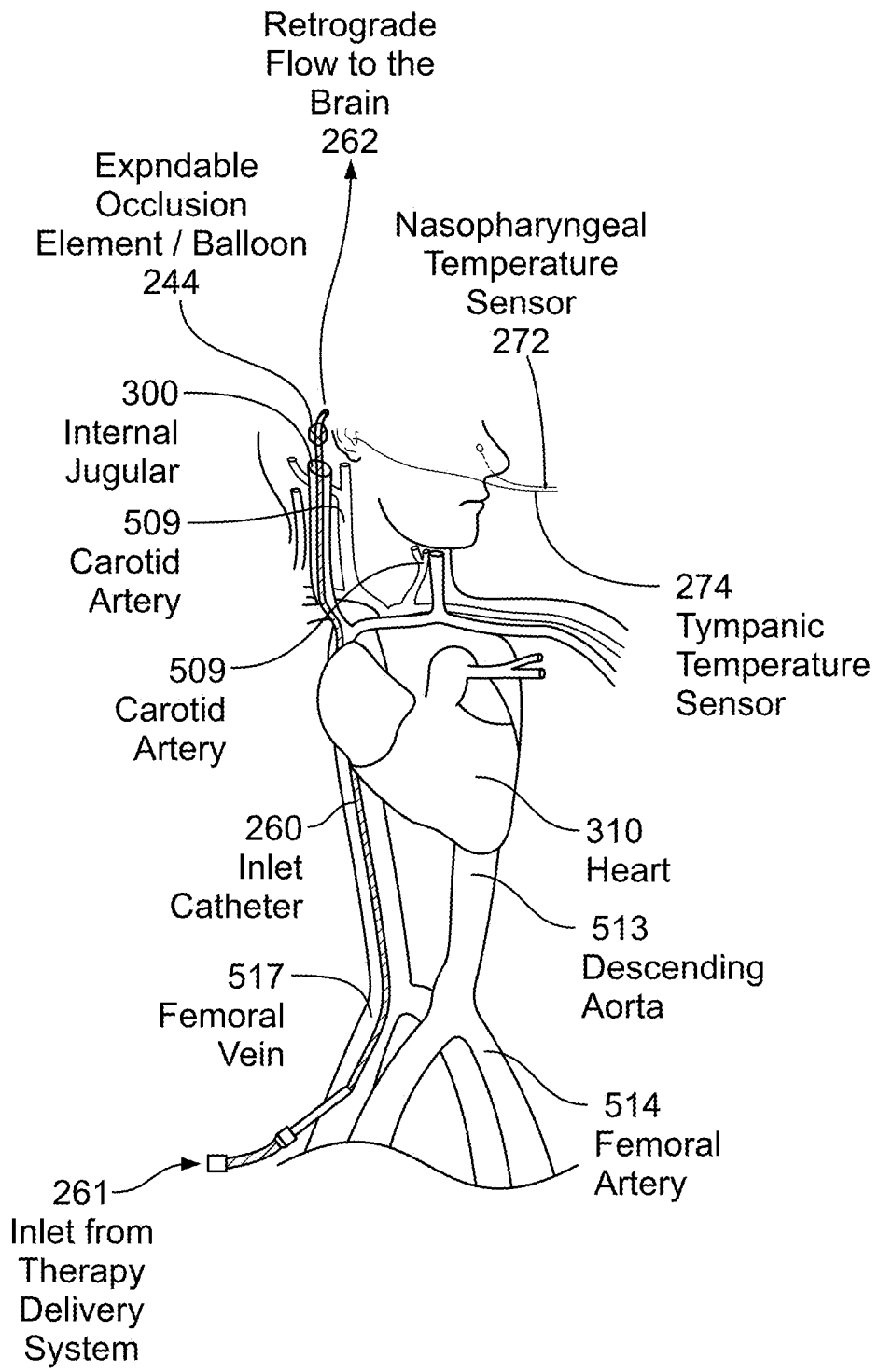
FIG. 30 illustrates a system using retrograde therapy with a catheter through the femoral vein and into the brain of a patient, in accordance with some embodiments of the disclosure.

FIG. 26 illustrates a system using retrograde therapy with a catheter via internal jugular vein of a patient, in accordance with some embodiments of the disclosure. In this instance, an infusion catheter may be placed in one of the internal jugular veins which drain blood from the brain. In other instances, the infusion catheter may be placed in other venous access sites, such as the femoral vein, subclavian vein, or cephalic vein, and may be navigated to a position in the internal jugular vein, or in another vein in which retrograde flow would allow perfusion of the target organ. FIG. 27 illustrates a system using retrograde therapy with a catheter via femoral vein of a patient, FIG. 28 illustrates a system using retrograde therapy with a catheter via subclavian vein of a patient, and FIG. 29 illustrates a system using retrograde therapy with a catheter via cephalic vein of a patient, in accordance with some embodiments of the disclosure. The infusion catheter may be placed in the femoral vein to allow retrograde flow into the brain. FIG. 30 illustrates a system using retrograde therapy with a catheter through the femoral vein and into the brain of a patient, in accordance with some embodiments of the disclosure. The infusion catheter may also be placed in the veins of the brain itself.

An expandable occluder, which may be part of the infusion catheter, may be expanded to occlude the internal jugular vein, or other vein in which the device may be placed and facilitate retrograde flow of delivered fluid. Flow and the characteristics of the flowing fluid in the infusion catheter may be modulated by the therapy delivery system, which may be in fluid communication with the infusion catheter. Therapeutic fluid, such as cooled autologous blood, oxygenated or non-oxygenated, or saline, may be infused through this catheter. In the case of cold autologous blood, the patient's own blood may be suctioned from another arterial or venous access site, cooled, oxygenated, or cooled and oxygenated, and then infused through the infusion catheter, described in more detail elsewhere in this document. Although the rest of the body may be cooled by this infusion, the majority of cooling may take place in the brain as the fluid will pass through this region before returning to the rest of the body. The flow path of fluid infused through the port cephalad to the expandable occluder of the infusion catheter may be retrograde through the internal jugular vein in which the device may be placed, through the venous sinuses and veins of the brain, flowing down the contralateral jugular veins.

In this instance, the arterial pressure in the arteries and capillaries of the brain may prevent the flow of blood retrograde from veins to arteries, and therefore the flow may remain in the venous system. The veins of the brain may act as a heat exchanger to achieve rapid, deep, neural cooling. Oxygenated blood, normothermic or otherwise, may be delivered to the brain retrograde to supply oxygen to tissues cut off from some amount of oxygenated blood from their supply arteries. It is worth noting that the veins of the brain have more collatoralization than the arteries of the brain, so retrograde flow may be more potent than therapy delivered antegrade. When placed in the internal jugular vein, the device may have lumens to allow it to deliver medicaments to the heart, similar to other central venous catheters placed in the central venous system. The method of insertion may be Seldinger technique. Insertion of this therapy device using a simple technique known to all doctors may enable the device to be placed and the brain to be cooled in hospitals with limited staff and resources, such as rural hospitals. In some instances, instead of autologous blood or saline, drugs or other neuroprotective agents may be delivered in this retrograde method to tissue receiving reduced amounts of oxygen in order to slow the rate of cellular damage, such as in acute ischemic stroke patients.

Counter warming measures, which serve to keep the body warm while the brain may be receiving cooling, may be implemented. These counter warming methods may include using warming blankets, heating pads, forced air heating blankets, or similar warming devices. These counter warming methods may serve to keep the body, especially the heart, close to normothermic, while the brain may be undergoing selective cooling. As described in association with the therapy delivery system, temperature sensors may be used to monitor and modulate the cooling from the infusion.

3.2.3 Retrograde Approach with Saline Infusion (See FIGS. 27-34)

Figure 31:
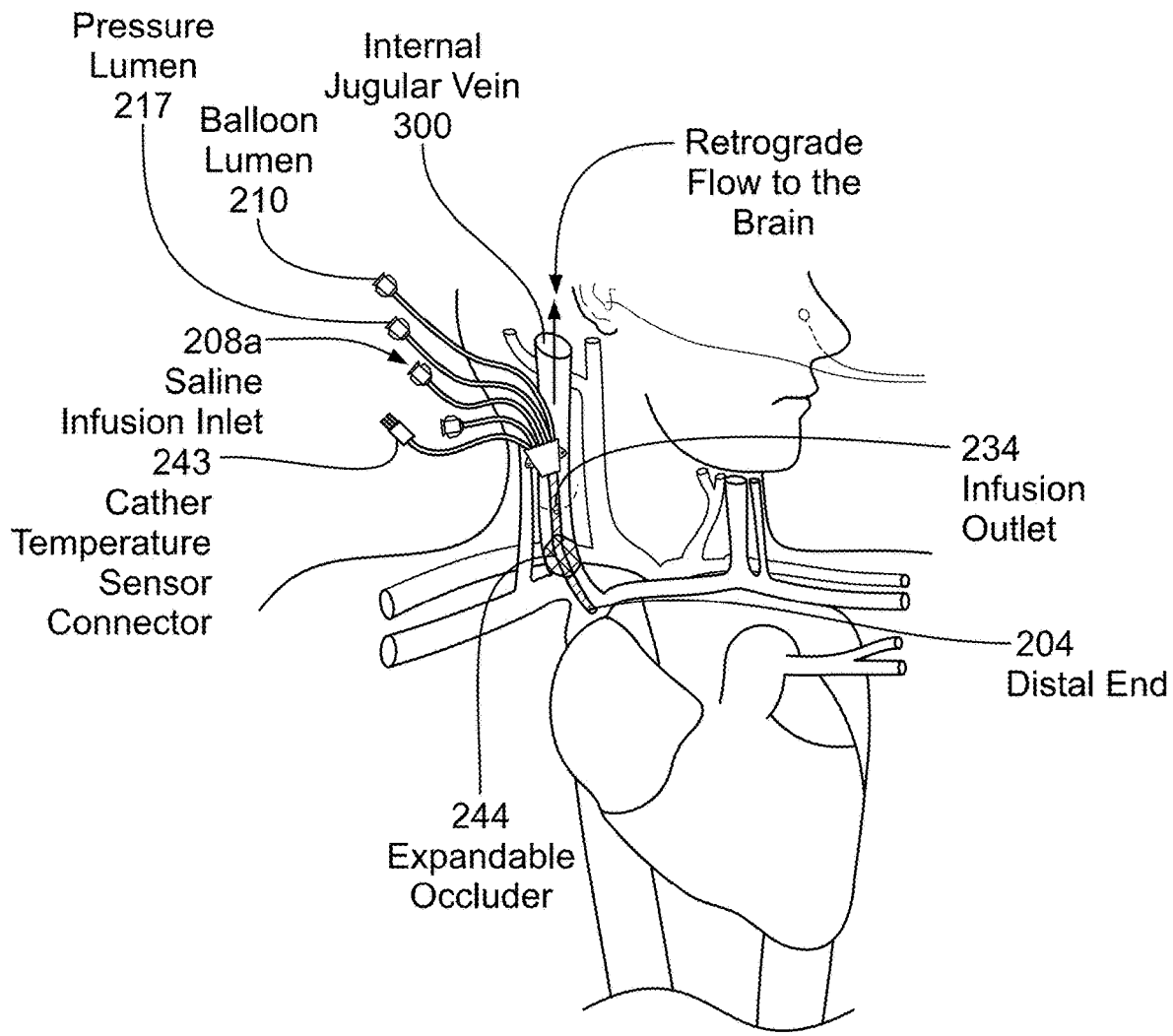
FIG. 31 illustrates a system using retrograde therapy using a saline infusion with a catheter via internal jugular vein of a patient, in accordance with some embodiments of the disclosure.

FIG. 31 illustrates a system using retrograde therapy using a saline infusion with a catheter via internal jugular vein of a patient, in accordance with some embodiments of the disclosure. In some instances, cooled saline, or other crystalloid fluid, may be used to cool all or a part of the body tissue. The patient may be monitored for hemodilution, so that their blood may not be diluted to dangerous levels during infusion of saline. In one instance, the saline may be infused retrograde through a device in the internal jugular vein. In this instance, an expandable occluder may be used to redirect the flow of the saline retrograde. The saline may be infused at a temperature greater than 0° C. and less than 37° C. and may allow for selective cooling of the brain.

Figure 32:
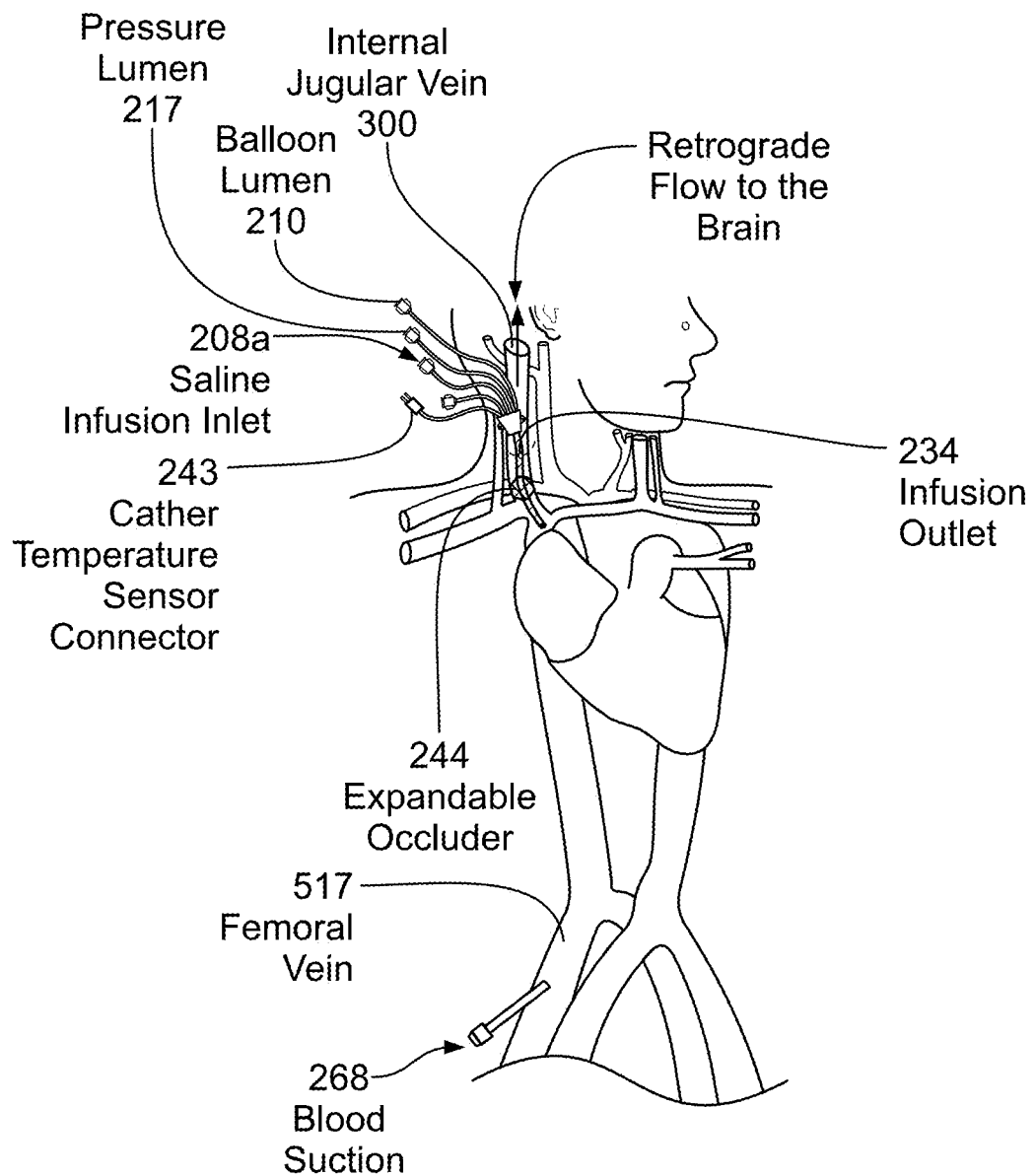
FIG. 32 illustrates a system using retrograde therapy using a saline infusion with a catheter via internal jugular vein of a patient with suction from the femoral vein, in accordance with some embodiments of the disclosure.
Figure 33:
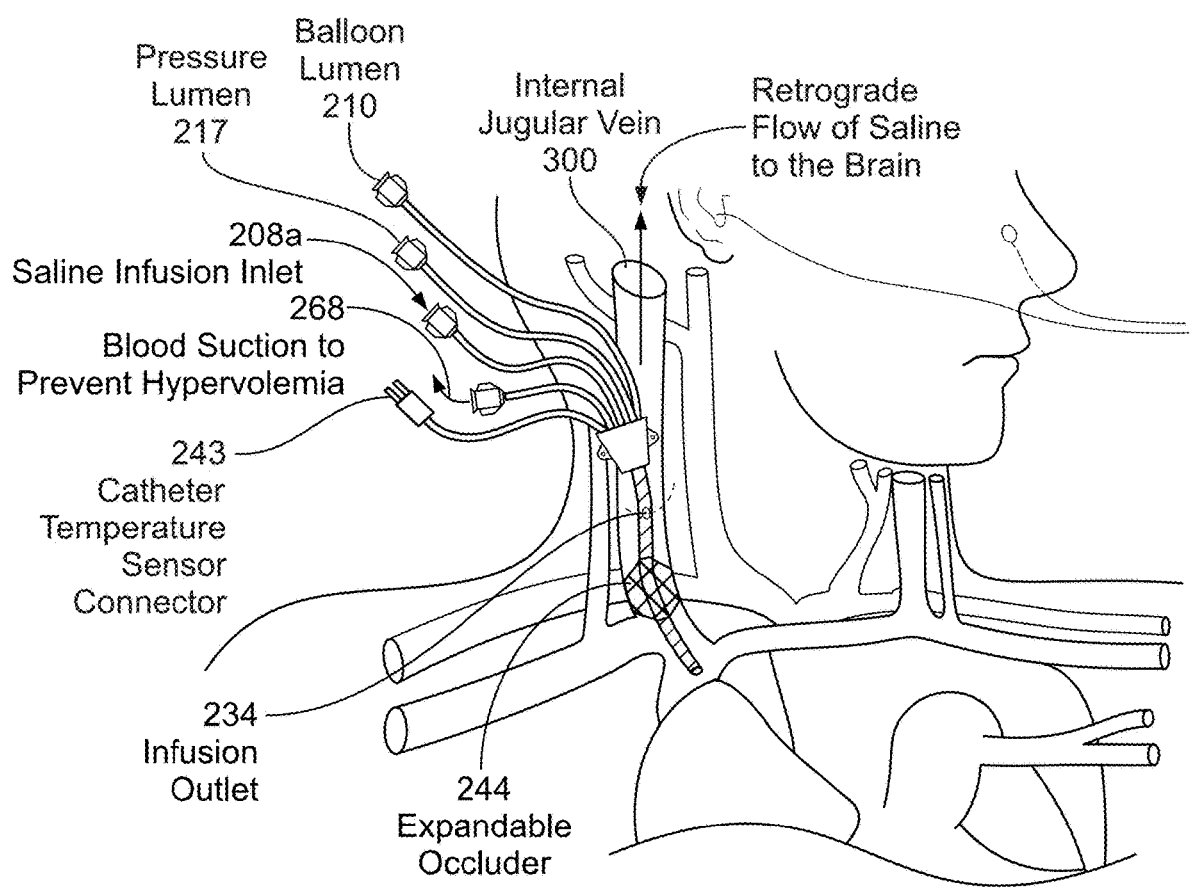
FIG. 33 illustrates a system using retrograde therapy using a saline infusion with a catheter via internal jugular vein of a patient with suction from the internal jugular vein, in accordance with some embodiments of the disclosure.

In some embodiments of this saline infusion method, blood may be suctioned from a separate lumen in the same device as the infusion lumen, or from a different device located in another blood vessel of the body, in order to prevent hypervolemia. FIG. 32 illustrates a system using retrograde therapy using a saline infusion with a catheter via internal jugular vein of a patient with suction from the femoral vein, while FIG. 33 illustrates a system using retrograde therapy using a saline infusion with a catheter via internal jugular vein of a patient with suction from the internal jugular vein. These methods may be used to quickly modify the brain temperature of a patient to a lower level, which may be desired during emergent ischemic events, such as stroke and cardiac arrest. Crystalloid fluid may be delivered via a bolus, sequential boluses, or continuous flow.

Figure 34:
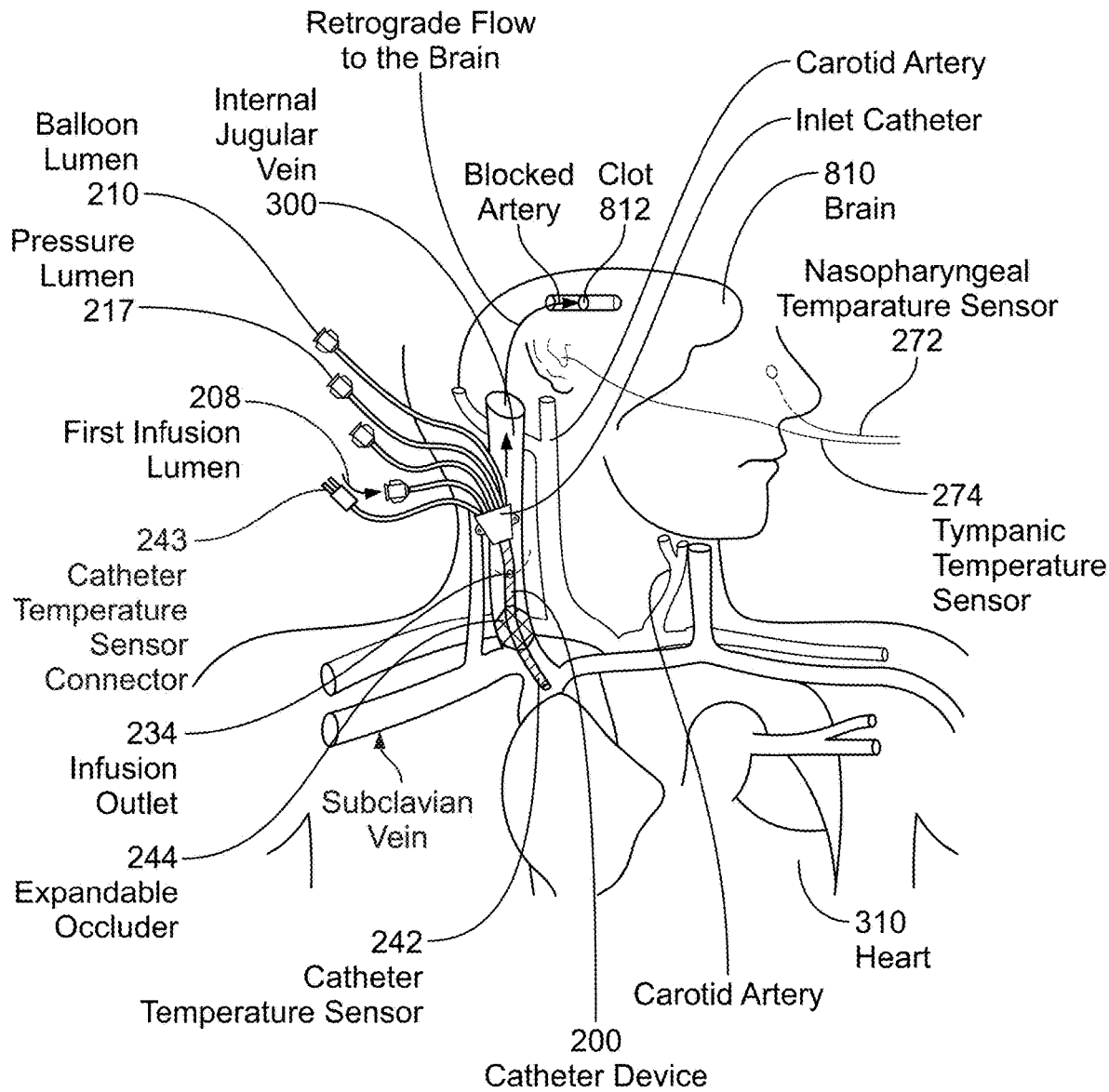
FIG. 34 illustrates a system using retrograde therapy using a saline infusion with a catheter using retrograde flow to dislodge a clot, in accordance with some embodiments of the disclosure.

In some embodiments, the present disclosure provides a method for using retrograde flow to assist in the removal of a blockage in a vessel. FIG. 34 illustrates a system using retrograde therapy using a saline infusion with a catheter using retrograde flow to dislodge a clot, in accordance with some embodiments of the disclosure. The retrograde flow may be provided by the infusion catheter. This flow can also have a cooling fluid, which can be used to cool the surrounding area of the blocked vessel. The retrograde flow may produce a force on a clot lodged in a blood vessel, such as in an artery of the brain, which may help dislodge the clot in the vessel. If an aspiration catheter or stent retriever is being used to remove the arterial blockage, the retrograde flow may provide additional force to assist in removal of the clot, and may offer additional benefits such as neuroprotective or therapeutic drug delivery to the portion of the brain affected by the stroke.

Figure 35:
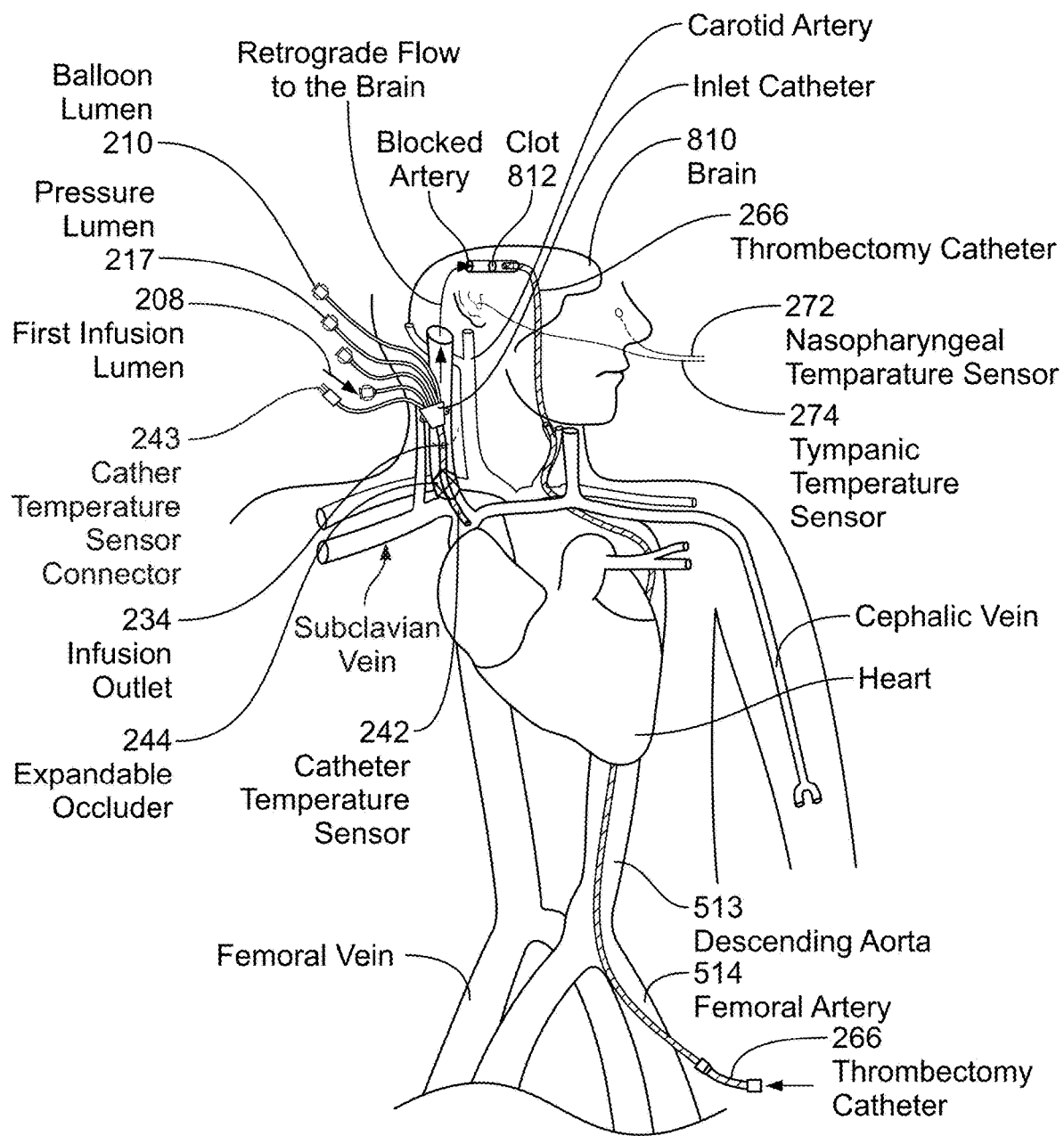
FIG. 35 illustrates a system using retrograde therapy using a saline infusion with a catheter using retrograde flow to dislodge a clot during thrombectomy, in accordance with some embodiments of the disclosure.
Figure 36:
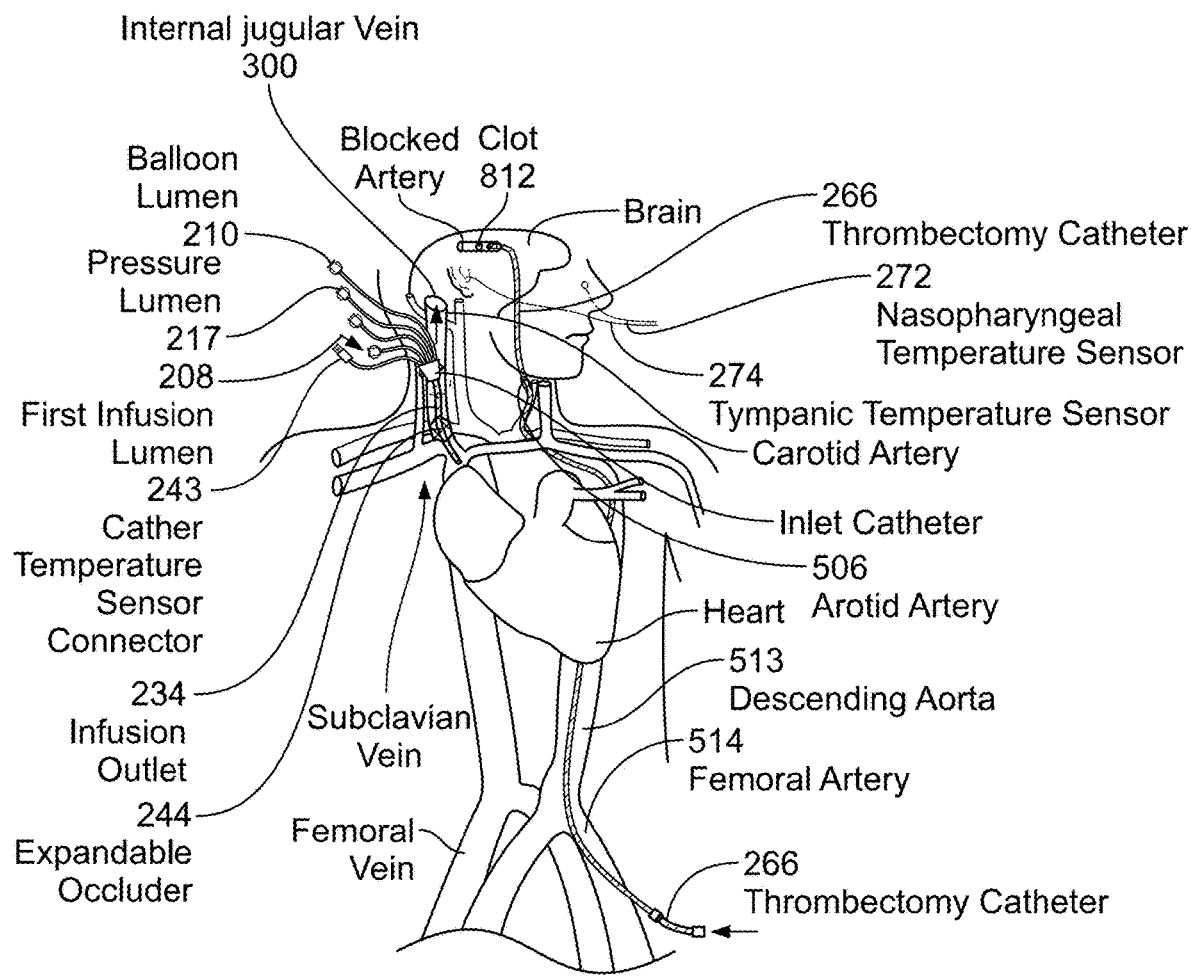
FIG. 36 illustrates a system using retrograde therapy using a saline infusion with a catheter using retrograde flow cool during thrombectomy, in accordance with some embodiments of the disclosure.

FIG. 35 illustrates a system using retrograde therapy using a saline infusion with a catheter using retrograde flow to dislodge a clot during thrombectomy, while FIG. 36 illustrates a system using retrograde therapy using a saline infusion with a catheter using retrograde flow cool during thrombectomy, in accordance with some embodiments of the disclosure. In some embodiments, a thrombectomy catheter, such as an aspiration or stent retriever catheter, may be used in tandem with the retrograde cooling methods. The thrombectomy catheter may be inserted into the femoral artery and navigated to the clot in the brain, while the retrograde cooling may be being delivered through a catheter in the jugular vein or other venous location.

Figure 37:
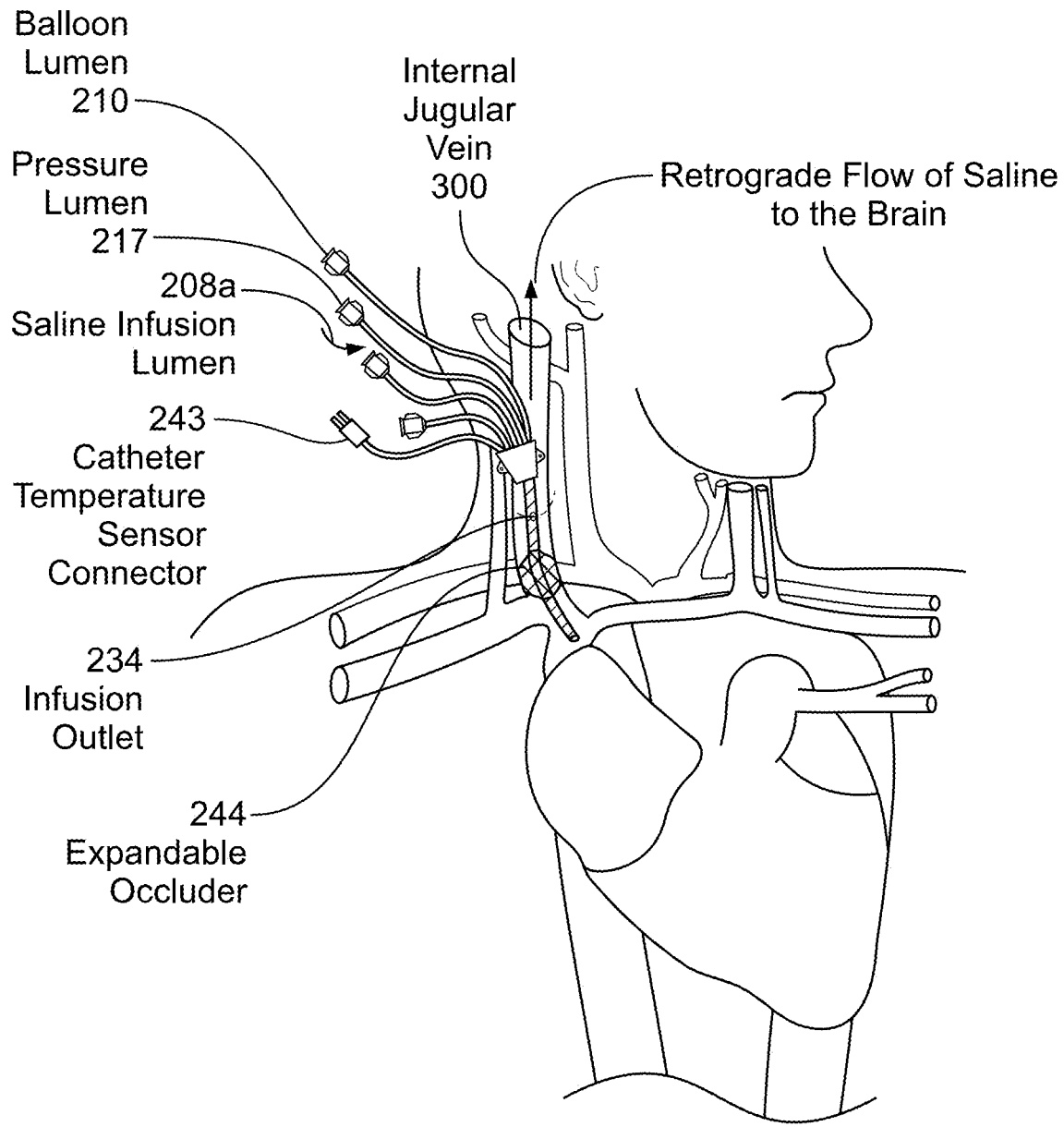
FIG. 37 illustrates a system using retrograde therapy using a saline infusion with a catheter via internal jugular vein of a patient, in accordance with some embodiments of the disclosure.
Figure 38:
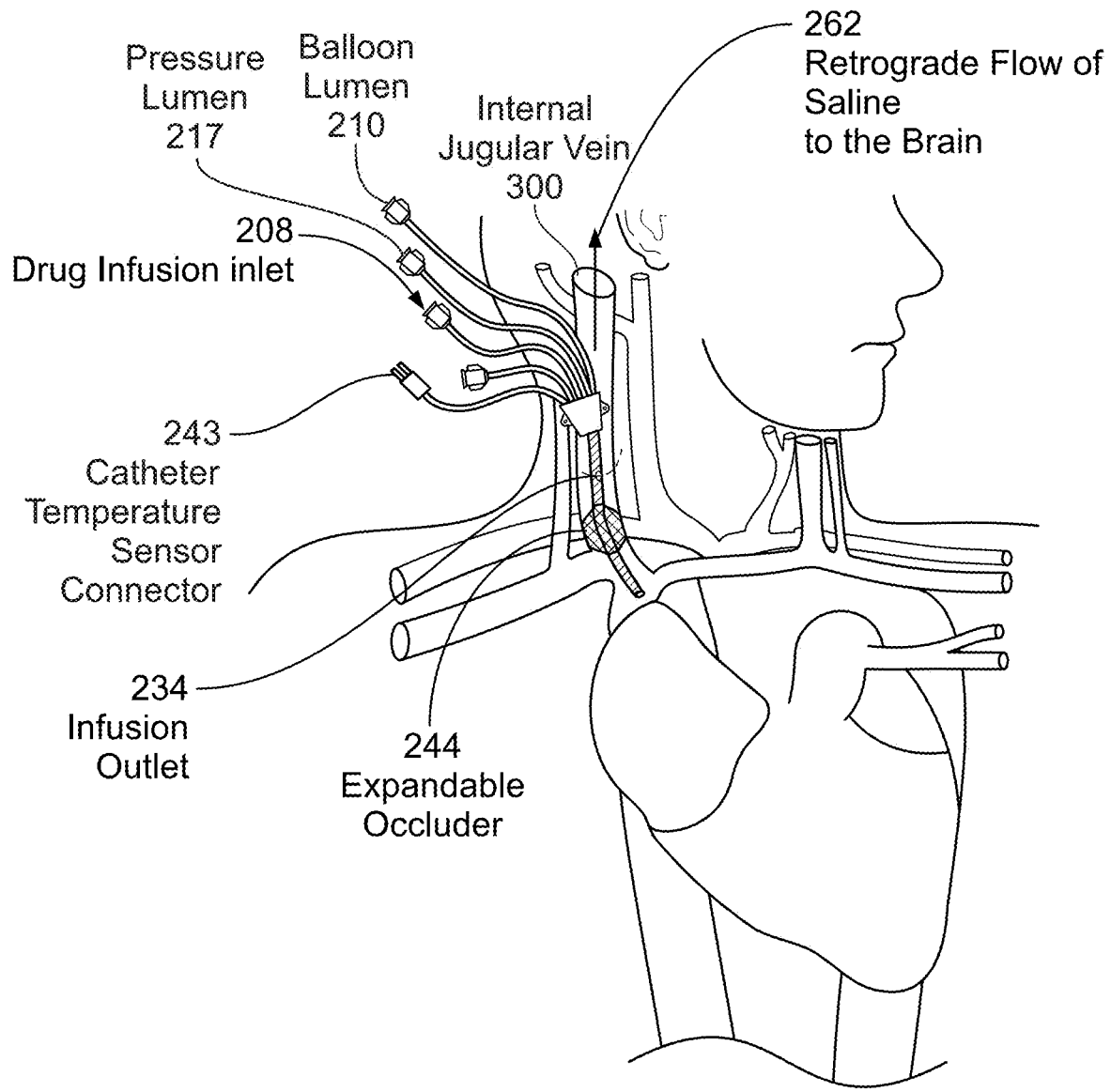
FIG. 38 illustrates a system using retrograde therapy with a catheter for drug delivery to the brain, in accordance with some embodiments of the disclosure.

In some embodiments, the infusion catheter may be connected to a source or infusate, such as a source of saline or blood, to be directly infused, and may be administered with the aid of a pressure bag, for immediate delivery of therapeutic fluids. FIG. 37 illustrates a system using retrograde therapy using a saline infusion with a catheter via internal jugular vein of a patient, in accordance with some embodiments of the disclosure;

FIG. 38 illustrates a system using retrograde therapy with a catheter for drug delivery to the brain, in accordance with some embodiments of the disclosure. In some embodiments, the infusion catheter may deliver neuroprotective drugs or other neuroprotective agents proximal to the expandable occluder, such that the flow of the drug or agent may be directed retrograde towards the brain. The flow rate of the infusion may be modulated based on input from a sensor or change in status of the patient with a blocked vessel. The retrograde drug delivery route may better be able to reach the ischemic portion of a brain undergoing an ischemic stroke, and therefore may be able to better deliver the neuroprotectant than an antegrade approach. The neuroprotective drug, or other neuroprotective agent, may be a calcium antagonist, cell membrane stabilizers, serotonin-receptor antagonists, xenon, radical scavengers, or the like.

3.3 Extracorporeal Circuits 3.3.1—Suction and Infusion in the Same Device (See FIGS. 35-41)

The present disclosure provides a method for suctioning blood, conditioning the blood extracorporeally, and then reinfusing the blood to deliver therapy, especially hypothermic therapy, targeted at a specific organ or group of organs. The blood may be suctioned through one or more catheters and reinfused through one or more catheters. The reinfusion methods may be any of the antegrade or retrograde infusion methods described herein. The one or more catheters may include the infusion catheter, described herein. It should be noted that the infusion catheter shall contain a suction and infusion lumen when used in this method. The suction lumen 216 may be larger than the reinfusion lumen to ensure steady flow can be achieved in the extracorporeal circuit. The suction lumen 216 may be between 1.25 and 3 times larger in surface area than the reinfusion lumen, in order to facilitate steady flow. The extracorporeal conditioning may be done by the therapy delivery system, described herein, or a similar system with some or all of its components. This method of selective therapy using one or more devices attached to an extracorporeal circuit may be used to treat an ischemic stroke patient. The therapy may be used before, during, or following thrombectomy, or independent of thrombectomy, in any stroke patient. The therapy, such as cooling, may allow for longer time windows of treatment eligibility in which the patient can receive additional treatments for stroke. Sensors, such as the temperature sensors described in association with the therapy delivery system, may be used to monitor the therapy, such as the hypothermic therapy.

In some methods the system may be instituted before, or during patient transfer, or some combination thereof. For instance, the system may be used to deliver therapy, such as therapeutic hypothermia, to a patient who has arrived at a first medical facility who may be intended to be transferred to a second medical facility. The therapy, such as neuroprotective therapy for patients with a stroke, may begin at the first location, and this therapy may reduce the brain damage incurred by this stroke patient during their transit from the first medical facility to the second medical facility. The therapy delivery may be continued on the vehicle used to transport the patient, which may be an ambulance, a car, a helicopter, or the like. Operators at the first center or in the transit vehicle may first place the one or more suction and reinfusion devices in a patient's blood vessels, such as a single suction and reinfusion catheter in the internal jugular vein, connect the device to an extracorporeal circuit, and then turn on the circuit to begin therapy. Sensors may be placed on the patient, like temperature and pressure sensors, to monitor the patient during therapy. The therapy may be monitored from a console, and the therapy modulated in response to readouts from the sensors. The extracorporeal circuit may be the aspect of the system modulated, by changing the flow rate, heat transfer rate to the blood passing through, or the like. Therapy may continue one the patient has reached the second medical center.

Figure 39:
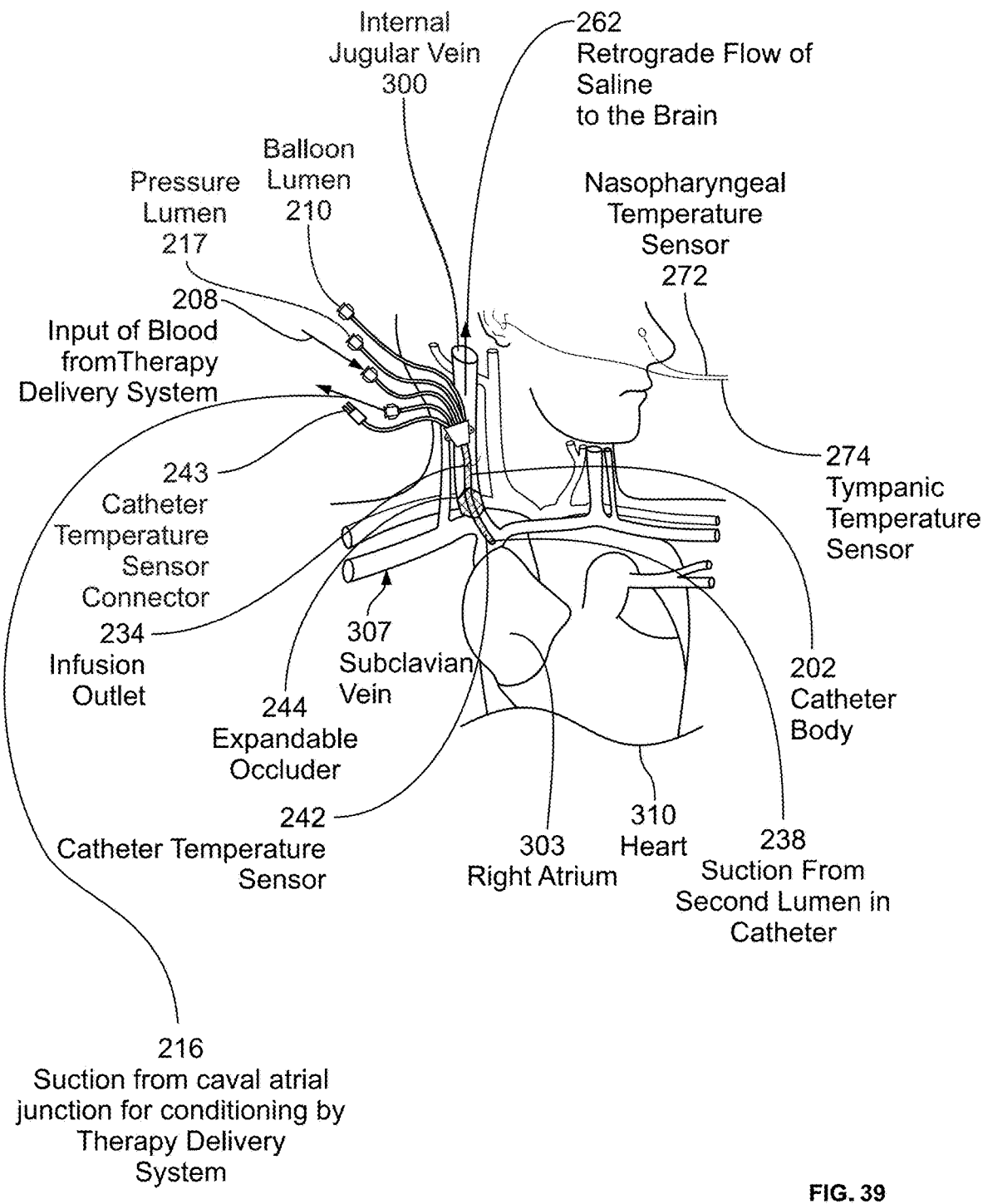
FIG. 39 illustrates a system for therapy with a catheter configured to suction fluid in the internal jugular vein of a patient and return fluid in the internal jugular vein, in accordance with some embodiments of the disclosure.
Figure 40:
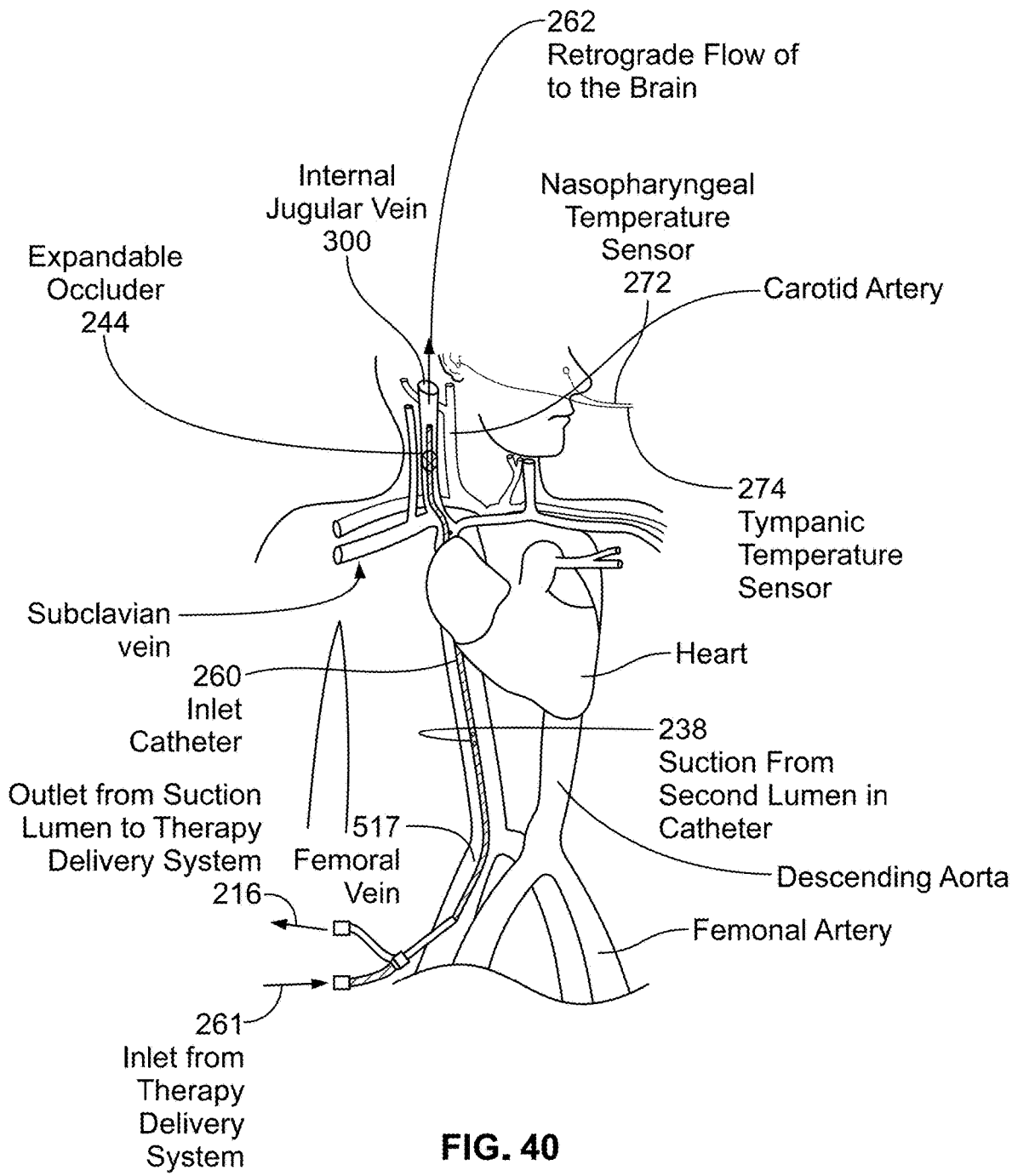
FIG. 40 illustrates a system for retrograde therapy with a catheter configured to suction fluid in the femoral vein of a patient and return fluid in the internal jugular vein, in accordance with some embodiments of the disclosure.
Figure 41:
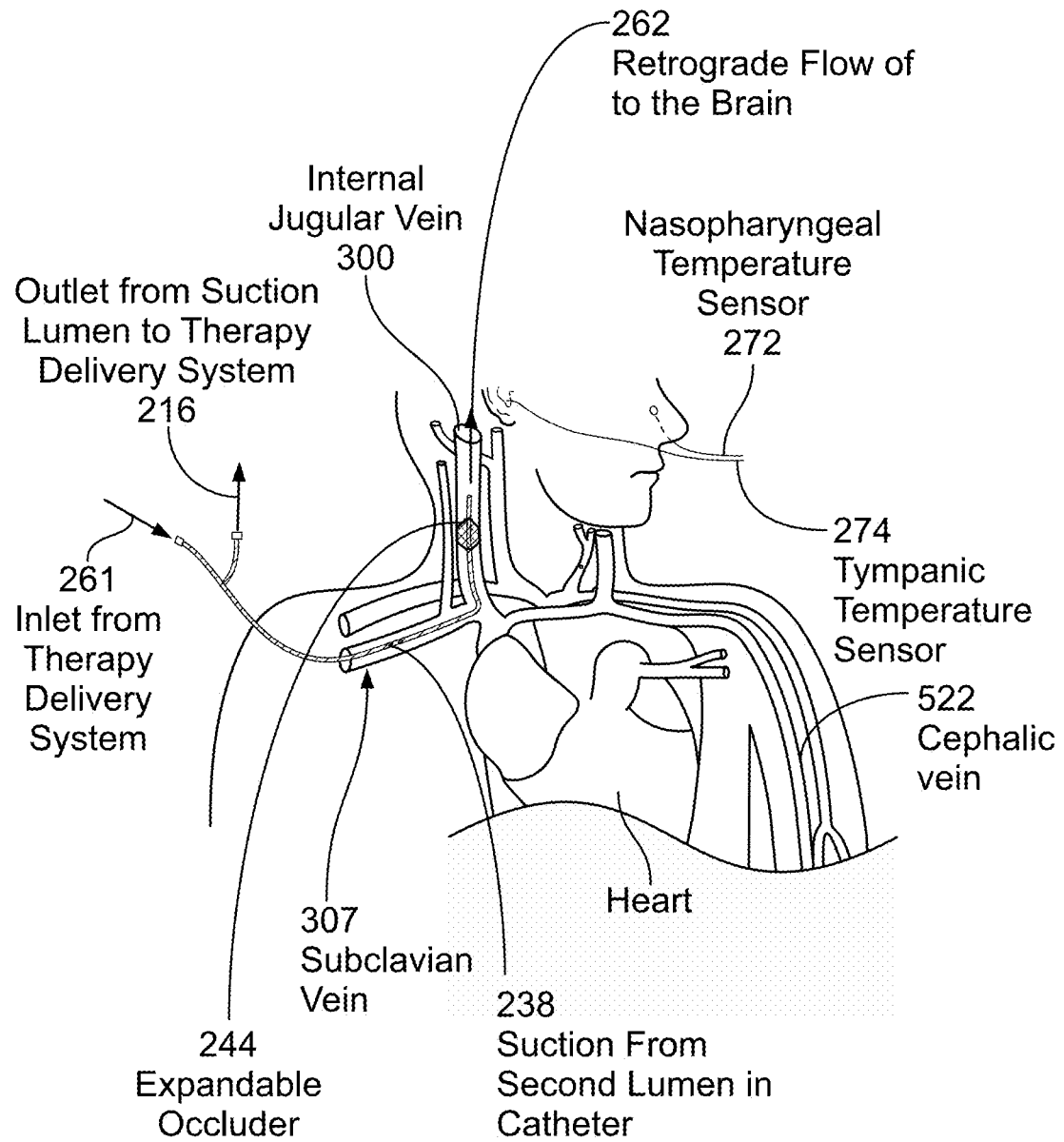
FIG. 41 illustrates a system for retrograde therapy with a catheter configured to suction fluid in the subclavian vein of a patient and return fluid in the internal jugular vein, in accordance with some embodiments of the disclosure.
Figure 42:
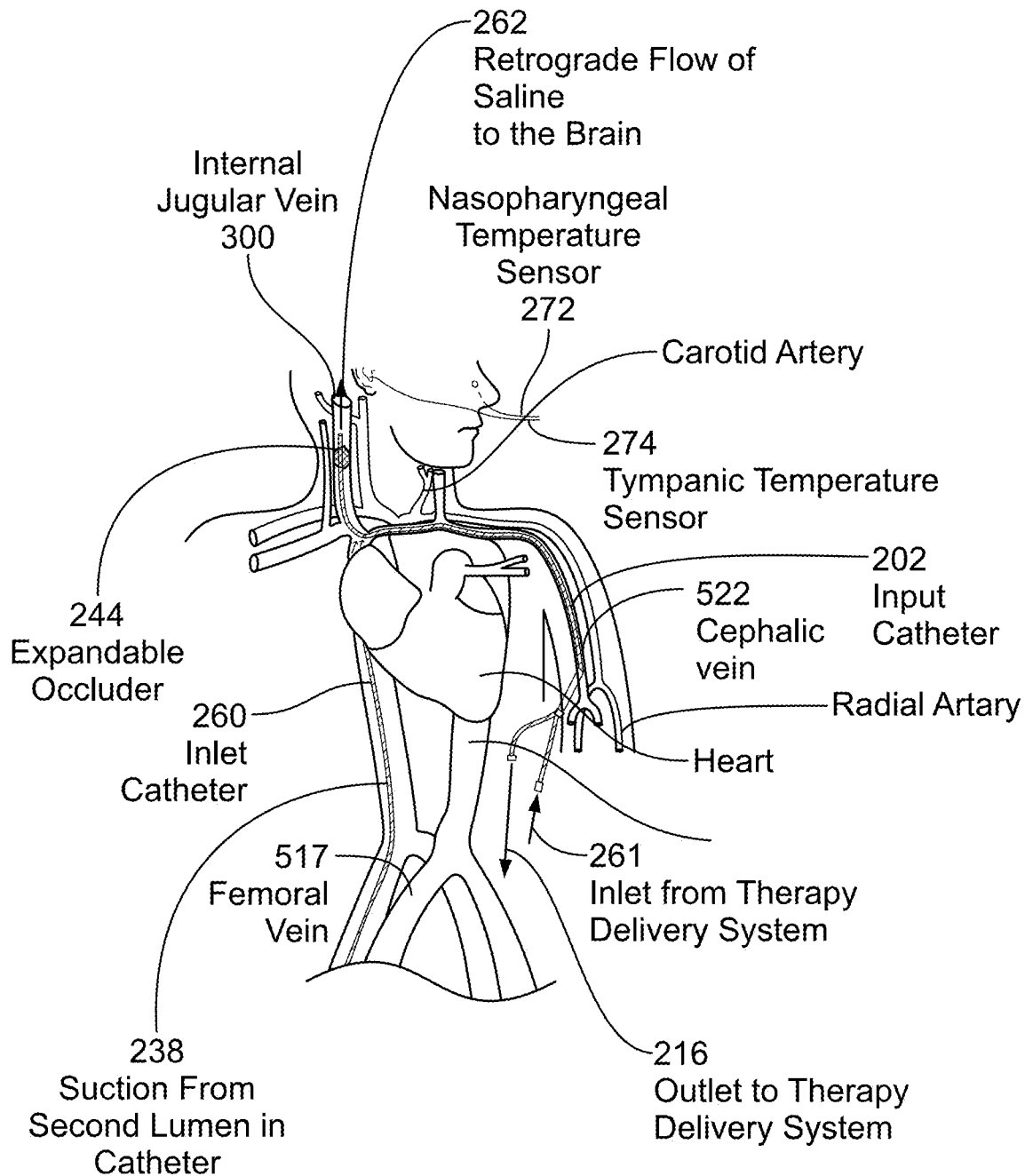
FIG. 42 illustrates a system for retrograde therapy with a catheter configured to suction fluid in the cephalic vein of a patient and return fluid in the internal jugular vein, in accordance with some embodiments of the disclosure.
Figure 43:
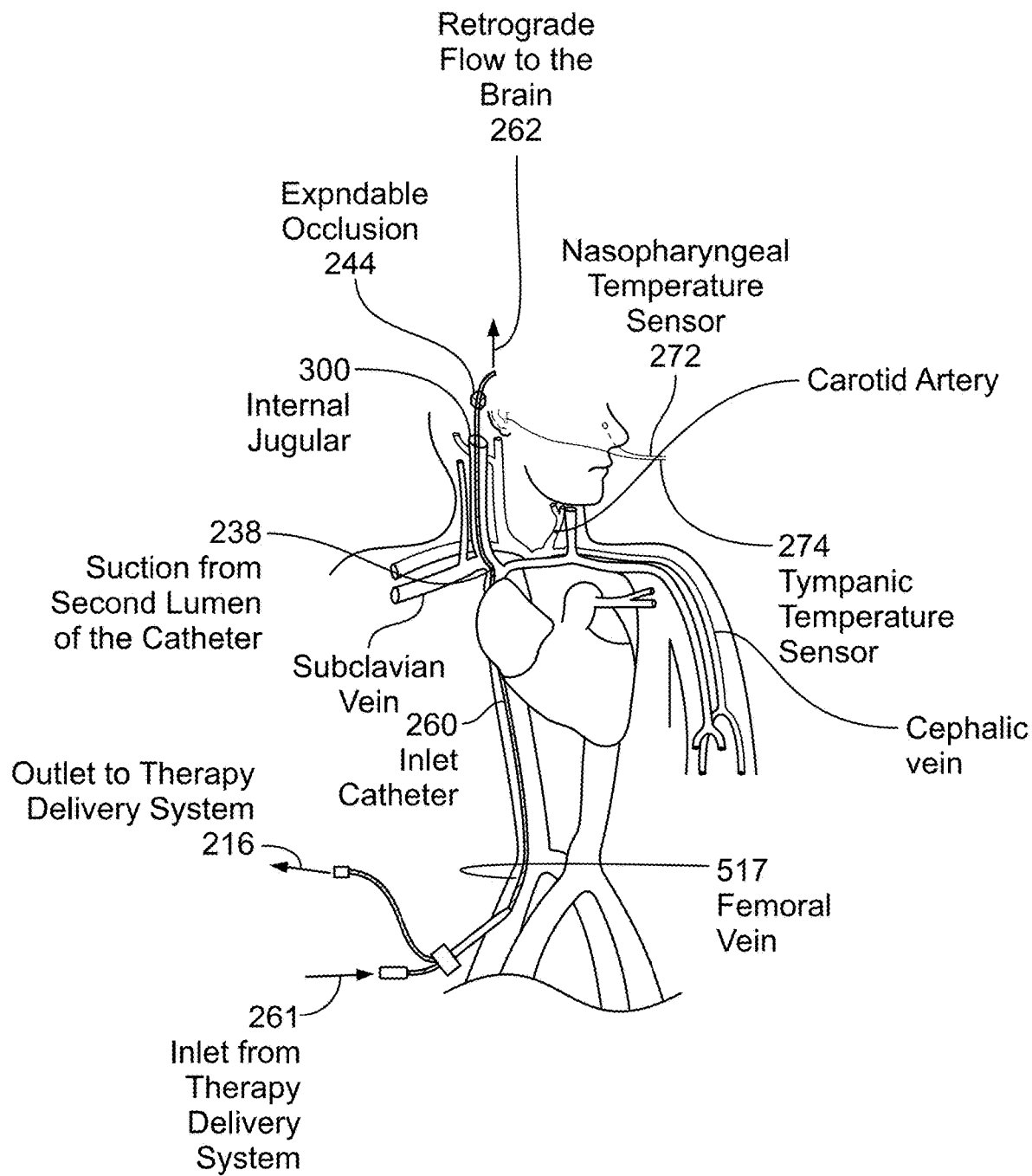
FIG. 43 illustrates a system for retrograde therapy with a catheter configured to suction fluid in the femoral vein of a patient and return fluid in the veins of the brain, in accordance with some embodiments of the disclosure.

In some instances, the methods used to suction and reinfuse the blood may be the same device. This device may be a central venous catheter, placed in a patient's internal jugular vein. FIG. 39 illustrates a system for therapy with a catheter configured to suction fluid in the internal jugular vein of a patient and return fluid in the internal jugular vein. The device may suction blood from near the cavoatrial junction or some other position along the body of the catheter, condition the blood extracorporeally, and then reinfuse the blood into the internal jugular vein or other location into which the device may be placed. The device may also be placed in the femoral vein, subclavian vein, cephalic vein, or some similar vein. FIG. 40 illustrates a system for retrograde therapy with a catheter configured to suction fluid in the femoral vein of a patient and return fluid in the internal jugular vein, FIG. 41 illustrates a system for retrograde therapy with a catheter configured to suction fluid in the subclavian vein of a patient and return fluid in the internal jugular vein, FIG. 42 illustrates a system for retrograde therapy with a catheter configured to suction fluid in the cephalic vein of a patient and return fluid in the internal jugular vein, and FIG. 43 illustrates a system for retrograde therapy with a catheter configured to suction fluid in the femoral vein of a patient and return fluid in the veins of the brain, in accordance with some embodiments of the disclosure. The suction and infusion ports may be separated in the vessel by an expandable occluder, such as a balloon. The infusion port may outlet proximal to the balloon such that flow out of this port proceeds retrograde to the brain. The extracorporeal conditioning may include cooling of the blood, heating of the blood, oxygenation of the blood, infusion of a drug into the blood, or the like, and may be done by the therapy delivery system. The device may be placed using the Seldinger technique method. The system may pull and reinfuse blood continuously or may modulate flow through this extracorporeal circuit in response to a sensor measurement of a physiologic parameter. The system may pull and reinfuse blood after the balloon has been inflated. Sensors, such as those described in association with the therapy delivery system, may be used to monitor the therapy. Physiologic parameters, which may be measured by sensors, include heart temperature, which may be measured by proxy via a temperature sensor, specifically a thermistor, near the cavoatrial junction, infusion pressure, which may be measured using a pressure port proximal to the expandable occluder on the infusion catheter, brain temperature, which may be measured non-invasively using either a tympanic membrane temperature sensor or a nasopharyngeal temperature sensor. If a measurement from one of these sensors indicates that a change may be needed in the system, if the temperature of the heart is too low, the infusion pressure is too high, or the temperature of the brain is too high, for example, the system may modulate flow taking actions such as increasing or decreasing the temperature of the blood reinfused, increasing or decreasing the flow rate of the reinfused blood, increasing or decreasing oxygenation of the blood being reinfused, completely stopping the flow through the extracorporeal system, or the like.

In some embodiments, the device may be an infusion catheter herein described placed in the internal jugular vein.

The device may suction blood from at or near the cavoatrial junction, deliver this blood to the therapy delivery system herein described where the temperature, flow rate, oxygenation, or some combination thereof may be modified, and then reinfused through the perfusion lumen on the infusion catheter. A temperature sensor at the tip may monitor the heart to ensure the reinfused blood cannot cool the heart to dangerous levels.

Figure 44:
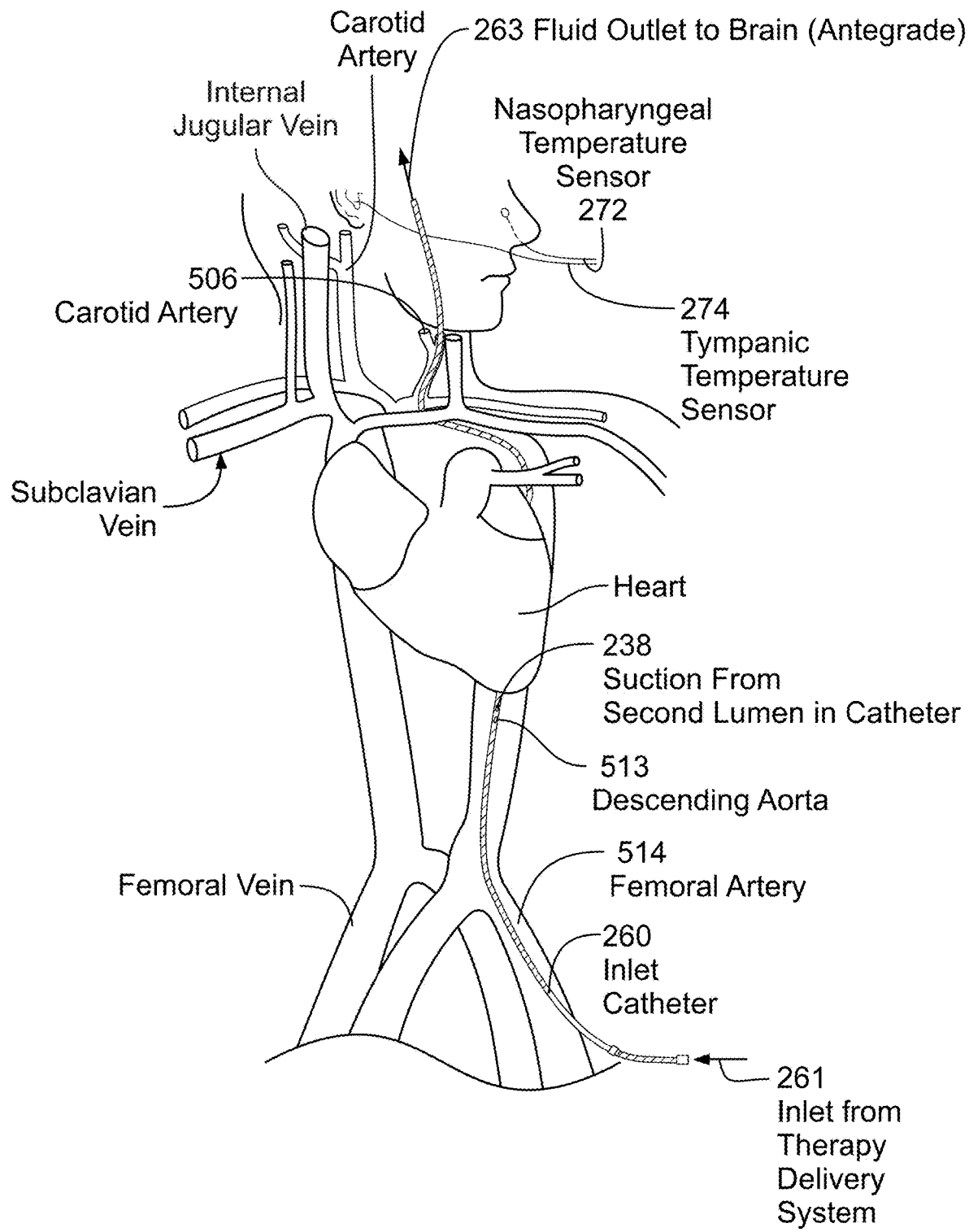
FIG. 44 illustrates a system for antegrade therapy with a catheter configured to suction fluid in the femoral vein of a patient and return fluid into the arteries of the brain, in accordance with some embodiments of the disclosure.
Figure 45:
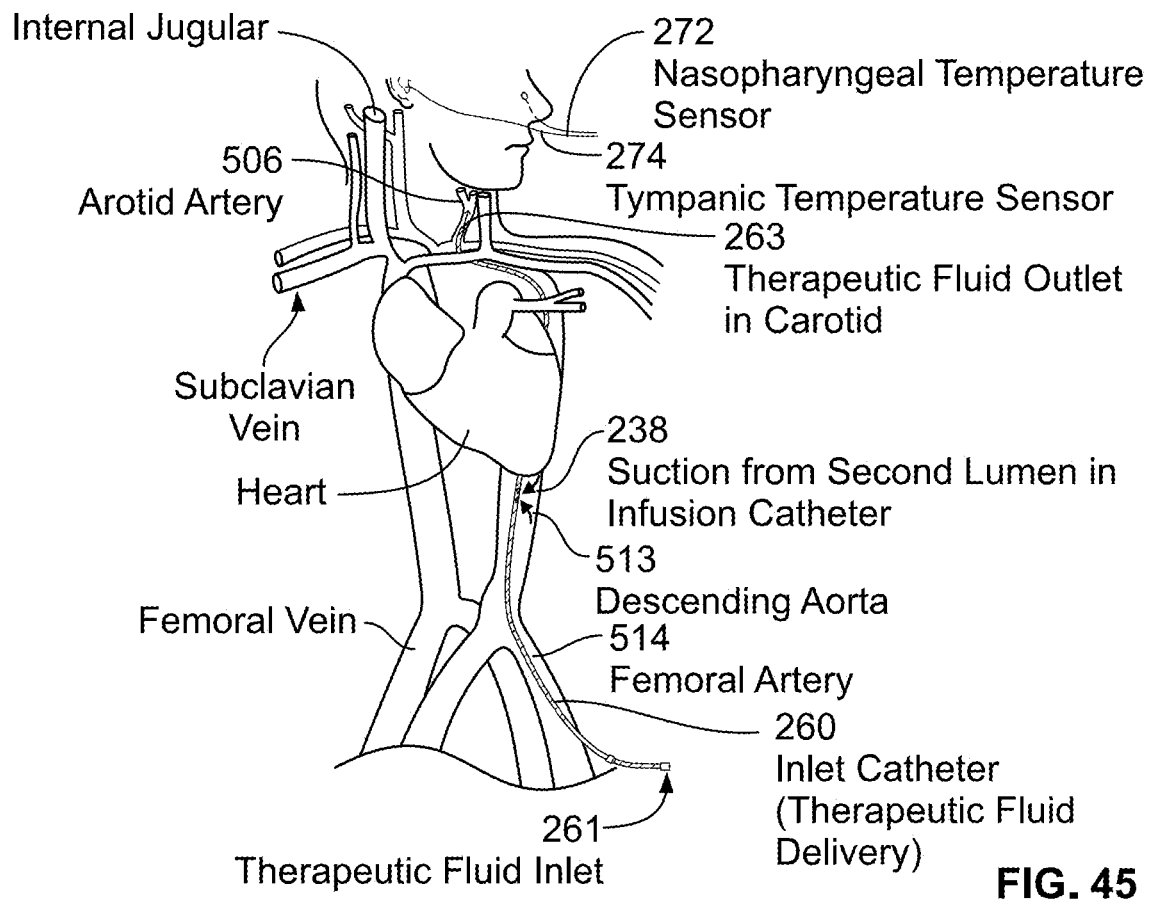
FIG. 45 illustrates a system for antegrade therapy with a catheter configured to suction fluid in the femoral vein of a patient and return fluid into the carotid artery, in accordance with some embodiments of the disclosure.

In another instance, the suctioning and reinfusing may be done in the same device, but the flow may be antegrade rather than retrograde. The infusion catheter may enter the femoral artery, carotid artery, brachial artery, or similar and be navigated to a placement near or in the arteries of the brain, near the site of an ischemic stroke. FIG. 44 illustrates a system for antegrade therapy with a catheter configured to suction fluid in the femoral vein of a patient and return fluid into the arteries of the brain and FIG. 45 illustrates a system for antegrade therapy with a catheter configured to suction fluid in the femoral vein of a patient and return fluid into the carotid artery, in accordance with some embodiments of the disclosure. Autologous blood may be suctioned from either the infusion catheter or from a different access site in the body, such as the femoral artery. In the case that the infusion catheter includes two or more lumens, the suction port 238 may be disposed proximal to an infusion port at or near the distal end 204 of the device, and the proximal suction port 238 may suction blood from other blood vessels, such as the aortic arch or descending aorta through which the device passes. The suctioned autologous blood may be treated by being cooled, oxygenated, or cooled and oxygenated. After treatment, the autologous blood may be reinfused to the body directly toward the brain, to the region affected by the stroke, through the outlet port of the infusion catheter. This direct infusion of cold fluid to the brain may cool the brain to therapeutic levels, which may have the noted benefits of hypothermia.

3.3.2 Suction and Infusion in Different Devices (See FIGS. 46-55)

In some instances, a first device may be used to suction blood from a first location and a second device may be used to reinfuse blood at a second location. The reinfusion location may be in a vein to produce retrograde flow in combination with an expandable occluder on the device, as described herein, such as a device in the internal jugular vein.

Figure 46:
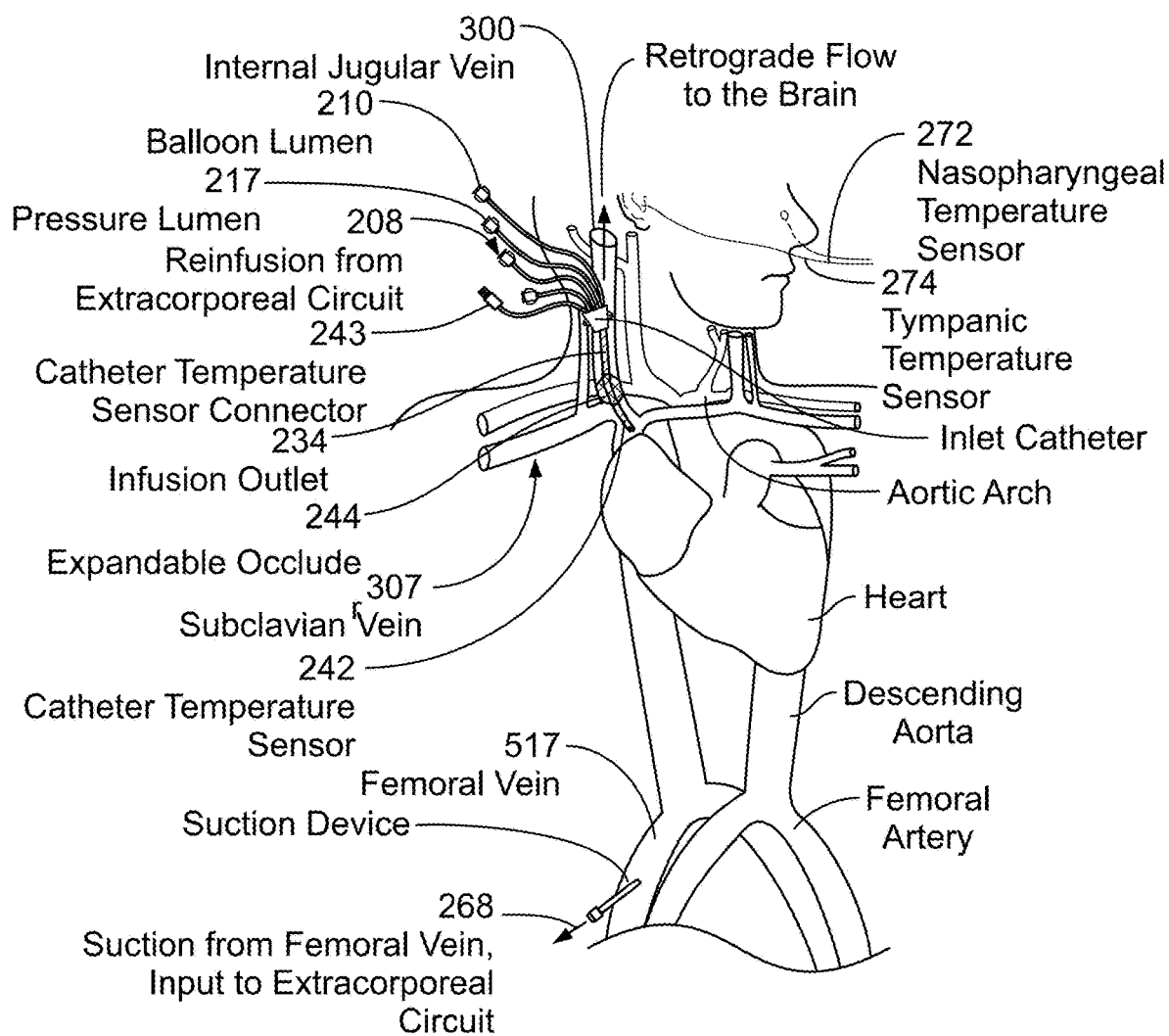
FIG. 46 illustrates a system for retrograde therapy with a device configured to suction fluid in the femoral vein of a patient and a catheter configured to return fluid in the internal jugular vein, in accordance with some embodiments of the disclosure.
Figure 47:
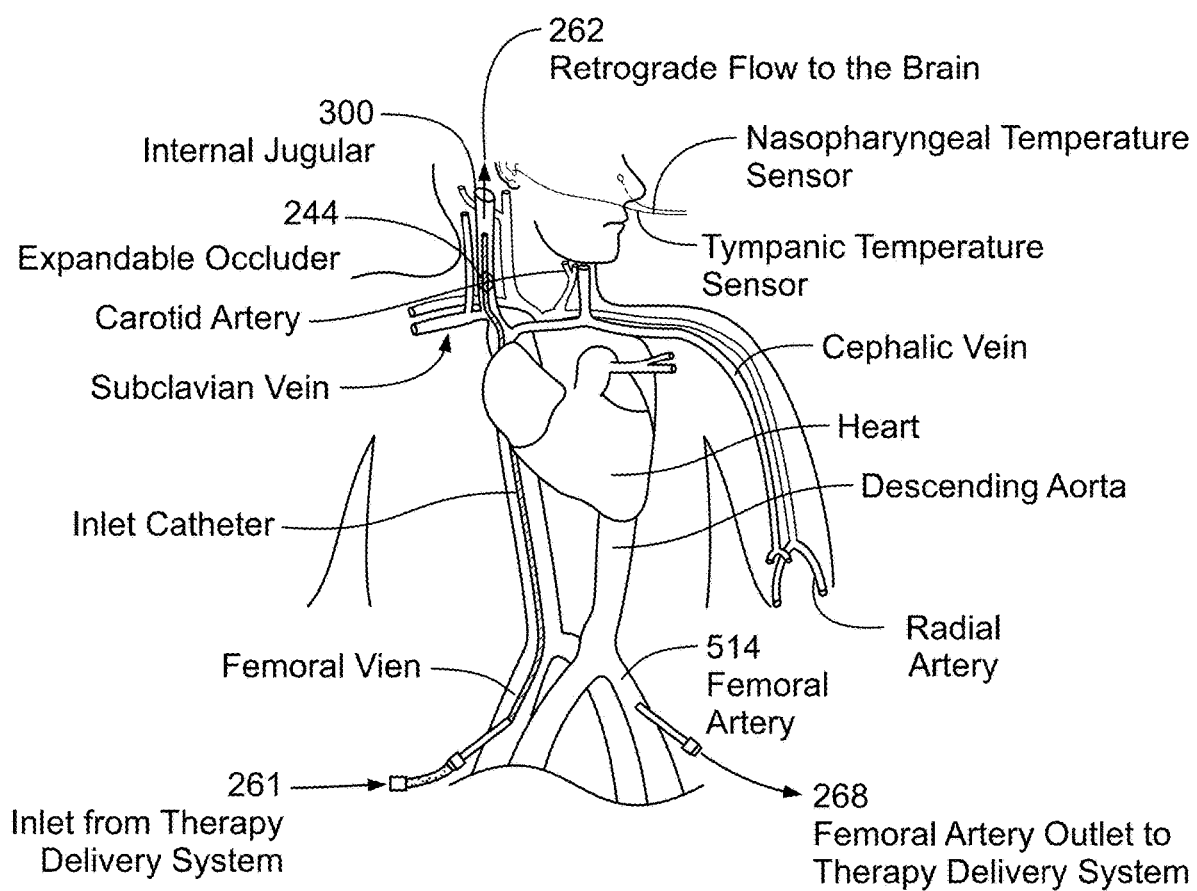
FIG. 47 illustrates a system for retrograde therapy with a device configured to suction fluid in the femoral artery of a patient and a catheter configured to return fluid in the femoral vein, in accordance with some embodiments of the disclosure.
Figure 48:
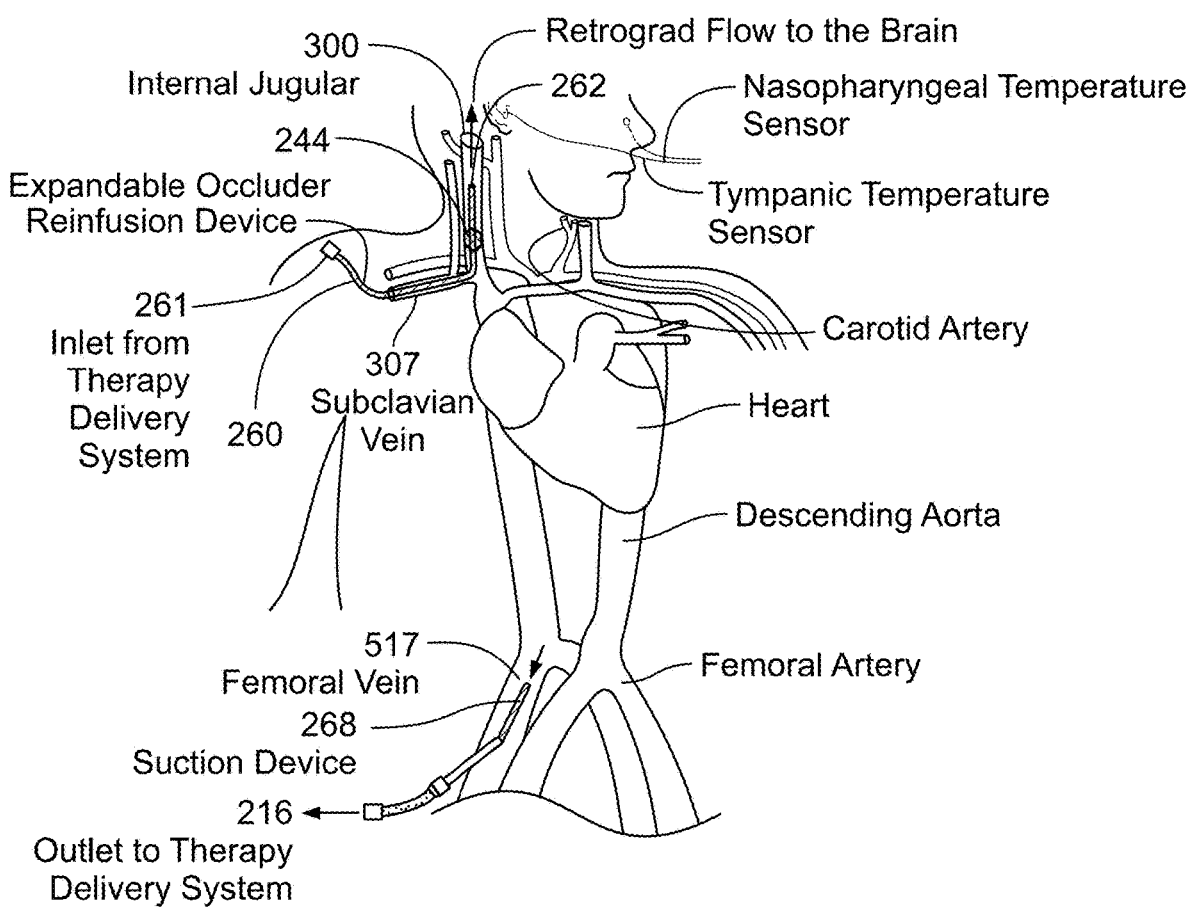
FIG. 48 illustrates a system for retrograde therapy with a device configured to suction fluid in the femoral vein of a patient and a catheter configured to return fluid in the subclavian vein, in accordance with some embodiments of the disclosure.

FIG. 46 illustrates a system for retrograde therapy with a device configured to suction fluid in the femoral vein of a patient and a catheter configured to return fluid in the internal jugular vein, in accordance with some embodiments of the disclosure. The reinfusion location may also be through one of the venous retrograde methods described herein, such as through a catheter placed in the femoral vein, subclavian vein, cephalic vein, or other venous vessel. FIG. 47 illustrates a system for retrograde therapy with a device configured to suction fluid in the femoral artery of a patient and a catheter configured to return fluid in the femoral vein and FIG. 48 illustrates a system for retrograde therapy with a device configured to suction fluid in the femoral vein of a patient and a catheter configured to return fluid in the subclavian vein, in accordance with some embodiments of the disclosure.

Figure 49:
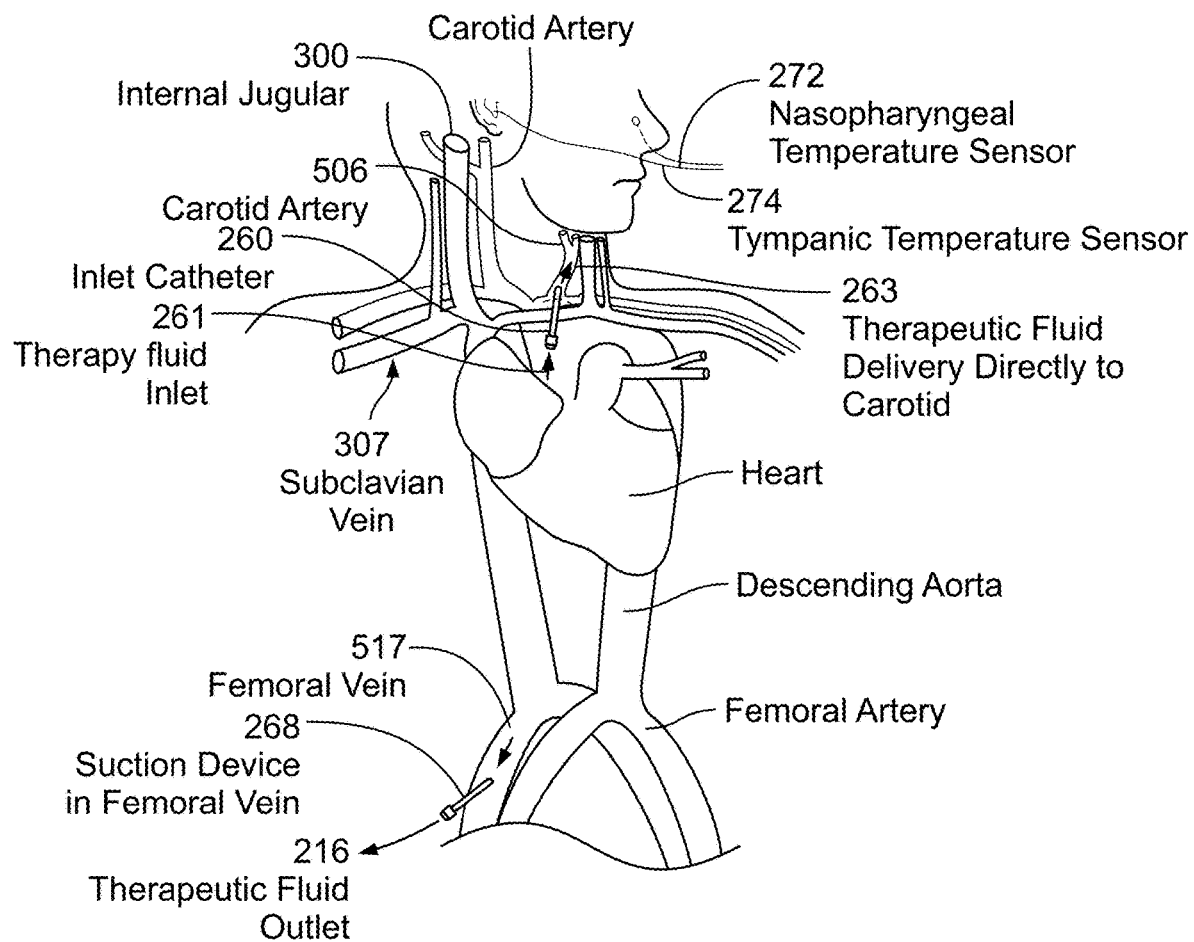
FIG. 49 illustrates a system for antegrade therapy with a device configured to suction fluid in the femoral vein of a patient and a catheter configured to return fluid in the carotid artery, in accordance with some embodiments of the disclosure.
Figure 50:
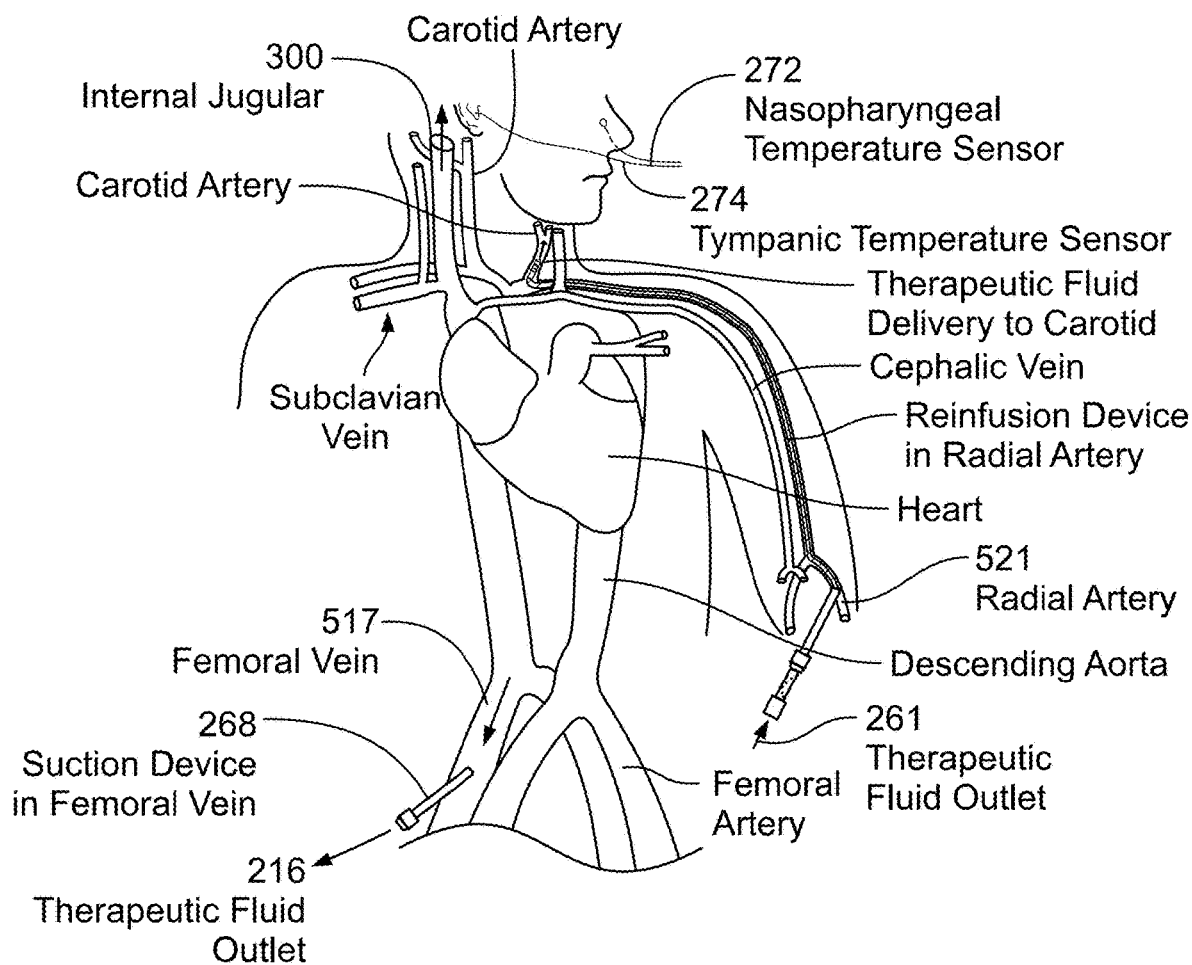
FIG. 50 illustrates a system for antegrade therapy with a device configured to suction fluid in the femoral vein of a patient and a catheter configured to return fluid in the radial artery, in accordance with some embodiments of the disclosure.
Figure 51:
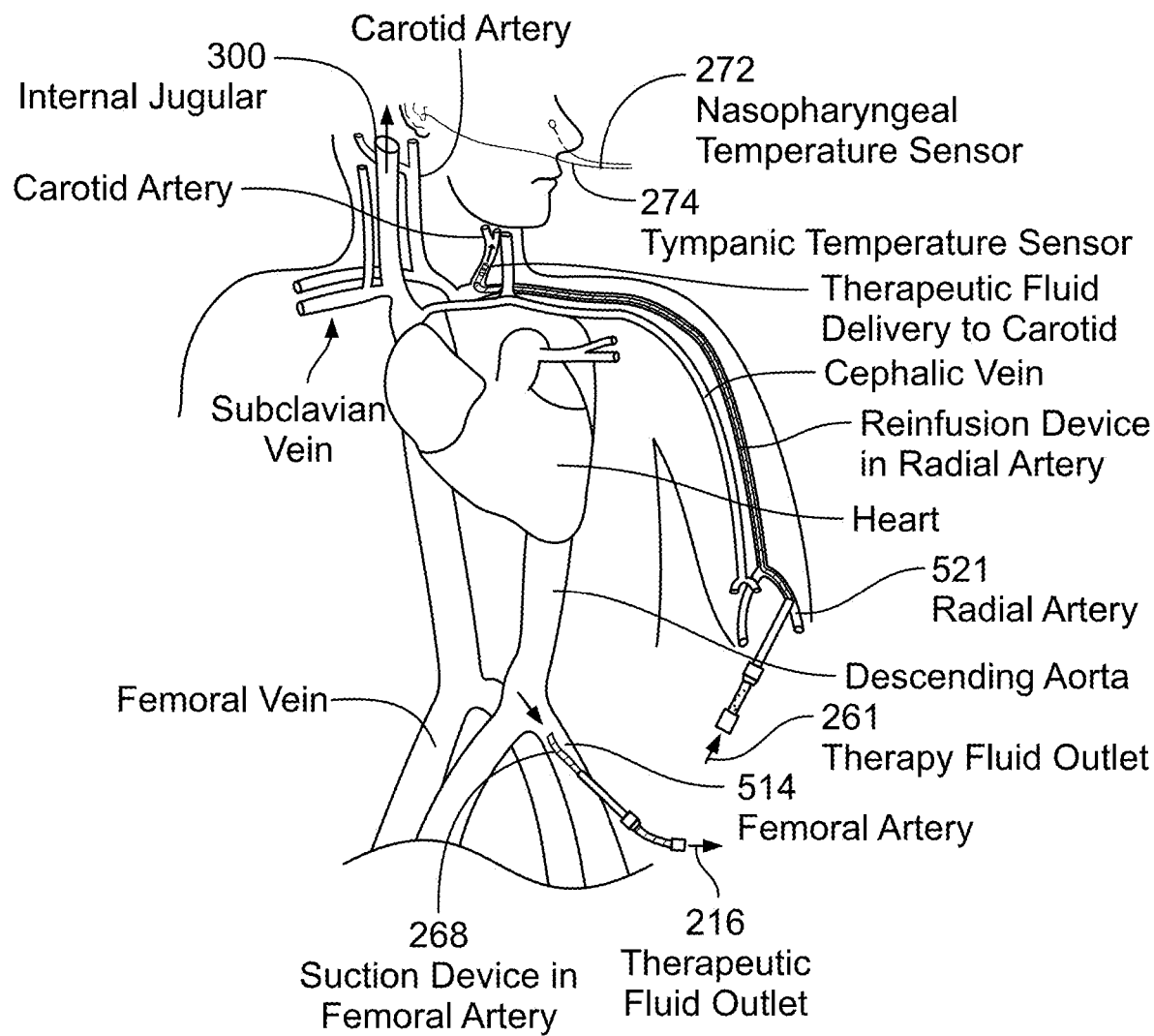
FIG. 51 illustrates a system for antegrade therapy with a device configured to suction fluid in the femoral artery of a patient and a catheter configured to return fluid in the radial artery, in accordance with some embodiments of the disclosure.

The reinfusion device may also be in an artery, using one of the arterial antegrade flow methods described herein, such as the internal carotid artery, femoral artery, radial artery, or other arterial vessel. FIG. 49 illustrates a system for antegrade therapy with a device configured to suction fluid in the femoral vein of a patient and a catheter configured to return fluid in the carotid artery, FIG. 50 illustrates a system for antegrade therapy with a device configured to suction fluid in the femoral vein of a patient and a catheter configured to return fluid in the radial artery, FIG. 51 illustrates a system for antegrade therapy with a device configured to suction fluid in the femoral artery of a patient and a catheter configured to return fluid in the radial artery, in accordance with some embodiments of the disclosure.

Figure 52:
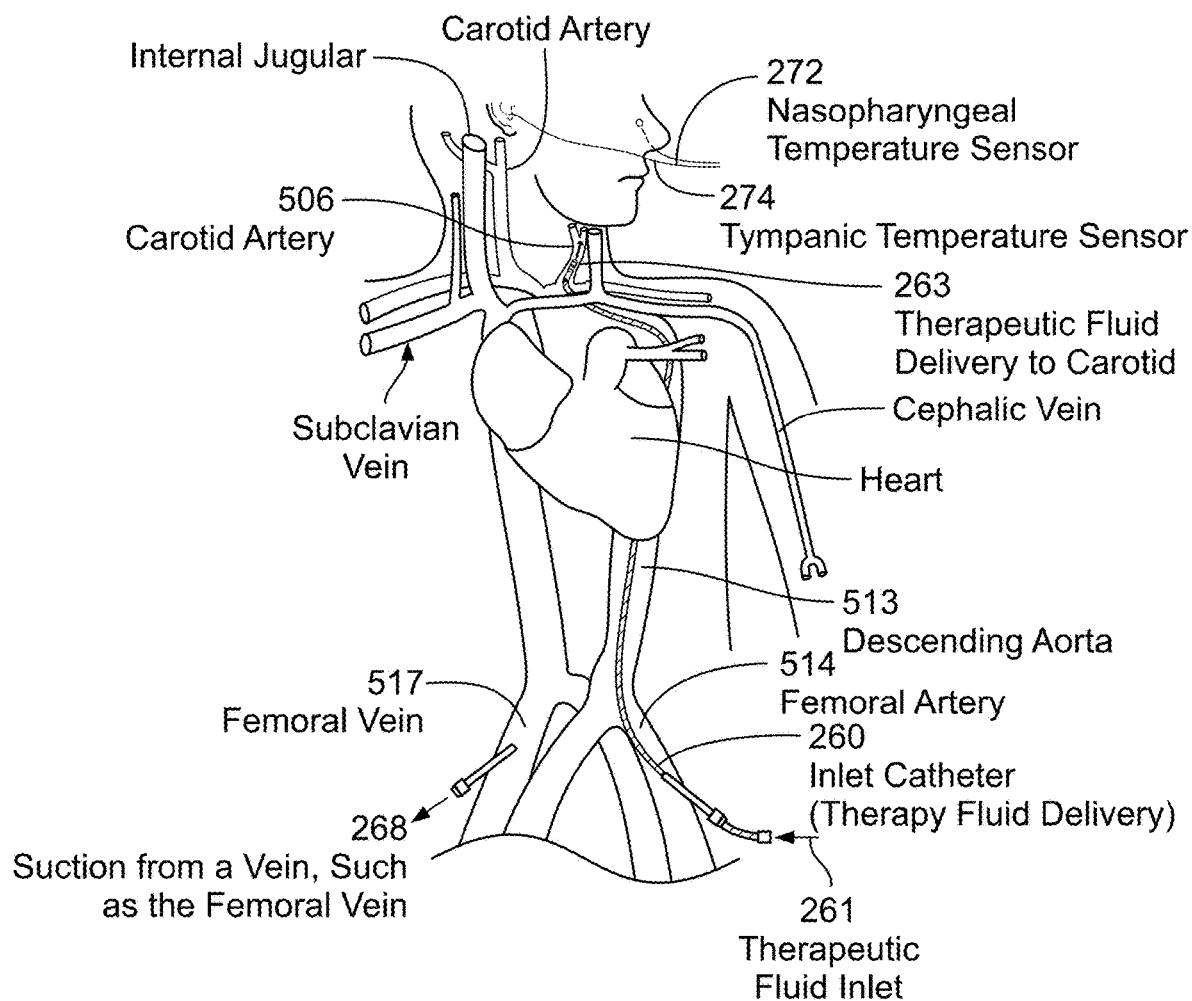
FIG. 52 illustrates a system for antegrade therapy with a device configured to suction fluid from any vein of a patient and a catheter configured to return fluid in the femoral artery, in accordance with some embodiments of the disclosure.

The suction location may be in one or more of any of a plurality of locations in the body; it may be placed anywhere vessel access can be established to suction blood. FIG. 52 illustrates a system for antegrade therapy with a device configured to suction fluid from any vein of a patient and a catheter configured to return fluid in the femoral artery. Common access points include the femoral vein or the femoral artery, the radial artery, subclavian vein, internal jugular veins, the carotid arteries, the cephalic vein, the radial artery or the like, or any combination thereof. It is understood that one or more of any combination of access points for suction may be used with one or more of any delivery points for reinfusion, even though all permutations are not pictured.

Figure 53:
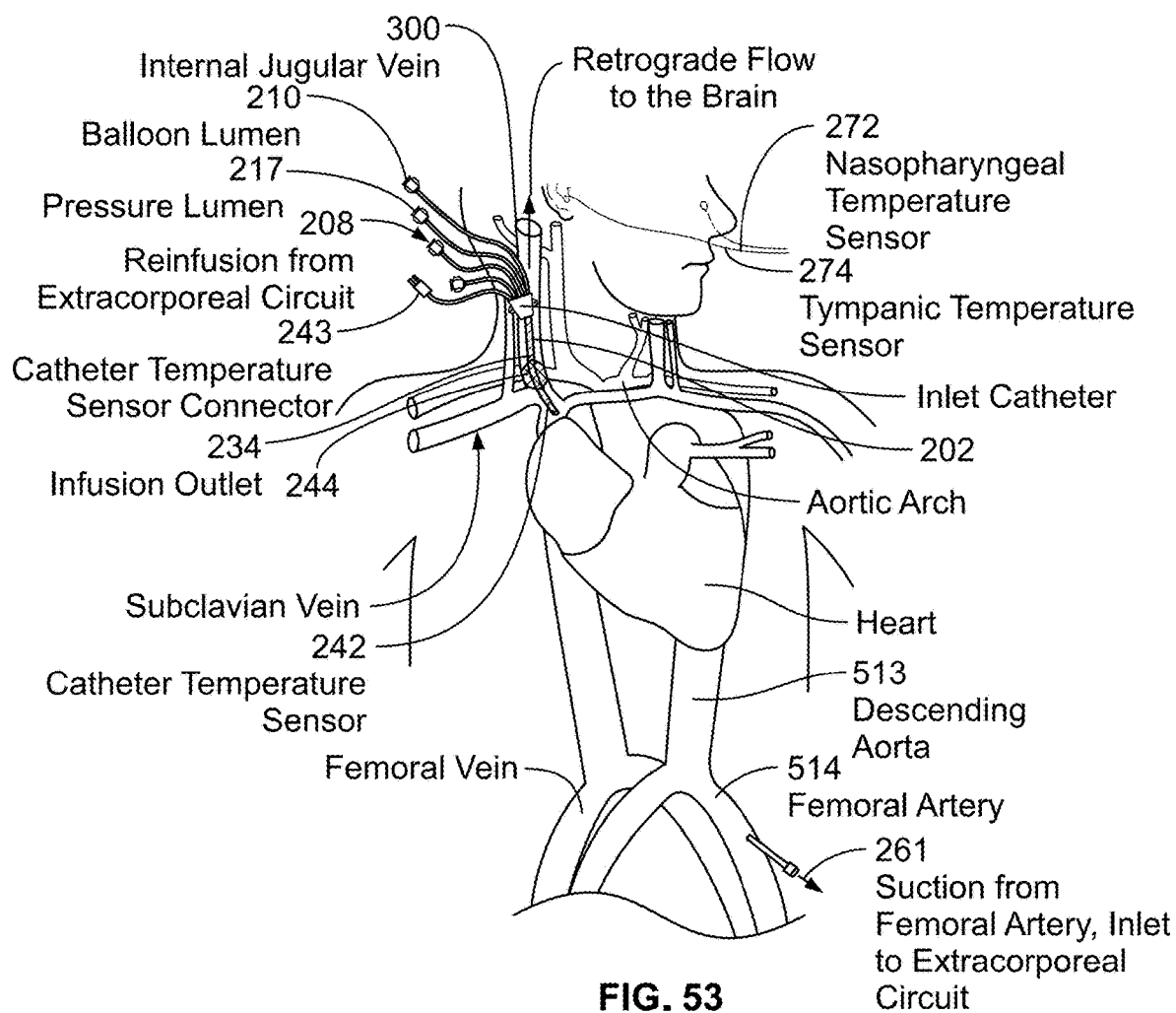
FIG. 53 illustrates a system for retrograde therapy with a device configured to suction fluid in the femoral vein of a patient and a catheter configured to return fluid in the internal jugular vein, in accordance with some embodiments of the disclosure.
Figure 54:
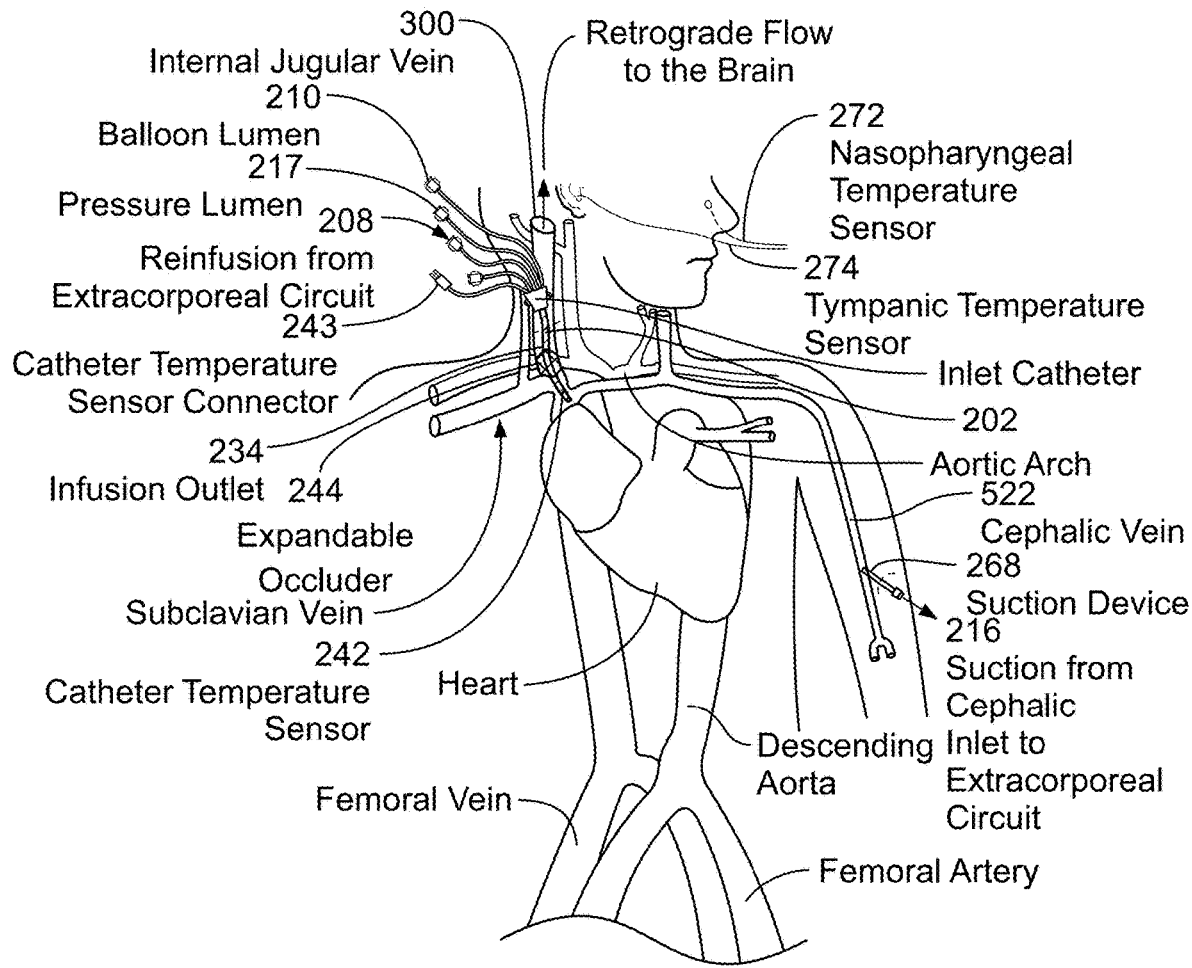
FIG. 54 illustrates a system for retrograde therapy with a device configured to suction fluid in the cephalic vein of a patient and a catheter configured to return fluid in the internal jugular vein, in accordance with some embodiments of the disclosure.

In some embodiments, a suction device may be placed in a femoral vessel, the flow may be suctioned to be run through the extracorporeal circuit, where it may be conditioned by cooling, oxygenation, flow rate modification, and the like, and then re-infused through a reinfusion device placed in the internal jugular vein. FIG. 53 illustrates a system for retrograde therapy with a device configured to suction fluid in the femoral vein of a patient and a catheter configured to return fluid in the internal jugular vein, in accordance with some embodiments of the disclosure. In such an instance, an expandable occluder may be occluding the internal jugular vein distal to the outlet of the reinfusion catheter, which may provoke retrograde flow towards the brain to deliver selective therapy. Common access points include the femoral vein or the femoral artery, the radial artery, subclavian vein, internal jugular veins, the carotid arteries, the cephalic vein, the radial artery or the like, or any combination thereof. FIG. 54 illustrates a system for retrograde therapy with a device configured to suction fluid in the cephalic vein of a patient and a catheter configured to return fluid in the internal jugular vein, in accordance with some embodiments of the disclosure.

In another embodiment, the suction device and reinfusion device may be separate lumens in the same device, such as a catheter that enters the body through the femoral vein and may be navigated to the internal jugular vein. Navigation of the catheter may make use of a guidewire to correctly place the device.

Figure 55:
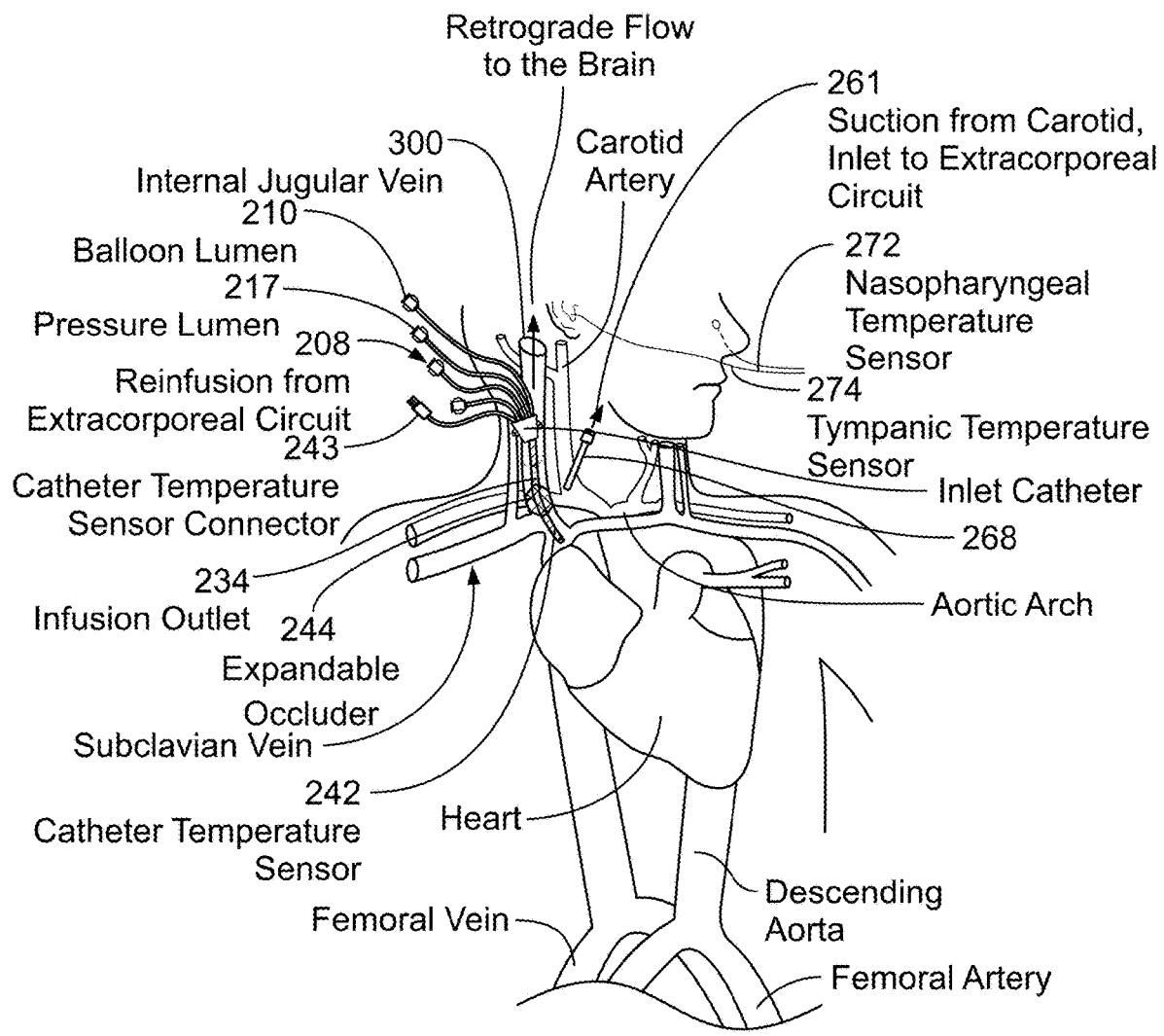
FIG. 55 illustrates a system for retrograde therapy with a device configured to suction fluid in the carotid artery of a patient and a catheter configured to return fluid in the internal jugular vein, in accordance with some embodiments of the disclosure.

In some embodiments, the suction device may be placed in the internal carotid artery and the infusion device placed in the internal jugular vein. FIG. 55 illustrates a system for retrograde therapy with a device configured to suction fluid in the carotid artery of a patient and a catheter configured to return fluid in the internal jugular vein, in accordance with some embodiments of the disclosure. In this instance, the extracorporeal circuit may not need a pump as the pressure differential between the carotid and jugular may be enough to provoke retrograde flow to the brain through the internal jugular vein. This method of blood transfer may be used to deliver oxygenated blood retrograde to the brain of a patient. The blood from the carotid may be extracorporeally or intracorporeally cooled.

In practice, the extracorporeal circuit may have a heat exchanger that cools blood to 0° C. or warmer. The pump may adjust its flow rate in a range of 0-5 L/min, for example, based on a tympanic temperature sensor or other sensor, which may be used as a proxy for brain temperature or the temperature of another organ. The system may have a heat exchanger that cools blood to 0° C. which may be autologous. The pump may adjust its flow rate in a potential range of 0-5 L/min, for example, based on input from both a tympanic temperature, as a proxy for brain temperature, and a distal tip 205 of the catheter temperature sensor, as a proxy for body temperature. The circuit may be the therapy delivery system described herein.

In another embodiment, blood may be shunted directly from an artery or vein to the infusion catheter, potentially being temperature modulated intracorporeally. As such, without passing through an extracorporeal conditioning system, arterial blood may be accessed from the carotid artery, for example, and infused cephalad to the expandable occluder, thereby supplying the brain with oxygenated blood. Additionally, intracorporeal cooling, as described herein, may be utilized to cool this shunted blood before infusion toward the brain.

Figure 56A:
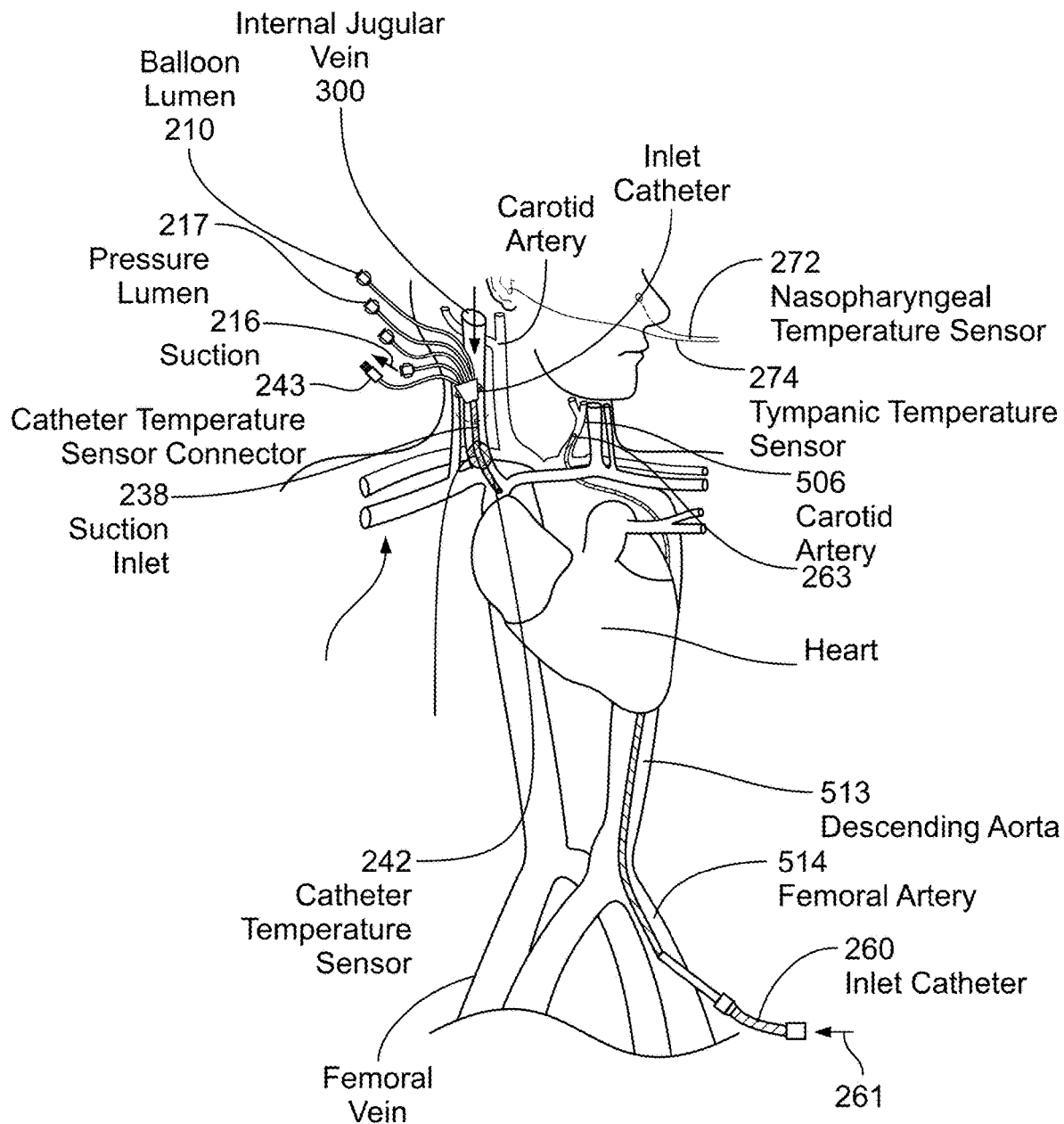
FIG. 56A illustrates a system for antegrade closed loop therapy, in accordance with some embodiments of the disclosure.
Figure 56B:
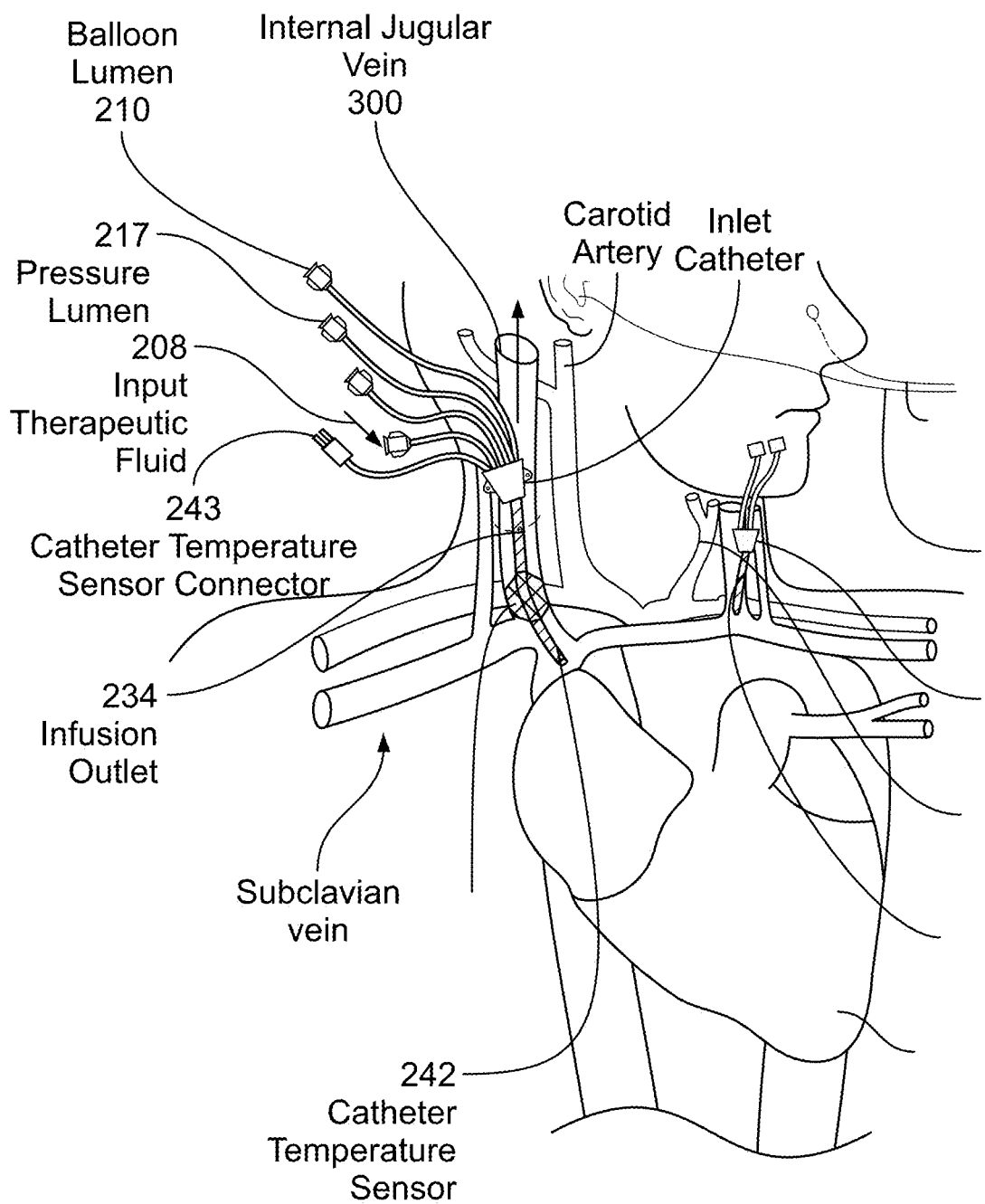
FIG. 56B illustrates a system for retrograde closed loop therapy, in accordance with some embodiments of the disclosure.

3.4 Closed Loop Organ Compartment Therapy (See FIGS. 56A-56B)

In some embodiments, therapeutic fluid may be administered to a target organ or organs through veins or arteries for selective therapy through one catheter at a first location, known as the inlet catheter, and then suctioned up by another catheter at a second location, known as the outlet catheter. Flow may be either retrograde or antegrade through the selected organ. One or both of the inlet and outlet catheters may be the infusion catheter, herein described. The inlet and outlet catheters may include one or more expandable occluders to occlude a blood vessel if desired.

3.4.1 Antegrade Approach

FIG. 56A illustrates a system for antegrade closed loop therapy, in accordance with some embodiments of the disclosure. In the case of antegrade therapy, the first location may be in the arteries feeding the selected organ and the second location may be in the veins draining the selected organ. In one instance, the brain may be the organ selected to be cooled, and an inlet catheter may be placed in one or both of the carotid arteries which deliver blood to the brain. Therapeutic fluid, such as cold autologous blood or saline, may be infused through these catheters to selectively cool the brain. In the one or both internal jugular veins, the veins draining blood from the brain, outlet catheters may be placed which suction the cold drainage from the brain to prevent cooling of the rest of the body. The outlet catheters may be the infusion catheter, described herein. Anatomical placement of the catheters may include the femoral artery, peripheral arteries, such as radial, carotid artery, or otherwise; and the catheter may be navigated to the target artery via these approaches.

3.4.2 Retrograde Approach

FIG. 56B illustrates a system for retrograde closed loop therapy, in accordance with some embodiments of the disclosure. In the case of retrograde therapy, the first location may be in the veins draining the selected organ and the second location may be in the arteries supplying the selected organ with blood. In one instance, the brain may be the organ selected to be cooled, and an inlet catheter may be placed in one or both of the internal jugular veins which drain blood from the brain. An expandable occluder, which may be a feature of the infusion catheter, may be expanded to occlude the internal jugular vein and facilitate retrograde flow of fluids infused cephalad to the occlusion. Therapeutic fluid, such as cold crystalloid or cooled autologous blood, may be infused through these catheters, which may selectively cool the brain. In either one or both of the carotid arteries, or in the contralateral internal jugular vein, for instance, outlet catheters may be placed which suction the fluid draining from the brain. This outlet catheter may communicate with an extracorporeal heater cooler apparatus to rewarm the fluid before administering back to the body. In this way, cooled fluid is delivered to the target organ, such as the brain, but removed, and possibly rewarmed and reinfused, upon outflow from the target organ, to potentially minimize systemic cooling. In the case of the outlet catheter being placed in the contralateral jugular vein, only one inlet catheter would be placed. The outlet catheter in the contralateral jugular may be the infusion device herein described, or may be a simple catheter without an expandable occluder. If present, an expandable occluder on the outlet device may prevent the therapeutic fluid from reaching the rest of the body, so that all of it may be suctioned through the outlet catheter. The flow path may be retrograde through the internal jugular vein in which the device may be placed, through the venous sinuses and veins of the brain, and out the contralateral internal jugular vein where it can outlet through the outlet catheter. In this instance, the arterial pressure in the arteries and capillaries of the brain may prevent the flow of blood retrograde through the vein from veins to arteries, and therefore the infused fluid may drain to the contralateral internal jugular vein.

If catheters with occlusive elements are used, the occlusive elements may be expanded to completely isolate the organ from the rest of the body's circulation, allowing closed loop flow to the selected organ. If catheters with no occlusion elements are used, the outlet catheter may draw fluid out of the body fast enough so that minimal cold fluid from the infusion lumen gets past the target organ region. This may allow the brain to be cooled selectively without cooling the heart or other organs. In some instances, instead of delivering therapeutic cooling agents like cooled autologous blood or cooled saline, the system may deliver oxygenated blood or a therapeutic drug. In the particular therapeutic area in which neuroprotection may be desired, and the brain is the target organ, such as in ischemic stroke, delivery of a neuroprotectant agent such as calcium antagonists, cell membrane stabilizers, xenon, serotonin-receptor antagonists or free radical scavengers or the like, may be delivered. The pressure at which the drug or agent may be perfused may be dictated by the severity and location of the blocked vessel, with higher pressures needed to reach clots in more distal locations of the brain.

Although one inlet and one outlet catheter are discussed, it is understood that multiple infusion, or inlet, and suction, or outlet, catheters may be used to accomplish selective cooling of the organ. The number needed may be determined based on the number of pertinent inflow and outflow vessels to the selected organ to be cooled.

Figure 57:
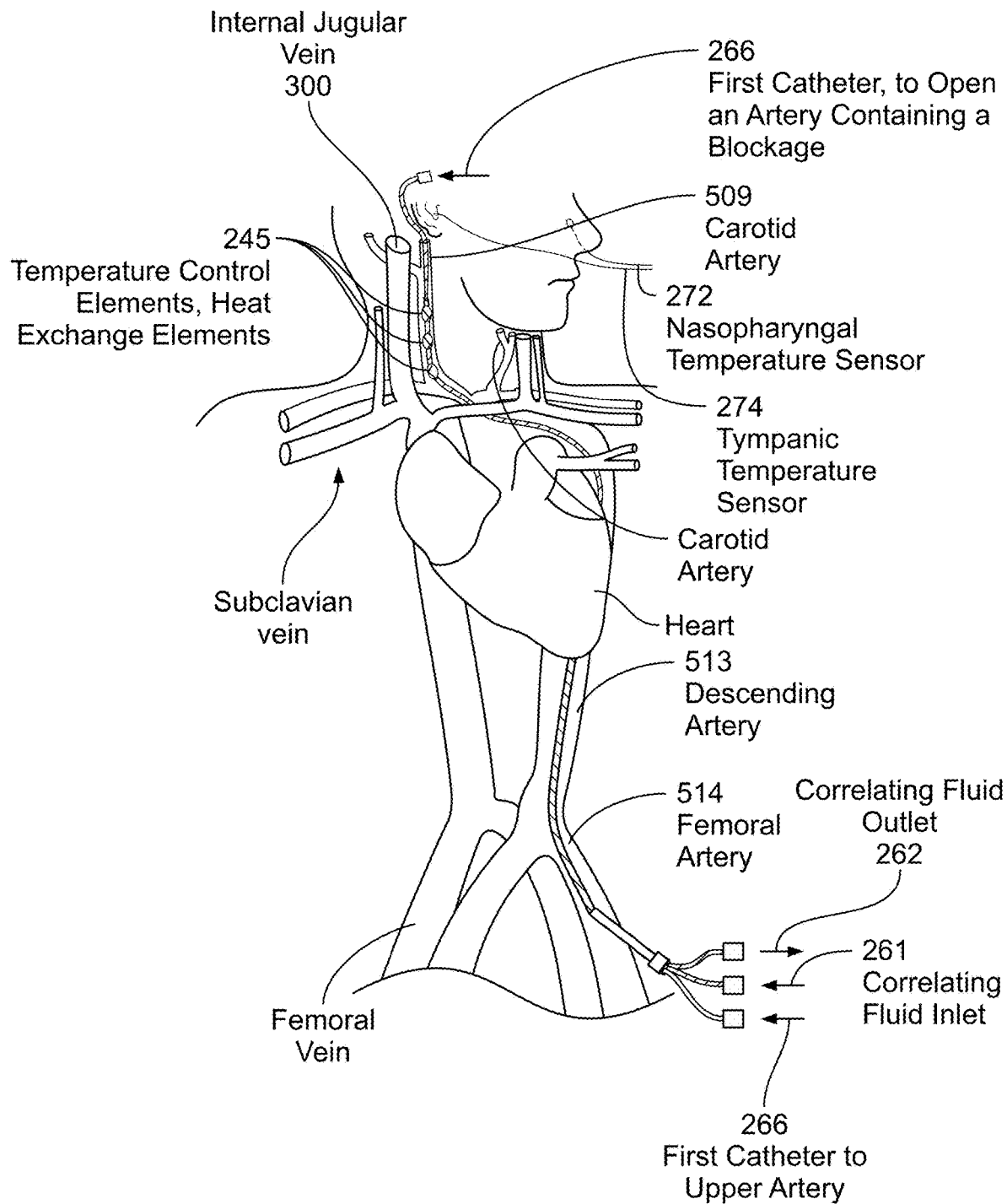
FIG. 57 illustrates a system for therapy used in thrombectomy procedures, in accordance with some embodiments of the disclosure.

3.5 Use in Thrombectomy (See FIG. 57)

FIG. 57 illustrates a system for therapy used in thrombectomy procedures, in accordance with some embodiments of the disclosure. In some embodiments, a system is described which can open a blood vessel containing a blockage, and control the temperature of blood at a specified location. The system may comprise a first catheter 266, which may be intended to open an artery containing a blockage, such as an artery in the brain or heart, a temperature control element, sensors, and a therapy circulating system. The first catheter 266 intended to open the blocked artery may be an aspiration catheter or a stent-retriever which may be intended to be used in thrombectomy procedures. A temperature control element can also have one or more heat exchange elements 245, that may be disposed on a catheter body 202. The heat exchange elements 245 may be expandable, and may be filled with circulating fluid. The circulating fluid may be cooled water, saline, or other coolant fluid.

The temperature control elements may be in thermal communication with blood flowing past the elements in a vessel, and may allow for the cooling of this fluid flowing past the temperature control elements. Sensors, such as temperature, flow or pressure sensors, may be used to monitor a change in response to the temperature control elements. Temperature sensors may be disposed on the catheter intended to open a blocked artery, may be external to a patient receiving therapy, may be internal to a patient receiving therapy, or may be on a catheter distal to the temperature control elements in a vessel. Temperature sensors on the catheter to open the blocked vessel or on a catheter distal to the temperature control elements may be used to sense the temperature of fluid that has passed by the temperature control elements. Internally and externally located temperature sensors on a patient receiving therapy may be placed to monitor the temperatures of the patient's body when the temperature control elements are modifying fluid temperature in vessels of the body. For example, the tympanic membrane temperature, the nasopharyngeal temperature, or the internal jugular temperature may be monitored by sensors to track temperature changes of these locations. The temperature sensors may be in communication with a therapy circulating system. The therapy circulating system may control the pressure, flow, or temperature of the fluid circulating through the temperature control element. The input from the temperature sensors may be used to modulate the flow, pressure, or temperature parameters of the fluid that the therapy circulating system circulates through the temperature control elements. A control system may be used to allow the therapy circulating system to modulate the temperature of a targeted part of the body, as measured by one of the temperature sensors described, to a level which may be therapeutic, such as therapeutic hypothermia in the range of 25-36° C.

Figure 58:
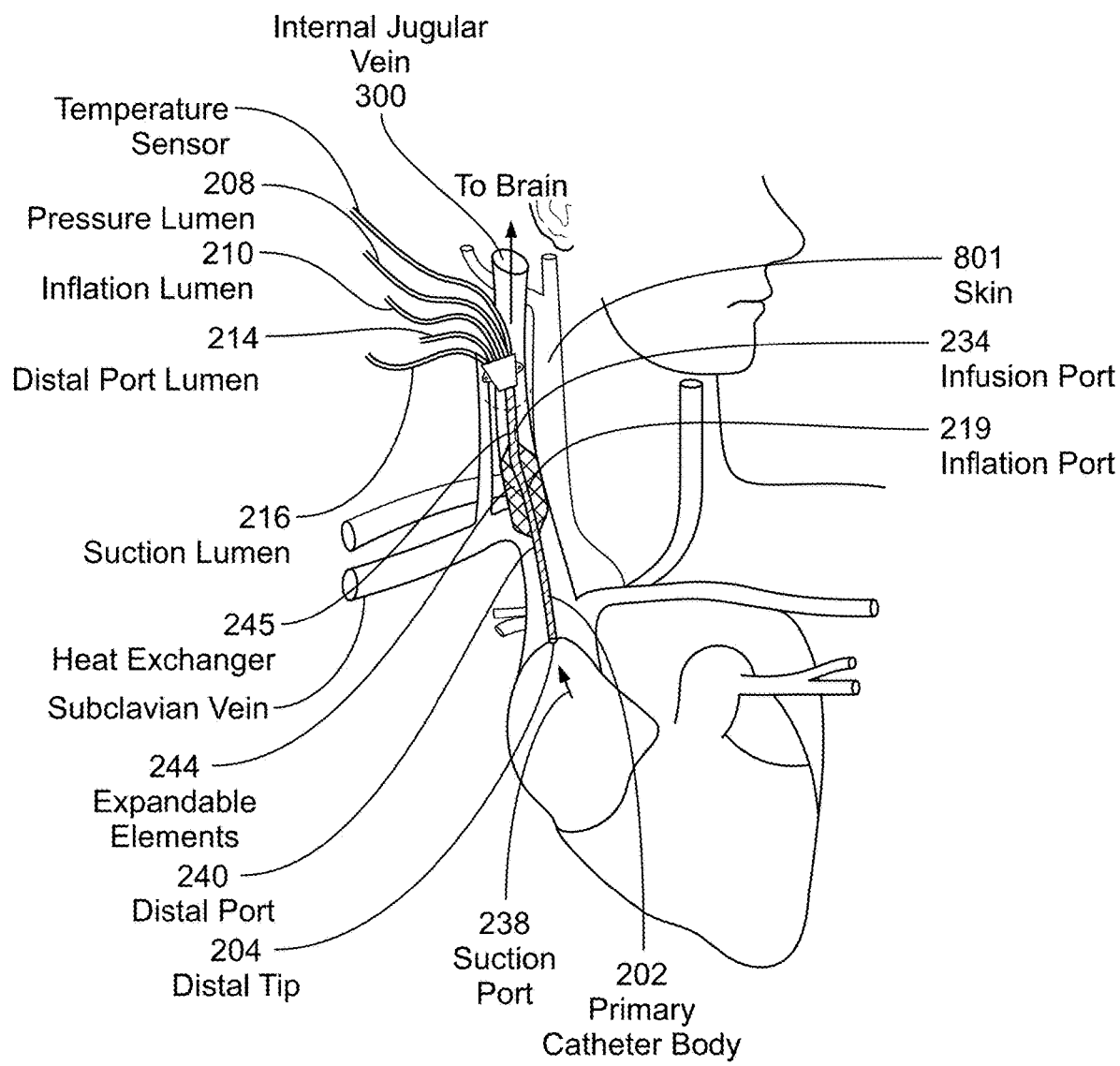
FIG. 58 illustrates a system for therapy with a catheter configured as an intracorporeal heat exchanger, in accordance with some embodiments of the disclosure.

3.6 Intracorporeal Heat Exchanger (See FIG. 58)

In some clinical scenarios, such as reduction of brain injury during ischemic events including ischemic stroke, cooling may be desired for neuroprotection. The cooling may be conducted by locally cooling blood, crystalloid, or another fluid (the working fluid) flowing through a lumen of the catheter device. The cooling catheter may comprise a flexible catheter with a lumen to deliver the working fluid to the target organ, and one or more coolant lumens which may be in thermal contact with the working fluid lumen. The catheter may allow an interventional tool, like a device intended for thrombectomy or angioplasty, to pass through to enable a method of use of the device during thrombectomy or angioplasty. The catheter may be used with a cooling loop system which may comprise a control module, a pump, a heat exchanger, a flow loop connecting the pump and heat exchanger and a catheter, such as the therapy delivery system described herein. A pressure, temperature, or flow probe may be in the fluid flow loop and may be used to measure the status of the cooling of the fluid in the catheter, or the cooling status of the body. The cooling status of the body may be measured by temperature sensors on a patient's body, such as nasopharyngeal or tympanic temperature sensors. These temperature sensors may be placed on or in the body of a human. These sensors may communicate with the control unit, which may use these measurements to determine the flow rate of the pump and the amount of heating/cooling to be transferred to the working fluid. The pump may move the fluid, the heat exchanger may heat or cool the fluid, and the control unit may adjust the flow rate of the pump and the heat exchange capacity.

In some embodiments, a catheter device may be used with this cooling loop system. FIG. 58 illustrates a system for therapy with a catheter configured as an intracorporeal heat exchanger, in accordance with some embodiments of the disclosure. The device may be placed in the venous system, or arterial system. After device placement, the device may be navigated into position for selective organ cooling. Navigation may comprise the use of a guidewire to navigate the vessels and continuous x-ray (fluoroscopy) in order to place the device in a position for selective organ cooling. The selected organ may be the brain, and it may be selected because it may be undergoing ischemic damage and would benefit from neuroprotective hypothermia. The catheter may be placed in the carotid artery so that flow exiting from the device goes directly to the brain. The fluid cooling loop pump may be started so that cold fluid is circulating within the device in the lumen or lumens in thermal contact with the working fluid channel. Working fluid, either cold saline, cold blood, or cooled and oxygenated blood may be pumped through the working fluid channel and delivered to the selected organ. The cooling loop may serve to keep this working fluid cold before it is outlet at the end of the catheter. This therapy may be maintained for long periods of time, such as 2-12 hours with a control system which monitors temperature and pressure, amongst other variables. The catheter may additionally include a balloon to anchor it in place and prevent it from moving during operation. The balloon may be occlusive in order to block flow to all or a portion of the selective organ.

In some instances, the blood may be taken from a first location, cooled intracorporeally, and then reinfused at a second location at the lower temperature. The active cooling of the blood may take place while the blood may be flowing through one or more lumens of a catheter inside the body. The cooling may be done using a heat exchange surface in thermal communication with one or more lumens carrying a cooling fluid. The heat exchange surface can have coolant circulating in other lumens of the catheter or may have elements externally disposed on the catheter which allow for cooling of the fluid in the lumen. The externally disposed elements may be balloons in which a coolant fluid may be circulated. For example, a suction catheter may be placed in the femoral artery, and an infusion catheter may be placed in the internal jugular vein. An intracorporeal circuit, connecting the suction and reinfusion catheters inside the body, may drive flow from the artery to the internal jugular vein. There may be additional channels in the intracorporeal conditioning device which allows cold fluid to be circulated, this cold fluid being in thermal communication with the blood passing through the intracorporeal conditioning device. The cold fluid may cool down the blood passing through the intracorporeal circuit, allowing the temperature to be lower when the blood is delivered to internal jugular vein. This allows for the administration of oxygenated, chilled blood which may be used to mitigate brain damage in stroke patients. In some instances, the catheter may need additional length to facilitate additional cooling of the fluid passing through the catheter.

Figure 59A:
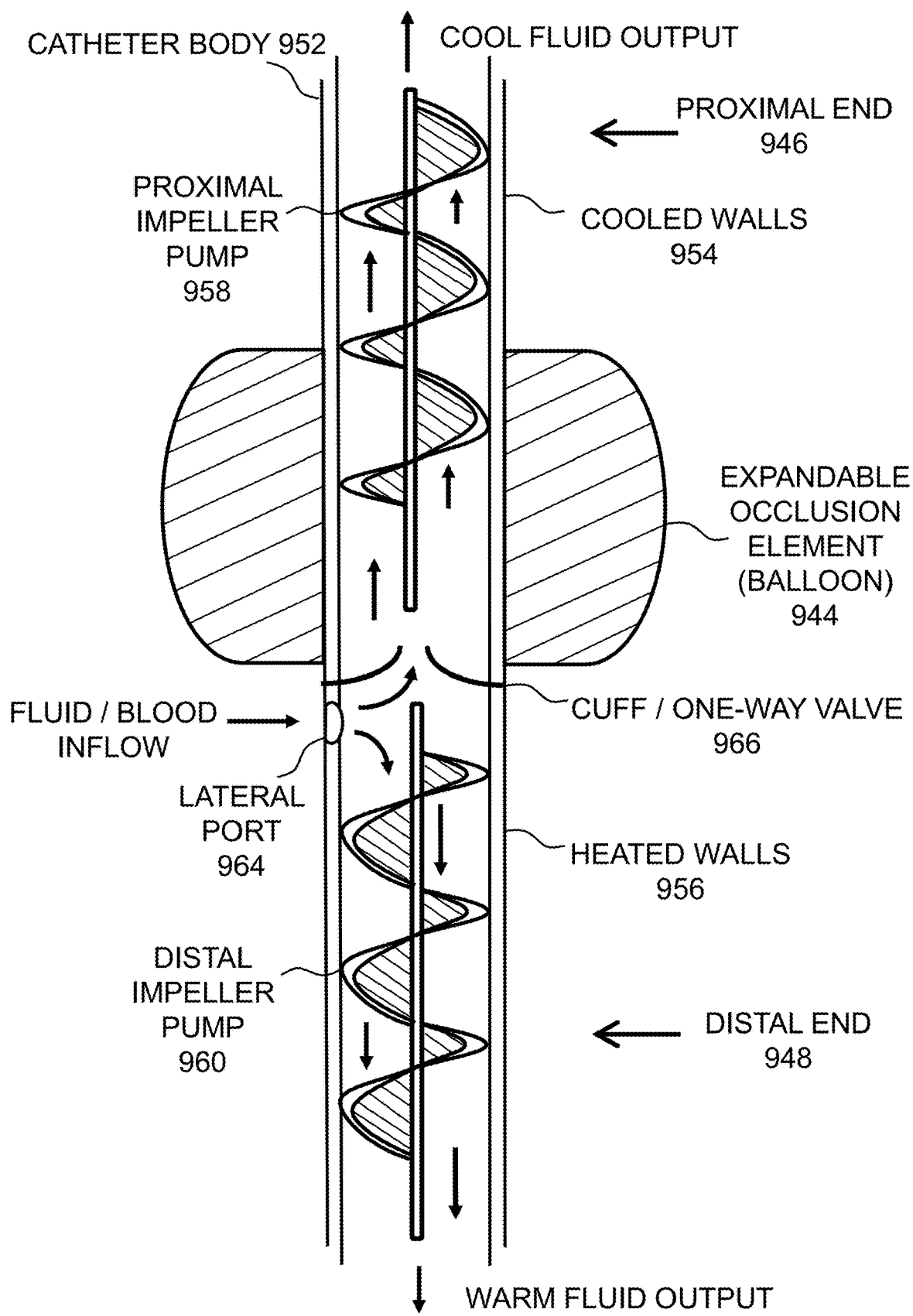
FIG. 59A illustrates an embodiment of a catheter with an impeller, in accordance with some embodiments of the disclosure.
Figure 59B:
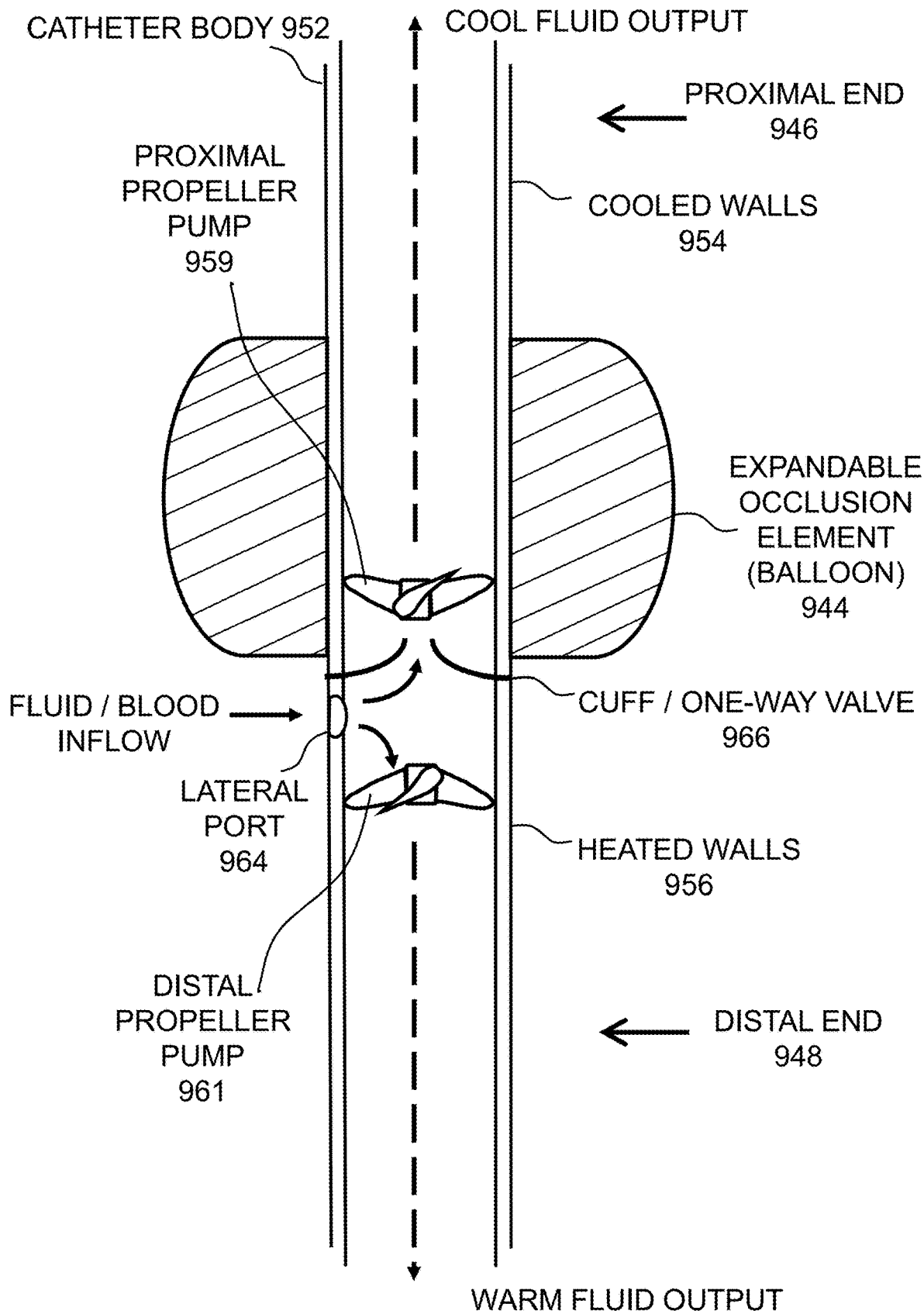
FIG. 59B illustrates an embodiment of a catheter with a propeller, in accordance with some embodiments of the disclosure.

3.7 Impeller Catheters (see FIGS. 59A and 59B)

FIG. 59A illustrates an embodiment of a catheter with an impeller, in accordance with some embodiments of the disclosure. FIG. 59A depicts catheter body 202 952 with a proximal end 206 946 and a distal end 204 948. In some embodiments, catheter body 202 948 may be inserted into a patient's vasculature to create an occlusion in the internal jugular vein and produce flows of cool fluid proximally and normothermic or hyperthermic fluid distally. For instance, catheter body 202 948 may be inserted with the distal end 204 948 positioned in the patient's superior vena cava or right atrium to direct normothermic or hyperthermic fluid toward a patient's heart and proximal end 206 946 may be positioned in a patient's internal jugular vein to create a retrograde flow of hypothermic fluid in the patient's cerebral vasculature. Catheter body 202 952 creates cool fluid output of the proximal end 206 946 and warm fluid output of distal end 204 948.

Separating proximal end 206 946 and distal end 204 948 are an expandable occlusion element 944 and cuff/one-way valve 966. Expandable occlusion element 944, typically an inflatable balloon, is secured to an external surface of elongated catheter body 202 952. Expandable occlusion element 944 can assume an expanded configuration and a contracted configuration, typically comprising a balloon structure fluidly connectable to a source of inflation fluid, e.g., saline. As catheter body 202 952 in inserted venously in a patient, expandable occlusion element 944 may be expanded to occlude blood flow outside of catheter body 202 952.

In catheter body 202 952, distal of expandable occlusion element 944 and cuff 966 is lateral port 964 which allows fluid/blood inflow. In some embodiments, as fluid enters lateral port 964, fluid may flow proximally through cuff 966. Fluid may be pulled proximally by proximal impeller pump 958. As fluid is moved proximally, cooled walls 954 cool the fluid. Cool fluid may be output through proximal end 206 946 to create a flow of hypothermic fluid, e.g., into a patient's cerebral vasculature.

In some embodiments, as fluid enters lateral port 964 fluid, may flow distally. Fluid may be pulled distally by distal impeller pump 960. As fluid is moved distally, heated walls 956 warm the fluid. Warm fluid may be output through distal end 204 946 to create a flow of normothermic or hyperthermic fluid, e.g., toward a patient's heart.

Cooled walls 954 and heated walls 956 may be cooled/heated in various ways. For instance, each wall could be made of a conductive material, separated from each other with a nonconductive barrier, and cooled or heated respectively. In some embodiments, each wall may be filled with cooled or warmed fluid, respectively. In some embodiments, cooled walls 954 and heated walls 956 may have additional insulation and/or safety coating. Each of proximal propeller pump 959, distal propeller pump 961, cooled walls 954, and heated walls 956 may be powered by, e.g., on-board batteries and/or extracorporeal electric circuits.

In some embodiments, one or more temperature probes may be incorporated in catheter body 202 952. For instance, thermistors or other sensors may be placed at proximal end 206 946 or distal end 204 948. A catheter may include a controller, e.g., with a processor and memory, to collect temperature data from temperature sensors and adjust flow rate by each of proximal impeller pump 958 or distal impeller pump 960, as well as temperatures of cooled walls 954 or heated walls 956.

In some embodiments, elongated impeller pumps 958 and 960 may be replaced by smaller pumps 959 and 961. FIG. 59B illustrates an embodiment of a catheter with a propeller, in accordance with some embodiments of the disclosure. Each of proximal propeller pump 959 and distal propeller pump 961 may be powered by, e.g., on-board batteries and/or extracorporeal electric circuits.

In some embodiments, in catheter body 202 952, distal of expandable occlusion element 944 and cuff 966 is lateral port 964 which allows fluid/blood inflow. As fluid enters lateral port 964, fluid may flow proximally through cuff 966. Fluid may be pulled proximally by proximal propeller pump 959. As fluid is moved proximally, cooled walls 954 cool the fluid. Cool fluid may be output through proximal end 206 946 to create a flow of hypothermic fluid, e.g., into a patient's cerebral vasculature.

In some embodiments, as fluid enters lateral port 964 fluid, may flow distally. Fluid may be pulled distally by distal propeller pump 961. As fluid is moved distally, heated walls 956 warm the fluid. Warm fluid may be output through distal end 204 946 to create a flow of normothermic or hyperthermic fluid, e.g., toward a patient's heart.

Figure 60:
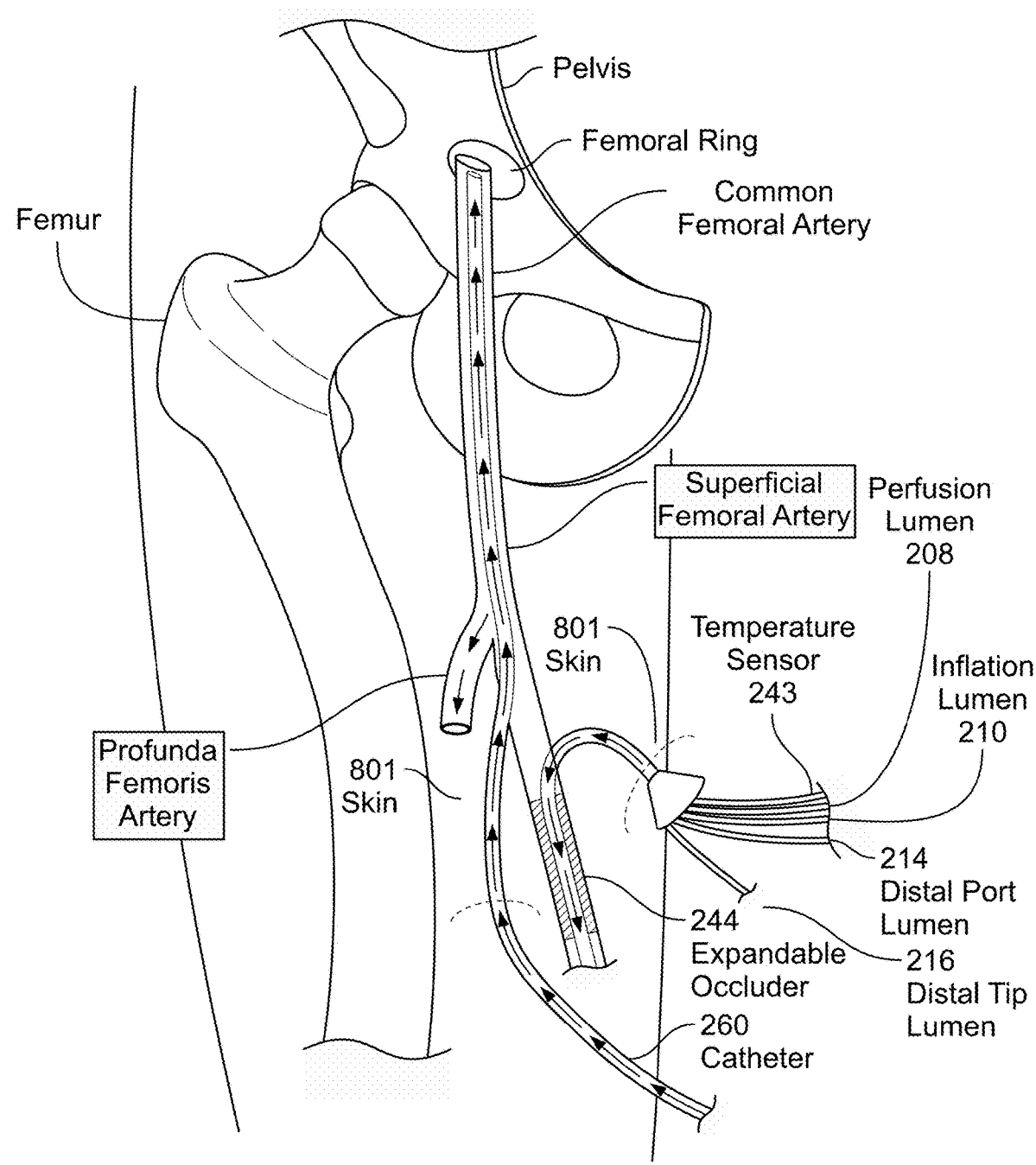
FIG. 60 illustrates a system for therapy with a catheter configured for limb perfusion, in accordance with some embodiments of the disclosure.

4.0 Methods of Catheter Use 4.1 Limb Perfusion (See FIG. 60)

Some embodiments may include a method for treating a patient comprising introducing a catheter into the patient's arterial vasculature, such as during extracorporeal membrane oxygenation. In some embodiments, the infusion catheter herein described may be placed in the patient's vasculature, possibly in the superficial femoral artery. FIG. 60 illustrates a system for therapy with a catheter configured for limb perfusion, in accordance with some embodiments of the disclosure. The device may be used to selectively occlude the vasculature via deployment of an expandable occluder on an exterior of the catheter within the patient's superficial femoral artery. In this specific instance, occluding the patient's superficial femoral artery may help to maintain blood flow from the common femoral artery to the femoral profunda, aiding in perfusion of the limb of the patient. The device may similarly be placed in the common femoral artery, and potentially navigated to the superficial femoral artery for occlusion and infusion of fluids.

Figure 61:
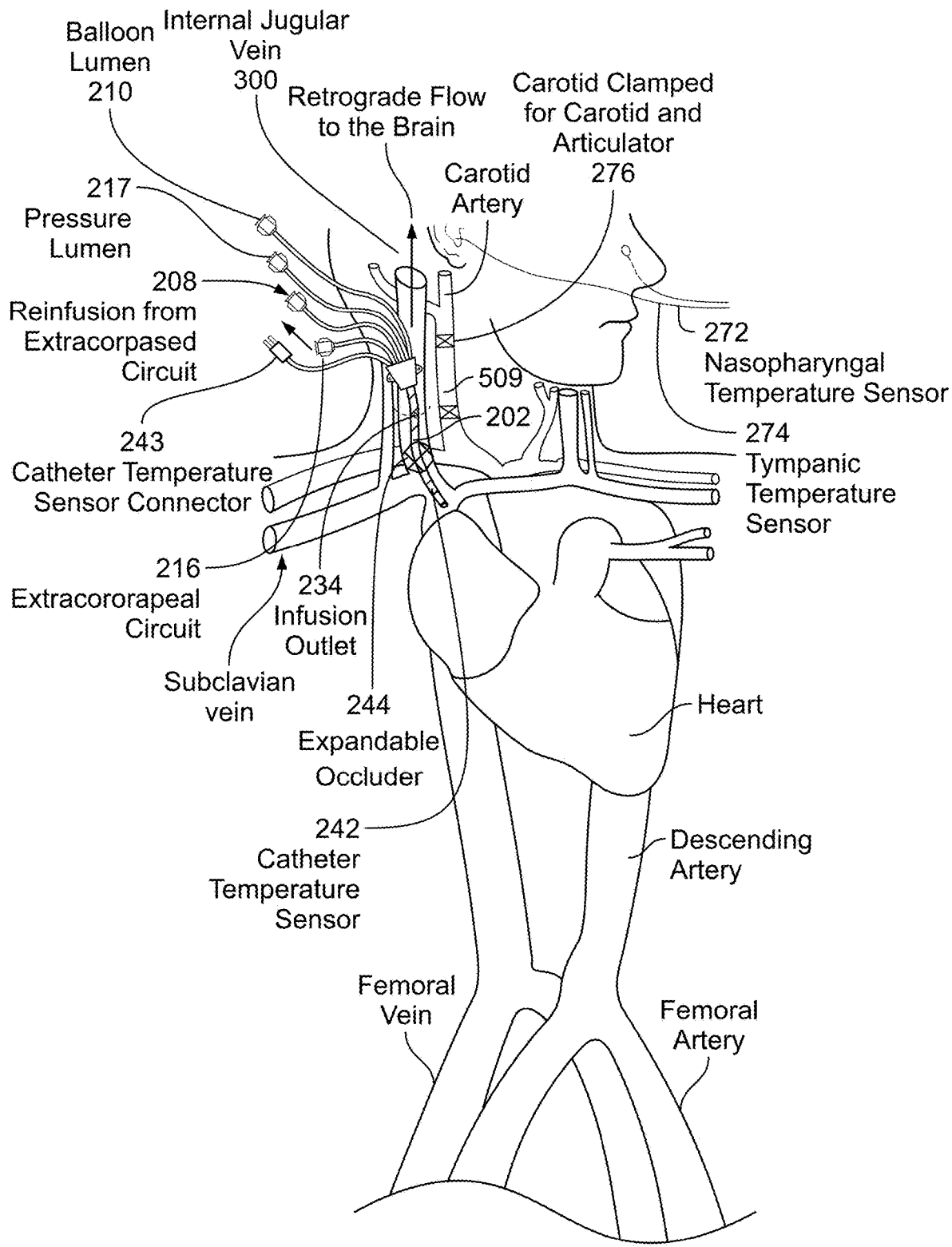
FIG. 61 illustrates a system for therapy with a catheter during a carotid endarterectomy procedure, in accordance with some embodiments of the disclosure.

4.2 Carotid Endarterectomy (See FIG. 61)

The systems and devices described herein may also be used to selectively cool the brain during a carotid endarterectomy procedure, in which plaque may be removed from the carotid artery. FIG. 61 illustrates a system for therapy with a catheter during a carotid endarterectomy procedure, in accordance with some embodiments of the disclosure. This procedure may involve a temporary ischemic event, during which cooling may be advantageous for neuroprotection. Selective retrograde neural cooling, neuroprotection using oxygenated blood or a drug, or the like, as described herein, may be used to mitigate potential risks of this procedure. Additionally, placement of the device in the setting of carotid endarterectomy may occur via surgical cut-down upon visualization of the internal jugular vein, rather than via a percutaneous approach.

Figure 62:
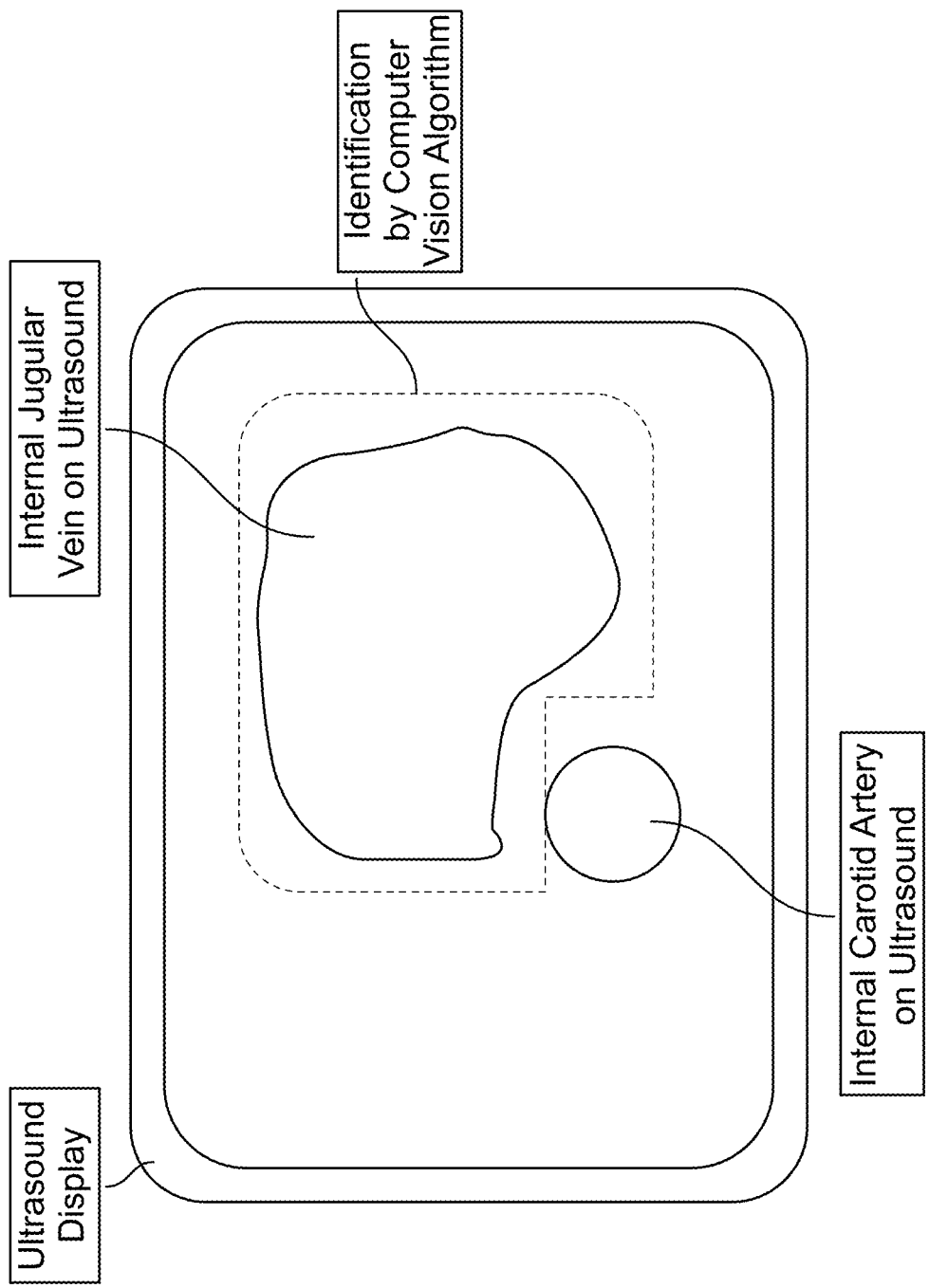
FIG. 62 illustrates a system for automated placement of a catheter, in accordance with some embodiments of the disclosure.
Figure 63:
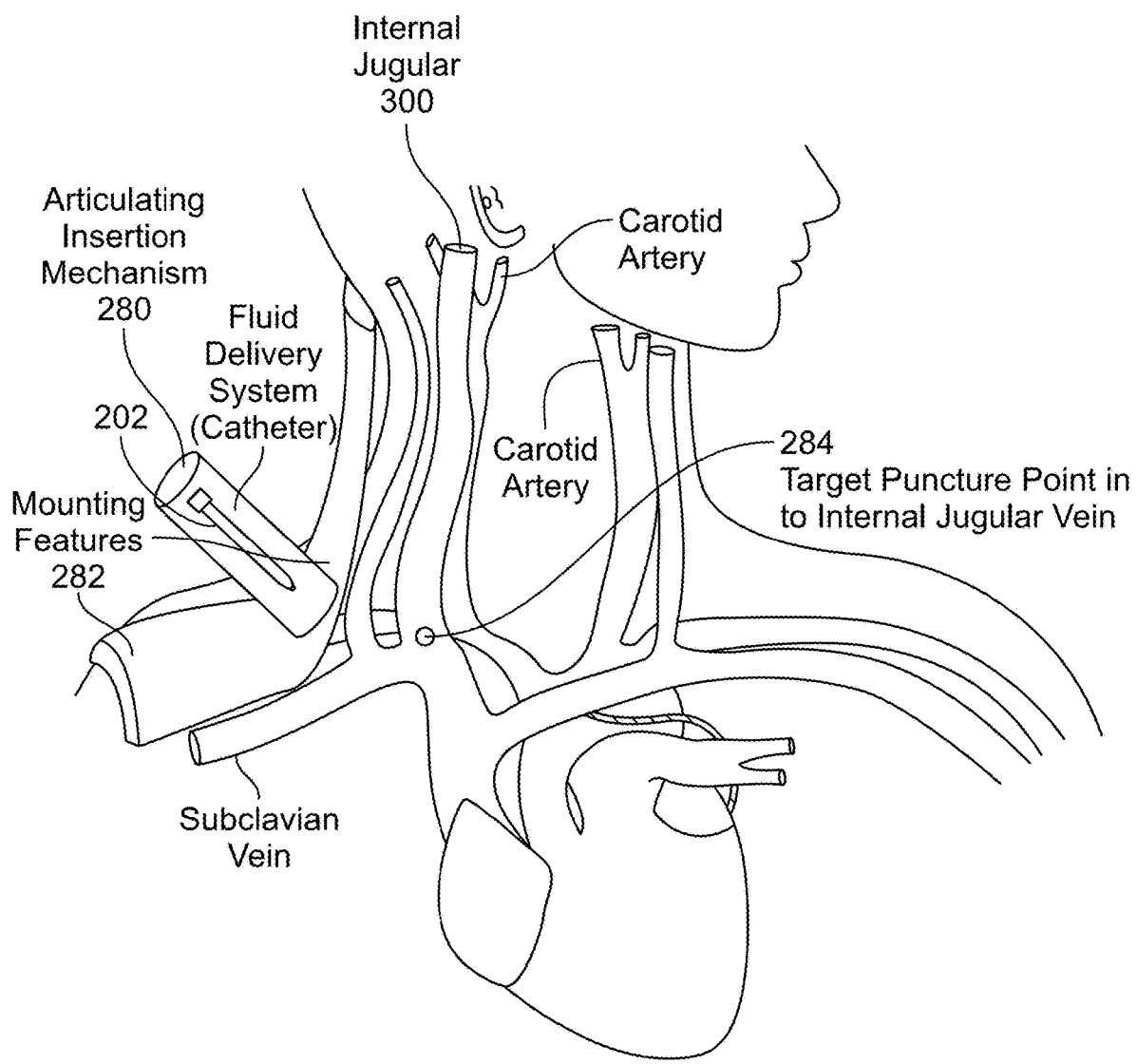
FIG. 63 illustrates a system for automated placement of a catheter, in accordance with some embodiments of the disclosure.

5.0 Automation of Catheter Placement (See FIGS. 62-63)

A system for fully or partially automating the insertion of a fluid delivery device into a fluidic system is described herein. The system may be known as the automated insertion system. The fluid delivery device may be an arterial or venous catheter, such as the perfusion catheter described herein. The fluidic system to which the device may be inserted may be a blood vessel of the human body. The delivered fluids may be therapeutic media, drugs, crystalloid, colloids, blood product, or the like. The automation elements of the system may include an algorithm for identifying regions on medical imaging data to identify a relevant structure in the fluidic system. Further automation elements may include an articulating insertion mechanism which can either assist in placing the device for delivery of fluids to the fluidic system or may be fully capable of placing the device for delivering fluids to the fluidic system. The system may be used for enabling percutaneous access of veins and arteries in a multitude of settings, especially unconventional settings for percutaneous access, especially outside of the hospital.

In some embodiments, the device for delivering fluids may be an arterial or venous catheter. The catheter may be an infusion catheter comprising an elongated catheter body 202 having one or more lumens. Flow of various media, described herein, may be passed through the lumens of the device. The device for delivering fluids may have an expandable occluder, which may be used to block off vessels in the fluidic system. The catheter may be the infusion catheter disclosed previously, or a similar catheter with an expandable occluder, however it is understood that there are iterations of the device which do not contain an expandable occluder. One or more lumens may be used for delivering fluids. The device may have a tapered tip to enable the device to be placed through an orifice by the automated insertion system. The device may have adhesive or other non-invasive attachment method to an external surface. For example, a catheter may have an adhesive coated portion which can be used to secure the catheter to the body of a patient so that the device does not need to be sutured onto the skin of the patient.

In some embodiments, the fluidic system into which the automated insertion system places the device may be a blood vessel of the human body. The blood vessel may be either a vein or artery. When inserted into the venous system, the device may be inserted into the central vasculature, such as the internal jugular vein, femoral vein, or a similar insertion point, or in to the peripheral vasculature, such as the subclavian vein, the cephalic vein, or similar insertion point. In some instances, the device placed into a vein may be capable of occluding the normal direction of blood flow, such as by using an expandable occlusion element, and, with the normal direction of flow occluded, flow through the device may be directed retrograde in the venous system. When inserted into the arterial system, the device may be inserted into the central vasculature, such as the internal carotid artery, femoral artery, or a similar insertion point, or in to the peripheral vasculature, such as the brachial artery, the radial artery, or similar insertion point. When placed in the artery, flow through the device may be directed in the antegrade direction. Both the antegrade arterial and retrograde venous flow may be used for selective cooling of one or more target organs.

In practice, the device may be a central venous catheter placed in the internal jugular vein. In another scenario, this device may be the infusion catheter herein described and may be used to cool the brain by blocking off flow in the internal jugular vein with an expandable occluder and directing the flow of cooled fluids to the brain.

In some instances, the delivered fluids may be therapeutic media, drugs, crystalloids, colloids, blood product, or the like. Mechanisms on the inserted catheter may be capable of directing the flow path of the delivered fluids. For instance, a catheter with an expandable occlusion element may occlude the vein it may be placed in, thereby facilitating retrograde flow in this vessel. The delivered fluids may be temperature modulated so as to induce cooling or warming of all of the fluidic system or a specified region of the fluidic system. The temperature modulation of fluids may be done by a heat exchanger. The delivered fluid may be delivered by the therapy delivery system disclosed herein, or by a system with some or all of the same features. The flow of the delivered fluids may be driven by a pump or pumping mechanism. The pump may be small enough to fit on an ambulance and may be between 0 cubic foot and 5 cubic feet in volume. The delivered blood may be oxygenated and may be oxygenated by an external oxygenator. The delivered fluid may be delivered by the therapy delivery system disclosed herein, or by a system with some or all of the same features.

In some instances, the automation elements of the system may include an algorithm for identifying regions on medical imaging. FIG. 62 illustrates a system for automated placement of a catheter using, e.g., an ultrasound, in accordance with some embodiments of the disclosure. The algorithm may be used to identify a relevant structure in the fluidic system. The relevant structure may be a blood vessel of the human body, such as the internal jugular vein. The blood vessel identified may be the vessel into which the fluid delivery device will be placed. The medical imaging used may be ultrasound, computer tomography, or fluoroscopy. The algorithm may make use of computer vision to identify the relevant structure. The algorithm may be a deep learning algorithm which may have trained on a dataset of labeled medical imaging scans and may be able to identify relevant structures to a high degree of accuracy. The deep learning algorithm may be a clustering algorithm, an object detection algorithm, or similar algorithm which can identify structures on video or pictures. A convolutional neural network may be implemented to identify the relevant structure on the medical imaging data. The outputs of the algorithm may include guidance and instructions for a user, and this output may be displayed on the screen on a console. The guidance and instructions may include directions on the optimal placement location to insert a fluid delivery device into a blood vessel of the body, a suggested angle of insertion into a blood vessel, the force or speed at which to puncture into the blood vessel, or similar instructions to facilitate correct placement, which may enable the device to be placed semi-autonomously and to be placed by a medical professional other than a doctor. Alternatively, the outputs of the algorithm may be used as inputs to the articulating insertion mechanism to allow it to place a fluid delivery device into a blood vessel fully autonomously.

In practice, the medical imaging algorithm may analyze a live stream of ultrasound data coming from an ultrasound probe. The algorithm may be used to identify the internal jugular vein in order to identify the insertion location for a central venous catheter. The algorithm may identify the internal jugular or other pertinent vessel on a screen. Instructions may then be given to the operator on the screen regarding an optimal location, angle, force, speed, or some combination thereof to use when inserting the central line. Alternatively, the outputs of the algorithm may be used as inputs to the articulating insertion mechanism to allow it to place a fluid delivery device into a blood vessel fully autonomously.

In some embodiments, automation elements may include an articulating insertion mechanism which can either assist in placing the device for delivery of fluids to the fluidic system or is fully capable of placing the device for delivering fluids to the fluidic system. FIG. 63 illustrates a system for automated placement of a catheter including an articulating insertion mechanism, in accordance with some embodiments of the disclosure. The articulating insertion mechanism may be controlled by a control system. The articulating insertion mechanism may be a robotic inserter capable of moving in at least 1 degree of freedom in order to align with an insertion point on the body. The articulating insertion mechanism control system may be computer numerically controlled, and this control system may control the feed rate, positioning, and speed of the articulating insertion mechanism. The articulating insertion mechanism may have an apparatus for maintaining the fluid delivery device, such as a catheter, such as a central venous catheter, in a first position, outside of the fluidic system, and this apparatus may be able to move the fluid delivery device to a second position, so that it may be inserted through an orifice and into the fluidic system. The fluidic system may a blood vessel of the human body, such as the internal jugular vein. Placement of the device may follow a technique similar to the Seldinger technique, in which access to the vein may be established with a needle puncture, the skin may be opened slightly with a small incision, a guidewire may be placed, and dilators used as needed to prepare the vessel for device placement, before the device may be introduced to the vessel over the guidewire. In some instances, the apparatus for holding the fluid delivery system may be a linear retraction mechanism which can advance or retract the fluid delivery device, which may be a central venous catheter, placed in the linear retraction mechanism. The orifice may be a hole or puncture in the skin of a patient, and the fluidic system may be the veins of said patient. The control system for the articulating inserter may take input from the algorithm for identifying a region on medical imaging to determine the optimal insertion point for the fluid delivery device. The articulating insertion mechanism may contain mounting features which allow it to be secured to an external structure. The external structure may be the human body, and the articulating insertion mechanism may be anchored to a specific location near a target blood vessel into which the fluid delivery device may be placed. The mounting features may allow for stabilization and calibration of the articulating insertion mechanism, to allow the insertion mechanism to consistently insert the device in a particular location, which may be a particular location on the human body. Before the fluid delivery device may be inserted, a placement probe, such as a needle, may be first used to puncture the fluidic system and ensure the fluid delivery device will be placed in the correct region of the fluidic system. A sensor, such as a pressure sensor, flow sensor, or temperature sensor may be used to detect when the placement probe or fluid delivery device may have been successfully placed into the fluidic system. In the instance where this fluidic system is the blood vessels of the human body, the sensor may detect a flow rate, pressure change or temperature change when the fluid delivery system, such as a catheter, punctures in a blood vessel. The puncture may produce a flash of blood flowing from the higher pressure system, such as the blood vessel, to the lower pressure system, such as the catheter, and this flash may indicate when the placement probing needle or fluid delivery device has successfully been placed in the correct vessel or unsuccessfully placed in the incorrect vessel. The control system may use the input from this sensor to determine if the fluid delivery device has been placed correctly in the fluidic system, and therefore does not need to be substantially moved, or if the fluid delivery device has not been placed correctly in the fluidic system, and therefore needs to be moved substantially.

In practice, the articulating insertion element may carry a catheter, potentially a central venous catheter, attached to a linear actuator to retract and extend the catheter for insertion into the central venous system. A secondary actuating system may be capable of moving in 1 or more degrees of freedom to control the feed rate, position, and angle of the linear actuator. This secondary system may take inputs from the algorithm for identifying regions on medical imaging, and position the linear actuator at a point identified to be optimal for placement of the catheter into the vein. A control system may control and coordinate the movements of the linear actuator and the secondary system, and this control system may also take input from a sensor which detects when the catheter or placement probe needle may have entered the correct vessel in the body. The sensor may detect pressure or flow readings that are too high for the venous system, in which case the device may likely be in place in an artery, so the control system may remove the placement probe or catheter and reposition it in the correct vessel.

The system may be used for enabling percutaneous access of veins and arteries in a multitude of settings, especially unconventional settings for percutaneous access, especially outside of the hospital. The system may be used by EMTs, nurses, or similarly trained medical professionals, either at the scene of an incident or during transport to the hospital. The system may be used to percutaneously place a device in the ambulance on the way to the hospital. The device may be placed in patients who are having a stroke to deliver therapy to potentially reduce brain damage sustained during transit. The system may also be used at the scene of an incident, to deliver therapy as soon after the incident as possible. In some instances, a person untrained in medicine may be able to place the system on a patient. In these situations, the automation of the system allows less skilled medical practitioners to begin delivery of therapy before a patient reaches the hospital. In addition to out-of-hospital stroke treatment, this approach may also be used for the treatment or cardiac arrest or traumatic brain injury, among other ischemic or traumatic events.

II. Gastric Lavage for Central Temperature Management

An additional device is herein disclosed and described which would aim to help maintain systemic body temperature near normothermic during intrajugular retrograde cooled infusion for targeted cerebral hypothermia. If the counterwarming mechanism described in the infusion catheter above may not achieve the desired level of brain-body temperature differential, an additional device is proposed to selectively warm the body while allowing for cerebral cooling to continue.

The use of gastric lavage as a method of central temperature management has been previously demonstrated in animal models of hypothermia; canine studies by Brunette et al. 1987 have shown that gastric lavage as a method of rewarming is significantly slower than pleural lavage with warm solution. Theoretically this may be due to the relatively small surface area to volume ratio of the stomach, as well as the relatively thick and well vascularized gastric wall. However, while this would prove to be a significant limitation with regard to rewarming a hypothermic patient, these anatomical characteristics may allow for the stomach to serve as the perfect organ for the maintenance of a desired central temperature. It is also possible that the location of the stomach relative to the inferior vena cava, as well as the diaphragm (and arguably the mediastinum) may serve to allow for the maintenance of central intravascular temperature prior to or at the time of regional cerebral hypothermia.

Figure 64:
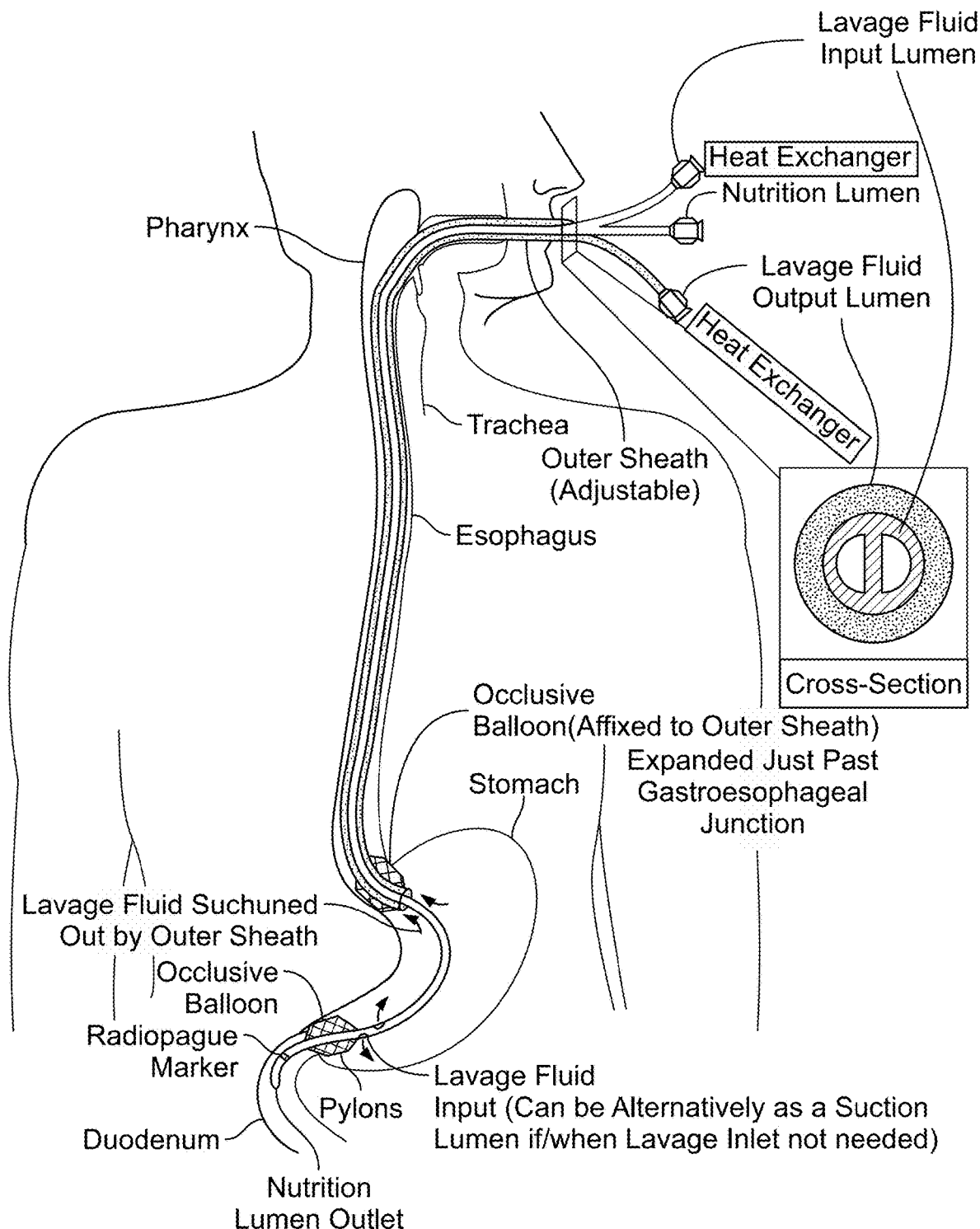
FIG. 64 illustrates a system for therapy gastric incorporating lavage for central temperature management, in accordance with some embodiments of the disclosure.
Figure 65:
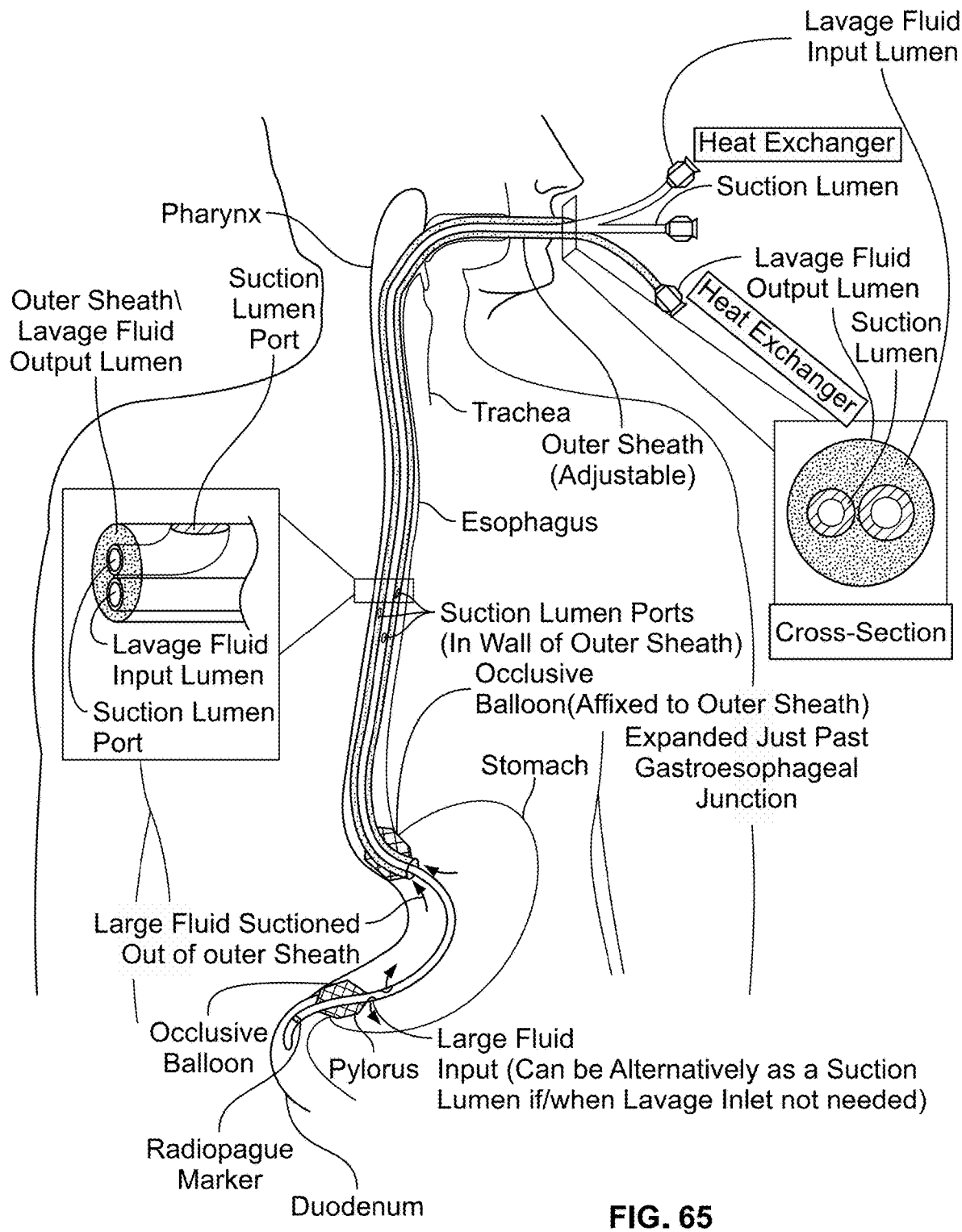
FIG. 65 illustrates a system for therapy incorporating gastric lavage for central temperature management with an outer sheath, in accordance with some embodiments of the disclosure.

The herein described multi-lumen gastric lavage tube can be used as an adjunct in central temperature management. FIG. 64 illustrates a system for therapy incorporating gastric lavage for central temperature management, in accordance with some embodiments of the disclosure. The gastric lavage tube comprises a multi-lumen device having a proximal and distal expandable occluder, referred to additionally as an occlusive balloon(s). The gastric lavage tube is designed with an outer diameter of sufficient size, possibly 36 Fr. The tube may have an outer sheath to allow for proximal and distal movement. Affixed to the body of this sheath is the proximal expandable occluder. FIG. 65 illustrates a system for therapy incorporating gastric lavage for central temperature management, with an outer sheath, in accordance with some embodiments of the disclosure. A proximal expandable occluder will be used to occlude the gastro-esophageal junction and prevent reflux of warmed contents into the esophagus.

A distal expandable occluder, affixed to the body of the gastric lavage tube, allows for occlusion of the pylorus. A radiopaque tip allows for placement of the tube under fluoroscopic guidance and/or ultrasound guidance. A distal port 240(s) allows for inflow of warm solution to be initiated prior to or at the time of regional cerebral hypothermia. A temperature probe can be placed in one port for accurate measurement of intra-gastric temperature additionally, or may be incorporated into the gastric lavage tube itself in some embodiments.

The most proximal ports (which are strategically placed just distal to the proximal expandable occluder) will allow for suction of perfusate and transfer to a heat exchanger for rewarming and return to the gastric lumen, thus allowing for maintenance of a constant intra-luminal temperature. Additional embodiments of this gastric lavage tube may contain lumen(s) outletting proximal to the proximal balloon (within the esophagus) for placement of an esophageal temperature probe and/or suction of esophageal contents to minimize the risk of aspiration. Another iteration may contain an additional lumen outletting distal to the distal expandable occluder at the pylorus, to allow for enteral feeding in the event that long term placement of the lavage tube is necessary.

Use of this gastric lavage tube may require endotracheal intubation given the risk of aspiration, a large volume of warm perfusate to sufficiently distend the stomach and achieve the desired temperature, require radiographic adjuncts to ensure adequate positioning of the tube.

Administration of warmed fluids through the gastric lavage tube may include crystalloids, blood product, medicaments, or a combination thereof. Such fluids, for the purposes of counterwarming the body at or around the time of targeted cerebral hypothermia therapy, may safely be delivered through the gastric lavage tube in the range of 39-40° C., based on existing canine study data.

While the technology described here can be used for counter warming during regional cerebral hypothermia, alternate uses may include maintenance of core hypothermia when desirable, use as an adjunct to active rewarming using other techniques, and for delivery of heated chemotherapeutic agents in the treatment of esophagogastric tumors.

III. Insulated Guide Catheter and Associated Method of Use

Figure 66:
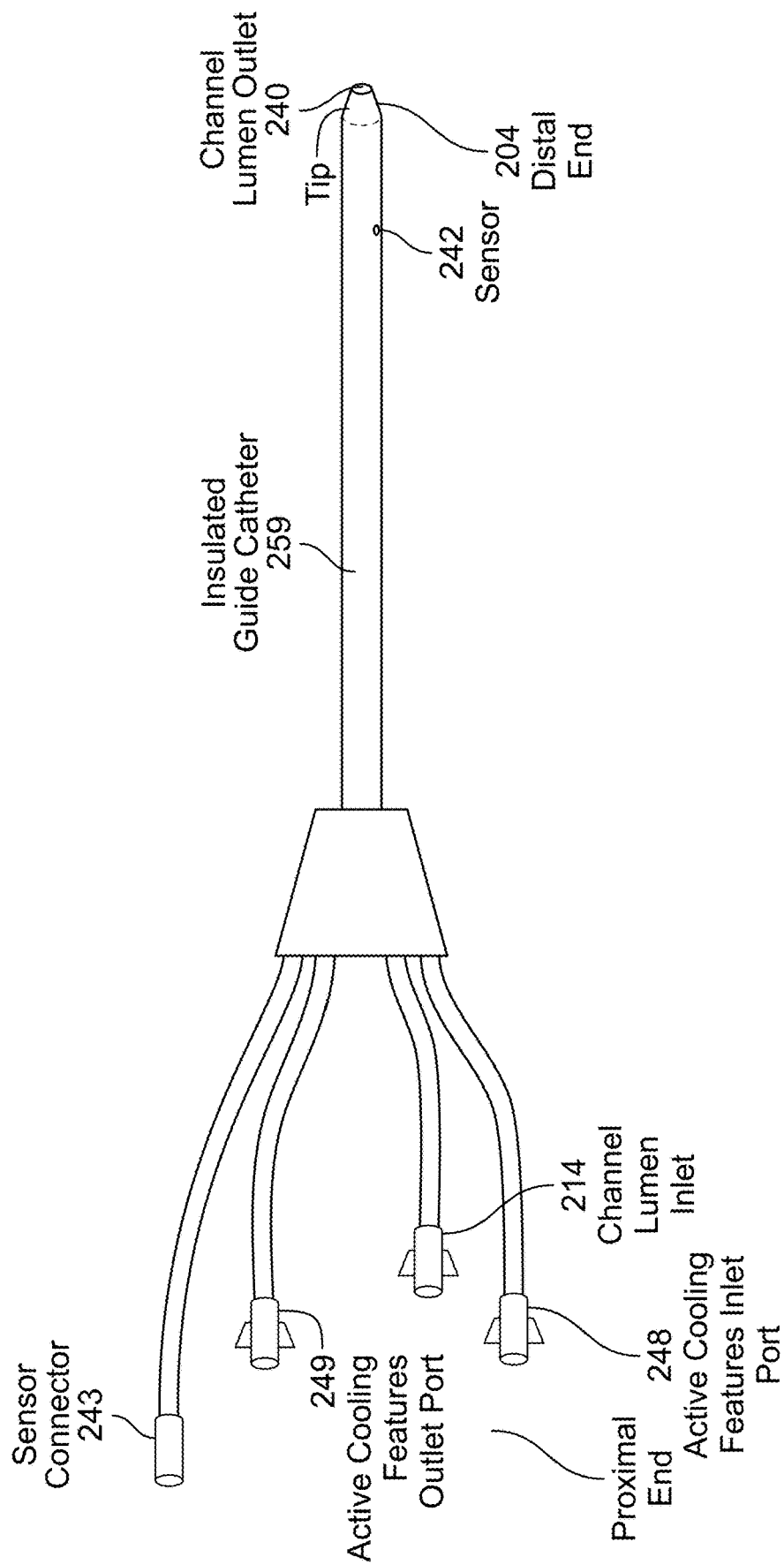
FIG. 66 depicts an exemplary external view of an insulated guide catheter, in accordance with some embodiments of the disclosure.
Figure 67:
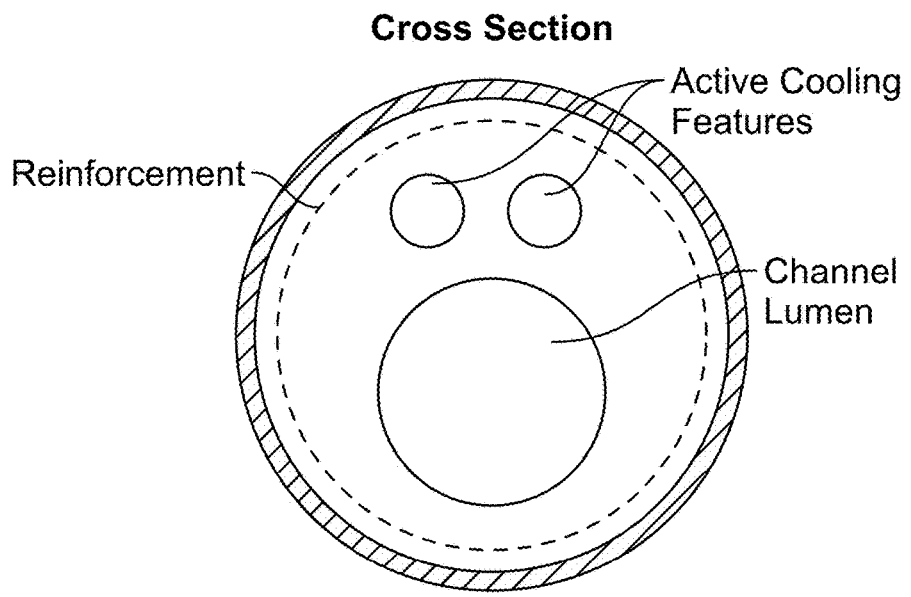
FIG. 67 depicts an exemplary cross-sectional view of an insulated guide catheter, in accordance with some embodiments of the disclosure.

According to some embodiments, the present disclosure provides an insulated guide catheter comprising an elongated catheter body 202 having one or more lumens, extending longitudinally between a proximal end 206 and a distal end 204. FIG. 66 depicts an exemplary external view of an insulated guide catheter and FIG. 67 depicts an exemplary cross-sectional view of an insulated guide catheter, in accordance with some embodiments of the disclosure. The elongated catheter body 202 may have a channel lumen that allows a one or more additional devices to pass through it, such as a thrombectomy catheter, guidewire, or other devices that may be placed coaxially. This channel lumen may also allow for the passage of fluid, which may be cooled fluid, in addition to or in lieu of the additional devices. The catheter may have insulation which may help prevent warming of the cooled fluid flowing through the channel of the catheter. The insulation may be aerogel or aerogel based, or some other similar insulative materials. The aerogel material may take advantage of the Knudsen effect to effectively insulate. The body of the catheter may be made of polymer. The walls of the polymer body may contain reinforcement, such as reinforcement from coiled or braided wire. The reinforcement may provide the catheter with kink resistance, column strength, hoop strength, or similar advantageous mechanical properties. The coiled or braided wire may be stainless steel, nitinol, a liquid crystal polymer (LCP), or some similar reinforcing material. The catheter may have active cooling features which actively lower the temperature of fluid flowing through the catheter. One such active cooling feature may be one or more lumens which may be used to circulate fluid, such as cooled fluid, inside the catheter, which may induce cooling or maintain the temperature of the fluid flowing through the channel. The one or more lumens to circulate fluid may receive an input of fluid to one or more inlet ports at the proximal end 206 of the device and output fluid from one or more outlet ports on the proximal end 206 of the device. The one or more fluid circulating lumens may direct fluid from the one or more proximal inlets, longitudinally to the distal end 204 of the device, and at the distal end 204 of the device the fluid may reach a direction-change point, at which point the fluid may change directions and flow longitudinally to the proximal end 206 of the device where it may outlet through the one or more outlet ports. The fluid flowing through the circulating lumens may be water, air, a refrigerant like R-134A, or some similar fluid. The cross-sectional shape of the circulating lumens may be circular, arcuate, ovular, or some other cross-sectional shape.

Figure 68:
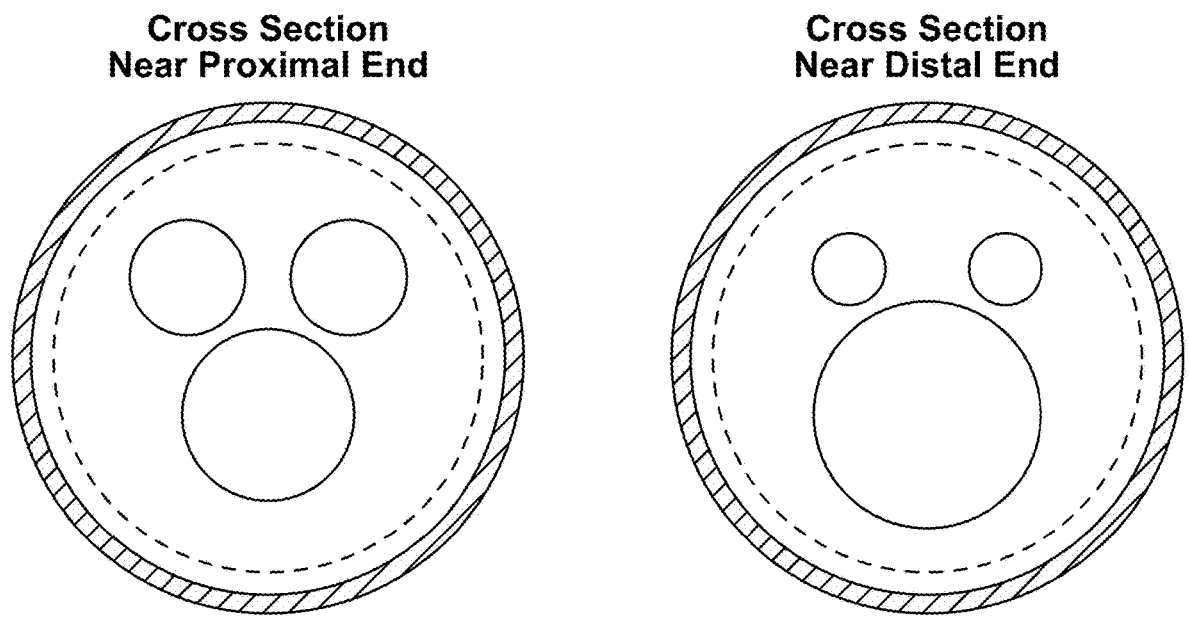
FIG. 68 depicts exemplary cross-sectional views of an insulated guide catheter, in accordance with some embodiments of the disclosure.

The size of the cross-sectional area may taper longitudinally, for instance the cross-sectional area may be larger at or near the proximal end 206 of the catheter, and the cross-sectional area may be smaller at or near the distal end 204 of the catheter. FIG. 68 depicts exemplary cross-sectional views of an insulated guide catheter near each of the proximal end 206 and distal end 204, in accordance with some embodiments of the disclosure. Alternatively, the cross-sectional area may be smaller at or near the proximal end 206 of the catheter, and the cross-sectional area may be larger at or near the distal end 204 of the catheter. The insulated guide catheter may have a tip which may allow the device to be inserted into a vessel without causing damage. The tip may be atraumatic and may allow for the catheter to enter a vessel, such as a blood vessel of the human body, with the intention to minimize damage upon insertion. The tip may also be radiopaque, so that it is visible when used in conjunction with medical imaging, such as x-ray or fluoroscopy. The distal end 204 of the catheter may also contain a distal flexible length, which may allow it to atraumatically navigate through vessels, such as the human vasculature. The catheter may contain one or more sensors to evaluate one or more parameters of the fluids in the catheter, the fluids in the channel, or the surroundings of the catheter. These sensors may include temperature, pressure, flow sensors, or the like. These sensors may allow the measurement of the exit velocity of the fluid flowing through the channel, the exit temperature of the fluid flowing through the channel, the pressure of the fluid flowing through the channel, the pressure of the fluid flowing through the one or more circulating lumens, the temperature of the fluid flowing through the circulating lumens, the temperature of the surrounding, or some similar parameter. The sensor may have an electrical connector, which may be at or near the proximal end 206 of the device, which may allow the device to exchange signals with an external system, such as a cooling console system.

Figure 69:
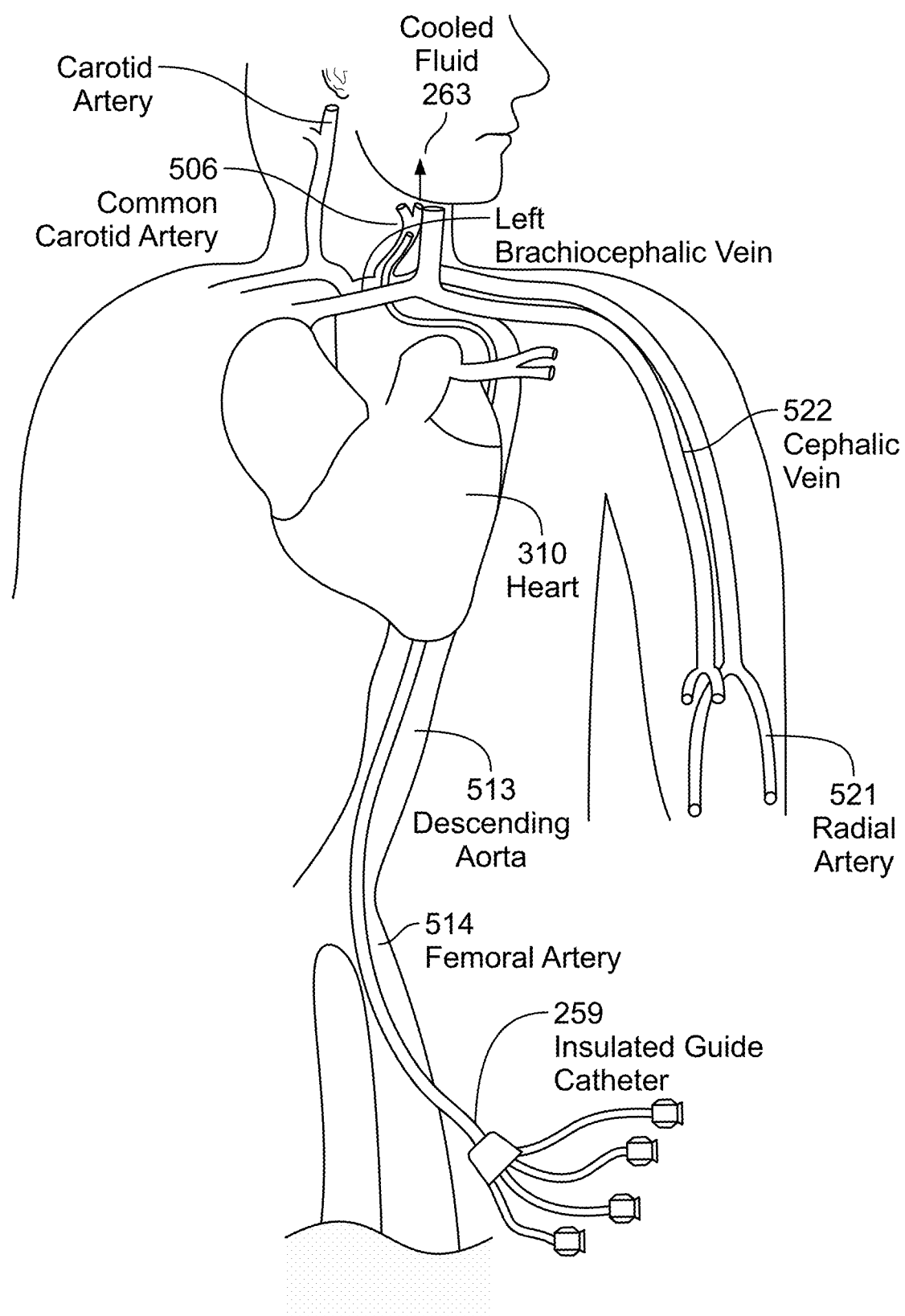
FIG. 69 illustrates a system for therapy incorporating an insulated guide catheter, in accordance with some embodiments of the disclosure.

The insulated guide catheter may be placed in a blood vessel, either a vein or artery of a patient, and may be used for delivering therapy. FIG. 69 illustrates a system for therapy incorporating an insulated guide catheter, in accordance with some embodiments of the disclosure. The channel lumen may be available for infusion of all types of media, including hypothermic, normothermic, hyperthermic and other temperature modulated media, blood products, drugs, medicaments, autologous blood and the like. The catheter may be placed inside a neurovascular support catheter. An example of such a neurovascular support catheter includes a Stryker FlowGate2 or Penumbra Neuron Max. In a preferred embodiment, the outer diameter of the insulated guide catheter is between 0.07-0.09 inches, preferably 0.081 inches, so that it is capable of fitting in the FlowGate2 or Neuron Max 088 neurovascular support catheters. The device may be used for infusion of cooled fluid into the body. The fluid may be infused through the channel lumen of the device, and the one or more active cooling features may circulate chilled fluid in order to cool or maintain the temperature of the fluid infused through the channel. The insulation may allow both the circulating fluid in the circulating lumen and the fluid infused through the channel to remain at a lower temperature than the device's surroundings. The device may be placed in the human body and may be used as a guide catheter for other medical devices, such as a thrombectomy catheter, a guidewire, or a similar medical device. The guide catheter may enter the body through the femoral artery, or some similar arterial access point. It may be used in combination with or in place of guide extension catheters like the Teleflex Guideliner. The device may be placed in the femoral artery and navigated to the common carotid artery (CCA) or internal carotid artery (ICA), or some other artery of the body. In some embodiments, the device may be used to decrease brain temperature during a thrombectomy, such as by selectively cooling the brain. The cooled fluid may be infused through the device, outletting at the distal end 204 of the device, into an artery, such as the common carotid artery or internal carotid artery, and the infused fluid may then flow antegrade towards the brain. When a proximal aspiration thrombectomy is being performed, the device may work with a balloon guide catheter or act as a balloon guide catheter. When a distal aspiration thrombectomy is being performed, a balloon guide catheter may not be needed, or the device may not need to act as a balloon guide catheter. The device may be used to administer cooled fluid after clot removal, or before clot removal. Cooled fluid may begin being administered before clot removal, and continue after clot removal. In some embodiments, the device may be used to cool the heart during myocardial infarction.

Figure 70:
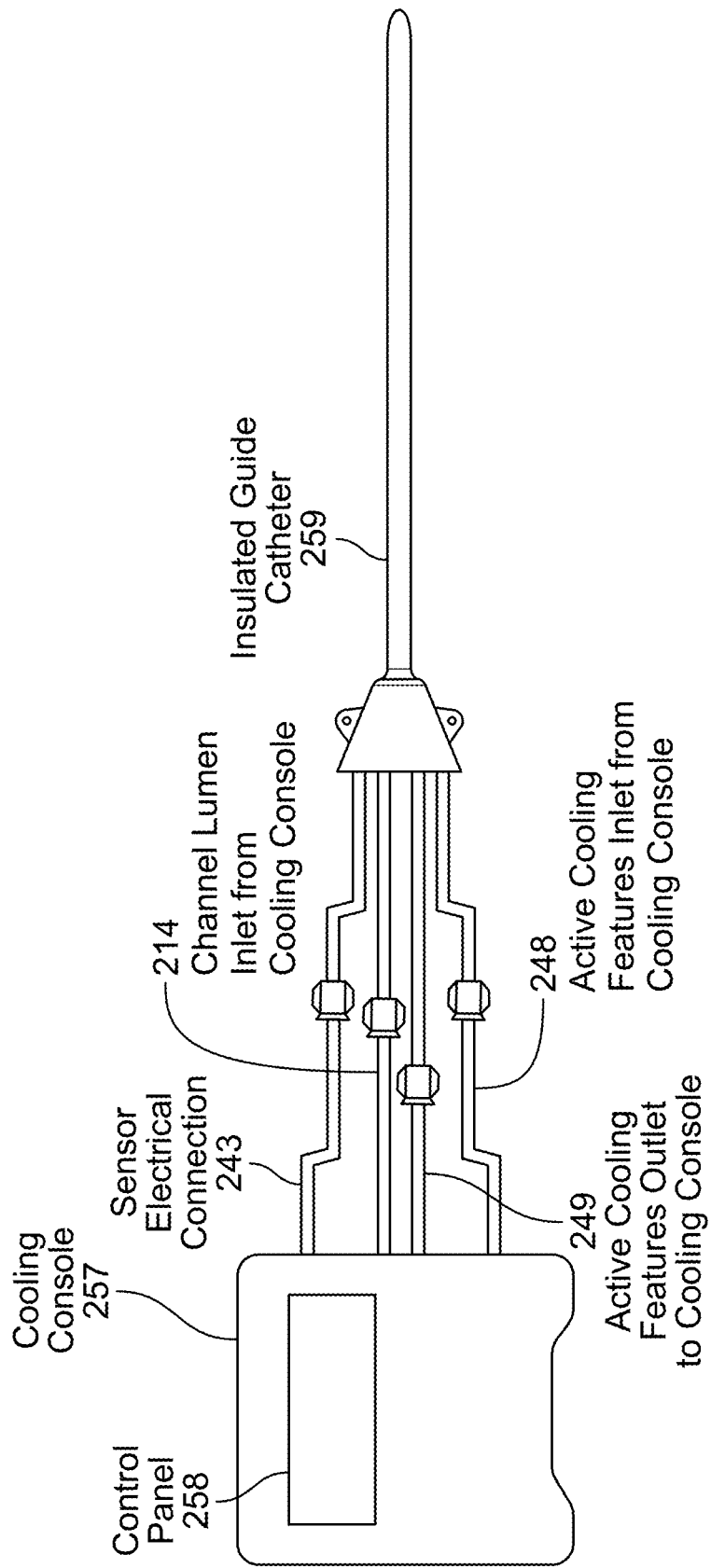
FIG. 70 illustrates a system for therapy incorporating an insulated guide catheter and a cooling console, in accordance with some embodiments of the disclosure.

The proximal portion of the device, the portion of the device which may be outside the human body during use, may be connected to an apparatus, such as a cooling console, which circulates cooled fluid through the active cooling features of the catheter, such as lumens to circulate fluid. FIG. 70 illustrates a system for therapy incorporating an insulated guide catheter and a cooling console, in accordance with some embodiments of the disclosure. The cooling console may provide chilled fluid to the inlet of a lumen of the device which circulates cooled fluid throughout the device. The console may also provide an outlet for the input fluid after it circulates through the system. The cooling console may have features to cool the fluid before it is inserted into the inlet of the catheter. These cooling features may be a cooling circuit which uses a heat exchanger to lower the temperature of the fluid. The cooling console may also be the source of inflow for the fluid infused through the channel lumen, intended to outlet at or near the distal end 204 of the device. The cooling console may have one or more pumps which allows for movement of the fluid throughout the system. The cooling console may have one or more control units which may allow a user to monitor the parameters of the system and may allow the user to modify the performance of the system, such as by changing the settings. The cooling console may be in communication with the one or more sensors of the device, and the output of these sensors may be displayed on the cooling console, such as on a control panel. The cooling console may modify its performance, such as through the use of a control module, or notify a user to modify its performance, if a measurement received from one or more of the one or more sensors of the device is outside a specified range. The pump may be operatively coupled to the control module to modify the fluid flow rate through the apparatus when directed by the control module. The cooling console, in combination with the insulated guide catheter, may be used to deliver hypothermic fluid to the body, which may be used for the treatment of reperfusion injury or ischemia of the brain or heart.

The system described may also be inserted through a vein, such as a femoral vein, and may be used to deliver cooled fluid retrograde. In this embodiment, the guide catheter may have a balloon to block flow in the venous system and allow for the delivery of retrograde flow.

IV. Reversible Catheter Embodiment

Figure 71:
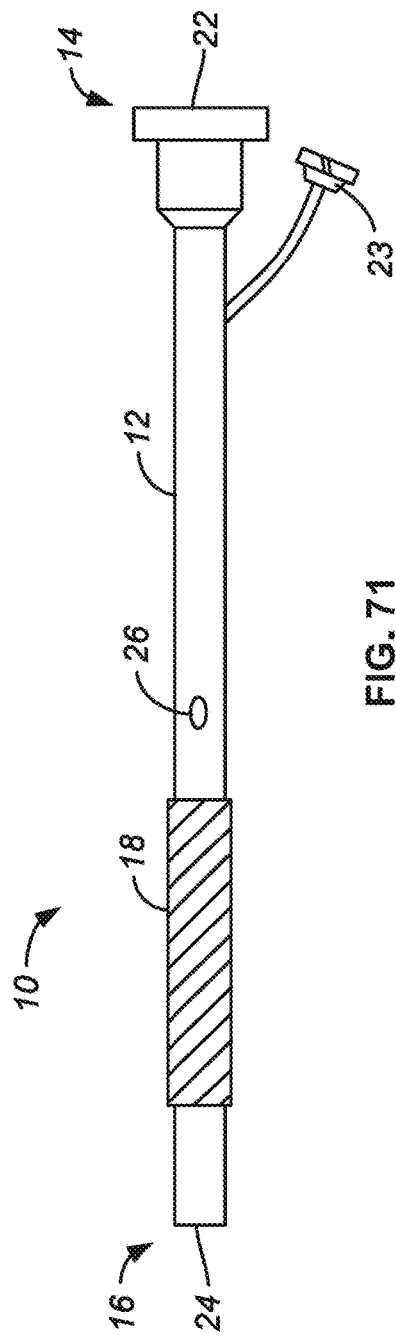
FIG. 71 is a side view of a first embodiment of a venous perfusion catheter constructed in accordance with the principles of the present invention, in accordance with some embodiments of the disclosure.
Figure 72:
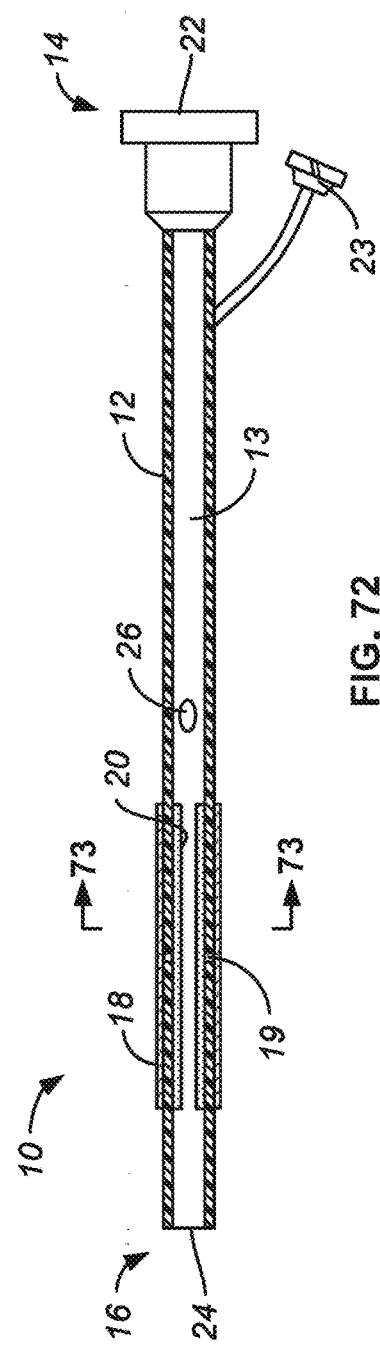
FIG. 72 is a cross-sectional view of the venous infusion catheter of FIG. 71, in accordance with some embodiments of the disclosure.
Figure 73:
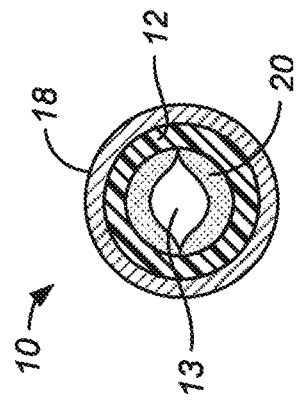
FIG. 73 is a front view of the venous infusion catheter of FIG. 71, in accordance with some embodiments of the disclosure.

FIGS. 71 to 73 illustrate a venous infusion catheter device 10 which comprises an elongated and hollow catheter body 12 which extends between a proximal end or hub 14 and a distal end 16. The venous infusion catheter 10 is further provided with at least one external inflatable balloon 18 secured to the external face of the elongated catheter body 12 and at least one internal inflatable balloon structure 20 secured to the internal face of the elongated catheter body 12. The elongated catheter body 12 is provided with an input port 22 located at the proximal hub 14, an output port 24 located at the distal end 16 and a lateral port 26 located on the wall of the elongated catheter body 12.

The external and internal balloons 18 and 20 are each secured at a respective position along the length of the elongated catheter body 12 and the lateral port is positioned at a given position along the length of the elongated catheter body 12 so that the lateral port 26 be located between the external balloon 18 and the proximal hub 14 of the elongated catheter body 12 and between the internal balloon 20 and the proximal hub 14 of the elongated catheter body 12 and between the internal balloon 20.

The proximal hub of the elongated catheter body 12 is fluidly connectable to a source of fluid, such as a liquid or other preservative medium, and the elongated catheter body 12 is adapted for propagating the fluid received from its proximal hub 14 along its length, typically through an axial or central lumen 13, and deliver the fluid via the output port 24 and the lateral port 26. At least a section of the elongated catheter body adjacent to the distal end 16 and comprising the lateral port 26 is insertable into a conduit such as a vein of a subject.

The external balloon 18 is inflatable so that it may change between a deflated state or configuration and an inflated state or configuration. Similarly, the internal balloon 20 is inflatable so that it may change between a deflated state or configuration and an inflated state or configuration. It should be understood that the external and internal balloons 18 and 20 illustrated in FIGS. 71 to 73 are each in the deflated state or configuration. As described below, the size and shape of the external and internal balloons 18 and 20 are chosen so that the external balloon 18 occludes the space between the elongated catheter body 12 and the venous lumen in which the venous infusion catheter 10 is inserted, and the internal balloon 20 occludes the lumen 13 of the elongated catheter body 12, when in the inflated configuration, and so that the external balloon 18 allows fluid to flow in the space between the elongated catheter body 12 and the conduit and the internal balloon 20 allows fluid to flow within the elongated catheter body, when in the deflated configuration.

When the external and internal balloons 18 and 20 are in the deflated configuration, fluid injected into the elongated catheter body 12 via the input port 22 flows into the elongated catheter body 12 while some of the fluid exits the elongated catheter body 12 via the lateral port 26 while the remaining fluid exits the elongated catheter body 12 via the output port 24.

Figure 74:
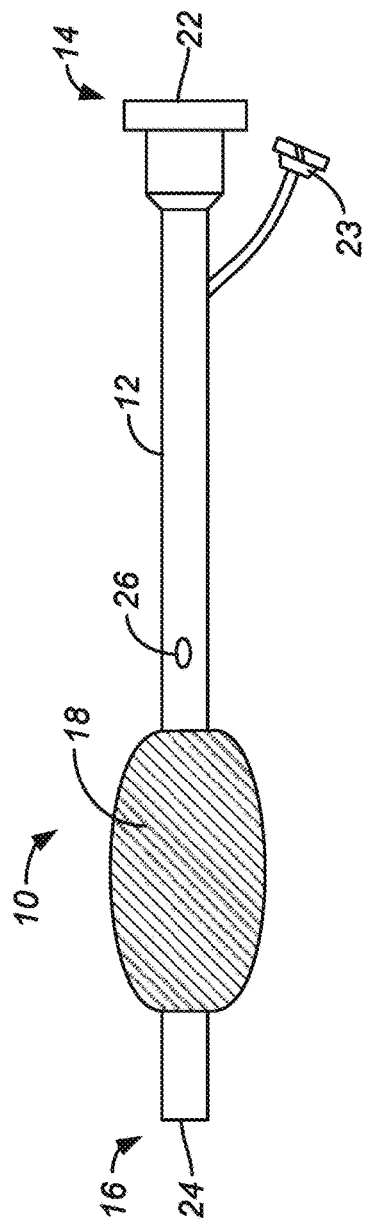
FIG. 74 is a side of a venous infusion catheter comprising balloons in an inflated configuration, in accordance with an embodiment, in accordance with some embodiments of the disclosure.
Figure 75:
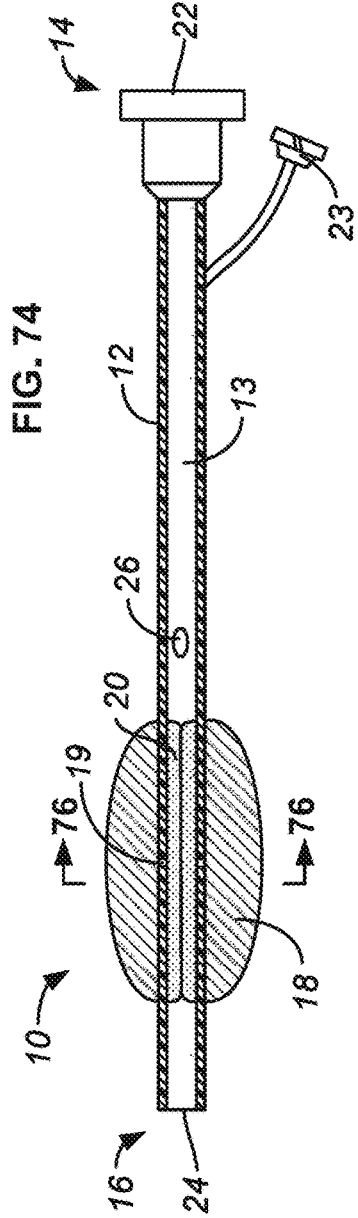
FIG. 75 is a cross-sectional view of the venous infusion catheter of FIG. 74, in accordance with some embodiments of the disclosure.
Figure 76:
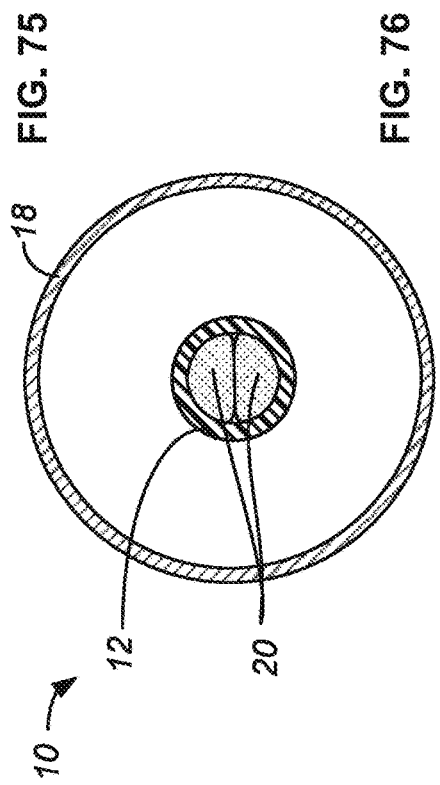
FIG. 76 is a front view of the venous infusion catheter of FIG. 74, in accordance with some embodiments of the disclosure.

FIGS. 74 to 76 illustrate the venous infusion catheter 10 when the balloons 18 and 20 are in the inflated configuration. The external balloon 18 is inflated around the circumference of the external face of the elongated catheter body 12. The diameter of the external balloon 18, when inflated, is chosen so as to abut the internal wall of the conduit into which the venous infusion catheter 10 is inserted. As a result, no fluid may flow outside of the elongated catheter body from the proximal hub 14 thereof towards the distal end 16 thereof. As illustrated in FIG. 75 and FIG. 76, the internal balloon 18, when inflated, form occludes the internal cavity of the elongated catheter body 12 so that no fluid may flow within the lumen 13 of elongated catheter body 12 from the proximal hub 14 thereof towards the distal end 16 thereof.

As a result, when the external and internal balloons 18 and 20 are inflated, any fluid injected into the elongated catheter body 12 via input port 22 is blocked by the inflated internal balloon 20 and therefore cannot flow down to the distal output port 24, also referred to as a medicament or infusion outlet port. As a result the fluid exits the elongated catheter body 12 via the lateral port 26. After exiting the elongated catheter body 12, the fluid cannot propagate outside of the elongated catheter body 12 towards the distal end 16 of the elongated catheter body 12 because of the inflated external balloon 20. As a result, the fluid flows outside of the elongated catheter body from the lateral port 26 towards the proximal hub 14 of the elongated catheter body 12.

It should be understood that the external and internal balloons 18 and 20 are each fluidly connectable to a source of fluid (not shown) for inflating the balloons 18 and 20. For example, the source of fluid may be adapted to deliver a pressurized fluid such as air or water, typically saline, into the balloons 18 and 20 so as to inflate the balloons 18 and 20. In one embodiment, the source of fluid is further configured to aspirate fluid from the balloons 18 and 20 so as to deflate the balloons 18 and 20. In one embodiment, a source of inflation medium, such as a saline-filled syringe (not shown), may couple to a inflation luer or other connector 23 to deliver the inflation medium simultaneously to the external and internal balloons 18 and 20 through a common inflation port 19 formed in a wall of the elongated catheter body 12. Typically, an axial inflation lumen (not illustrated) will also be formed in the wall of elongated catheter body 12 to pass the inflation medium from the connector 23 to the common inflation port 19.

While in the illustrated embodiment, the hollow body 12 has a tubular shape, it should be understood that the body 12 may be provided with any other adequate cross-sectional shape such as an oval cross-sectional shape.

While in the illustrated embodiment, the internal balloon 20 and the external balloon 18 are positioned substantially at the same longitudinal position along the length of the elongated catheter body 12, it should be understood that the balloons 18 and 20 may be positioned at different longitudinal positions as long as the external and internal balloons 18 and 20 are positioned between the distal end 16 of the elongated catheter body 12 and the lateral port 26.

In one embodiment, the elongated catheter body 12 is made of a flexible material. For example, including but not limited to, radiopaque polyurethane, silicone, polyethylene, polyvinylchloride, polytetrafluoroethylene, nylon, or a material with favorable interactions with whole blood and its components such as red blood cell, platelets, and inflammatory mediators.

While in the above description the external balloon 18 has a cylindrical shape when in the deflated and inflated configurations, it should be understood that the balloon 18 may have on ovoid, irregular, or tulip-shaped, or other configuration in order to optimize retrograde flow path of fluid administered proximal to the expandable occluder so long as it can be inflated to conform to seal against an inner wall of the vein when inflated therein. Often the external balloon 18 may be formed wholly or partly from an elastomeric or other compliant material to promote conformance to and sealing against the inner vessel wall.

While the internal balloon structure 20 is illustrated as a pair of opposed, D-shaped kissing balloons so that meet and occlude the internal lumen 13 of the elongated catheter body 12 when inflated, as shown in FIG. 76, it will be appreciated that the balloon could have any one of a variety of specific configurations which would provide full luminal occlusion when inflated.

The venous infusion catheter 10 may comprise more than one external balloon 18 and/or more than one internal balloon structure 20. The number, position and shape of the external balloon(s) 18 are chosen so that no fluid may flow in the space surrounding the elongated catheter body 12 between the proximal and distal ends 14 and 16 of the elongated catheter body 12 when the external balloons) 18 are inflated. Similarly, the number, position and shape of the internal balloons structures 20 are chosen so that no fluid may flow through the lumen 13 the elongated catheter body 12, and in particular will be prevented from flowing from the inlet port 22 to the outlet port 24 at the distal end of the elongated catheter body 12.

While the above description refers to a single source of inflation fluid for inflating both the external and internal balloons 18 and 20, it should be understood that the external balloon 18 may be connected to a first source of inflation fluid and the internal balloon 20 may be connected to a second and different source of inflation fluid.

In an alternative embodiment (not illustrated), the elongated catheter body 12 comprises no output port 24. In this case, the distal outlet port 24 of the elongated catheter body 12 is a closed end so that fluid flowing from the input port 22 into the elongated catheter body 12 may exit the elongated catheter body 12 only via the lateral port 26. In this case, the venous infusion catheter 10 may comprise no internal balloon 20 and only comprise at least one external balloon 18.

While the above description refers to a single lateral port 26, it should be understood that the elongated catheter body 12 may be provided with more than one lateral port having any adequate shape and size distributed along as the lateral wall of the elongated catheter body 12. Similarly, the elongated catheter body 12 may be provided with more than one output port of which the position, shape and size may vary as long as the output ports are located at the distal end 16 of the elongated catheter body 12 or between the distal end 16 and the internal balloon 20.

Figure 77:
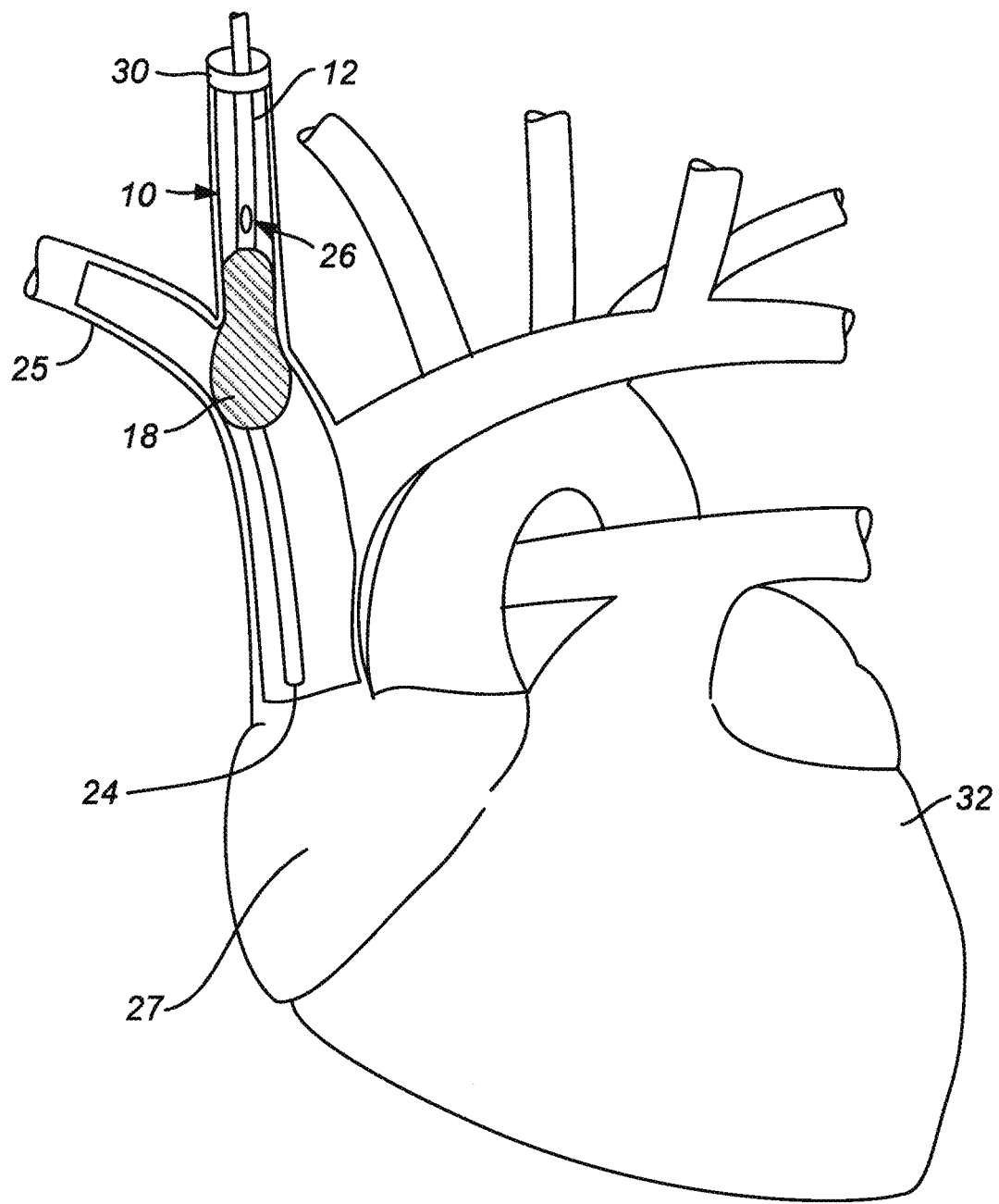
FIG. 77 illustrates a venous infusion catheter installed in an internal jugular vein, in accordance with an embodiment, in accordance with some embodiments of the disclosure.

In other embodiments, the venous infusion catheter such as the catheter 10 may be used as a central venous catheter both to provide access to the right atrium for the delivery of medicaments and to provide retrograde cerebral perfusion during an emergency, such as cardiopulmonary arrest, a stroke, during cardiac surgery when the heart has been intentionally stopped, or the like. In such cases, as illustrated in FIG. 77, the venous infusion catheter 10 is percutaneously introduced into the patient's internal jugular vein 30 and into the brachiocephalic vein 25, also known as an innominate vein, so that the distal outlet port 24 is above the right atrium 27 of the patient's heart 32. The lateral port 26 remains in the internal jugular vein 30 while the external balloon 18 is positioned at the junction between the internal jugular vein 30 and into the brachiocephalic vein 25. Normally, both the external and internal balloons 18 and 20 will remain deflated, and the venous perfusion catheter 10 can be used as a central venous catheter in the usual manner with medicaments and other substances delivered into the right atrium 27 through the inlet port 22. In the event that the patient suffers a cardiopulmonary or other emergency, however, the external and internal balloons 18 and 20 will be inflated to redirect the flow path through the catheter so that a preservative medium may be infused through the inlet port 22 to exit through lateral port 26 and flow in a retrograde direction through the internal jugular vein 30 into the cerebral vasculature to protect the brain tissue from damage in cardiac arrest, as described below.

When used as a central venous catheter, the balloons 18 and 20 remain in their deflated configurations, and the proximal hub 14 of the venous infusion catheter 10 is fluidly connected to a source of fluid to direct a first fluid, such as a preservative, towards the heart of the subject. Examples of preservative fluids include crystalloid solution, blood, oxygenated blood, oxygen carrying fluids, colloids, or the patient's own blood. Examples of medicaments that may be delivered include fluids, blood products, and nutritional media.

The distal section of the venous infusion catheter 10 is inserted into the internal jugular vein 30 of the subject so that the port 26 of the elongated catheter body 10 be located inside the internal jugular vein 30, and once in place, the venous infusion catheter 10 is secured onto the subject. Once the catheter has been installed in the internal jugular vein 30 of the subject, the source of fluid may be activated to deliver the first fluid. The first fluid reaches the input port 22 and propagates into the elongated catheter body 12. The first fluid then exits the elongated catheter body 12 via the lateral port 26 and the output port 24 before propagating into the heart 32.

If an emergency is detected, e.g. the heart and/or lungs go into arrest, the venous infusion catheter 10 which is already in place in the subject may be used for perfusing the brain of the subject. To do so, the external and internal balloons 18 and 20 are inflated using the source(s) of inflation fluid. When inflated, the internal balloon 20 substantially hermetically obstructs the passageway within the elongated catheter body 12 so that no fluid within the lumen 13 of elongated catheter body 12 from the input port 22 may propagate up to the distal end 16 of the elongated catheter body 12 and exit the elongated catheter body 12 via the output port 24. The fluid coming from the input port 22 will redirected (diverted) to exit the elongated catheter body 12 via the lateral port 26 only.

When inflated, the external balloon 18 extends in the space between the external face of the elongated catheter body 12 and the internal wall of the internal jugular vein 30 and abuts against the internal wall of the jugular vein 30 so as to substantially hermetically obstruct the passageway between the external face of the elongated catheter body 12 and the internal wall of the internal jugular vein 30. The fluid exiting the elongated catheter body 12 via the lateral port 26 cannot therefore propagate towards the heart 32 because of the inflated external balloon 18 and may then propagate in an opposite direction towards the brain.

In one embodiment, a second fluid different from the first fluid may be delivered once the external and internal balloons 18 and 20 have been inflated. In this case, the proximal hub 14 of the venous infusion catheter 10 is fluidly connected to a source of second fluid.

In another embodiment, the same fluid, i.e. the first fluid, may be delivered to the brain after the inflation of the external and internal balloons 18 and 20.

In one embodiment, the second fluid to be delivered to the brain after the inflation of the external and internal balloons 18 and 20 comprises a crystalloid fluid. Such a crystalloid fluid can cool and protect a brain and is usually available in an intensive care unit (ICU). In case of emergency, a non-sub specialized person, such as a nurse, may then inflate the external and internal balloons 18 and 20, connect the catheter to a source of crystalloid fluid to the proximal hub 14 of the venous infusion catheter 10, and direct the flow of crystalloid fluid towards the brain of the subject.

In another embodiment, the second fluid may be an oxygen carrying fluid such as blood.

It should be understood that any adequate means may be used for fluidly connecting the external and/or internal inflatable balloons 18 and 20 to at least one source of inflation fluid. For example, a first conduit or pipe may have a first end connect to a first source of inflation fluid and a second end fluidly connected to the external balloon 18. The first conduit is then located outside of the elongated catheter body 12. A second conduit or pipe inserted into the elongated catheter body 12 has a first end connected to a second source of inflation fluid and a second end fluidly connected to the internal balloon 20.

Figure 78:
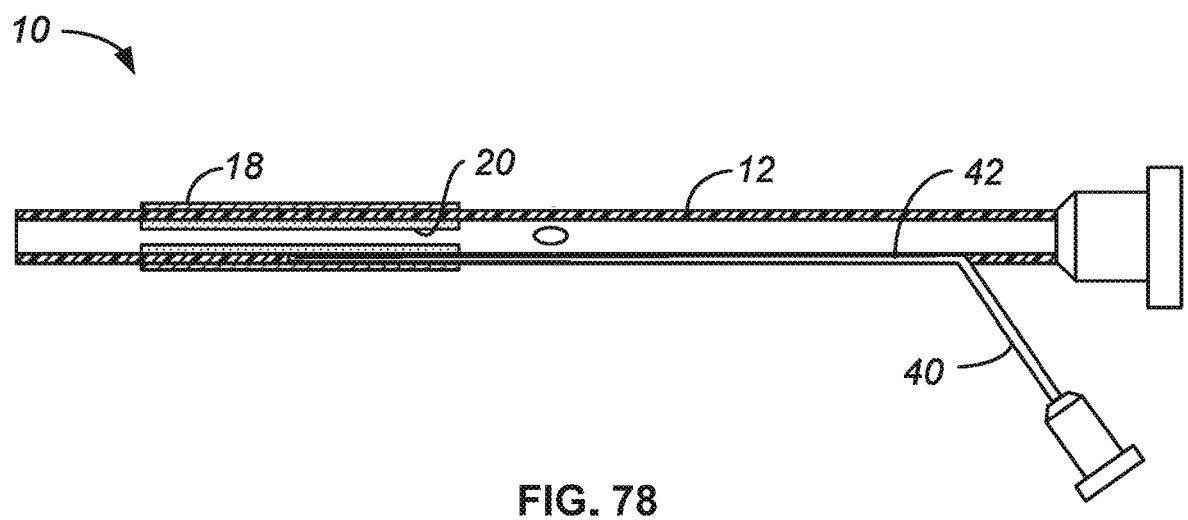
FIG. 78 illustrates a venous infusion catheter comprising a conduit for delivering an inflation fluid to balloons, the balloons being in a deflated state, in accordance with an embodiment, in accordance with some embodiments of the disclosure.
Figure 79:
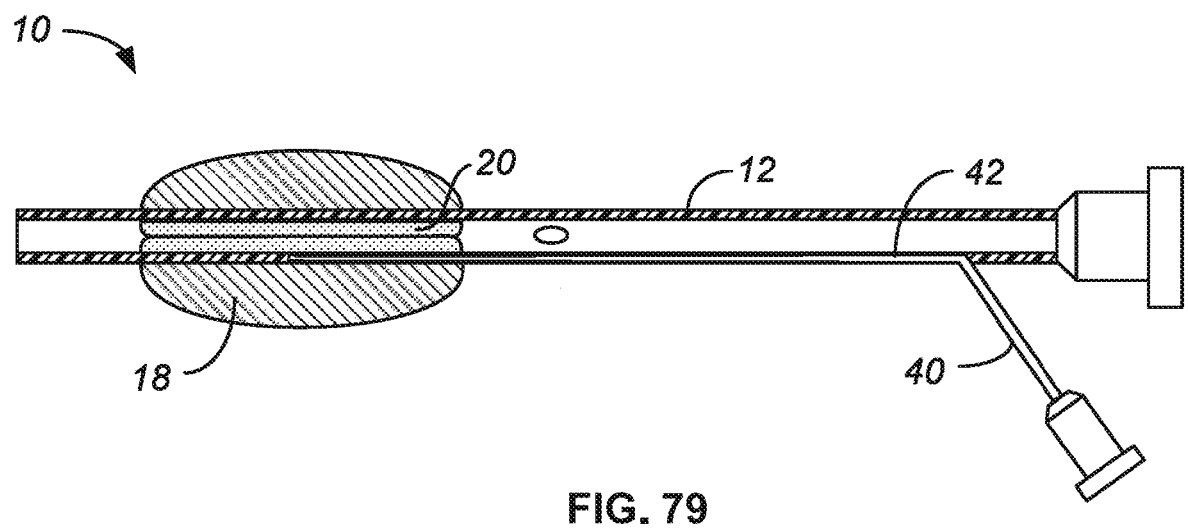
FIG. 79 illustrates the venous infusion catheter of FIG. 78 with the balloons in an inflated state, in accordance with some embodiments of the disclosure.

FIG. 78 and FIG. 79 illustrate another configuration for fluidly connecting the external and internal balloons 18 and 20 to a source of inflation fluid. In this embodiment, a single conduit 40 is used for fluidly connecting the source of inflation fluid to both the external and internal balloons 18 and 20. In this embodiment, the wall of the elongated catheter body 12 is provided with an internal cavity 42 which extends along a section from a proximal position adjacent to the proximal hub 14 to a distal position that faces the external and internal balloons 18 and 20. The conduit 40 is inserted into the cavity 42 via a proximal aperture present in the elongated catheter body 12. The distal end of the conduit 40 is fluidly connected to the external and internal balloons so as to deliver thereto the inflation fluid.

Figure 80:
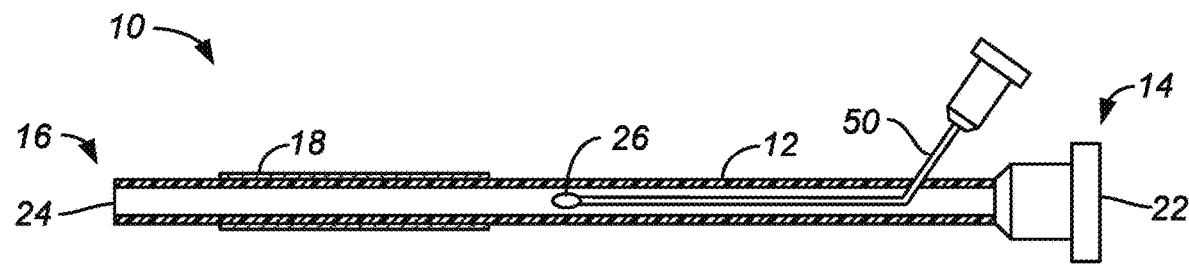
FIG. 80 illustrates a catheter comprising only an external balloon and conFIG.d for concurrently delivering two fluids in opposite directions, the external balloon being in a deflated state, in accordance with some embodiments of the disclosure.
Figure 81:
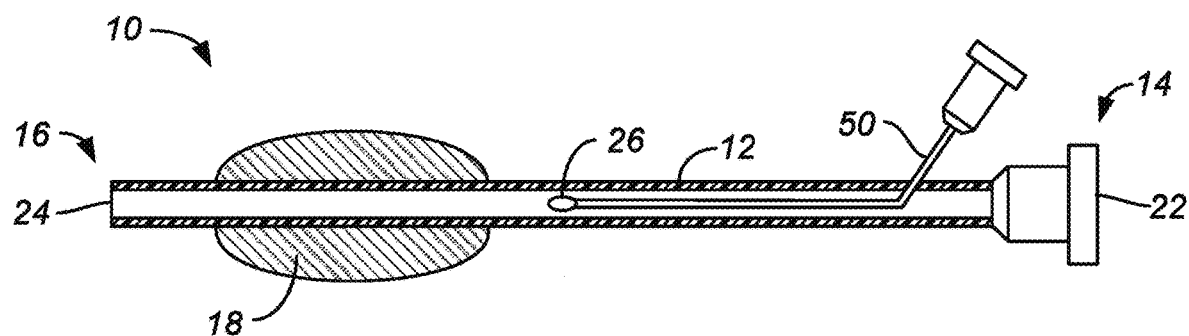
FIG. 81 illustrates the catheter of FIG. 80 with the external balloon in an inflated state, in accordance with some embodiments of the disclosure.

FIG. 80 and FIG. 81 illustrate an embodiment of a catheter configured for delivering two fluids concurrently. For example, this catheter may be used for delivering a first fluid towards the heart of a subject and a second fluid towards the brain of the subject. This catheter comprises no internal balloon but comprises a conduit 50 having a distal end connected to the lateral port 26 from the inside of the elongated catheter body 12 and a proximal hub connectable to a source fluid. As a result, when a fluid is injected into the elongated catheter body 12 via its proximal port, the fluid exits the elongated catheter body 12 via the distal port. When a fluid is injected into the conduit 50, the fluid exits the catheter via the lateral port 26.

In one embodiment, the catheter may be used for concurrently providing a first fluid to the heart of a subject and irrigating the brain of the subject. The catheter is inserted in the internal jugular vein as described above. The elongated catheter body 12 may be used for delivering a first fluid towards the heart of the subject by injecting the first fluid via the proximal port of the elongated catheter body 12. In case of emergency, the external balloon 18 is inflated and a second fluid is injected via the conduit 50. The second fluid exits the catheter via the lateral port 26. Since the inflated external balloon 18 prevents the second fluid from propagating towards the heart of the subject, the second fluid flows in the reverse direction towards the brain of the subject. It should be understood that the first fluid can still be delivered to the heart while the second fluid is delivered to the brain of the subject.

A further exemplary catheter device 20, illustrated in FIGS. 82A-82B and FIGS. 83A-83D, comprises an elongated catheter body 102 having a distal end 104 and proximal end 106. As shown in particular in FIGS. 83A-83D, the elongated catheter body 102 includes a perfusion lumen 108, an inflation lumen 110, a first drug lumen 112, and second drug lumen 114. Each lumen has a corresponding connector attached via a proximal hub 118. More specifically, the inflation lumen 110 is typically connected to an inflation connector 120, the perfusion lumen 108 is connected to a perfusion connector 122, the first drug lumen 112 is connected to a first drug connector 126, and the second drug lumen 114 is connected to a second drug connector 128. Each of the connectors will include a luer or other conventional terminal element to be removably attached to an appropriate material source, such as a perfusate, drugs, a protective medium, or an inflation source, such as a syringe.

Each of the internal lumens within the catheter body 102 terminates in a port on the catheter body. In particular, the perfusion lumen 108 terminates in a lateral perfusion port 134. The inflation lumen 110 terminates in an inflation port 132, and the first and second drug lumens 112 and 114 terminate in a first drug port 138 and a second drug port 140, respectively. In this way, it will be appreciated that fluids, drugs, inflation media, and the like, may be delivered from each of the connectors to their respective outlet ports in the elongated catheter body 102 by connection to the appropriate fluid or inflation source.

The catheter 100 also includes an expandable occlusion element 144, typically an inflatable balloon, positioned on the exterior surface of the catheter body 102 between the perfusion port 134 and the drug delivery ports 138 and 140. As will be described hereinafter, having the expandable occlusion element 144 between these ports allows flow from each port to be selectively directed in an antegrade or retrograde flow direction in a vein when the occlusion element 144 is expanded.

Figure 82A:
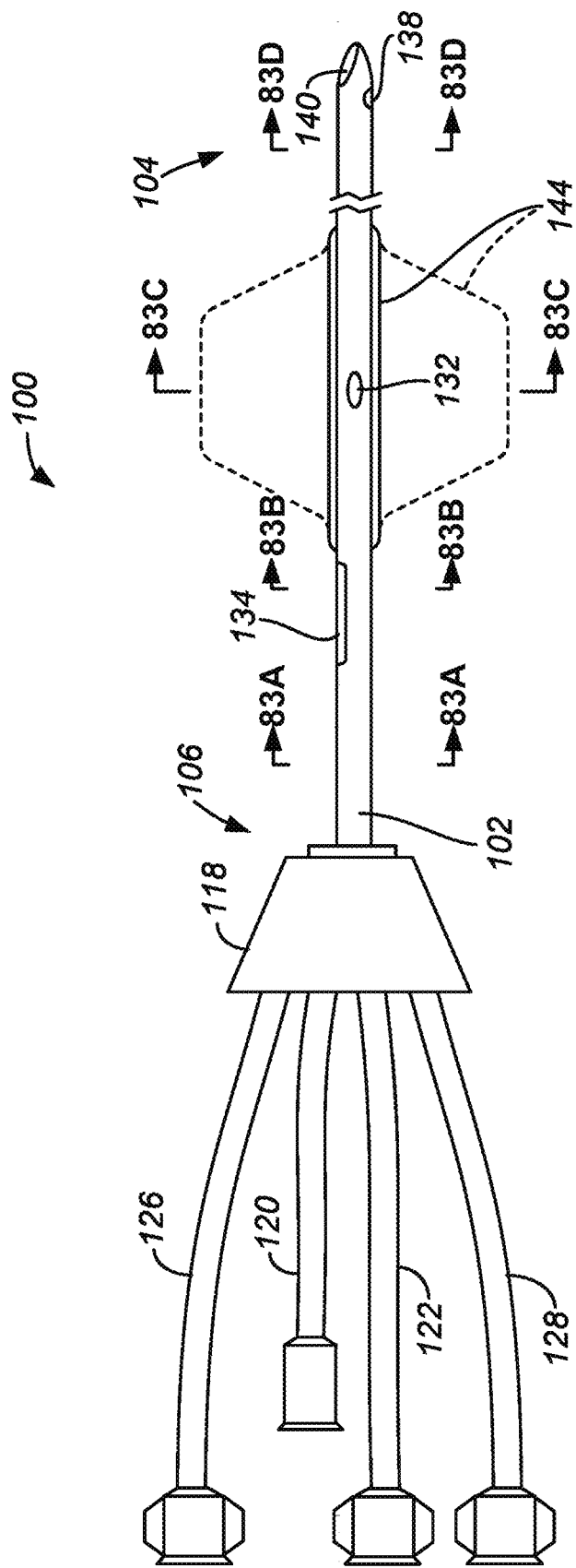
FIG. 82A is a side view of an embodiment of a venous perfusion catheter, in accordance with the principles of the present invention, in accordance with some embodiments of the disclosure.
Figure 82B:
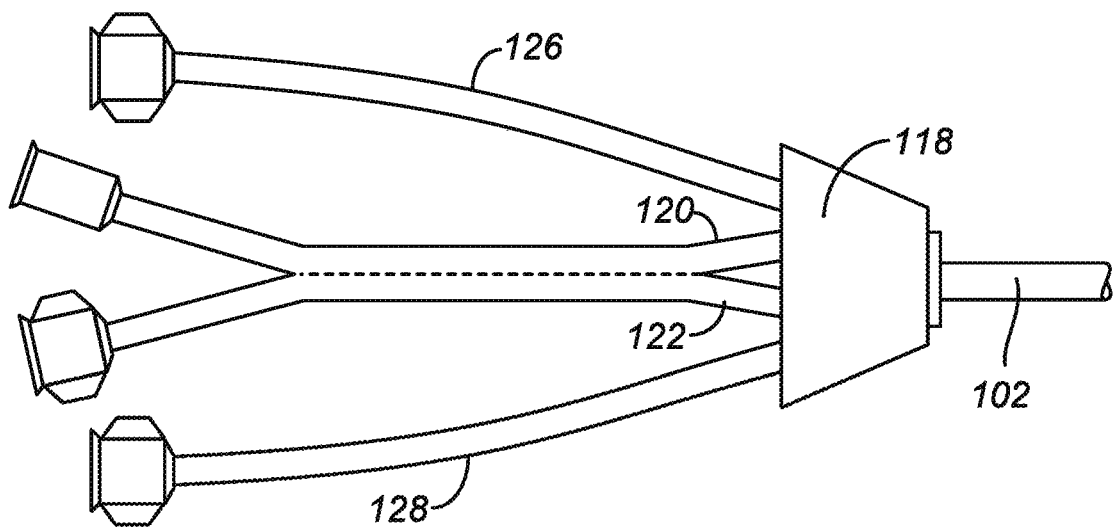
FIG. 82B illustrates an alternative hub and connector assembly for the catheter of FIG. 82, in accordance with some embodiments of the disclosure.

Referring now to FIG. 82A, in some embodiments the inflation connector 120 and the perfusion connector 122 may be fused or otherwise joined together to facilitate connection management during use. In particular, by having the perfusion connection and the inflation connector together, the user may easily identify both connectors when there is a need to inflate the external occlusion element 144 and deliver a protective medium through the perfusion connector 122.

Figure 84A:
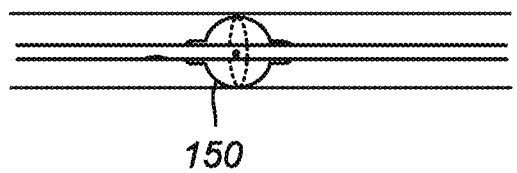
FIG. 84A illustrates external occlusion elements having alternative configurations, in accordance with some embodiments of the disclosure.
Figure 84B:
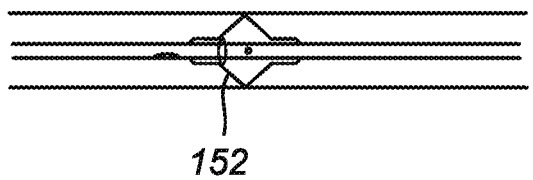
FIG. 84B illustrates external occlusion elements having alternative configurations, in accordance with some embodiments of the disclosure.
Figure 84C:
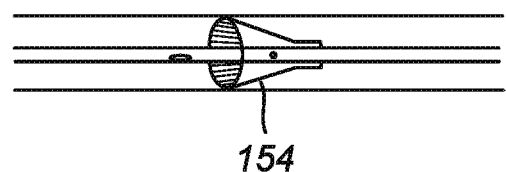
FIG. 84C illustrates external occlusion elements having alternative configurations, in accordance with some embodiments of the disclosure.
Figure 83A:
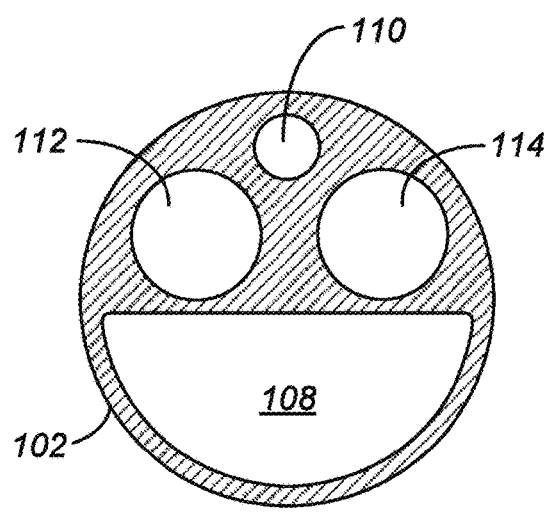
FIG. 83A is a cross-sectional view taken along line 83A of FIG. 82A, in accordance with some embodiments of the disclosure.
Figure 83B:
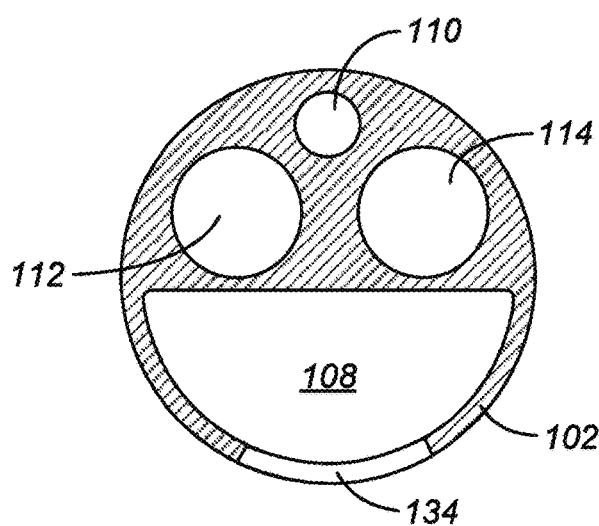
FIG. 83B is a cross-sectional view taken along line 83B of FIG. 82A, in accordance with some embodiments of the disclosure.
Figure 83C:
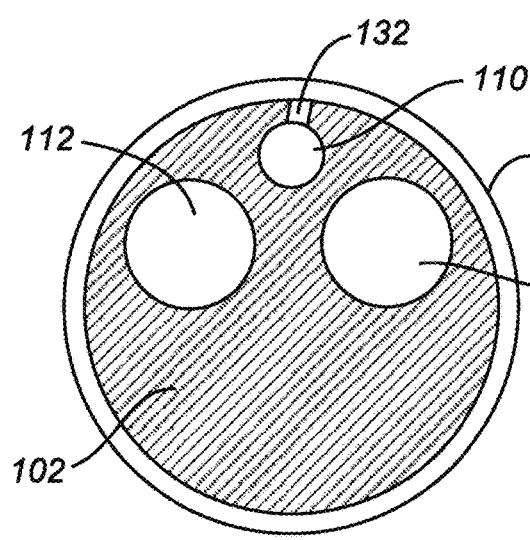
FIG. 83C is a cross-sectional view taken along line 83C of FIG. 82A, in accordance with some embodiments of the disclosure.
Figure 83D:
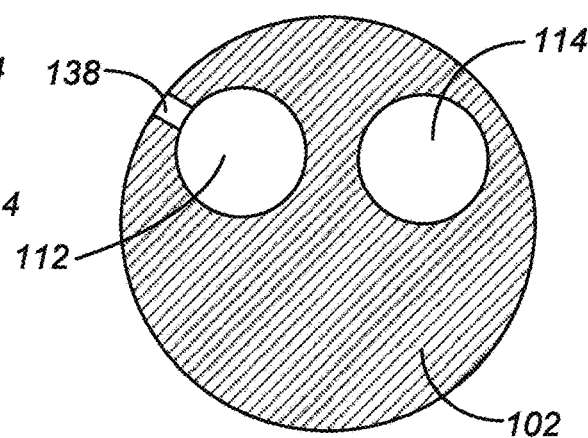
FIG. 83D is a cross-sectional view taken along line 83D of FIG. 82A, in accordance with some embodiments of the disclosure.

As illustrated in FIG. 82A, the expandable occlusion element 144 is an inflatable balloon having a deflated configuration shown in full line. The balloon may be inflated to a generally cylindrical shape, as shown in broken line. As shown in FIGS. 84A-84C, the expandable occlusion elements may have a variety of shapes, such as spherical balloons 150 (FIG. 84A), inflatable elements having a circumscribing ridge as shown at 152 in FIG. 84B, and tulip-shaped 154 as shown in FIG. 84C. Such tulip-shaped occlusion elements 154 will typically have a concave surface oriented in an upstream direction so that blood flow will cause the conical structure to expand and further seal against the venous wall.

Figure 85:
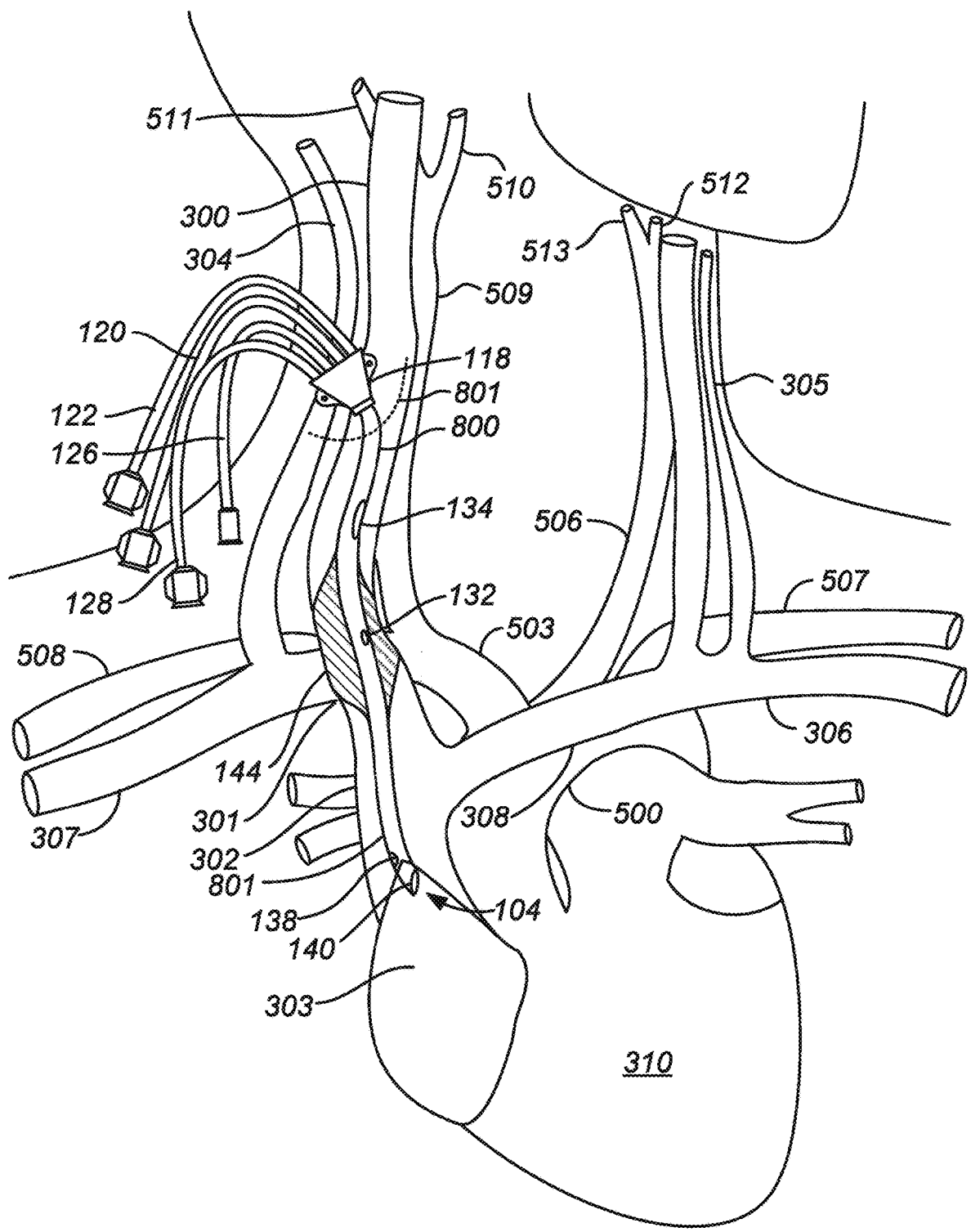
FIG. 85 illustrates the venous perfusion catheter of FIG. 82A placed in a patient's venous vasculature, in accordance with some embodiments of the disclosure.

Placement and use of the catheter 100 is illustrated in FIG. 85, where both the patient's venous and arterial vasculatures are shown. Venous blood flows caudally from the right internal jugular vein 300 through the right brachiocephalic vein 301 into the superior vena cava 302, and into the right atrium 303 of the heart 310. Venous blood is also returned to the right atrium of the heart 303 via the left 308 and right 301 brachiocephalic veins, collecting from the right 304 and left 305 external jugular veins and the left 306 and right 307 subclavian veins. Arterial flow is directed from the aorta 500 through the brachiocephalic artery 503, left common carotid artery 506, and left subclavian artery 507. From the brachiocephalic artery 503, arterial blood flows to both the right subclavian artery 508, and cranially, through the right common carotid 509, splitting into the right internal common carotid 510 and right external common carotid 511. Arterial blood additionally flows from the left common carotid artery 506 to the left external carotid artery 512 and left internal carotid artery 513.

As further shown in FIG. 85, the catheter 100 is located, as typical of central venous catheters, with the distal end 104 sitting in the superior vena cava 302 at the entrance to the right atrium 303. The device hub 118 is sutured to the skin 801 for secure placement, with each of the four connectors 120, 122, 126, and 128 located externally for access by medical team. The elongated catheter body 102 is introduced through a lumen of the right internal jugular vein 300, with the expandable occlusion element 144 in an unexpanded configuration. The expandable occlusion element 144 will typically be positioned above the junction with the right subclavian vein 307 and be left in the unexpanded configuration until a need arises for the delivery of a protective perfusion medium to the patient's brain, e.g. during an in-hospital cardiac arrest (IHCA). While in this configuration, the catheter 100 may be used for delivering drugs or other substances to heart though either drug lumen 112 and 114 and drug port 138 and 140 in the same manner as a conventional central venous catheter.

When IHCA or other need arises for the delivering of a protective perfusion medium to the patient's brain, the expandable occlusion element 144 is expanded to provide full occlusion of the right internal jugular vein 304. Partial or full occlusion of the right subclavian vein 307 may also occur. As illustrated in this embodiment, the expandable occlusion element 144 is an inflatable balloon, and expansion is caused by delivering saline or other inflation medium though the inflation connector 120 and inflation lumen 110, typically using a syringe. While specific reference has been made to intervention into the right internal jugular vein, it will be appreciated that other portions of the vasculature could also be accessed.

By occluding the right internal jugular vein 301 and optionally right subclavian vein 307, antegrade venous flow through the right internal jugular vein 301 is arrested and retrograde flow of the protective medium (such as a cooled crystalloid fluid) to the cerebral venous vasculature may occur.

Drug delivery to the heart may continue as appropriate to occur through the second drug lumen 114 and port 140 or through the first drug lumen 112 and port 138. Countercurrent heat exchange may then occur between the right internal jugular vein 300 and the right carotid arteries 509, 510, 511 as this potentially cooled fluid is administered through the perfusion lumen 108 and port 134. Arterial flow through vessels, none of which are occluded, will continue despite IHCA or other use indication, including intentional cardiac arrest during cardiac surgery, and the patient will experience blood flow during the chest compressions associated with CPR. This arterial blood flow will further accommodate temperature exchange through this countercurrent heat exchange, supplementary to the temperature modulation achieved by direct exposure in the venous system to potentially cooled fluids.

Figure 86:
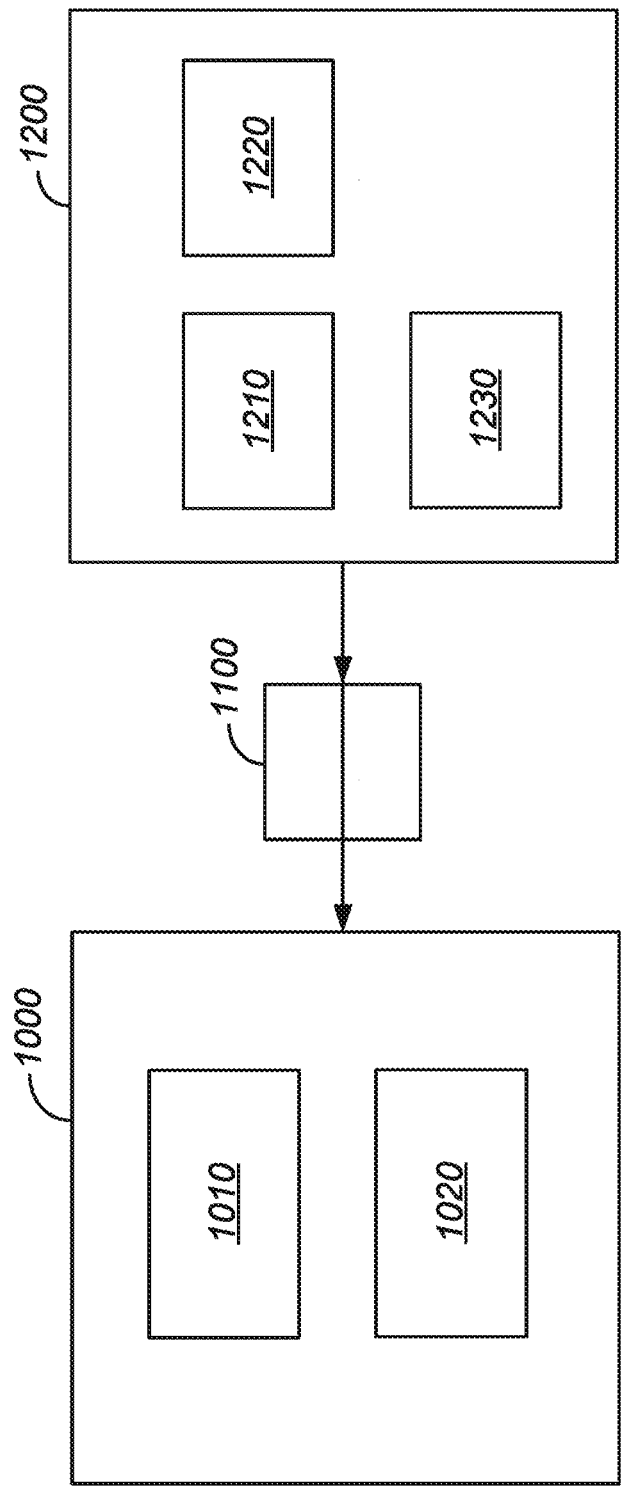
FIG. 86 is a block diagram illustrating components of a therapeutic system, in accordance with some embodiments of the disclosure.
Figure 88A:
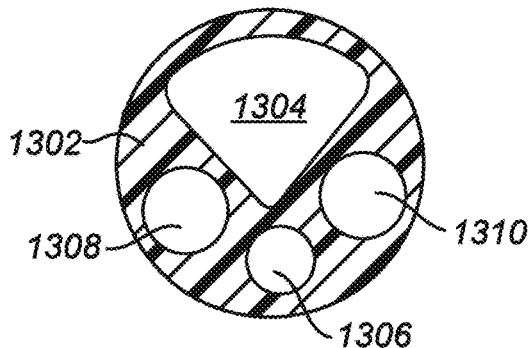
FIG. 88A is a cross-sectional view taken along line 88A of FIG. 87A, in accordance with some embodiments of the disclosure.
Figure 88B:
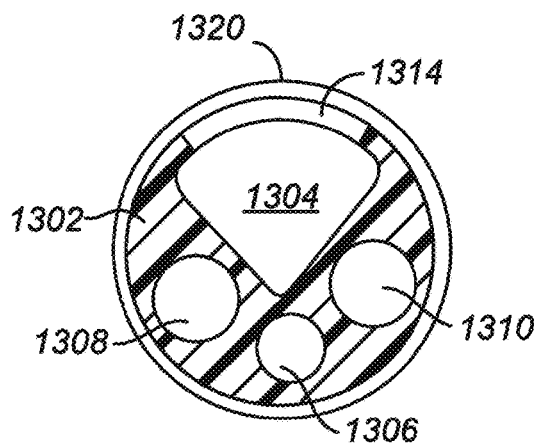
FIG. 88B is a cross-sectional view taken along line 88B of FIG. 87A, in accordance with some embodiments of the disclosure.
Figure 88C:
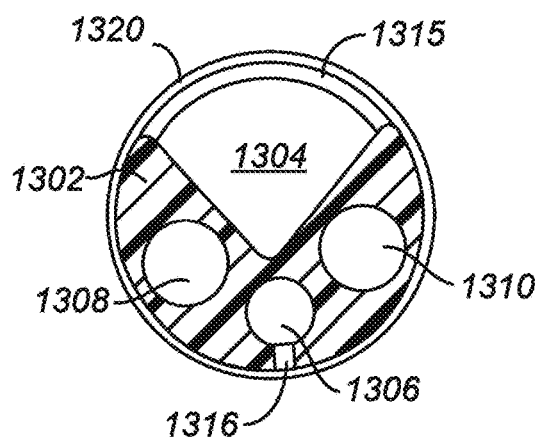
FIG. 88C is a cross-sectional view taken along line 88C of FIG. 87A, in accordance with some embodiments of the disclosure.
Figure 88D:
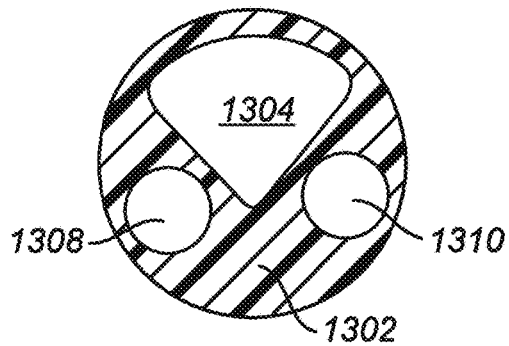
FIG. 88D is a cross-sectional view taken along line 88D of FIG. 87A, in accordance with some embodiments of the disclosure.

Referring now to FIG. 86, systems of the present invention typically comprise patient-interface components 1000, extracorporeal components 1200, and fluid transfer components 1100 between the patient-interface components and the extracorporeal components. The patient-interface components 1000 typically include a venous perfusion catheter 1010 and an associated temperature sensor 1020. The extracorporeal components 1200 include a crystalloid or other fluid 1210 to be housed within a specialized temperature-modulating receptacle 1220, and a readout feature 1230 of the temperature sensor. The fluid transfer components 1100 typically include temperature-modulating tubing, and the fluid 1210 to be administered will flow through the temperature-modulating tubing to the venous perfusion catheter 1010 where it will be released into the patient's vasculature and directed cranially. Temperature fluctuation data will be communicated from the patient-interfacing system 1000 to the extracorporeal system 1200.

Referring now to FIGS. 87A-87B, FIGS. 88A-88D and FIGS. 89A-89B, an alternative distribution system for a venous perfusion catheter in accordance with the principles of the present invention will be described. The flow of distribution system 1300 may be incorporated into a venous perfusion catheter of the type previously disclosed. The flow distribution system 1300 utilizes a double-acting balloon configuration to simultaneously occlude venous flow and divert flow through the perfusion lumen from the distal or downstream side of the expanded balloon to the proximal or upstream side of the balloon.

An elongated catheter body 1302 includes a perfusion lumen 1304, an inflation lumen 1306, a first drug lumen 1308, and a second drug lumen 1310. The drug lumens 1308 and 1310 are visible only in the lateral cross-sectional views of FIGS. 88A-88D and FIGS. 89A-89B and are not visible in the axial cross-sectional views of FIGS. 87A-87B.

The perfusion lumen 1304 terminates in a distal port (not illustrated) for delivery of drugs, substances, or the like to the heart when the perfusion lumen is open (not occluded by the double-acting balloon as described below or other mechanical occlusion means). The perfusion lumen 1304 also has a second or cerebral perfusion port 1314 for delivery of perfusion medium, typically a protective perfusion medium, to the cerebral venous vasculature when the double-acting balloon is inflated.

As shown in FIG. 87A and FIGS. 88A-88D, an expandable occlusion element 1320 in the form of an inflatable balloon is in a deflated configuration. When deflated, a proximal segment of the balloon 1320 covers the proximal perfusion port 1314 as well as the occlusion port 1315.

Figure 89A:
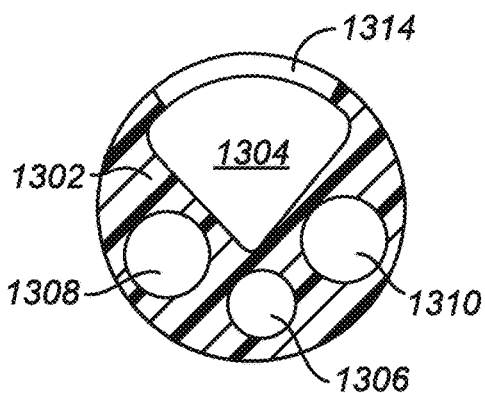
FIG. 89A is a cross-sectional view taken along line 89A of FIG. 87B, in accordance with some embodiments of the disclosure.
Figure 89B:
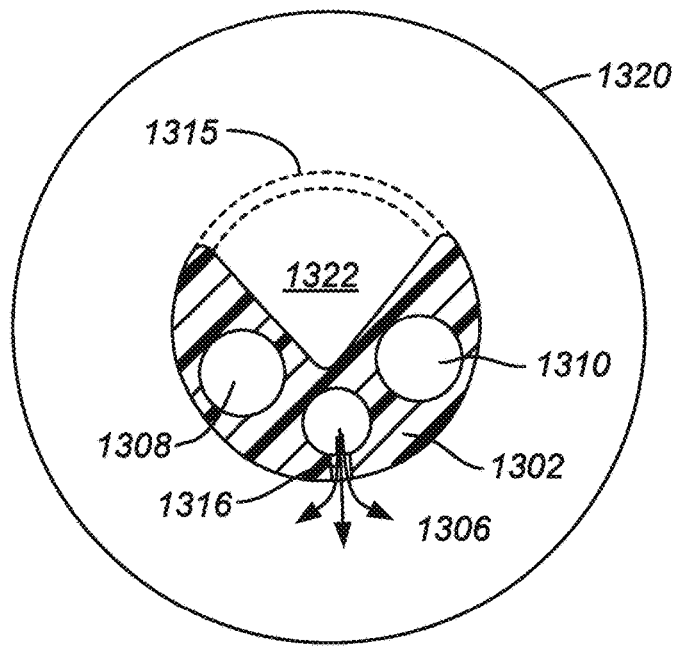
FIG. 89B is a cross-sectional view taken along line 89B of FIG. 87B, in accordance with some embodiments of the disclosure.

As shown in FIGS. 87B and 89B, however, when the expandable occlusion balloon 1320 is inflated by delivery of an inflation medium through inflation lumen 1306, the balloon inflates and peels away to uncover the proximal perfusion port 1314. In addition, an occlusion protrusion 1322 of the balloon expands radially inwardly through the occlusion port 1315 in the sidewall of the elongated catheter body 1302. Thus, flow of the perfusion medium through the perfusion lumen 1304 is blocked by the expanded occlusion element 1320 and diverted through the uncovered perfusion port 1314 so that it can flow in a retrograde manner into the patient's cerebral venous vasculature, as described previously.

Figure 90A:
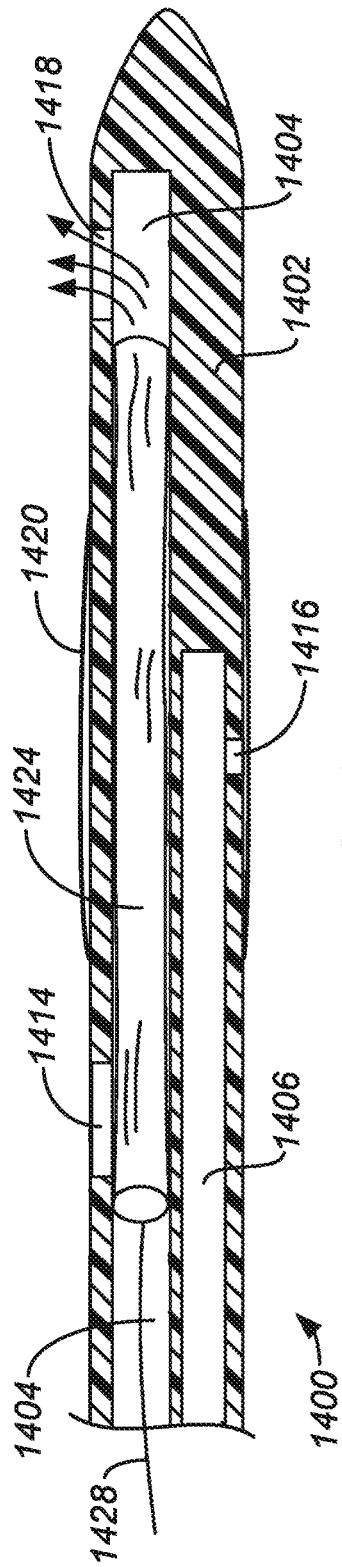
FIG. 90A illustrates an embodiment of a venous perfusion catheter, in accordance with some embodiments of the disclosure.
Figure 90B:
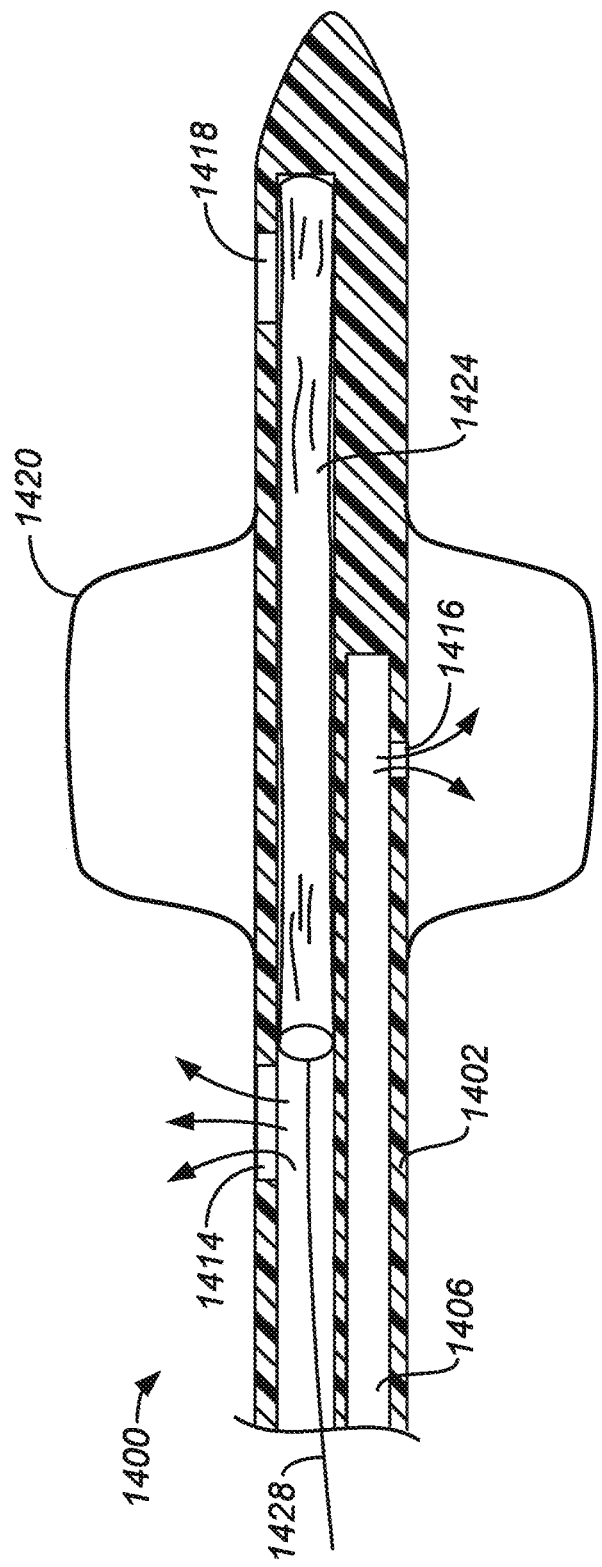
FIG. 90B illustrates an embodiment of a venous perfusion catheter, in accordance with some embodiments of the disclosure.

Referring now to FIG. 90A and FIG. 90B, a venous perfusion catheter 1400 having a tubular flow diverter is illustrated. The venous perfusion catheter 1400 includes an elongated catheter body 1402 having a perfusion lumen 1404 and an inflation lumen 1406. The catheter will typically also include one or more additional drug delivery lumens, but such lumens are not visible in the axial cross-sectional views of FIG. 90A and FIG. 90B.

The perfusion lumen 1404 includes a proximal or cerebral perfusion port 1414 and a distal or cardiac perfusion port 1418. The inflation lumen 1406 includes an inflation port 1416 positioned to inflate a balloon-like expandable occlusion element 1420 in a manner similar to prior embodiments.

As shown in FIG. 90A, a tubular flow diverter 1424 is in a proximally retracted position so that it covers the proximal or cerebral perfusion port 1414. That is, when the tubular flow diverter 1424 is proximally retracted, flow through the perfusion lumen 1404 cannot pass outwardly through the proximal or cerebral perfusion port 1414. Instead, flow through the perfusion lumen 1404 will pass through an interior passage of the tubular flow diverter 1424 so that it may pass out of the distal or cardiac perfusion port 1418.

In order to divert the perfusion flow to the proximal or cerebral perfusion port 1414, the tubular flow diverter 1424 is distally advanced to cover the distal or cardiac infusion port 1418, as shown in FIG. 90B. The proximal or cerebral perfusion port 1414 is simultaneously uncovered so that flow may then pass radially outwardly through the proximal port. In order to assure that the flow from the proximal port 1414 flows in a retrograde manner, the balloon-like expandable occlusion element 1420 is inflated by delivering an inflation medium through the inflation lumen 1406 and outwardly through the inflation port 1416 to occlude the vein as previously described.

Referring now to FIGS. 21A and 21B, a perfusion balloon catheter 1500 is illustrated. The perfusion balloon catheter 1500 includes an elongated catheter body 1502 having a combination perfusion/inflation lumen 1504 and at least one additional drug or other fluid delivery lumen 1506. When used as a central access catheter, an expandable occlusion element in the form of the perfusion balloon 1520 remains uninflated, as shown in FIG. 91A. Drugs or other substances may be delivered through the drug delivery lumen 1506 and outwardly through a drug infusion port 1508, as shown in FIG. 91A. Drugs may also be released through a second drug infusion port 1510, as shown in FIG. 91B.

When it is desired to deliver a perfusion medium, such as a cerebral protection medium, in a retrograde direction from the perfusion balloon catheter 1500, the protective or other perfusion medium is delivered through the combined perfusion/inflation lumen 1504 so that it inflates the balloon occlusion element 1520, as shown in FIG. 91B. A plurality of drug release apertures 1524 formed on a proximal or cerebral side of the inflated balloon open to release the inflating perfusion medium from the balloon in a retrograde direction, typically toward the patient's brain. If desired, drugs may be delivered through any of the available drug delivery lumens in the catheter.

The embodiments of the invention described above are intended to be exemplary only. The scope of the invention is therefore intended to be limited solely by the scope of the appended claims. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Any elements described herein as singular can be pluralized (i.e., anything described as "one" can be more than one). Any species element of a genus element can have the characteristics or elements of any other species element of that genus. (e.g., "Central Venous Catheter" is used as an exemplary medical device throughout the disclosure, but can be any medical device or combinations thereof. "Heat exchanger" is used as an exemplary method of cooling matter throughout the disclosure but can be any method of cooling matter or combinations thereof.) The above-described configurations, elements or complete assemblies and methods and their elements for carrying out the invention, and variations of aspects of the invention can be combined and modified with each other in any combination.

We claim:

1. A venous infusion catheter assembly comprising:
    an elongated catheter body having a proximal end and a distal end;
    a hemicylindrical occluder disposed on the elongated catheter body for fluid delivery;
    at least one infusion lumen, wherein:
        the at least one infusion lumen extends from the proximal end of the catheter body to a proximal infusion port positioned on the catheter body proximally of the hemicylindrical occluder,
        the at least one infusion lumen extends from the proximal end of the catheter body to a distal infusion port positioned on the catheter body distally of the hemicylindrical occluder, and
        the fluid delivery is through the proximal infusion port or through the distal infusion port based on an orientation of the hemicylindrical occluder;
    a suction lumen extending from the proximal end of the catheter body to at least one suction port positioned on the catheter body; and
    wherein the proximal infusion port and the distal infusion port are spaced relative to the hemicylindrical occluder such that when the catheter is introduced into vasculature of a patient, the suction port is positioned in the patient's superior vena cava to draw blood flowing through the patient's vena cava, the distal infusion port is positioned in the patient's superior vena cava or right atrium to direct normothermic or hyperthermic fluid toward the patient's heart, and the proximal infusion port is positioned in the patient's internal jugular vein to create a retrograde flow of hypothermic fluid in the patient's cerebral vasculature.

2. The venous infusion catheter assembly of claim 1 further comprising an inflation lumen extending from the proximal end of the catheter body to the hemicylindrical occluder.

3. The venous infusion catheter assembly of claim 1 further comprising a positional marker positioned on the catheter body at or proximally adjacent to at least one of the at least one suction port, the proximal infusion port, the distal infusion port.

4. The venous infusion catheter assembly of claim 3, wherein the positional marker is a radiopaque marker or an ultrasonically opaque marker.

5. The venous infusion catheter assembly of claim 1 further comprising a positional marker on the distal end of the catheter body, the positional marker comprising a radiopaque marker or an ultrasonically opaque marker.

6. The venous infusion catheter assembly of claim 1 further comprising a heat exchange assembly fluidly connected with the suction lumen and the at least one infusion lumen.

7. The venous infusion catheter assembly of claim 6 further comprising a controller communicatively connected to the heat exchange assembly.

8. The venous infusion catheter assembly of claim 7, wherein the heat exchange assembly further comprises a pump with adjustable flow rate connected to the controller.

9. The venous infusion catheter assembly of claim 8, wherein the controller is configured to adjust at least one of flow rate of the pump or temperature of the heat exchange assembly.

10. The venous infusion catheter assembly of claim 8, wherein the controller is further configured to:
    receive a brain temperature and a heart temperature; and
    adjust at least one of flow rate of the pump or temperature of the heat exchange assembly based on the brain temperature and the heart temperature.

11. The venous infusion catheter assembly of claim 7, wherein the controller controls the heat exchange assembly to output hypothermic fluid to the infusion controller controls the heat exchange assembly to output hypothermic fluid to the at least one infusion lumen through the proximal infusion port.

12. The venous infusion catheter assembly of claim 7, wherein the controller controls the heat exchange assembly to output normothermic or hyperthermic fluid to the at least one infusion lumen through the distal infusion port.

13. The venous infusion catheter assembly of claim 7, wherein the heat exchange assembly and the controller are integrated in a housing.

14. The venous infusion catheter assembly of claim 1 further comprising a temperature sensor positioned on or in the catheter body distally of the hemicylindrical occluder or in suction tubing.

15. The venous infusion catheter assembly of claim 1 further comprising a guidewire extending from the proximal end of the catheter body to the distal end of the catheter body.

16. The venous infusion catheter assembly of claim 1 further comprising an expandable element disposed on the elongated catheter body and positioned on the catheter body distally of the hemicylindrical occluder between the hemicylindrical occluder and the at least one suction port such that the at least one suction port is not occluded by the patient's vein wall.

17. The venous infusion catheter assembly of claim 16, wherein the expandable element is nonocclusive.

18. The venous infusion catheter assembly of claim 1, wherein the normothermic or hyperthermic fluid comprises blood of temperature between 36 degrees Celsius and 42 degrees Celsius.

19. The venous infusion catheter assembly of claim 1, wherein the hypothermic fluid comprises blood of temperature between 0 degrees Celsius and 36 degrees Celsius.

20. The venous infusion catheter assembly of claim 1, wherein the at least one infusion lumen comprises a layer of insulation.

21. The venous infusion catheter assembly of claim 1, wherein the normothermic or hyperthermic fluid comprises suctioned blood.

22. The venous infusion catheter assembly of claim 1, wherein the hypothermic fluid comprises cooled suctioned blood.

23. The venous infusion catheter assembly of claim 1, wherein one or more of the at least one infusion lumen, the suction lumen, or a pressure lumen extending through the catheter body comprises a reinforcement coil or hypotube.

24. The venous infusion catheter assembly of claim 1 further comprising a pressure lumen extending from the proximal end of the catheter body to a port positioned proximally of the hemicylindrical occluder.

25. The venous infusion catheter assembly of claim 1 further comprising a mounting fixture.

26. The venous infusion catheter assembly of claim 1 further comprising a tapered tip positioned at the distal end of the catheter body.

27. The venous infusion catheter assembly of claim 26 wherein the tapered tip is constructed of a material of lower durometer than the catheter body.

28. The venous infusion catheter assembly of claim 1 further comprising a second suction port, different from the at least one suction port, that is fluidly connected to the suction lumen and positioned on the catheter body distally of the hemicylindrical occluder between the hemicylindrical occluder and the distal infusion port.

29. The venous infusion catheter assembly of claim 1 further comprising a second suction port, different from the at least one suction port, that is fluidly connected to the suction lumen and positioned on the catheter body distally of the distal infusion port.

30. The venous infusion catheter assembly of claim 1, wherein the elongated catheter body is introduced into vasculature of the patient in a first direction to deliver a flow of fluid through the catheter and directed in a direction opposite of the first direction.

* * * * *

UNITED STATES PATENT AND TRADEMARK OFFICE
CERTIFICATE OF CORRECTION

| | | |
|---|---|---|
| PATENT NO. | : 12,097,345 B2 | Page 1 of 1 |
| APPLICATION NO. | : 17/031511 | |
| DATED | : September 24, 2024 | |
| INVENTOR(S) | : Robert D. Schultz et al. | |

It is certified that error appears in the above-identified patent and that said Letters Patent is hereby corrected as shown below:

In the Claims

Claim 11, Column 78, Line 45-47, delete "infusion controller controls the heat exchange assembly to output hypothermic fluid to the".

Signed and Sealed this
Twenty-ninth Day of October, 2024

Katherine Kelly Vidal
*Director of the United States Patent and Trademark Office*